(12) United States Patent
Aicher et al.

(10) Patent No.: US 7,384,934 B2
(45) Date of Patent: Jun. 10, 2008

(54) PIPERAZINE SUBSTITUTED ARYL BENZODIAZEPINES

(75) Inventors: Thomas Daniel Aicher, Superior, CO (US); Zhaogen Chen, Noblesville, IN (US); Yvan LeHuerou, Boulder, CO (US); Fionna Mitchell Martin, Basingstoke (GB); Marta Maria Pineiro-Nunez, Brownsburg, IN (US); Vincent Patrick Rocco, Indianapolis, IN (US); Kevin Michael Ruley, Indianapolis, IN (US); John Mehnert Schaus, Zionsville, IN (US); Patrick Gianpietro Spinazze, Avon, IN (US); David Edward Tupper, Basingstoke (GB)

(73) Assignee: Eli Lilly and Company, Indianapolis, IN (US)

( * ) Notice: Subject to any disclaimer, the term of this patent is extended or adjusted under 35 U.S.C. 154(b) by 21 days.

(21) Appl. No.: 10/523,147

(22) PCT Filed: Jul. 28, 2003

(86) PCT No.: PCT/IB03/03583

§ 371 (c)(1),
(2), (4) Date: Oct. 18, 2005

(87) PCT Pub. No.: WO2004/014895

PCT Pub. Date: Feb. 19, 2004

(65) Prior Publication Data

US 2006/0084643 A1 Apr. 20, 2006

Related U.S. Application Data

(60) Provisional application No. 60/401,297, filed on Aug. 5, 2002.

(51) Int. Cl.
C07D 403/04 (2006.01)
C07D 495/04 (2006.01)
C07D 513/04 (2006.01)
A61K 31/55 (2006.01)
A61P 25/18 (2006.01)

(52) U.S. Cl. ............... 514/219; 514/220; 540/555; 540/557

(58) Field of Classification Search ........... 514/219, 514/220; 540/555, 557
See application file for complete search history.

(56) References Cited

U.S. PATENT DOCUMENTS

| 4,115,568 A | 9/1978 | Chakrabarti et al. | 514/220 |
| 5,602,121 A | 2/1997 | Fu | 514/211.13 |
| 5,824,676 A | 10/1998 | Tehim et al. | 514/220 |

FOREIGN PATENT DOCUMENTS

| EP | 0354781 | 2/1990 |
| EP | 1016664 A | 7/2000 |
| WO | WO 03082877 | 10/2003 |

OTHER PUBLICATIONS

Chakrabarti J K et al: "Effects of Conformationally Restricted 4-Piperazinyl-10h-Thienobenzod Iazepine Neuroleptics on Central Dopamingergic and Cholinergic Systems," Journal of Medicinal Chemistry, American Chemical Society. Washington, US, vol. 25, No. 10, Oct. 1, 1982, pp. 1133-1140.

(Continued)

Primary Examiner—Brenda L Coleman
(74) Attorney, Agent, or Firm—Robert D. Titus; John A. Cleveland, Jr.

(57) ABSTRACT

Described herein are compounds of formula (I) wherein: is an optionally benzo-fused five or six member aromatic ring having zero to three hetero atoms independently selected from N, S, and O; Alk is $(C_{1-4})$ alkylene or hydroxy substituted $(C_{1-4})$ alkylene; X is oxygen or sulfur; $R^1$ is hydrogen, $(C_{1-6})$ fluroalkyl, $(C_{3-6})$ cycloalkyl, or $(C_{1-4})$ alkyl, wherein the $(C_{1-4})$ alkyl is unsubstituted or substituted with hydroxy, methoxy, ethoxy, $OCH_2CH_2OH$, or —CN; $R^2$ is H, halogen, $(C_{1-6})$ fluoroalkyl, $(C_{1-6})$ cycloalkyl, $OR^4$, $SR^4$, $NO_2$, CN, $COR^4$, $C(O)OR^4$, $CONR^5R^6$, $NR^5R^6$, $SO_2NR^5R^6$, $NR^5COR^4$, $NR^5SO_2R^4$, optionally substituted aromatic, or $(C_{1-6})$ alkyl, wherein $(C_{1-6})$ alkyl is unsubstituted or substituted with a hydroxy group; $R^3$ is hydrogen $(C_{1-6})$ fluoroalkyl, $(C_{2-6})$ alkenyl, Ar, $(C_{1-4})$alkyl-Ar, or $(C_{1-4})$ alkyl wherein $(C_{1-4})$ alkyly is unsubstituted or substituted with a phenyl; $R^4$ is hydrogen, $(C_{1-6})$ alkyl, $(C_{1-6})$ fluoroalkyl, or optionally substituted aromatic; $R^5$ and $R^6$ are independently hydrogen, $(C_{1-6})$ alkyl, or optionally substituted aromatic, $R^7$ is hydrogen, $(C_{1-6})$ alkyl, $(C_{1-6})$ fluoroalkyl, or optionally substituted aromatic; $R^8$ and $R^9$ are independently hydrogen, $(C_{1-6})$ alkyl, or optionally substituted aromatic; Ar is optionally substituted phenyl, napthyl, monocyclic heteroaromatic or bicyclic heteroaromatic; $Z^1$ and $Z^2$ are independently selected from hydrogen, halogen, $(C_{1-6})$ alkyl, $(C_{1-6})$ fluoroalkyl, $OR^7$, $SR^7$, $NO^2$, CN, $COR^7$, $CONR^8R^9$, $NR^8R^9$, and optionally substituted aromatic; and all salts, solvates, optical and geometric isomers, and crystalline forms thereof. Also, described are the use of the compounds of formula (I) as antagonists of the dopamine D2 receptor and as agents for the treatment of psychosis and bipolar disorders, and pharmaceutical formulations of the compounds of formula (I)

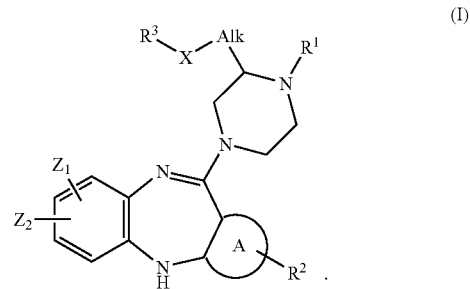

(I)

21 Claims, No Drawings

OTHER PUBLICATIONS

Rasmussen et al., Preclinical Pharmacology of FMPD [6-Fluoro-10-[3-(2-methoxyethyl)-4-methyl-piperazin-1-yl]-2-methyl-4$H$-3-thia-4,9-diaza-benzo[$f$]azulene]: A Potential Novel Antipsychotic with Lower Histamine $H_1$ Receptor Affinity Than Olanzapine, *The Journal of Pharmacology and Experimental Therapeutics*, 2005, pp. 1265-1277, vol. 315, No. 3.

PIPERAZINE SUBSTITUTED ARYL BENZODIAZEPINES

This is a 371 of PCT/IB03/03583 filed Jul. 28, 2003, which claims priority to U.S. Provisional Application No. 60/401,297 filed Aug. 5, 2002.

BACKGROUND OF THE INVENTION

Currently there are many drugs available for the treatment of disorders of the central nervous system. Among these drugs is a category known as antipsychotics which are used for treating serious mental conditions such as schizophrenia and schizophreniform illnesses. Currently available treatments for such conditions are often associated with undesirable adverse events. As such, there remains a need for new compounds that control or eliminate the symptoms of such mental conditions with improved adverse event profiles.

Patients suffering from schizophrenia, a condition of unknown etiology, exhibit a group of both positive and negative symptoms. Positive symptoms include delusions, hallucinations, disordered thoughts, and disorganized speech, while negative symptoms include flat affect, anhedonia, social withdrawal, emotional detachment, cognitive deficits, and poverty of speech. Not only does schizophrenia cause personal suffering by the patient, it also severely affects the patient's occupational and social functions, so that often the patient must be institutionalized, which results in a high cost to society.

A leading hypothesis suggests that the positive symptoms of schizophrenia can be effectively treated by compounds that act as antagonists at certain dopamine receptors. Currently, five principal dopamine receptors ($D_1$-$D_5$) have been identified. Antipsychotic efficacy has been most closely associated with blockade of the $D_2$ class of dopamine receptors. One class of antipsychotic agents known as "typical" antipsychotic agents (eg. haloperidol) are effective in controlling the positive symptoms of schizophrenia. However, they do not adequately treat the negative symptoms and are associated with significant adverse events, principally hyperprolactinemia, tardive dyskinesia, and extrapyramidal side effects (EPS).

One approach to developing better antipsychotic agents, involves the identification of compounds that combine $D_2$ receptor blockade with actions at other receptors. One such agent is clozapine.

Clozapine was the first drug identified as an "atypical" antipsychotic, i.e., a drug effective in treating both the positive and negative symptoms of schizophrenia. Additionally, it has a decreased propensity to induce EPS, hypolactinemia, and tardive dyskinesia seen with classical, "typical" antipsychotics. Although clozapine is an effective drug, its utility in treating schizophrenia has been limited because of the clinical observation that 1-2% of treated patients developed a potentially fatal blood disorder, agranulocytosis. More recently, olanzapine has been widely accepted as an atypical antipsychotic with relatively few adverse events.

However, weight gain has been observed during treatment with many of the atypical antipsychotic compounds (Wetterling, "Body Weight Gain with Atypical Antipsychotics, A Comparative Review", Drug Safety 24, 59-73 (2001); Wirshing, et al, "Novel Antipsychotics: Comparison of Weight Gain Liabilities", J. Clin. Psychiatry 60, 358-363 (1999); Allison, et al, "Antipsychotic-Induced Weight Gain: A Comprehensive Research Synthesis" Am. J. Psychiatry 156, 1686-1696 (1999); Ganguli, R. Weight gain associated with antipsychotic drugs. J. Clin. Psychiatry 60(suppl. 2), 20-24, (1999). Drugs with the clinical efficacy and safety profile of the atypical antipsychotics but with decreased propensity to induce weight gain would represent improved agents for the treatment of schizophrenia, bipolar disorder, and related disorders.

Atypical antipsychotics like clozapine and olanzapine are $D_2$ receptor antagonists but also interact with other neurotransmitter receptors, including other subtypes for dopamine, and certain receptor subclasses for serotonin, norepinephrine, histamine, and acetylcholine. It is believed that some of these additional receptor activities are responsible for the improved efficacy of the atypical antipsychotics and the adverse events of these agents may be mediated by interactions with others. In particular, it has been suggested that the weight gain effects of the atypical antipsychotics may be due to the blockade of the histamine H1 receptor (Wetterling, "Body Weight Gain with Atypical Antipsychotics, A Comparative Review", Drug Safety 24, 59-73 (2001); Wirshing, et al, "Novel Antipsychotics: Comparison of Weight Gain Liabilities" J. Clin. Psychiatry 60, 358-363 (1999); Kroeze, et al, "H1 Histamine Receptor Affinity Predicts Short-Term Weight Gain for Typical and Atypical Antipsychotic Drugs", Neuropsychopharmacology 28, 519-526 (2003); Orthen-Gambill, N. Antihistaminic drugs increase feeding, while histidine suppresses feeding in rats. Pharmacol. Biochem. Behav. 31, 81-86, (1988). Hence, the development of atypical antipsychotics with decreased affinity for the histamine $H_1$ receptor represents one mechanism for identifying antipsychotics with improved adverse event profiles.

The present invention provides antipsychotic compounds and methods of using those compounds to treat psychotic disorders, in particular, schizophrenia and mood disorders, such as bipolar disorders. These compounds offer certain improvements and advantages over the currently available antipsychotic agents, as for example, but not limited to, improved adverse event profiles. In particular, many of the compounds of this invention have reduced propentsity to cause weight gain because of their decreased affinity for the $H_1$ receptor.

BRIEF SUMMARY OF THE INVENTION

One aspect the present invention provides compounds of formula (I):

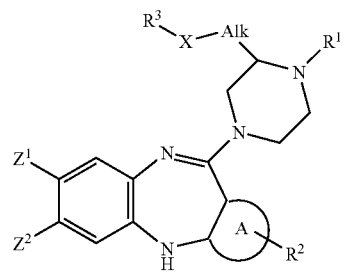

wherein:

is an optionally benzo-fused five or six member aromatic ring having zero to three hetero atoms independently selected from N, S, and O;

Alk is $(C_{1-4})$ alkylene or hydroxy substituted $(C_{1-4})$ alkylene;

X is oxygen or sulfur, $R^1$ is hydrogen, $(C_{1-6})$ fluoroalkyl, $(C_{3-6})$ cycloalkyl, or $(C_{1-4})$ alkyl, wherein the $(C_{1-4})$ alkyl is unsubstituted or substituted with hydroxy, methoxy, ethoxy, —OCH$_2$CH$_2$OH, or —CN;

$R^2$ is H, halogen, $(C_{3-6})$ cycloalkyl, $(C_{1-6})$ fluoroalkyl, OR$^4$, SR$^4$, NO$_2$, CN, COR$^4$, C(O)OR$^4$, CONR$^5$R$^6$, NR$^5$R$^6$, SO$_2$NR$^5$R$^6$, NR$^5$COR$^4$, NR$^5$SO$_2$R$^4$, optionally substituted aromatic, or $(C_{1-6})$ alkyl, wherein $(C_{1-6})$ alkyl is unsubstituted or substituted with a hydroxy group;

$R^3$ is hydrogen, $(C_{1-4})$ fluoroalkyl, $(C_{2-6})$ alkenyl, Ar, or $(C_{1-4})$ alkyl, wherein $(C_{1-4})$ alkyl is unsubstituted or substituted with a Ar group;

$R^4$ is hydrogen, $(C_{1-6})$ alkyl, $(C_{1-6})$ fluoroalkyl, or optionally substituted aromatic;

$R^5$ and $R^6$ are independently hydrogen, $(C_{1-6})$ alkyl, or optionally substituted aromatic, $R^7$ is hydrogen, $(C_{1-6})$ alkyl, $(C_{1-6})$ fluoroalkyl, or optionally substituted aromatic;

$R^8$ and $R^9$ are independently hydrogen, $(C_{1-6})$ alkyl, or optionally substituted aromatic;

Ar is optionally substituted phenyl, napthyl, monocyclic heteroaromatic or bicyclic heteroaromatic;

$Z^1$ and $Z^2$ are independently selected from hydrogen, halogen, $(C_{1-6})$ alkyl, $(C_{1-6})$ fluoroalkyl, OR$^7$, SR$^7$, NO$_2$, CN, COR$^7$, CONR$^8$R$^9$, NR$^8$R$^9$, and optionally substituted aromatic;

and all salts, solvates, optical and geometric isomers, and crystalline forms thereof.

Preferred among the compounds of formula (I) are those wherein:

$R^1$ is hydrogen or $(C_{1-4})$ alkyl unsubstituted or substituted with hydroxy, methoxy, ethoxy, —OCH$_2$CH$_2$OH, or —CN;

$R^2$ is H, $(C_{1-6})$ alkyl, halogen, $(C_{1-6})$ fluoroalkyl, —OR$^4$, —SR$^4$, —NO$_2$, —CN, —COR$^4$, —C(O)OR$^4$, —CONR$^5$R$^6$, —NR$^5$R$^6$, —SO$_2$NR$^5$R$^6$, —NR$^5$COR$^4$, —NR$^5$SO$_2$R$^4$, or optionally substituted aromatic; and $R^3$ is H, $(C_{1-4})$ alkyl, Ar, or $(C_{1-4})$alkyl Ar.

Also preferred among the compounds of formula (I) are those of formula (Ia):

(Ia)

wherein:

Alk is $(C_{1-4})$ alkylene;

$R^1$ is hydrogen, $(C_{1-6})$ fluoroalkyl, $(C_{3-6})$ cycloalkyl, or $(C_{1-4})$ alkyl wherein $(C_{1-4})$ alkyl is unsubstituted or substituted with hydroxy, methoxy, ethoxy, —OCH$_2$CH$_2$OH, or —CN;

$R^2$ is H, halogen, $(C_{1-6})$ fluoroalkyl, $(C_{3-6})$ cycloalkyl, —OR$^4$, —SR$^4$, —NO$_2$, —CN, —COR$^4$, —C(O)OR$^4$, —CONR$^5$R$^6$, phenyl, or $(C_{1-6})$ alkyl, wherein the $(C_{1-6})$ alkyl is unsubstituted or substituted with a hydroxyl group;

$R^3$ is hydrogen, $(C_{1-6})$ fluoroalkyl, $(C_{2-6})$ alkenyl, phenyl, or $(C_{1-4})$ alkyl, wherein $(C_{1-4})$ alkyl is unsubstituted or substituted with a phenyl group;

$R^4$ is hydrogen, $(C_{1-6})$ alkyl, or $(C_{1-6})$ fluoroalkyl;

$R^5$ and $R^6$ are independently hydrogen or $(C_{1-6})$ alkyl;

$R^7$ is hydrogen, $(C_{1-6})$ alkyl, or $(C_{1-6})$ fluoroalkyl;

$Z^1$ and $Z^2$ are independently selected from hydrogen, halogen, $(C_{1-6})$ alkyl, $(C_{1-6})$ fluoroalkyl, —OR$^7$, —SR$^7$, —NO$_2$, —CN, and —COR$^7$; and phenyl is unsubstituted or substituted with one to three substituents independently selected from hydrogen, halogen, $(C_{1-6})$ alkyl, $(C_{1-6})$fluoroalkyl, —OH, $(C_{1-6})$ alkoxy, $(C_{1-6})$ fluoroalkoxy, $(C_{1-6})$ alkylthio, $(C_{1-6})$ acyl, $(C_{1-4})$alkylsulfonyl, —OCF$_3$, —NO$_2$, —CN, carboxamido which may be substituted on the nitrogen by one or two $(C_{1-4})$ alkyl groups, and —NH$_2$ in which one of the hydrogens may be replaced by a $(C_{1-4})$ alkyl group and the other hydrogen may be replaced by either a $(C_{1-4})$ alkyl group, a $(C_{1-6})$ acyl group, or a $(C_{1-4})$ alkylsulfonyl group.

Also preferred among the compounds of formula (I) are those wherein the stereo configuration is "S" about the carbon of the piperazine group bound to Alk. More preferred are those "S"-configuration compounds wherein Alk is $(C_{2-4})$ alkylene.

Also preferred among the compounds of formula (I) are those wherein the stereo configuration is "R" about the carbon of the piperazine group bound to Alk. More preferred are those "R"-configuration compounds wherein Alk is methylene.

Also preferred among the compounds of formula (I) are those wherein Alk is —CH$_2$—, —CH$_2$CH$_2$—, —CH$_2$CH$_2$CH$_2$—, —CH$_2$CH(CH$_3$)— or —CH$_2$C(CH$_3$)$_2$—. More preferred are compounds wherein Alk is —CH$_2$CH$_2$CH$_2$— or —CH$_2$CH$_2$—.

Also preferred among the compounds of formula (I) are those wherein X is O.

Also preferred among the compounds of formula (I) are those wherein $R^1$ is $(C_{1-4})$ alkyl. More preferred are compounds wherein $R^1$ is methyl.

Also preferred among the compounds of formula (I) are those wherein $R^2$ is $(C_{1-6})$ alkyl or $(C_{1-6})$ fluoroalkyl. More preferred are compounds wherein $R^2$ is —CF$_3$, methyl or isopropyl.

Also preferred among the compounds of formula (I) are those wherein $R^3$ is $(C_{1-4})$ alkyl. More preferred are compounds wherein $R^3$ is methyl or ethyl.

Also preferred among the compounds of formula (I) are those wherein $Z^1$ and $Z^2$ are independently selected from hydrogen and halogen. More preferred are compounds wherein at least one of $Z^1$ and $Z^2$ is halogen. Even more preferred are those compounds wherein the halogen is fluorine.

Also preferred among the compounds of formula (I) are those wherein is

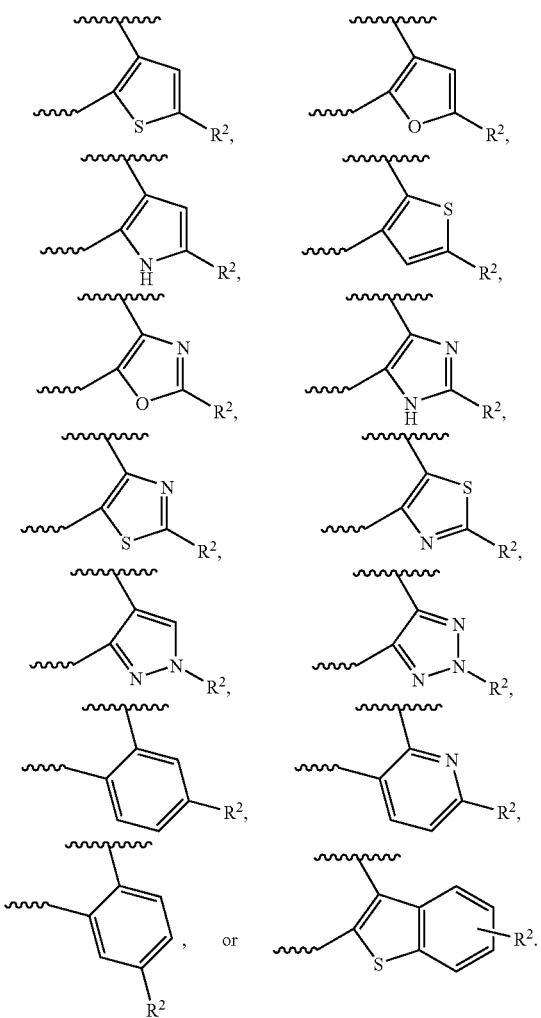

More preferred are compounds wherein

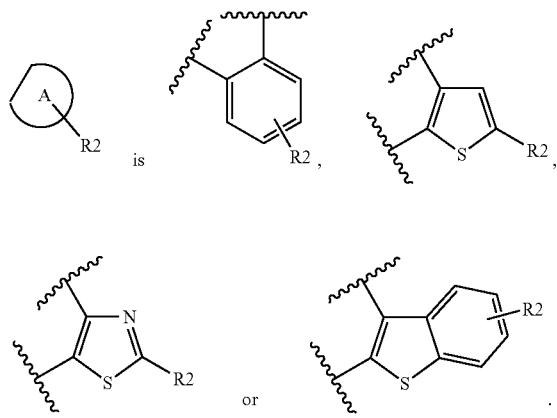

Another aspect of the invention provides a pharmaceutical composition comprising an effective amount of a compound of formula (I) in association with a pharmaceutically acceptable carrier, diluent or excipient.

Another aspect of the invention provides a pharmaceutical composition comprising a compound of formula (I) in an amount effective to antagonize $D_2$ receptor stimulation, and a pharmaceutically acceptable carrier, diluent or excipient.

Another aspect of the invention provides a pharmaceutical composition comprising a compound of formula (I) in an amount effective to antagonize 5-$HT_{2A}$ receptor stimulation, and a pharmaceutically acceptable carrier, diluent or excipient.

Another aspect of the invention provides a pharmaceutical composition, comprising a compound of formula (I) in an amount effective to antagonize 5-$HT_6$ receptor stimulation, and a pharmaceutically acceptable carrier, diluent or excipient.

Another aspect of the invention provides a method for antagonizing dopamine, receptor $D_2$, comprising administering to a mammal an effective amount of a compound of formula (I).

Another aspect of the invention provides a method for antagonizing a 5-$HT_{2A}$ receptor, comprising administering to a mammal an effective amount of a compound of formula (I).

Another aspect of the invention provides a method for antagonizing a 5-$HT_6$ receptor, comprising administering to a mammal an effective amount of a compound of formula (I).

Another aspect of the invention provides a method for treating a psychotic disorder, comprising administering to a mammal in need thereof an effective amount of a compound of formula (I). In a preferred embodiment, the psychotic disorder is schizophrenia, schizophreniform, or schizoaffective disorder.

Another aspect of the invention provides a compound of formula (I) for use in treating a psychotic disorder. In a preferred embodiment, the psychotic disorder is schizophrenia, schizophreniform, or schizoaffective disorder.

Another aspect of the invention provides use of a compound of formula (I) for the manufacture of a medicament for the treatment of a psychotic disorder. In a preferred embodiment, the psychotic disorder is schizophrenia, schizophreniform, or schizoaffective disorder.

Another aspect of the invention provides a method for treating a mood disorder, comprising administering to a mammal in need thereof an effective amount of a compound of formula (I). In a preferred embodiment, the mood disorder is a bipolar disorder. In a more preferred embodiment, the bipolar disorder is acute mania or bipolar depression.

Another aspect of the invention provides a compound of formula (I) for use in treating a mood disorder. In a preferred embodiment, the mood disorder is a bipolar disorder. In a more preferred embodiment, the bipolar disorder is acute mania or bipolar depression.

Another aspect of the invention provides use of a compound of formula (I) for the manufacture of a medicament for the treatment of a mood disorder. In a preferred embodiment, the mood disorder is a bipolar disorder. In a more preferred embodiment, the bipolar disorder is acute mania or bipolar depression.

Another aspect of the invention provides compounds of formula (VIz)

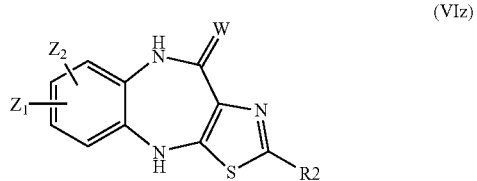

wherein:

$R^2$ is H, $(C_{1-6})$ alkyl, halogen, $(C_{1-6})$ fluoro alkyl, $OR^4$, $SR^4$, $NO_2$, $CN$, $COR^4$, $C(O)OR^4$, $CONR^5R^6$, $SO_2NR^5R^6$, $NR^5R^6$, $NR^5COR^4$, $NR^5SO_2R^4$, or optionally substituted phenyl, $R^4$ is hydrogen, $(C_{1-6})$ alkyl, $(C_{1-6})$ fluoro alkyl, or optionally substituted phenyl, $R^5$ and $R^6$, are independently hydrogen, $(C_{1-6})$ alkyl, or optionally substituted phenyl;

$Z^1$ and $Z^2$ are independently selected from hydrogen, halogen, $(C_{1-6})$ alkyl, $(C_{1-6})$ fluoro alkyl, $OR^7$, $SR^7$, $NO_2$, $CN$, $COR^7$, $CONR^8R^9$, $SO_2NR^8R^9$, $NR^8SO_2R^7$, $NR^8R^9$, or optionally substituted phenyl, $R^7$ is hydrogen, $(C_{1-6})$ alkyl, $(C_{1-6})$ fluoro alkyl, or optionally substituted phenyl, $R^8$ and $R^9$ are independently hydrogen, $(C_{1-6})$ alkyl, or optionally substituted phenyl;

W is oxygen or sulfur;

and tautomers and acid addition salts thereof, which are useful as intermediates in the preparation of compounds of this invention.

Another aspect of the invention provides compounds of formula (Vz)

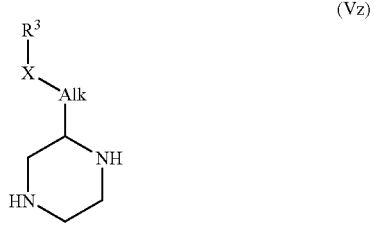

wherein:

X is oxygen or sulfur;

Alk is $-CH_2CH_2-$ optionally substituted by one or two methyl groups or one ethyl group;

$R^3$ is $(C_{1-4})$ alkyl, Ar, or $(C_{1-4})$ alkyl Ar where in Ar is optionally substituted phenyl, napthyl, monocyclic heteroaromatic or bicycle heteroaromatic; and acid addition salts thereof, which are useful as intermediates in the preparation of compounds of this invention.

Another aspect of the invention involves improved adverse event profiles (e.g., reduced weight gain) over currently available antipsychotic agents and/or better dopamine $D_2$ binding.

DETAILED DESCRIPTION OF THE INVENTION

Terms and symbols used herein have meanings consistent with usage in contemporary chemical literature unless otherwise noted.

For example, the term "$(C_{1-6})$ alkyl" includes saturated alkyl groups that may be branched or unbranched such as methyl, ethyl, n-propyl, isopropyl, n-butyl, isobutyl, sec-butyl, tert-butyl, pentyl, 2-pentyl, 3-pentyl, neopentyl, n-hexyl and the like.

The term "$(C_{1-4})$ alkyl" includes saturated and that may be branched or unbranched such as methyl, ethyl, n-propyl, isopropyl, n-butyl, isobutyl, sec-butyl, tert-butyl and the like.

The term "$(C_{2-6})$ alkenyl" includes unsaturated alkyl groups that may be branched or unbranched having from two to six carbon atoms such as vinyl, allyl, 1-buten-4-yl, 2-buten-4-yl, $-CHC(=CH_2)CH_3$, $-CH=CH_2CH_2CH_3$, $-CH=C(CH_3)_2$, $-CH=CH-CH_2CH_2CH_3$, $-CH=CHCH_2CH_2CH_3$ and the like.

The term "$(C_{1-4})$ alkylene" refers to straight chain alkylene groups such as $-CH_2-$, $-CH_2CH_2-$, $-CH_2CH_2CH_2-$, $-CH_2CH_2CH_2CH_2-$, or branched alkylene groups such as $-CH_2C(CH_3)_2-$, or $-CH_2CH(CH_3)-$, $-CH_2CH_2CH(CH_3)-CH_2CH(CH_3)CH_2-$, and the like.

The term "$(C_{3-6})$ cycloalkyl" refers to cyclopropyl, cyclobutyl, cyclopentyl, and cyclohexyl.

The term "halogen" includes fluoro, chloro, bromo and iodo.

The term "$(C_{1-6})$ fluoroalkyl" refers to a $(C_{1-6})$ alkyl group which is substituted with one to six fluorines, such as, fluoromethyl, difluoromethyl, trifluoromethyl, 2-fluoroethyl, 2,2,2-trifluoroethyl, 1,1,2,2,2-pentafluoroethyl, 3-fluoropropyl, 3,3,3-trifluoropropyl, 1,1,1,3,3,3-hexafluoroprop-2-yl, and 6-fluorohexyl and the like.

The term "$(C_{1-6})$ alkoxy" includes such groups as methoxy, ethoxy, isopropoxy, sec-butoxy, tert-butoxy, 2-pentoxy, 3-hexyloxy, and the like.

The term "$(C_{1-6})$ fluoroalkoxy" refers to a $(C_{1-6})$ fluoroalkyl group which is attached to an oxygen.

The term "$(C_{1-6})$ alkylthio" includes such groups as methylthio, ethylthio, isopropylthio, sec-butylthio, tert-butylthio, 1-hexylthio, and the like.

The term "acyl" includes, for example, formyl, acetyl, propanoyl, butanoyl, 2-methylpropanoyl, hexanoyl, and the like.

The term "$(C_{1-4})$alkylsulfonyl" includes methanesulfonyl, ethanesulfonyl, propanesulfonyl, isopropanesulfonyl, 1-butanesulfonyl and the like.

The term "optionally substituted aromatic" refers to a phenyl, napthyl, monocyclic heteroaromatic or bicyclic heteroaromatic group which may be substituted with one to three substituents independently selected from hydrogen, halogen, $(C_{1-6})$ alkyl, $(C_{1-6})$ fluoroalkyl, $-OH$, $(C_{1-6})$ alkoxy, $(C_{1-6})$ fluoroalkoxy, $(C_{1-6})$alkylthio, acyl, $(C_{1-4})$ alkylsulfonyl, $-NO_2$, $-CN$, carboxamido which may be substituted on the nitrogen by one or two $(C_{1-4})$ alkyl groups, and $NH_2$ in which one of the hydrogens may be replaced by a ($C_{1-4}$) alkyl group and the other hydrogen may be replaced by either a ($C_{1-4}$) alkyl group, an acyl group or a ($C_1$-$C_4$ alkyl)sulfonyl group.

The term "monocyclic heteroaromatic" refers to a five or six membered aromatic ring containing one to three heteroatoms selected from N, O, and S. Recognize that if one of the heteroatoms is O or S, the heteroaromatic ring must be a five membered ring and that any other heteroatoms contained therein-must be N. Examples of such monocyclic heteroaromatic systems include furan, thiophene, pyridine, pyrimidine, thiazole, 1,2,3-triazole, and the like.

The term "bicyclic heteroaromatic" refers to a bicyclic aromatic system containing one to three heteroatoms selected from N, O, and S. Examples include indole, benzofuran, benzothiophene, quinoline, isoquinoline, indazole, benzothiazole, and the like.

The term "optionally substituted phenyl" refers to phenyl which may be substituted with one to three substituents independently selected from hydrogen, halogen, ($C_{1-6}$) alkyl, ($C_{1-6}$) fluoroalkyl, —OH, ($C_{1-6}$) alkoxy, ($C_{1-6}$) fluoroalkoxy, ($C_{1-6}$) thioalkyl, acyl, ($C_{1-4}$)alkylsulfonyl, —$NO_2$, —CN, carboxamido which may be substituted on the nitrogen by one or two ($C_{1-4}$) alkyl groups, and $NH_2$ in which one of the hydrogens may be replaced by a ($C_{1-4}$) alkyl group and the other hydrogen may be replaced by either a ($C_{1-4}$) alkyl group, an acyl group, or a ($C_{1-4}$) alkylsulfonyl group.

The term "optionally substituted phenyl, naphthyl, monocyclic heteroaromatic, or bicyclic heteroaromatic" refers to phenyl, naphthyl, monocyclic heteroaromatic, or bicyclic heteroaromatic which may be substituted with one to three substituents independently selected from hydrogen, halogen, ($C_{1-6}$) alkyl, ($C_{1-6}$)fluoroalkyl, —OH, ($C_{1-6}$) alkoxy, ($C_{1-6}$) fluoroalkoxy, ($C_{1-6}$) thioalkyl, acyl, ($C_{1-4}$)alkylsulfonyl, —$NO_2$, —CN, carboxamido which may be substituted on the nitrogen by one or two ($C_{1-4}$) alkyl groups, and $NH_2$ in which one of the hydrogens may be replaced by a ($C_{1-4}$) alkyl group and the other hydrogen may be replaced by either a ($C_{1-4}$) alkyl group, an acyl group, or a ($C_{1-4}$) alkylsulfonyl group.

In the case of optionally benzo-fused five or six member aromatic ring having zero to three hetero atoms independently selected from N, O, and S, the two atoms of the aromatic ring which are fused to the adjoining seven member ring are constrained to both be carbon. If the aromatic ring contains two additional adjacent carbon atoms, a benzene ring may be fused to the aromatic ring at those two adjacent carbon atoms. Examples of optionally benzo-fused five or six member aromatic rings having zero to three hetero atoms independently selected from N, S, and O include benzene, pyridine, furan, pyrrole, thiophene, thiazole, oxazole, pyrazole, imidazole, 1,2,3-triazole, naphthylene, quinoline, isoquinoline, indole, benzofuran, benzothiophene, and the like.

The compounds of the present invention may, depending upon their structure and manner of synthesis and isolation, exist as a pharmaceutically acceptable solvate. These solvates include water, methanol, and ethanol. Solvated forms of the compounds of the present invention represent a further embodiment of the present invention.

The compounds of the present invention may, depending upon their structure and manner of synthesis and isolation, exist as a pharmaceutically acceptable hydrates. Hydrated forms of the compounds of the present invention represent a further embodiment of the present invention.

The present invention also provides novel crystalline forms of the compounds of formula (I). Novel crystalline forms may be prepared by crystallization under controlled conditions. Crystallization from a solution and slurrying techniques are contemplated to be within the scope of the present process. In practice, a number of factors can influence the form obtained, including temperature, solvent composition and also optional seeding. Seed crystals can be obtained from previous synthesis of the compound in which crystals were isolated. The novel crystalline forms of the present invention may also be prepared by dissolving compounds of formula (I) in a solvent and then forming the hydrochloride salt by the addition of a solution containing hydrochloric acid and then allowing crystallization while controlling the temperature. Also the novel crystalline forms of the present invention may also be prepared by dissolving the anhydrate salt form of compounds of formula (I) in water and seeding with a crystalline form.

A number of methods are available to characterize crystalline forms of organic compounds. For example, methods include differential scanning calorimetry, solid state NMR spectrometry, infra-red spectroscopy, and X-ray powder diffraction. Among these X-ray powder diffraction and solid state NMR spectroscopy are very useful for identifying and distinguishing between crystalline forms.

Differential thermal/thermogravimetric analyses (DTA/TGA) are carried out on a TA simultaneous DTA/TGA unit (Model SDT2960). Samples are heated in open aluminum pans from 25 to 295° C. at 10° C./min with a nitrogen purge of 150 mL/min. The temperature is calibrated with indium. The weight calibration is performed with manufacturer-supplied standards and verified against sodium tartrate desolvation.

X-ray powder diffraction analysis are performed by a variety of methods known to the skilled person. These methods can be varied to increase sensitivity by sample preparation techniques and by using more intense radiation, smaller scan steps, and slower scan rates. One method is as follows. Either with or without lightly grinding the sample with an agate mortar and pestle, the sample is loaded into a sample holder for the X-ray powder diffraction measurement. Micro X-ray powder diffraction (μ-xrpd) patterns are obtained on a BrukerAXS X-ray powder diffractometer, equipped with a CuKα source (λ=1.54056 angstrom) and a Hi star Area Detector, operating at 40 kV and 50 mA. The instrument is configured with a single Göebel mirror on the incident beam, a 0.05 mm collimator, and a sample to detector distance of 15 cm. Data is integrated over the range of 5.5 to 35° 2θ.

It is well known in the crystallography art that, for any given crystal form, the relative intensities and peak widths of the diffraction peaks may vary due to a number of factors, including the effects of preferred orientation and/or particle size. Where the effects of preferred orientation and/or particle size are present, peak intensities may be altered, but the characteristic peak positions of the polymorph are unchanged. See, e.g., The United States Pharmacopoeia #24, National Formulary #19, pages 1843-1844, 2000.

Grinding may be used to minimize peak intensity. However, if grinding significantly alters the diffractogram or alters the crystalline state of the sample, then the diffractogram of the unground sample should be used. Grinding is done in a small agate mortar and pestle. The mortar is held during the grinding and light pressure was applied to the pestle.

Thus, a properly prepared sample crystalline compound of formula I may be characterized by one or more 2θ values in an X-ray diffraction pattern obtained as described above.

Crystalline compounds of formula I may also be characterized by solid state NMR spectroscopy. Solid state $^{13}C$ chemical shifts reflect not only the molecular structure of but also the electronic environment of the molecule in the crystal.

The compounds of formula (I) can exist in optically isomeric forms, i.e., stereoisomeric forms. That is, these compounds have a least one chiral, i.e., asymmetric, center at the carbon atom of the piperazine ring to which "Alk" is attached. Such asymmetry gives raise to at least one pair of enantiomers. An equal mixture of enantiomers is known as a "racemic" mixture or a "racemate." The representation of formula (I) is intended to represent each of those stereoisomers and mixtures thereof.

The terms "R" and "S" are used herein as commonly used in organic chemistry to denote specific configuration of a chiral center. It is understood that compounds of the present invention may exist as stereoisomers. As such, all enantiomers, diastereomers, and mixtures thereof, are included within the scope of the present invention. Where specific stereochemistries are identified in this application, the Cahn-Prelog-Ingold designations of (R)- and (S)- and the cis and trans designation of relative stereochemistry are used to refer to specific isomers and relative stereochemistry. Some of the compounds of formula (I) may have two or more chiral centers.

Some of the compounds of the present invention may also be isomeric with respect to one or more double bonds, which introduces geometric, i.e., cis and trans, isomers. A discussion of optical and geometric isomers can be found in standard organic chemistry text books such as *March's Advanced Organic Chemistry*, 5$^{th}$ Ed., Chapter 4, Wiley-Interscience, John Wiley & Sons, Inc., New York (2001), hereinafter, "March". Herein, when a compound of the present invention is named, or its structure presented, without an indication of asymmetric form, all of the possible asymmetric forms are intended. This invention is not limited to any particular isomer but includes all possible individual isomers and racemates.

The compounds of formula (Ie) listed in Table 1 are of particular interest:

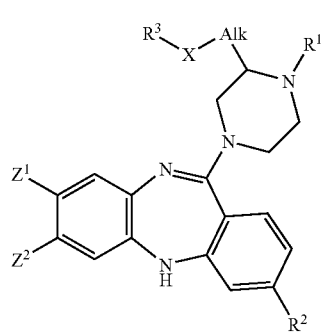

(Ie)

The absolute configuration being "S" about the carbon of the piperazine group bound to Alk unless otherwise indicated.

TABLE 1

| Ex. No.: | Alk-X—R$^3$ | R$^1$ | R$^2$ | Z$^1$ | Z$^2$ |
|---|---|---|---|---|---|
| 198 | CH$_2$CH$_2$OCH$_3$ | H | CH$_3$ | H | H |
| 217 | CH$_2$CH$_2$OCH$_3$ | CH$_3$ | CH$_3$ | H | H | all salts, solvates, optical and geometric isomers, and crystalline forms thereof. Ex. No.: corresponds to the example number in the Examples section.

The compounds of formula (If) listed in Table 2 are of particular interest:

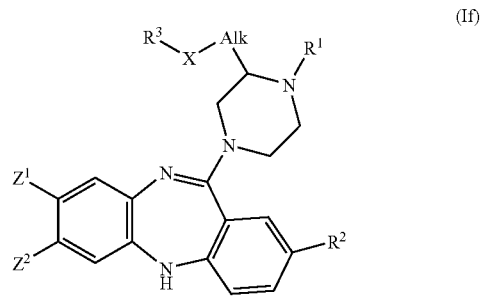

(If)

The absolute configuration being "S" about the carbon of the piperazine group bound to Alk unless otherwise indicated.

TABLE 2

| Ex. No. | Alk-X—R$^3$ | R$^1$ | R$^2$ | Z$^1$ | Z$^2$ |
|---|---|---|---|---|---|
| 199 | CH$_2$CH$_2$OCH$_3$ | H | CH$_3$ | H | H |
| 200 | CH$_2$CH$_2$OCH$_3$ | H | CH(CH$_3$)$_2$ | H | H |
| 201 | CH$_2$CH$_2$CH$_2$OCH$_3$ | H | CH(CH$_3$)$_2$ | H | H |
| 202 | CH$_2$CH$_2$OCH$_3$ | H | CF$_3$ | H | H |
| 203 | CH$_2$CH$_2$CH$_2$OCH$_3$ | H | CF$_3$ | H | H |
| 204 | CH$_2$CH$_2$OCH$_3$ | H | CH$_3$ | Cl | H |
| 205 | CH$_2$CH$_2$OCH$_3$ | H | CH(CH$_3$)$_2$ | Cl | H |
| 206 | CH$_2$CH$_2$OCH$_3$ | H | CH$_3$ | F | H |
| 207 | CH$_2$CH$_2$OCH$_3$ | H | CF$_3$ | F | H |
| 208 | CH$_2$CH$_2$OCH$_3$ | H | CH(CH$_3$)$_2$ | F | H |
| 209 | CH$_2$CH$_2$OCH$_3$ | H | CH(CH$_3$)$_2$ | H | F |
| 210 | CH$_2$CH$_2$OCH$_3$ | H | CF$_3$ | H | F |
| 211 | CH$_2$CH$_2$CH$_2$OCH$_3$ | H | CF$_3$ | H | F |
| 212 | CH$_2$CH$_2$CH$_2$OCH$_3$ | H | CF$_3$ | F | F |
| 213 | CH$_2$CH$_2$OCH$_3$ | H | cyclopropyl | H | F |
| 214 | CH$_2$CH$_2$OCH$_3$ | H | CF$_3$ | F | F |
| 215 | CH$_2$CH$_2$OCH$_3$ | H | CF$_3$ | Cl | H |
| 215a | CH$_2$CH$_2$OCH$_3$ | H | Cl | H | H |
| 216 | CH$_2$CH$_2$OCH$_3$ | CH$_3$ | CH$_3$ | H | H |
| 218 | CH$_2$CH$_2$OCH$_3$ | CH$_3$ | CH(CH$_3$)$_2$ | H | H |
| 219 | CH$_2$CH$_2$CH$_2$OCH$_3$ | CH$_3$ | CH(CH$_3$)$_2$ | H | H |

TABLE 2-continued

| Ex. No. | Alk-X—R$^3$ | R$^1$ | R$^2$ | Z$^1$ | Z$^2$ |
|---|---|---|---|---|---|
| 221 | CH$_2$CH$_2$OCH$_3$ | CH$_3$ | CF$_3$ | H | H |
| 222 | CH$_2$CH$_2$CH$_2$OCH$_3$ | CH$_3$ | CF$_3$ | H | H |
| 224 | CH$_2$CH$_2$OCH$_3$ | CH$_3$ | CH$_3$ | Cl | H |
| 225 | CH$_2$CH$_2$OCH$_3$ | CH$_3$ | CH(CH$_3$)$_2$ | Cl | H |
| 227 | CH$_2$CH$_2$OCH$_3$ | CH$_3$ | CH$_3$ | F | H |
| 228 | CH$_2$CH$_2$OCH$_3$ | CH$_3$ | CF$_3$ | F | H |
| 229 | CH$_2$CH$_2$OCH$_3$ | CH$_3$ | CH(CH$_3$)$_2$ | F | H |
| 230 | CH$_2$CH$_2$OCH$_3$ | CH$_3$ | CH(CH$_3$)$_2$ | H | F |
| 231 | CH$_2$CH$_2$OCH$_3$ | CH$_3$ | CF$_3$ | H | F |
| 232 | CH$_2$CH$_2$CH$_2$OCH$_3$ | CH$_3$ | CF$_3$ | H | F |
| 233 | CH$_2$CH$_2$CH$_2$OCH$_3$ | CH$_3$ | CF$_3$ | F | H |
| 234 | CH$_2$CH$_2$OCH$_3$ | CH$_3$ | cyclopropyl | H | F |
| 235 | CH$_2$CH$_2$OCH$_3$ | CH$_3$ | CF$_3$ | F | F |
| 236 | CH$_2$CH$_2$OCH$_3$ | CH$_3$ | CF$_3$ | Cl | H |
| 236a | CH$_2$CH$_2$OCH$_3$ | CH$_3$ | Cl | H | H | all salts, solvates, optical and geometric isomers, and crystalline forms thereof. Ex. No.: corresponds to the example number in the Examples section The compounds of formula (Ig) listed in Table 3 are of particular interest:

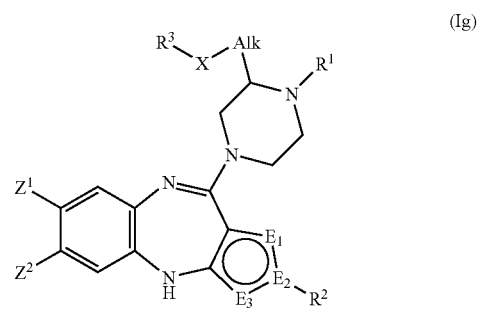

wherein:
the absolute configuration being "S" about the carbon of the piperazine group bound Alk unless otherwise indicated; and
E$_2$ is C and E$_3$ is S.

TABLE 3

| Ex No.: | E$_1$ | Alk-X—R$^3$ | R$^1$ | R$^2$ | Z$^1$ | Z$^2$ |
|---|---|---|---|---|---|---|
| 237 | CH | (R)CH$_2$OH | H | CH$_3$ | H | H |
| 238 | CH | (R)CH$_2$OCH$_3$ | H | CH$_3$ | H | H |
| 239 | CH | (R)CH$_2$OCHC(=CH$_2$)(CH$_3$) | H | CH$_3$ | H | H |
| 240 | CH | CH$_2$CH$_2$OH | H | CH$_3$ | H | H |
| 241 | CH | (R)CH$_2$CH$_2$OH | H | CH$_3$ | H | H |
| 241a | CH | CH$_2$CH$_2$OCH$_3$ | H | H | H | H |
| 242 | CH | CH$_2$CH$_2$OCH$_3$ | H | CH$_3$ | H | H |
| 242a | CH | CH$_2$CH$_2$Ophenyl | H | CH$_3$ | H | H |
| 243 | CH | CH$_2$CH$_2$OCH$_2$CH$_3$ | H | CH$_3$ | H | H |
| 244 | CH | (R)CH$_2$OPh | H | CH$_3$ | H | H |
| 245 | CH | CH$_2$CH$_2$OCH$_3$ | H | CH(CH$_3$)$_2$ | H | H |
| 246a | CH | CH$_2$CH$_2$CH$_2$OCH$_3$ | H | H | H | H |
| 246b | CH | CH$_2$CH$_2$CH$_2$OCH$_3$ | H | CH$_3$ | H | H |
| 247 | CH | CH$_2$CH$_2$CH$_2$CH$_2$OCH$_3$ | H | CH$_3$ | H | H |
| 247a | CH | CH$_2$CH$_2$OCH$_3$ | H | H | H | F |
| 247b | CH | CH$_2$CH$_2$CH$_2$OCH$_3$ | H | H | H | F |
| 248 | CH | CH$_2$CH$_2$OCH$_3$ | H | CH$_3$ | H | F |
| 248c | CH | CH$_2$CH$_2$CH$_2$OCH$_3$ | H | CH$_3$ | H | F |
| 249 | CH | CH$_2$CH$_2$OCH$_3$ | H | CH$_3$ | F | H |
| 249a | CH | CH$_2$CH$_2$CH$_2$OCH$_3$ | H | CH$_3$ | F | H |
| 249b | CH | CH$_2$CH$_2$OH | H | CH$_3$ | H | F |
| 250 | CH | CH$_2$CH$_2$OCH$_2$CH$_3$ | H | CH$_3$ | H | F |
| 251 | CH | CH$_2$CH$_2$OCH$_2$CH$_3$ | H | CH$_3$ | F | H |
| 252 | CH | CH$_2$CH$_2$OCH$_3$ | H | CH$_2$CH$_3$ | H | F |
| 253 | CH | CH$_2$CH$_2$OCH$_3$ | H | CH(CH$_3$)$_2$ | H | F |
| 253a | CH | CH$_2$CH$_2$OCH$_3$ | H | H | F | F |
| 254 | CH | CH$_2$CH$_2$OCH$_3$ | H | CH$_3$ | F | F |
| 254d | CH | CH$_2$CH$_2$OH | H | CH$_3$ | F | F |
| 255 | CH | CH$_2$CH$_2$OCH$_2$CH$_3$ | H | CH$_3$ | F | F |
| 256 | CH | CH$_2$CH$_2$OCH$_3$ | H | CH$_2$CH$_3$ | F | F |
| 257 | CH | CH$_2$CH$_2$OCH$_3$ | H | CH$_3$ | H | Cl |
| 257a | CH | CH$_2$CH$_2$OCH$_3$ | H | H | Cl | H |
| 257b | CH | CH$_2$CH$_2$CH$_2$OCH$_3$ | H | H | Cl | H |
| 258 | CH | CH$_2$CH$_2$OCH$_3$ | H | CH$_3$ | Cl | H |
| 258b | CH | CH$_2$CH$_2$OH | H | CH$_3$ | Cl | H |
| 259 | CH | (R)CH$_2$OH | CH$_3$ | CH$_3$ | H | H |
| 260 | CH | (R)CH$_2$OCH$_3$ | CH$_3$ | CH$_3$ | H | H |
| 261 | CH | (R)CH$_2$OCH$_2$CH$_3$ | CH$_3$ | CH$_3$ | H | H |
| 262 | CH | (R)CH$_2$OCH$_2$CH=CH$_2$ | CH$_3$ | CH$_3$ | H | H |
| 263 | CH | (R)CH$_2$OCH$_2$CH$_2$CH$_3$ | CH$_3$ | CH$_3$ | H | H |
| 264 | CH | (R)CH$_2$OCH$_2$C(=CH$_2$)(CH$_3$) | CH$_3$ | CH$_3$ | H | H |

TABLE 3-continued

| Ex No.: | $E_1$ | Alk-X—$R^3$ | $R^1$ | $R^2$ | $Z^1$ | $Z^2$ |
|---|---|---|---|---|---|---|
| 265 | CH | (R)CH$_2$Ophenyl | CH$_3$ | CH$_3$ | H | H |
| 266 | CH | CH$_2$CH$_2$OH | CH$_3$ | CH$_3$ | H | H |
| 266a | CH | CH$_2$CH$_2$OCH$_3$ | CH$_3$ | H | H | H |
| 266b | CH | CH$_2$CH$_2$CH$_2$OCH$_3$ | CH$_3$ | H | H | H |
| 267 | CH | CH$_2$CH$_2$OCH$_3$ | CH$_3$ | CH$_3$ | H | H |
| 268 | CH | CH$_2$CH$_2$OCH$_2$CH$_3$ | CH$_3$ | CH$_3$ | H | H |
| 269 | CH | CH$_2$CH$_2$Ophenyl | CH$_3$ | CH$_3$ | H | H |
| 270 | CH | (R)CH$_2$OCH$_2$phenyl | CH$_3$ | CH$_3$ | H | H |
| 271 | CH | (R)CH$_2$Ophenyl | CH$_3$ | CH$_3$ | H | H |
| 272 | CH | CH$_2$CH$_2$OCH$_3$ | CH$_3$ | CH(CH$_3$)$_2$ | H | H |
| 273a | CH | CH$_2$CH$_2$CH$_2$OCH$_3$ | CH$_3$ | CH$_3$ | H | H |
| 274 | CH | CH$_2$CH$_2$CH$_2$CH$_2$OCH$_3$ | CH$_3$ | CH$_3$ | H | H |
| 276 | CH | CH$_2$CH$_2$OCH$_3$ | CH$_3$ | CF$_3$ | H | H |
| 277 | CH | CH$_2$CH$_2$CH$_2$OCH$_3$ | CH$_3$ | CF$_3$ | H | H |
| 278a | CH | CH$_2$CH$_2$OCH$_3$ | CH$_3$ | H | H | F |
| 278b | CH | CH$_2$CH$_2$CH$_2$OCH$_3$ | CH$_3$ | H | H | F |
| 278c | CH | CH$_2$CH$_2$OH | CH$_3$ | CH$_3$ | H | F |
| 279 | CH | CH$_2$CH$_2$OCH$_3$ | CH$_3$ | CH$_3$ | H | F |
| 280 | CH | CH$_2$CH$_2$OCH$_3$ | CH$_3$ | CH$_2$CH$_3$ | H | F |
| 281 | CH | CH$_2$CH$_2$OCH$_2$CH$_3$ | CH$_3$ | CH$_3$ | H | F |
| 282 | CH | CH$_2$CH$_2$OCH$_3$ | CH$_3$ | CH(CH$_3$)$_2$ | H | F |
| 283 | CH | CH$_2$CH$_2$CH$_2$OCH$_3$ | CH$_3$ | CH$_3$ | H | F |
| 283a | CH | CH$_2$CH$_2$CH$_2$OCH$_3$ | CH$_3$ | CH$_3$ | F | H |
| 284 | CH | CH$_2$CH$_2$OCH$_3$ | CH$_3$ | CF$_3$ | H | F |
| 285 | CH | CH$_2$CH$_2$CH$_2$OCH$_3$ | CH$_3$ | CF$_3$ | H | F |
| 286 | CH | CH$_2$CH$_2$OCH$_3$ | CH$_3$ | CH$_3$ | F | H |
| 287 | CH | CH$_2$CH$_2$OCH$_2$CH$_3$ | CH$_3$ | CH$_3$ | F | H |
| 287a | CH | CH$_2$CH$_2$OH | CH$_3$ | CH$_3$ | F | F |
| 288 | CH | CH$_2$CH$_2$OCH$_3$ | CH$_3$ | CH$_3$ | F | F |
| 289 | CH | CH$_2$CH$_2$OCH$_2$CH$_3$ | CH$_3$ | CH$_3$ | F | F |
| 290 | CH | CH$_2$CH$_2$OCH$_3$ | CH$_3$ | CH$_2$CH$_3$ | F | F |
| 290a | CH | CH$_2$CH$_2$OCH$_3$ | CH$_3$ | H | F | F |
| 290b | CH | CH$_2$CH$_2$OCH$_3$ | CH$_3$ | CF$_3$ | F | F |
| 291 | CH | CH$_2$CH$_2$OCH$_3$ | CH$_3$ | CH$_3$ | H | Cl |
| 291a | CH | CH$_2$CH$_2$OCH$_3$ | CH$_3$ | H | Cl | H |
| 291b | CH | CH$_2$CH$_2$CH$_2$OCH$_3$ | CH$_3$ | H | Cl | H |
| 291c | CH | CH$_2$CH$_2$OH | CH$_3$ | CH$_3$ | Cl | H |
| 292 | CH | CH$_2$CH$_2$OCH$_3$ | CH$_3$ | CH$_3$ | Cl | H |
| 293 | CH | CH$_2$CH$_2$OCH$_3$ | CH$_3$ | CF$_3$ | Cl | H |
| 294 | CH | CH$_2$CH$_2$CH$_2$OCH$_3$ | CH$_3$ | CF$_3$ | Cl | H |
| 295 | CH | CH$_2$CH$_2$SPhenyl | H | CH$_3$ | H | H |
| 296 | CH | CH$_2$CH$_2$SPhenyl | CH$_3$ | CH$_3$ | H | H |
| 297 | CH | CH$_2$CH$_2$SCH$_3$ | CH$_3$ | CH$_3$ | H | F |
| 300 | N | CH$_2$CH$_2$OH | H | CH$_3$ | H | H |
| 301 | N | CH$_2$CH$_2$OCH$_3$ | H | CH$_3$ | H | H |
| 302 | N | CH$_2$CH$_2$OCH$_2$CH$_3$ | H | CH$_3$ | H | H |
| 303 | N | CH$_2$CH$_2$OCH$_3$ | H | CH$_2$CH$_3$ | H | H |
| 304 | N | CH$_2$CH$_2$OCH$_3$ | H | CH$_2$CH$_2$CH$_3$ | H | H |
| 305 | N | CH$_2$CH$_2$OCH$_3$ | H | CH$_2$CH$_2$CH$_2$CH$_3$ | H | H |
| 307 | N | CH$_2$CH$_2$OH | H | CH(CH$_3$)$_2$ | H | H |
| 308 | N | CH$_2$CH$_2$OCH$_3$ | H | CH(CH$_3$)$_2$ | H | H |
| 309 | N | CH$_2$CH$_2$OCH$_2$CH$_3$ | H | CH(CH$_3$)$_2$ | H | H |
| 310 | N | CH$_2$CH$_2$CH$_2$OCH$_3$ | H | CH(CH$_3$)$_2$ | H | H |
| 311 | N | CH$_2$CH$_2$OCH$_3$ | H | Cyclopentyl | H | H |
| 312 | N | CH$_2$CH$_2$OCH$_3$ | H | CH$_2$OH | H | H |
| 313 | N | CH$_2$CH$_2$OCH$_3$ | H | C(O)OCH$_2$CH$_3$ | H | H |
| 314 | N | CH$_2$CH$_2$OCH$_3$ | H | CF$_3$ | H | H |
| 316 | N | CH$_2$CH$_2$OCH$_3$ | H | CF$_2$H | H | H |
| 318 | N | CH$_2$CH$_2$OCH$_3$ | H | CH$_2$CH$_2$CF$_3$ | H | H |
| 319 | N | CH$_2$CH$_2$OH | CH$_3$ | CH$_3$ | H | H |
| 320 | N | CH$_2$CH$_2$OCH$_3$ | CH$_3$ | CH$_3$ | H | H |
| 321 | N | CH$_2$CH$_2$OCH$_2$CH$_3$ | CH$_3$ | CH$_3$ | H | H |
| 322 | N | CH$_2$CH$_2$OCH$_3$ | CH$_3$ | CH$_2$CH$_3$ | H | H |
| 323 | N | CH$_2$CH$_2$OCH$_3$ | CH$_3$ | CH$_2$CH$_2$CH$_3$ | H | H |
| 324 | N | CH$_2$CH$_2$OCH$_3$ | CH$_3$ | (CH$_2$)$_3$CH$_3$ | H | H |
| 326 | N | CH$_2$CH$_2$OH | CH$_3$ | CH(CH$_3$)$_2$ | H | H |
| 327 | N | CH$_2$CH$_2$OCH$_3$ | CH$_3$ | CH(CH$_3$)$_2$ | H | H |
| 328 | N | CH$_2$CH$_2$OCH$_2$CH$_3$ | CH$_3$ | CH(CH$_3$)$_2$ | H | H |
| 329 | N | CH$_2$CH$_2$CH$_2$OCH$_3$ | CH$_3$ | CH(CH$_3$)$_2$ | H | H |
| 331 | N | CH$_2$CH$_2$OCH$_3$ | CH$_3$ | Cyclopentyl | H | H |
| 332 | N | CH$_2$CH$_2$OCH$_3$ | CH$_3$ | CH$_2$OH | H | H |
| 333 | N | CH$_2$CH$_2$OCH$_3$ | CH$_3$ | C(O)OCH$_2$CH$_3$ | H | H |
| 334 | N | CH$_2$CH$_2$OCH$_3$ | CH$_3$ | CF$_3$ | H | H |
| 336 | N | CH$_2$CH$_2$OCH$_3$ | CH$_3$ | CF$_2$H | H | H |
| 338 | N | CH$_2$CH$_2$OCH$_3$ | CH$_3$ | CH$_2$CH$_2$CF$_3$ | H | H |
| 339 | N | CH$_2$CH$_2$OCH$_3$ | cyclopropyl | CH(CH$_3$)$_2$ | H | H |
| 340 | N | CH$_2$CH$_2$OCH$_3$ | CH$_2$CH$_3$ | CH(CH$_3$)$_2$ | H | H |

TABLE 3-continued

| Ex No.: | $E_1$ | Alk-X—$R^3$ | $R^1$ | $R^2$ | $Z^1$ | $Z^2$ |
|---|---|---|---|---|---|---|
| 341 | N | $CH_2CH_2OCH_3$ | $CH_2CH_2CH_3$ | $CH(CH_3)_2$ | H | H |
| 342 | N | $CH_2CH_2OCH_3$ | $CH_2CH_2OH$ | $CH(CH_3)_2$ | H | H |
| 343 | N | $CH_2CH_2OCH_3$ | $CH_2CH_2OCH_3$ | $CH(CH_3)_2$ | H | H |
| 344 | N | $CH_2CH_2OCH_3$ | $CH_2CH_3$ | $CF_3$ | H | H |
| 346 | N | $CH_2CH_2OCH_3$ | $(CH_2)_2CH_3$ | $CF_3$ | H | H |
| 348 | N | $CH_2CH_2OCH_3$ | $C(O)CH_2F$ | $CF_3$ | H | H |
| 349 | N | $CH_2CH_2OCH_3$ | $CH_2CH_2F$ | $CF_3$ | H | H |
| 351 | N | $CH_2CH_2OCH_3$ | $CH_2CH_2CH_2F$ | $CF_3$ | H | H |
| 353 | N | $CH_2CH_2OCH_3$ | $CH_2CH_2OH$ | $CF_3$ | H | H |
| 355 | N | $CH_2CH_2OCH_3$ | $CH_2CH_2CH_2OH$ | $CF_3$ | H | H |
| 357 | N | $CH_2CH_2OCH_3$ | $CH_2CH_2OCH_2CH_2OH$ | $CF_3$ | H | H |
| 359 | CH | *$CH_2CH(CH_3)OCH_3$ | H | $CH_3$ | H | H |
| 360 | CH | *$CH_2CH(CH_3)OCH_3$ | $CH_3$ | $CH_3$ | H | H |
| 361 | N | *$CH_2CH(CH_3)OCH_3$ | H | $CH(CH_3)_2$ | H | H |
| 362 | N | (S,S)$CH_2CH(CH_3)OCH_3$ | H | $CH(CH_3)_2$ | H | H |
| 363 | N | (S,R)$CH_2CH(CH_3)OCH_3$ | H | $CH(CH_3)_2$ | H | H |
| 364 | N | *$CH_2CH(CH_3)OCH_3$ | $CH_3$ | $CH(CH_3)_2$ | H | H |
| 365 | N | (S,S)$CH_2CH(CH_3)OCH_3$ | $CH_3$ | $CH(CH_3)_2$ | H | H |
| 366 | N | (S,R)$CH_2CH(CH_3)OCH_3$ | $CH_3$ | $CH(CH_3)_2$ | H | H |
| 367 | N | $CH_2C(CH_3)_2OH$ | H | $CH(CH_3)_2$ | H | H |
| 368 | N | $CH_2C(CH_3)_2OH$ | $CH_3$ | $CH(CH_3)_2$ | H | H |
| 369 | CH | $CH_2C(CH_3)_2OH$ | H | $CH_3$ | H | H |
| 370 | CH | $CH_2C(CH_3)_2OH$ | $CH_3$ | $CH_3$ | H | H |
| 371 | CH | *$CH_2CH(CH_3)OH$ | H | $CH_3$ | H | H |
| 372 | CH | (S,S)$CH_2CH(CH_3)OH$ | H | $CH_3$ | H | H |
| 373 | CH | (S,R)$CH_2CH(CH_3)OH$ | H | $CH_3$ | H | H |
| 374 | CH | Isomer 1 | $CH_3$ | $CH_3$ | H | H |
| 375 | CH | Isomer 2 | $CH_3$ | $CH_3$ | H | H | all salts, solvates, optical and geometric isomers, and crystalline forms thereof.
Ex. No.: corresponds to the example number in the Examples section.
*Mixture of diastereoisom The compounds of formula (Ih) listed in Table 4 are of particular interest:

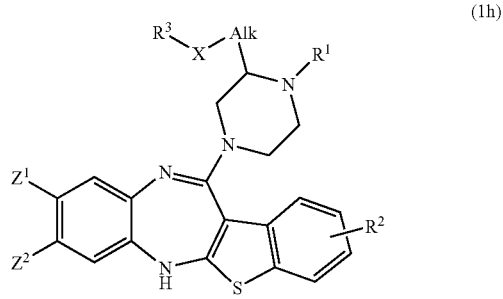

(Ih)

The absolute configuration being "S" about the carbon of the piperazine group bound to Alk unless otherwise indicated.

TABLE 4

| Ex. No.: | Alk-X—$R^3$ | $R^1$ | $R^2$ | $Z^1$ | $Z^2$ |
|---|---|---|---|---|---|
| 380 | $CH_2CH_2OCH_3$ | H | H | $CF_3$ | H |
| 382 | $CH_2CH_2OCH_3$ | $CH_3$ | H | $CF_3$ | H |
| 384 | $CH_2CH_2OCH_3$ | H | H | H | H |
| 385 | $CH_2CH_2OCH_3$ | $CH_3$ | H | H | H |
| 387 | $CH_2CH_2OCH_3$ | H | H | F | H |
| 388 | $CH_2CH_2OCH_3$ | $CH_3$ | H | F | H |
| 390 | $CH_2CH_2OCH_3$ | H | H | H | F |
| 391 | $CH_2CH_2CH_2OCH_3$ | H | H | H | F |
| 392 | $CH_2CH_2OCH_3$ | $CH_3$ | H | H | F |
| 393 | $CH_2CH_2CH_2OCH_3$ | $CH_3$ | H | H | F |
| 395 | $CH_2CH_2OCH_3$ | H | H | F | F |
| 396 | $CH_2CH_2OCH_3$ | $CH_3$ | H | F | F | all salts, solvates, optical and geometric isomers, and crystalline forms thereof. Ex. No.: corresponds to example number in the Examples section.

Since the compounds of this invention are basic in nature, they react with any of a number of inorganic and organic acids to form acid addition salts. For the therapeutic utility taught herein, the salt of the claimed compounds must be pharmaceutically acceptable. Acids commonly employed to form pharmaceutically acceptable salts are inorganic acids such as hydrochloric acid, hydrobromic acid, hydroiodic acid, sulfuric acid, phosphoric acid, and organic acids, such as p-toluenesulfonic acid, methanesulfonic acid, oxalic acid, p-bromo-phenylsulfonic acid, carbonic acid, succinic acid, citric acid, benzoic acid, acetic acid, lactic acid, maleic acid, tartaric acid, and the like. For further details on pharmaceutically acceptable salts, see *Journal of Pharmaceutical Science*, 66, 1 (1977). Salts that are not pharmaceutically acceptable may be used as intermediates to prepare other compounds of formula (I) or a pharmaceutically acceptable salt of compounds of formula (I) and are within the scope of the present invention. Particular pharmaceutically acceptable salts are those formed with hydrochloric acid, sulfuric acid, fumaric acid, or phosphoric acid.

Salts of compounds of formula (I) are known to exist in anhydrate forms and various hydrated forms.

The intermediates and final products described herein may be isolated and purified by the conventional techniques known to artisans of organic chemistry. For example, the well-known techniques of chromatography, recrystallization, distillation, and sublimation may be used singularly and sequentially.

General Synthetic Methods

Compounds of formula (I) of this invention can be prepared by several methods generally known in the art of organic chemistry. Starting materials, the preparation of which are not described, are commercially available or can be readily prepared by known techniques from commercially available starting materials.

As shown in Scheme 1, compounds of formula (I) may be conveniently prepared from compounds of formula (II a), by removal of the protecting group "ProG" from the amine nitrogen of the seven-member ring of the tricyclic ring system. The methods for introducing and removing these protecting groups are known in the art. See T. W. Green, *Protective Groups in Organic Synthesis*, John Wiley and Sons, Inc., (1981). Examples of such ProG groups include benzyl, acetyl, t-butoxycarbonyl, methanesulfonyl, and the like.

diisopropylethylamine or an inorganic base such as potassium carbonate. Solvents include methanol, ethanol, THF, and DMF. This transformation can also be accomplished by reductive alkylation of the piperazine by treatment with an aldehyde or ketone under reducing conditions. Examples of suitable aldehydes include formaldehyde, acetaldehyde, propionaldehyde, butyraldehyde, isobutyraldehyde, and the like. Suitable ketones include acetone, methylethylketone, and the like. Reductive alkylations are often performed under catalytic hydrogenation conditions. Other reducing agents include formic acid, sodium borohydride, sodium cyanoborohydride, and sodium triacetoxyborohydride. This transformation can also be accomplished by acylation of the piperazine nitrogen to form an amide and reduction of the amide to yield the alkylated piperazine. Examples of acylating agents include acyl halides such as acetyl chloride, propionyl chloride, pivaloyl chloride, and cyclopropylcarbonyl chloride, carboxylic acid anhydrides such as formylacetic anhydride and acetic anhydride, and carboxylic acids in the presence of an activating agent such as dicyclohexylcarbodiimide or carbonyldiimidazole. The resulting amides may be reduced to the tertiary amines with reducing agents such as lithium aluminum hydride or borane.

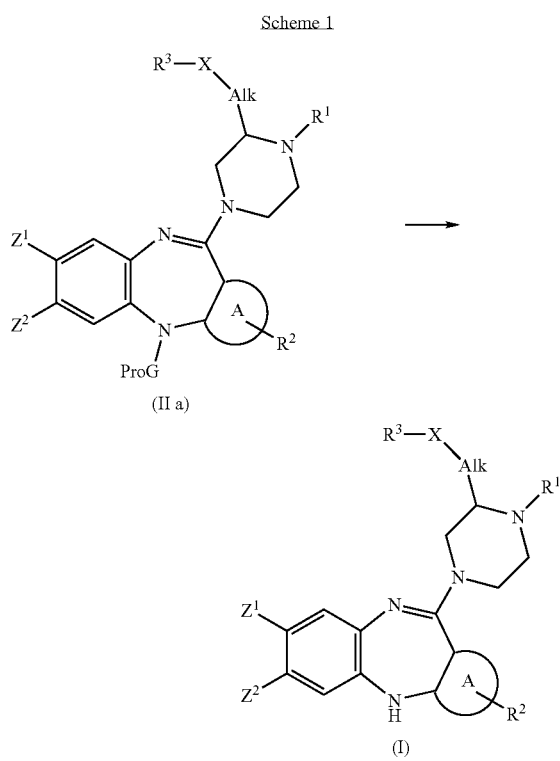

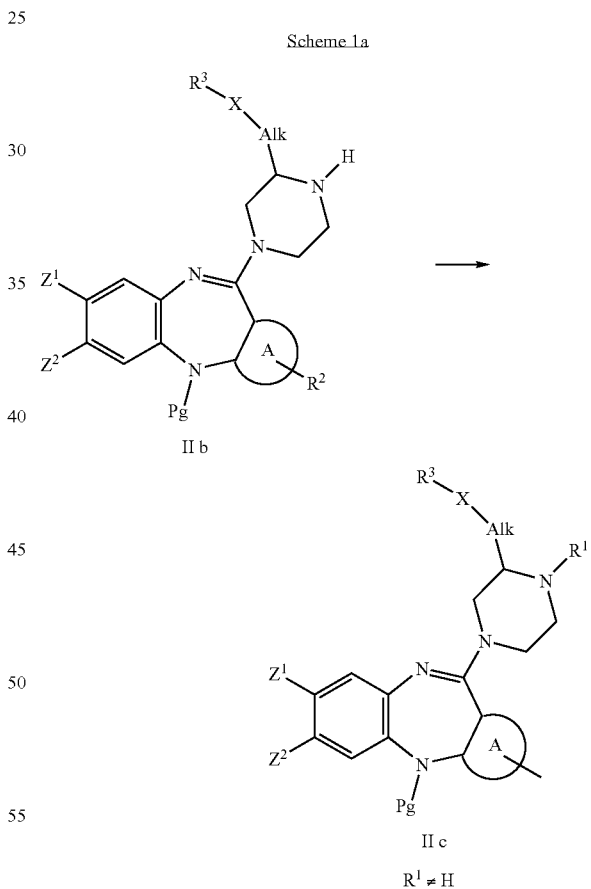

As used herein, "Pg" represents either hydrogen or an amine protecting group ProG. For those examples in which Pg is an amine protecting group, the penultimate intermediate can be converted to the compound of formula (I) by removal of the protecting group. In the following text, for those intermediates containing a group Pg in which Pg is an amine protecting group, the protecting group may be removed to give the unprotected amine. Similarly, for those intermediates in which Pg is hydrogen, an amine protecting group may be incorporated into the intermediate.

Compounds of formula (II b) in which $R^1$ is hydrogen can be converted to compounds of formula (II c) in which $R^1$ is $(C_{1-4})$ alkyl optionally substituted with a substitutent selected from the group consisting of hydroxy, methoxy, ethoxy, or $OCH_2CH_2OH$ or —CN. This transformation can be accomplished, as shown in Scheme 1a, by treatment of formula (II b) with an alkylating agent. Alkylating agents include alkyl halides and alkyl sulfonate esters. Examples include methyl iodide, 1-bromobutane, 2-propyl methanesulfonate, and bromoethylmethyl ether. This reaction is usually performed in the presence of a base and solvent. The base can be either an organic base such as pyridine or As shown in Scheme 2, compounds of formula (II) may be prepared by reacting an appropriately substituted piperazine of formula (V) with a tricyclic intermediate of formula (IV). "LG" represents a leaving group examples of which include $NH_2$, halo, $OY_1$, or $SY_1$, wherein $Y_1$ is lower alkyl such as methyl, ethyl, or propyl or optionally substituted phenyl or $OP(=O)R^{10}$. $R^{10}$ can be morpholine. This reaction may conveniently be performed with heating in a solvent such as DMSO, toluene, IPA, DMF, and N-methylpyrrolidinone or a mixture of solvents such as DMSO and toluene in ratios of (1:2, 1:3, or 1:4). For compounds of formula (II) when LG is $SY_1$, the equivalence of piperazine maybe reduced to 1 to 2 when heating in IPA.

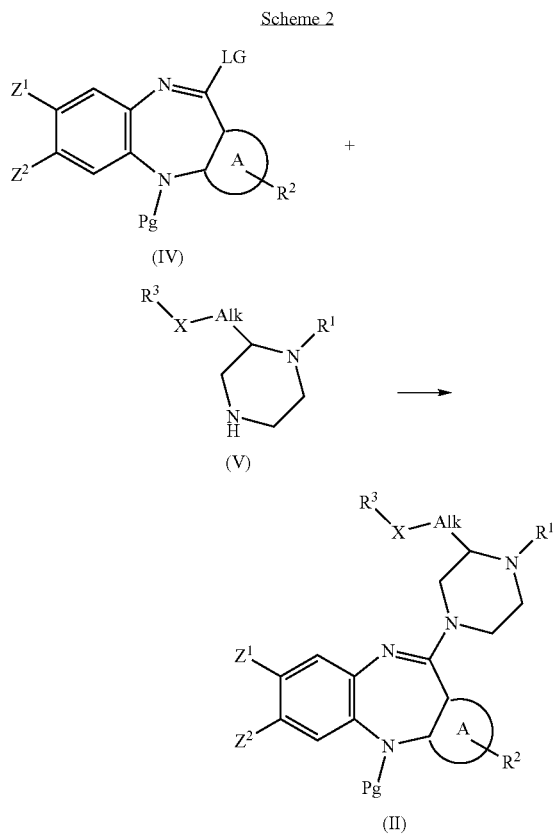

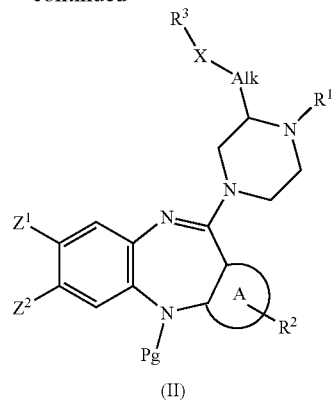

In Scheme 4, compounds of formula (VI b), wherein $X_1$ is S, may be prepared from compounds of formula (VI a), wherein $X_1$ is O, by treatment with a dehydrative thiolating agent in the presence of an inert solvent. Examples of such dehydrative thiolating agents include $P_2S_5$ and Lawesson's reagent (2,4-bis(4-methoxyphenyl)-1,3dithia-2,4-diphosphetane-2,4-disulfide). For a description of Lawesson's reagent and its use, see M. P. Cava and M. I. Levinson, *Tetrahedron*, 41, 5061 (1985).

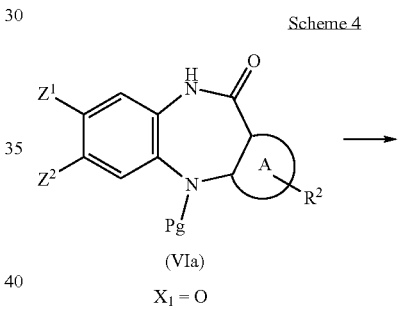

Alternatively, as shown in Scheme 3, tricyclic amide and thioamide intermediates of formula (VI) wherein $X_1$ is O or S, respectively, can react with substituted piperazines of formula (V) to give corresponding compounds of formula (II). This reaction is conveniently performed in a polar solvent such as pyridine and methylene chloride and may be performed in the presence or absence of a Lewis acid such as $TiCl_4$.

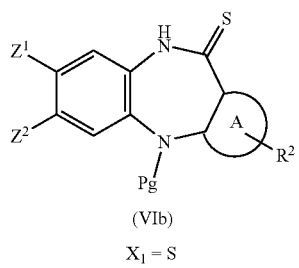

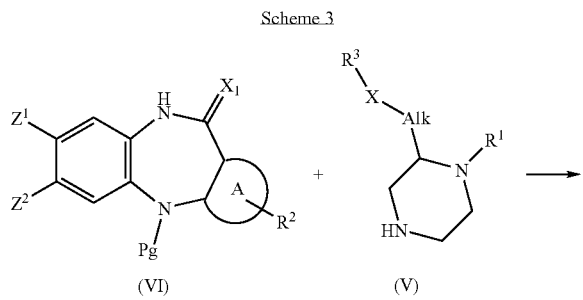

As shown in Scheme 5, tricyclic intermediates of formula (IV) can be prepared from the corresponding tricyclic amide and thioamide intermediates of formula (VI). O-alkylation of an amide of formula (VI a) ($X_1$=O) provides an iminoether of formula (IV) (LG=$OY_1$). Suitable alkylating agents include Meerwein's reagent and methyl fluorosulfonate. Iminothioethers of formula (IV), wherein LG is $SY_1$, may be prepared by S-alkylation of thioamides of formula (VI b) ($X_1$=S). Suitable alkylating agents include alkyl halides, alkyl sulfonates such as methyl trifluoromethanesulfonate, Meerwein's reagent and methyl fluorosulfonate. Reaction of an amide of formula (VI a) ($X_1$=O), with a dehydrative halogenating agent provides an iminohalide of formula (IV), wherein LG is a halo group. Suitable dehydrative halogenating agents include POCl$_3$, SOCl$_2$, PCl$_3$, PCl$_5$, PBr$_3$, PPh$_3$/Br$_2$, P(OPh)$_3$/I$_2$ and PPh$_3$/MeI.

Scheme 5

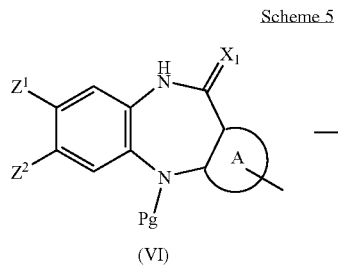

(VI)

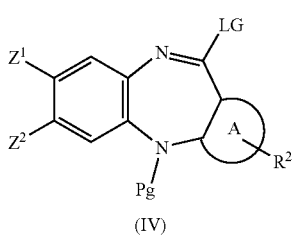

(IV)

Compounds of formula (IV) in which LG is NH$_2$, OY$_1$ or SY$_1$ may be prepared from compounds of formula (VI), wherein LG is halo, by reaction with a suitable nucleophile, such as ammonia, an alcohol, or a thiol to give compounds of formula (IV), wherein LG is NH$_2$, OY$_1$ or SY$_1$, respectively. This reaction may be conveniently performed in a solvent such as DMF and under basic conditions such as K$_2$CO$_3$.

As shown in Scheme 6, compounds of formula (II) may also be prepared by ring closure of an intermediate of formula (XIII a). This reaction may be effected by treatment of an amide of formula (XIII a) with an activating agent in the presence of an inert solvent. Examples of such activating agents include TiCl$_4$, POCl$_3$, P$_2$S$_5$, and Lawesson's reagent.

Scheme 6

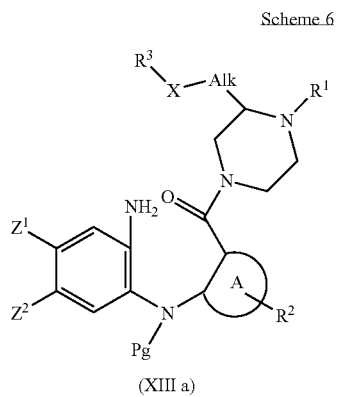

(XIII a)

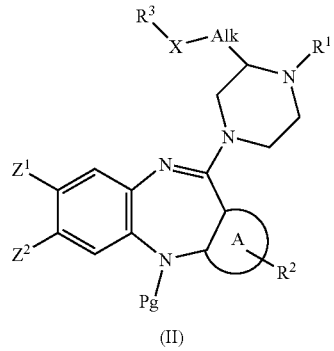

(II)

According to Scheme 7, compounds of formula (VI a), may be prepared by cyclization of an amine compounds of formula (XIII b) in which Y$_2$ is OY$_7$ or NY$_8$Y$_9$ wherein Y$_7$, Y$_8$ and Y$_9$ are independently, hydrogen or lower alkyl such as methyl, ethyl, or propyl.

Scheme 7

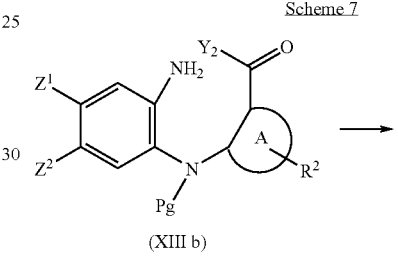

(XIII b)

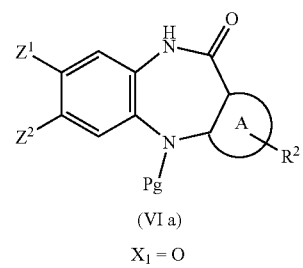

(VI a)

X$_1$ = O

As seen in Scheme 8, amines of formula (XIII b) may be prepared from compounds of formula (XIII c). The symbol Y$_3$ represents a group that may be converted to an amino group, such as NO$_2$, COOH, and NHCOOY$_4$, wherein Y$_4$ may be an optionally substituted alkyl such as, but not limited to, methyl, ethyl, 2-phenylethyl, t-butyl, 2-(trimethylsilyl)ethyl, 2,2,2-trichloroethyl, vinyl, allyl or optionally substituted benzyl group such as, but not limited to, benzyl, p-methoxybenzyl, p-nitrobenzyl, or diphenylmethyl.

Scheme 8

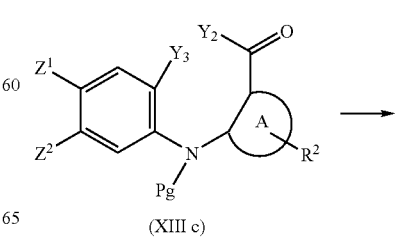

(XIII c)

-continued

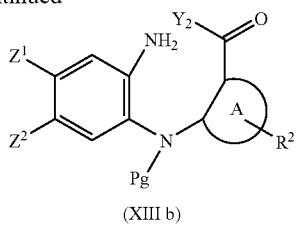

(XIII b)

If $Y_3$ is $NO_2$, treatment of compounds of formula (XIII c) under reducing conditions will provide corresponding compounds of formula (XIII b). Examples of such reducing conditions include catalytic hydrogenation conditions or $SnCl_2$. Compounds of formula (XIII c), wherein $Y_3$ is $NHCOOY_4$, may be converted to the corresponding compounds of formula (XIII b) under conditions that allow for removal of the $COOY_4$ group. If $Y_4$ is optionally substituted alkyl, such conditions may include hydrolysis under acidic or basic conditions. If $Y_4$ is optionally substituted benzyl, treatment under reducing conditions, preferably catalytic hydrogenation conditions, provides the corresponding compound of formula (XIII b). If $Y_4$ is t-butyl, treatment with acid provides a compound of formula (XIII b). If $Y_4$ is 2,2,2-trichloroethyl, reducing conditions, preferably zinc metal in acidic medium, yield a compound of formula (XIII b). If $Y_4$ is 2-(trimethylsilyl)ethyl, treatment with fluoride ion yield a compound of formula (XIII b).

Compounds of formula (XIII b) may also be prepared by Curtius rearrangement of the correspondent compound of formula (XIII c) in which $Y_3$ is COOH. The Curtius rearrangement occurs by thermal rearrangement of the acylazide of formula (XIII c) in which $Y_3$ is $CON_3$ to yield the isocyanate of formula (XIII c) in which $Y_3$ is NCO. This isocyanate may be hydrolyzed either directly or through the urethane in which $Y_3$ is $NHCO_2Y_4$, to yield the corresponding compound of formula (XIII b).

According to Scheme 9 compounds of formula (IV a) in which LG is $NH_2$ may be prepared by cyclization of aminonitrile compounds of formula (XIII d).

Scheme 9

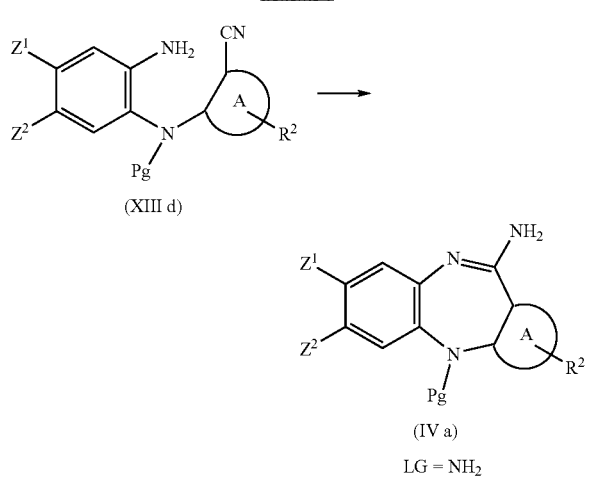

According to Scheme 10, aminonitrile compounds of formula (XIII d) may be prepared from corresponding compounds of formula (XIII e), in the manner described for Scheme 8. Alternatively, compounds of formula (XIII d) may be prepared by Curtius rearrangement under conditions also described for Scheme 8.

Scheme 10

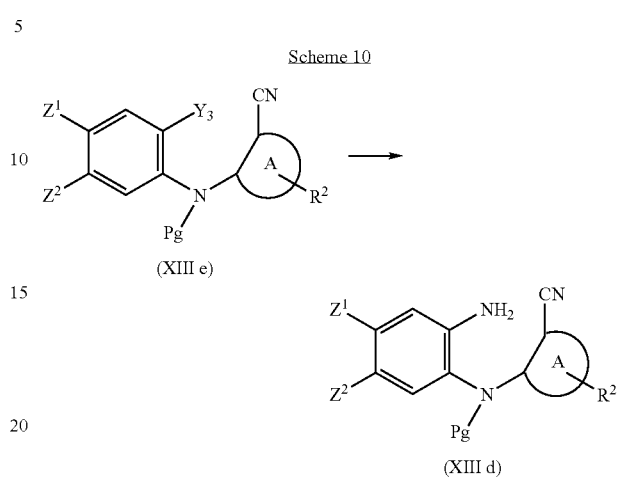

As shown in Scheme 11, compounds of formula (XIII a), wherein all groups are defined as above, may be prepared from corresponding compounds of formula (XIII f) in which $Y_3$ is a group that may be converted to an amino group.

Scheme 11

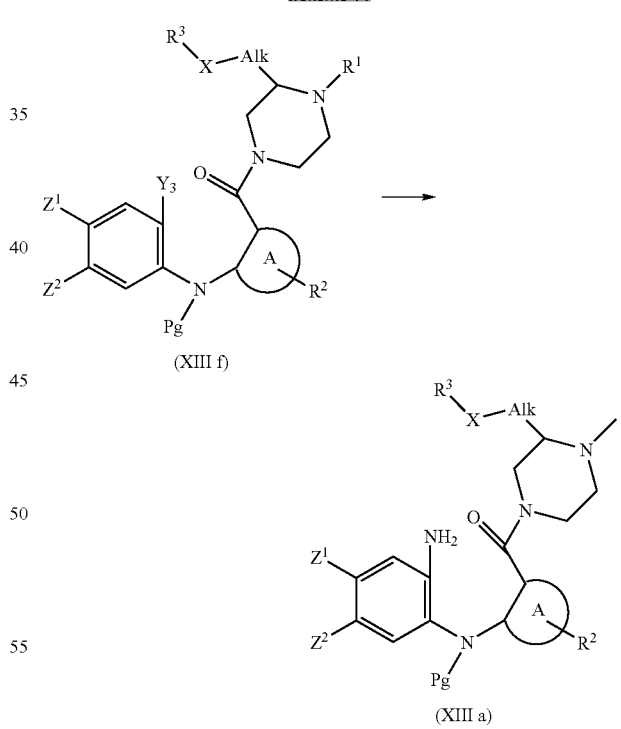

According to Scheme 12, compounds of formula (XIII f), wherein $Y_3$ is a group that may be converted to an amino group as defined above, and all other groups are as defined above, may be prepared by coupling a compound of formula (V) with a compound of formula (XIII g). Such coupling reactions may be performed under conditions commonly employed to form amide bonds. Coupling reagents include Scheme 12

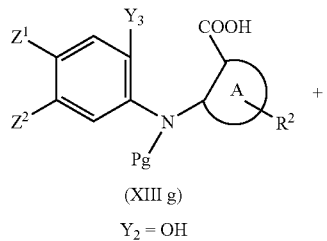

(XIII g)

$Y_2$ = OH

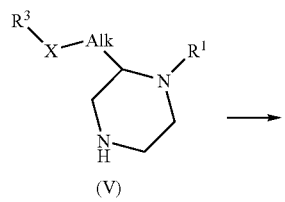

(V)

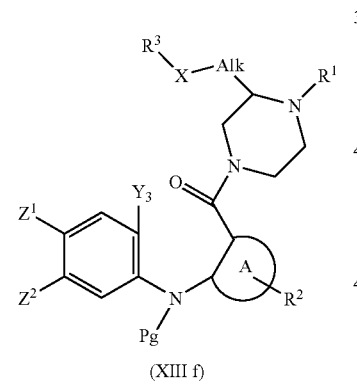

(XIII f)

compounds of formula (XV a) to yield a compound of formula (XIII) may also be performed in the presence of a metal catalyst. Conditions for this transformation may be found in Hartwig, *Angew. Chem. Int. Ed.* 37, 2046-2067 (1998), Wolff, et al., *Acc. Chem. Res.* 31, 805-818 (1998), Yang and Buchwald, *J. Organomet. Chem.* 576, 125-146 (1999), U.S. Pat. No. 6,271,225, U.S. Pat. No. 6,455,542, and references cited therein.

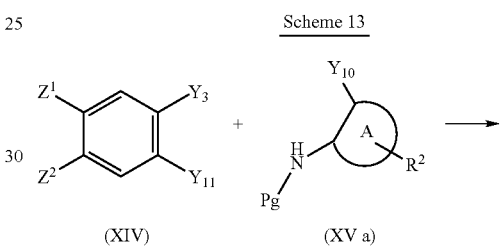

Scheme 13

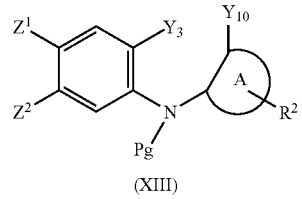

(XIII)

As shown in Scheme 13, compounds of formula (XIII) in which $Y_3$ may be $NH_2$ or a group that may be converted to an amino group as described above, $Y_{10}$ may be hydrogen, CN, $COOY_7$ or $CONY_8Y_9$, in which $Y_7$, $Y_8$, and $Y_9$ may independently be hydrogen or lower alkyl, or $NY_5Y_9$ is the group (XVI), may be prepared by reaction of compounds of formula (XIV) in which $Y_{11}$ may be a halo group or $OSO_2CF_3$ with compounds of formula (XV a). This reaction may be performed under basic conditions in a polar, aprotic solvent. Suitable bases include NaH, KH, potassium tert-butoxide, lithium hydroxide and cesium carbonate. Suitable solvents include DMF, N-methylpyrrolidinone, DMSO, and THF. The coupling of compounds of formula (XIV) with Compounds of formula (XIV) may be prepared by methods known in the art.

Alternatively as shown in Scheme 14, compounds of formula (XIII) in which $Y_3$ may be $NH_2$ or a group that may be converted to an amino group as described above, $Y_{10}$ may be hydrogen, CN, $COOY_7$ or $CONY_8Y_9$, in which $Y_7$, $Y_8$, and $Y_9$ may independently be hydrogen or lower alkyl, or $NY_8Y_9$ is the group (XVI), and the other groups are defined as above, may also be prepared by reaction of compounds of formula (XIVa) with compounds of formula (XV) in which $Y_{12}$ may be a halo group or $OSO_2CF_3$. This reaction may be performed under basic conditions in a polar, aprotic solvent. Suitable bases include NaH, KH, potassium tert-butoxide, lithium hydroxide, and cesium carbonate. Suitable solvents include DMF, N-methylpyrrolidinone, DMSO, and THF.

The coupling of compounds of formula (XIVa) with compounds of formula (XV) to yield a compound of formula (XIII) may also be performed in the presence of a metal catalyst. Conditions for this transformation may be found in Hartwig, *Angew. Chem. Int. Ed.* 37, 2046-2067, (1998), Wolff, et al., *Acc. Chem. Res.*, 31, 805-818, (1998), and Yang and Buchwald, *J. Organomet. Chem.* 576, 125-146, (1999), and references cited therein.

Scheme 14

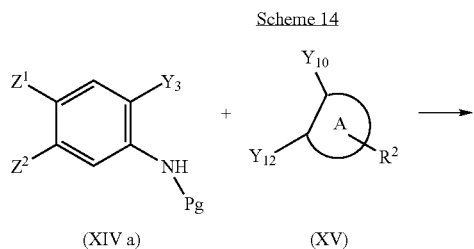

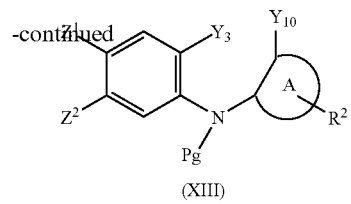

(XIII)

Compounds of formula (XIVa) may be prepared by methods known in the art.

According to Scheme 15, a compound of formula (VIa) can also be prepared by cyclization of isocyanate (XIIIh) under acidic conditions. Isocyanate (XIIIh) may be prepared from compounds of formula (XIII) in which $Y_{10}$ is hydrogen and $Y_3$ is an amino group by reaction with formic acetic anhydride and dehydration of the resulting formamide with a dehydrating agent such as $POCl_3$ or $P_2O_5$. Isocyanate (XIIIh) may also be prepared from compounds of formula (XII) in which $Y_{10}$ is hydrogen and $Y_3$ is COOH by Curtius rearrangement as described before. Alternatively, a compound of formula (IIb) may also be prepared by reaction urea (XIIIi) in the presence of a Lewis acid. Urea (XIIIi) may be prepared by reaction of isocyanate (XIIIh) with an amine of formula (V).

Scheme 15

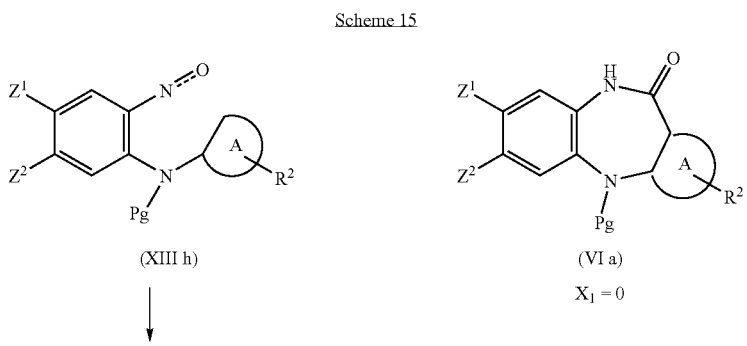

$X_1 = O$

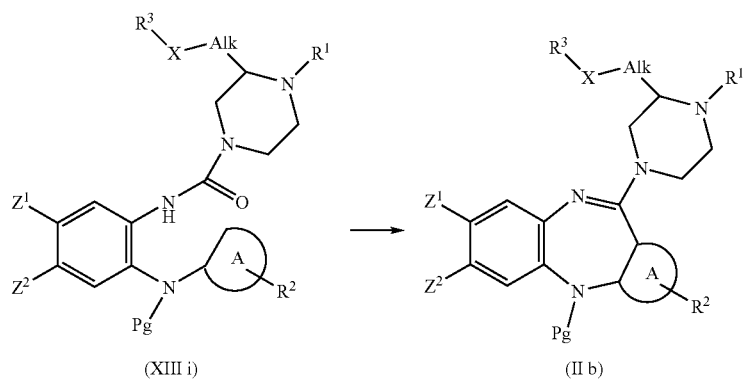

In Scheme 16, compounds of formula (VI c), the aromatic ring,

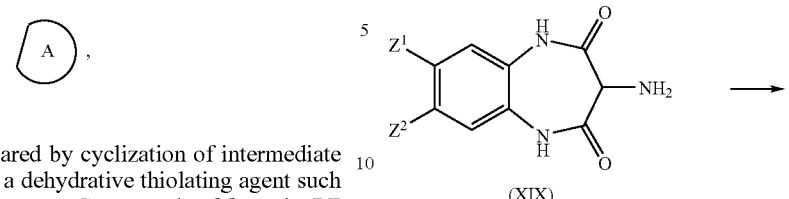

is thiazole, may be prepared by cyclization of intermediate of formula (XVIII) with a dehydrative thiolating agent such as $P_2S_5$ or Lawesson's reagent. Compounds of formula (VI d), the aromatic ring, is an oxazole ring, may be prepared by cyclization of intermediate of formula (XVIII) with a dehydrating agent such as $P_2O_5$ or $PPh_3/Tf_2O$.

Scheme 17

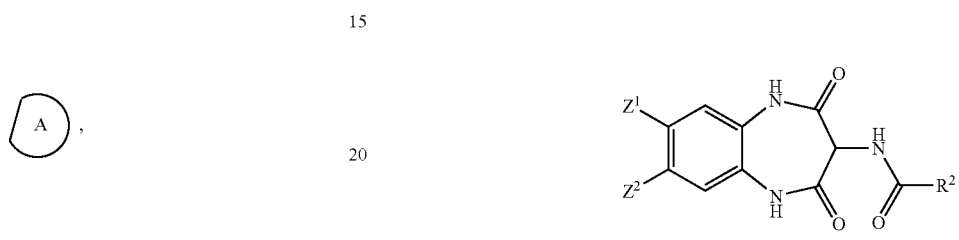

Scheme 16

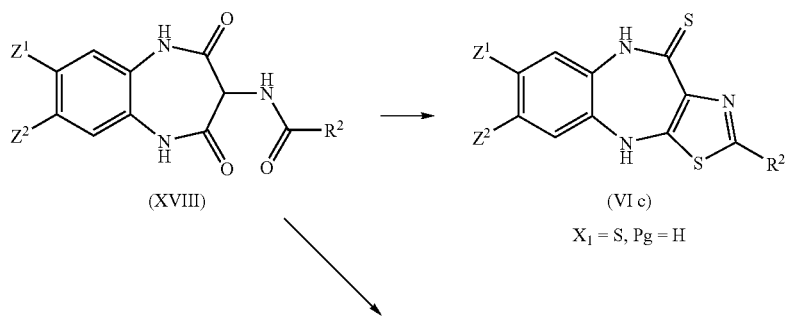

According to Scheme 17, compounds of formula (XVIII) are prepared by acylation of an amine of formula (XIX). This reaction is usually performed by treatment of formula of (XIX) with an acid chloride, or acid anhydride in the presence of a base in an inert solvent. Methods for the synthesis of compounds of formula (XIX) are known in the art; see, for example, Hagishita, et al., *Bioorg. Med. Chem.*, 5(7), 1433-1446, (1997).

As shown in Scheme 18, compounds of formula (VI e), the A ring,

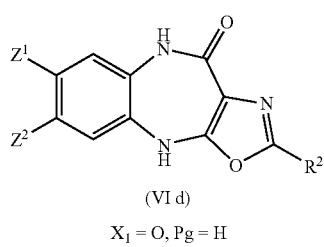

is pyrazole, or (VI f) the A ring, is pyrimidine, may also be prepared by reaction of compounds of formula (XX) with a substituted hydrazine or an amidine, respectively. Compounds of formula (XX) are prepared as described in Roma, et al., *Farmaco, Ed. Sci.*, 38, 546-558 (1983).

The skilled artisan will recognize that substituents $R^2$ and $Z^1$ and $Z^2$ in the compounds of formula (I) may be present in the precursor molecules of formulas (XIV), (XIVa), (XVb), and (XVc). Alternatively, these substituents may be introduced at any convenient point during the synthesis

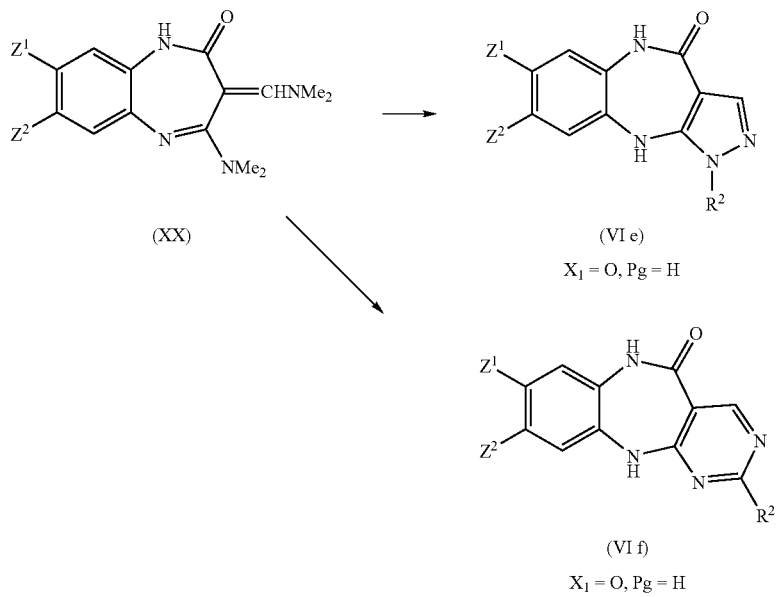

Methods for the preparation of compounds of formula (XV b) and formula (XV c) are known in the art and vary depending on the nature of the aromatic ring A, either by replacement of a hydrogen (through, for example, an electrophilic aromatic substitution reaction) or by conversion of an existing substituent into the substituents present in the compounds of formula (I). Examples of electrophilic aromatic substitution reactions include halogenation, nitration, Friedel-Crafts acylation, and electrophilic trifluoromethylation under conditions described in the literature. Examples of conversion of an existing substituent into one present in the final compound include conversion of a Br substituent into a substituent such as $SR^{11}$ or $COR^{11}$ by metallation with an organolithium reagent and reaction with an electrophile such as $R^{11}SSR^{11}$ or $R^{11}COOMe$. $R^{11}$ may be $(C_{1-6})$alkyl, $(C_{1-6})$ fluoroalkyl, benzyl, or optionally substituted phenyl" Additionally, a Br substituent can be converted to an optionally substituted aromatic ring by reaction with an optionally substituted phenylboronic acid in the presence of a palladium catalyst. Many other such functional group transformations are reported in the literature.

General methods and specific examples of the synthesis of these compounds can be found in the following references: Chakrabarti, et al., *J. Med. Chem.*, 23, 878-884; (1980), Chakrabarti, et al., *J. Med. Chem.*, 23, 884-889; (1980), Chakrabarti, et al., *J. Med. Chem.*, 25, 1133-1140; (1982), Chakrabarti, et al., *J. Med. Chem.*, 32, 2573-2582; (1989), Liegeois, et al., *J. Med. Chem.*, 36, 2107-2114; (1993), Liegeois and Delarge, U.S. Pat. No. 5,393,752 (1995);

Chakrabarti and Hotten, Eur. Pat. Appl., EP 354781; (1990),
Bolton, et al., PCT Int. Appl., WO 9700252; (1997),
Chakrabarti, et al., Eur. Pat. Appl., EP 27390; (1981),
Tehim, et al., U.S. Pat. No. 5,602,124 (1998);
Tehim, et al., U.S. Pat. No. 5,824,676 (1998);
Eilingsfeld and Swybold, Ger. Offen. DE 2713573; (1978),
Gallemaers, et al., *Tetrahedron Lett.*, 693-694; (1976),
Durnow and Abele, *Chem. Ber.*, 97, 3349-3353, (1964),
Klempier, et al., *J. Heterocyclic Chem.*, 29, 93-95, (1992).

In Scheme 19, compounds of formula (XV d) may be prepared by regioselectively nitrating 3-bromobenzothiophene compounds to afford the 2-nitro-3-bromobenzothiophene compounds of formula (XVe). Suitable nitrating conditions include nitric acid (optionally in the presence of another acid, such as trifluoroacetic acid, sulfuric acid, or acetic acid, or in the presence of an inert solvent such as dichloromethane or water), fuming nitric acid, or sidium nitrite in the presence of an acid. Displacement of the 3-bromo-group with cyanide can be accomplished using CuCN in the presence of a polar solvent like DMF or N-methylpyrrolidinone to give compounds of formula (XV f). Reduction of the nitro group to the amine can be accomplished by reducing agents such as $SnCl_2/HCl$, $Zn/HOAc$ and $Pd$—$C/H_2$ to give compounds of formula (XV d) in which Pg is hydrogen. A protecting group may be subsequently introduced.

Scheme 19

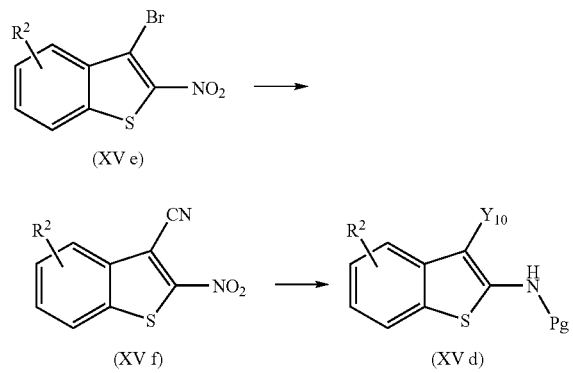

Compounds of formula (V) of this invention may be prepared from compounds of formula (XXIV b), as shown in Scheme 20, in which one of the nitrogens in the piperazine ring may be protected by an amine protecting group, by removal of this protecting group. In this equation, $ProG_2$ represents an amine protecting group. Examples of such $ProG_2$ groups include benzyl, acetyl, t-butoxycarbonyl, methanesulfonyl, and the like. Examples of additional $ProG_2$ groups and methods for the introduction and removal of such groups can be found in T. W. Green, *Protective Groups in Organic Synthesis*, John Wiley and Sons, Inc. (1981). In the subsequent text, $Pg_2$ represents either hydrogen or an amine protecting group $ProG_2$. In the following text, for those intermediates containing a group $Pg_2$ in which $Pg_2$ is an amine protecting group, the protecting group may be removed to give the unprotected amine. Similarly, for those intermediates in which $Pg_2$ is hydrogen, an amine protecting group may be incorporated into the intermediate. The methods for introducing and removing these protecting groups are known in the art.

Scheme 20

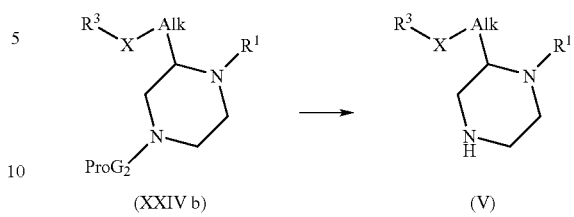

According to Scheme 21, compounds of formula (XXIV a) of this invention may be prepared from compounds of formula (XXV a) by removal of the amine protecting group $ProG_1$. Examples of such $ProG_1$ amine protecting groups include benzyl, acetyl, t-butoxycarbonyl, methanesulfonyl, and the like. Examples of additional $ProG_1$ groups and methods for the introduction and removal of such groups can be found in T. W. Green, *Protective Groups in Organic Synthesis*, John Wiley and Sons, Inc. 1981. It will be recognized that in some instances, in compounds of formula (XXV a), $Pg_2$ and $ProG_1$ may both be protecting groups that are removed under the same reaction conditions. In those cases, deprotection of this compound will yield compounds of formula (V) in which $R^1$ is hydrogen. In compounds of formula (XXIV a), if $Pg_2$ is an amine protecting group, $ProG_2$, then alkylation of formula (XXIV a) will yield compounds of formula (XXIV), in which $R^1$ is $(C_{1-4})$ alkyl optionally substituted with a substituent selected from the group consisting of hydroxy, methoxy, ethoxy, —$OCH_2CH_2OH$, or —CN.

Scheme 21

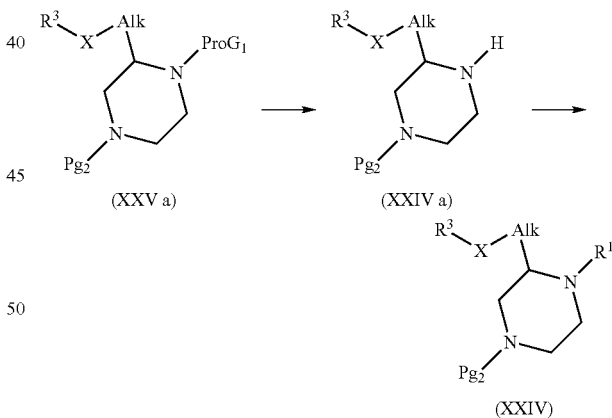

In Scheme 22, compounds of formula (XXV), in which all groups are defined as above, may be prepared by reduction of either a ketopiperazine of formula (XXVI) or a diketopiperazine of formula (XXVII). $Pg_1$ represents either hydrogen, is $(C_{1-4})$ alkyl optionally substituted with a substituent selected from the group consisting of hydroxy, methoxy, ethoxy, —$OCH_2CH_2OH$, —CN, or an amine protecting group $ProG_1$. Suitable reducing agents for this transformation include lithium aluminum hydride and borane. Methods for the synthesis of ketopiperazines and diketopiperazines are known in the art.

Scheme 22

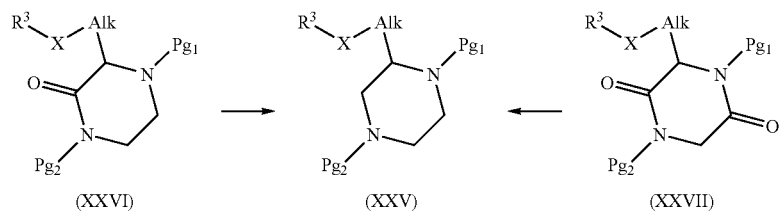

As shown in Scheme 23, compounds (XXVI) and (XXVII) may be prepared by alkylation of the corresponding ketopiperazine (XXVIII) and diketopiperazine (XXIX), respectively, with an alkylating agent of the formula Lg-Alk-X—$R^3$, in which Lg is a leaving group such as a halogen, alkylsulfonyloxy, or arylsulfonyloxy group. Examples of alkylsulfonyloxy groups include methanesulfonyloxy and ethansulfonyloxy and examples of arylsulfonyloxy groups include toluenesulfonyloxy and benzenesulfonyloxy groups. This alkylation reaction is performed in the presence of a base. Suitable bases include lithium diisopropoxide, lithium hexamethyldisilazide, sodium hydride, potassium t-butoxide, and the like.

Scheme 23

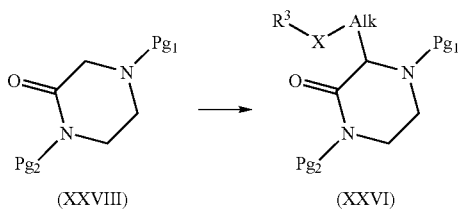

-continued

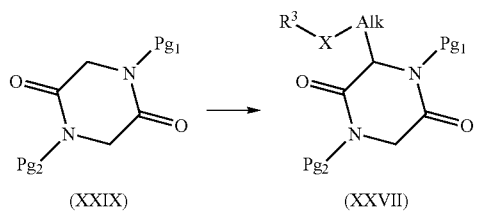

Further, as shown in Scheme 24, compounds of formula (XXV b) in which Alk is —$CH_2CH_2$—, —$CH_2CH_2CH_2$—, and —$CH_2CH_2CH_2CH_2$— may be prepared from a suitably protected 2-substituted piperazine of formula (XXX) by employing a hydroboration/oxidation sequence.

Scheme 24

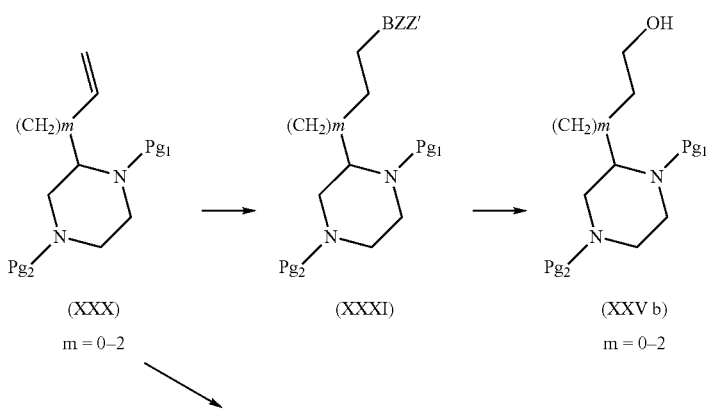

-continued

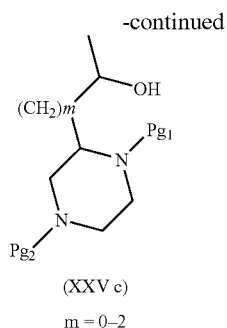

(XXVc)

m = 0–2

Thus, reaction of formula (XXX) with a borane HBZZ', in which Z and Z' are independently H, alkyl such as methyl, ethyl, propyl, or alkoxy such as methoxy, ethoxy, or propoxy provides an organoborane of formula (XXXI). Suitable boranes HBZZ' include, borane, trisiamylborane, catecholborane, and 9-borabicyclo[3,3,0]nonane (9-BBN). The resulting organoborane is then oxidized to the alcohol (XXVb) using an oxidant such as hydrogen peroxide or t-butylhydroperoxide.

Compounds of formula (XXVc) may be formed from compounds (XXX) by hydration of the olefin. This hydration is typically performed under acidic conditions or may also be performed through an oxymercuration/reduction sequence. The oxymercuration is typically performed by treatment of the olefin with a mercury(II) salt such as Hg(OAc)$_2$. The mercury atom is removed from the intermediate compound through reduction with NaBH$_4$.

It should be noted that compounds (XXVb) and (XXVc) are regioisomers of one another. Mixtures of these compounds can result from either the hydroboration/oxidation, acid catalyzed hydration, or oxymercuration/reduction sequences if the regiochemical control of these processes is limited.

Compounds of formula (XXX) (m=0) may be prepared by the method described in Tsuda, et al., *J. Org. Chem.*, 55, 3388-3390, (1990), and Uozumi, et al., *J. Org. Chem.*, 58, 6826-6832, (1993).

In Scheme 25 compounds of formula (XXX) (m=1, 2) may be prepared by an alkylation of formula (XXVIII) with an allyl halide or a homoallyl halide and to give compounds of formula (XXXII) and reduction with lithium aluminum hydride to give compounds of formula (XXX) (m=1, 2).

-continued

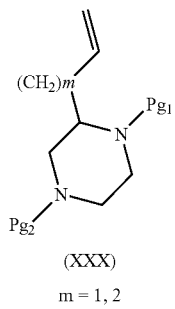

(XXX)

m = 1, 2

As shown in Scheme 26, compounds of the formula (XXVb) (m=0, 1) and (XXVc) (m=0,1) may be oxidized to the corresponding aldehyde (XXXIII) (m=0, 1) and ketone (XXXIV) (m=0, 1), respectively. Suitable oxidizing reagents include pyridinium chlorochromate, DMSO/oxalyl chloride (Swern oxidation) and dimethylsulfide/N-chlorosuccinimide (Corey-Kim oxidation). Compounds (XXXIII) and (XXXIV) may be treated with an organoalkyl reagent, MR$^{12}$ to provide alcohols (XXVc) (m=0, 1) and (XXVe) (m=0, 1), respectively. Suitable organoalkyl reagents include organolithium reagents such as methyllithium and ethyllithium, Grignard reagents such as methylmagnesium bromide and ethylmagnesium chloride, and the like.

Scheme 25

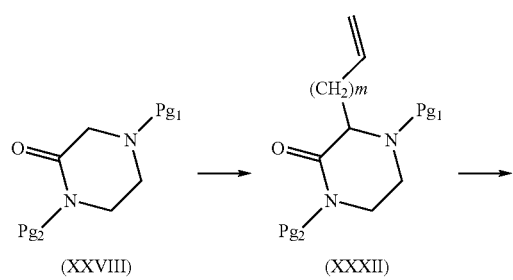

Scheme 26

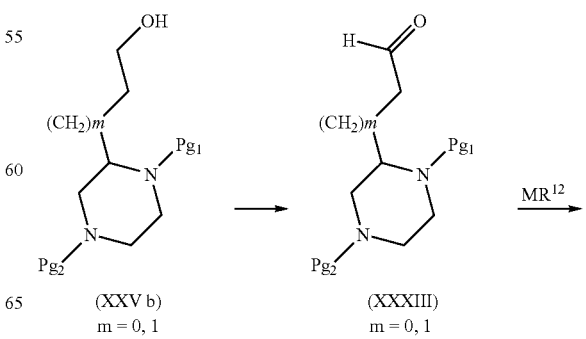

-continued

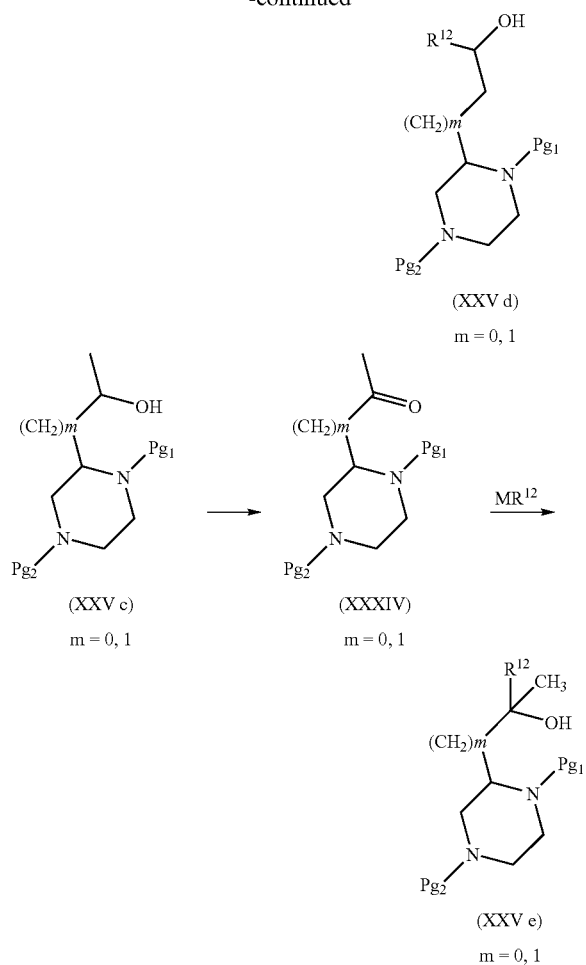

(XXV d)
m = 0, 1

(XXV c)
m = 0, 1

(XXXIV)
m = 0, 1

(XXV e)
m = 0, 1

As shown in Scheme 27, an alcohol of the formula (XXV f) may be transformed to the corresponding ethers and thioethers (XXV h) (X=O, S) and (XXV g) through a number of methods. The oxygen of alcohol (XXV f) may be treated with an alkylating agent to form ether (XXV g) in which $R^3$ is an alkyl group. Suitable alkylating agents include dimethyl sulfate, alkyl halides such as methyl iodide, ethyl bromide, and benzyl chloride, and sulfonate esters such as methyl tosylate, ethyl methanesulfonate, and methyl trifluoromethanesulfonate. This alkylation is usually performed under basic conditions.

Alternatively as depicted in Scheme 27, compound (XXV f) may be converted into a compound of structure (XXXV) in which Lg is a leaving group. Examples of leaving groups Lg include halogen, the alkylsulfonyloxy group, and the arylsulfonyloxy group. Examples of alkylsulfonyloxy groups include methanesulfonyloxy and ethansulfonyloxy and examples of arylsulfonyloxy groups include toluenesulfonyloxy and benzenesulfonyloxy groups. Compounds in which Lg is a halogen such as chlorine or bromine may be prepared from (XXV f) by reaction with an inorganic halide such as thionyl chloride, phosphorus pentachloride, or phosphorus tribromide. Compounds in which Lg is an alkylsulfonyloxy group or arylsulfonyloxy group may be prepared by reaction of (XXV f) with the corresponding alkylsulfonyl halide, arylsulfonyl halide, alkylsulfonic anhydride or arylsulfonic anhydride in the presence of a base. Reaction of (XXXV) with an alcohol $R_3OH$ or a thiol $R_3SH$ provides the corresponding ethers and thioethers (XXV h) (X=O, S). This reaction is typically performed under basic conditions in an inert solvent. Suitable bases include sodium hydride, sodium hydroxide, and potassium hydride.

Scheme 27

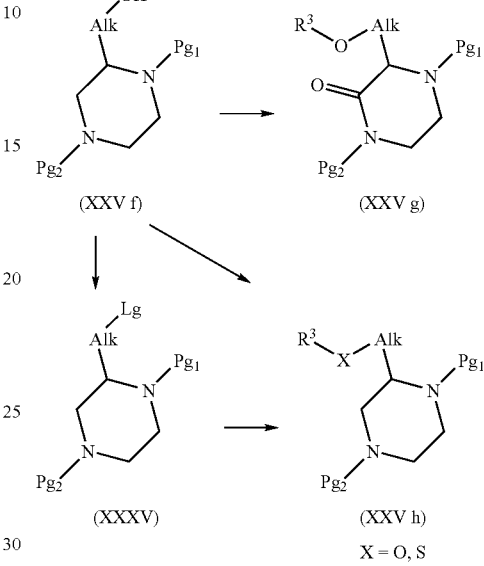

(XXV f)

(XXV g)

(XXXV)

(XXV h)
X = O, S

Alternatively, as also shown in Scheme 27, (XXV f) may be converted directly into (XXV h) (X=O, S) by treatment with an alcohol $R_3OH$ or thiol $R_3SH$ under Mitsunobu conditions. Classical Mitsunobu conditions employ triphenylphosphine and diethyl azodicarboxylate. The Mitsunobu reaction has been reviewed in the following references:

David L. Hughes, *Organic Reactions*, 42, 335-656 (1992);

David L. Hughes, *Organic Preparations and Procedures International*, 28, 127-164 (1996).

As shown in Scheme 28, thioethers (XXV i) may be converted into the corresponding sulfoxides, (XXV j) m=1, and sulfones, (XXV j) m=2, by reaction with an appropriate oxidizing agent. Oxidizing agents include molecular oxygen, hydrogen peroxide, t-butyl hydroperoxide, peroxyacetic acid, meta-chloroperoxybenzoic acid, ozone, and oxone (potassium peroxymonosulfate).

Scheme 28

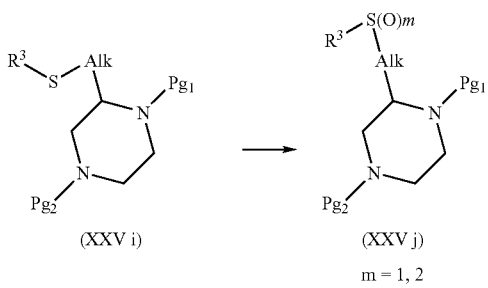

(XXV i)

(XXV j)
m = 1, 2

The skilled artisan will appreciate that many of the aforementioned reactions may be performed in any convenient order. Similarly, for those compounds that contain an asymmetric center, the skilled artisan will recognize that the aforementioned reactions may be performed either on pure isomers or on a mixture of isomers. The isomers may be separated at any convenient stage during the synthesis.

Pharmacological Activity

Compounds of the formula (I) have moderate to high binding affinity for multiple neurotransmitter receptors, and in particular, the dopamine receptors. Those skilled in neuropharmacology and related disciplines have recognized dopamine receptor binding activity as indicative of antipsychotic, in particular, antischizophrenic properties. See P. Seeman, et al., *Nature*, 261, 717-718 (1976); P. Seeman, *Synapse*, 1, 133 (1987); H. Howard, et al., 28, 39 (1993); and J. Schaus. Et al., *Annual Reports in Medicinal Chemistry*, 33, 1 (1998). Cloning studies have currently demonstrated five principal dopamine receptor subtypes that fall into two major classes, $D_1$-like and $D_2$-like. The $D_1$-like class includes the $D_1$ and $D_5$ subtypes, and the $D_2$-like class encompasses the $D_2$, $D_3$, and $D_4$ subtypes. Table 5 shows the relative binding affinity of selected compounds of formula (I) for the $D_2$ receptor. The experimental protocol for the assay generating this data is in the Example section below.

TABLE 5

Relative $D_2$ Receptor Binding Affinity For Compounds of Formula (I)

| Comp. No. | Affinity $K_i$* | Comp. No. | Affinity $K_i$ | Comp. No. | Affinity $K_i$ | Comp. No. | Affinity $K_i$ |
|---|---|---|---|---|---|---|---|
| 198 | + | 324 | +++ | 269 | +++ | 340 | +++ |
| 199 | ++ | 314 | ++++ | 242 | +++ | 341 | +++ |
| 216 | ++ | 334 | ++++ | 267 | +++ | 343 | ++ |
| 303 | ++++ | 346 | ++++ | 319 | +++ | 342 | +++ |
| 304 | ++++ | 344 | ++++ | 327 | ++++ | 359 | +++ |
| 313 | ++ | 351 | +++ | 320 | +++ | 360 | ++ |
| 318 | ++++ | 316 | ++++ | 326 | ++++ | 361 | ++++ |
| 322 | +++ | 336 | ++++ | 331 | +++ | 367 | ++++ |
| 323 | +++ | 355 | +++ | 309 | +++ | 368 | ++++ |
| 333 | ++ | 353 | +++ | 328 | +++ | 369 | ++ |
| 338 | +++ | 357 | +++ | 302 | +++ | 370 | ++ |
| 312 | ++ | 240 | +++ | 268 | +++ | | |
| 327 | +++ | 241 | ++ | 321 | ++ | | |
| 305 | +++ | | | 339 | +++ | | |

*$K_i$ is generally defined as the binding affinity constant (i.e., dissociation constant) of an unlabeled ligand in a radioligand-binding assay. See, for example, Neurotransmitter Receptor Binding, Second Edition, Eds H. I. Yamamura, S. J. Enna, and M. J. Kuhar, Raven Press (1985).
*++++ = <10 nM; +++ = 10-100 nM; ++ = 100-1000 nM; + = >1000 nm Using the relative $K_i$ scale of Table 5, clozapine has a ++ affinity and olanzapine has a +++ affinity. Thus, many of the compounds of formula (I) exhibit $D_2$ receptor affinity greater than both clozapine and olanzapine. The compounds of formula (I) have a desirable $D_2$ binding affinity of preferably less than or equal to 1000 nM, more preferably less than or equal to 200 nM, and even more preferably less than or equal to 50 nM.

Like clozapine and olanzapine, the compounds of formula (I) also exhibit affinity for the 5-$HT_6$ receptor. Because clozapine and olanzapine have greater efficacy in treating the cognitive disturbances of schizophrenia than typical antipsychotics (Purdon, et al., *Arch. Gen. Psych.*, 57, 249 (2000)) and selective 5-$HT_6$ antagonists are active in models of cognitive enhancement, this activity is desirable in an antipsychotic drug.

Many atypical antipsychotics have a high affinity for the 5-$HT_{2A}$ receptor. Researchers believe that high affinity for the 5-$HT_{2A}$ receptor helps in treating the negative symptoms of schizophrenia and preventing some of the motor side effects (H. Meltzer, et al., *J. Pharm. Exp. Ther.* 25, 238 (1989)). However, selective 5-$HT_{2A}$ antagonists are not effective antipsychotics as monotherapy. Thus, 5-$HT_{2A}$ antagonism would likely be among the other neuroreceptor affinities of a superior antipsychotic compound. The compounds of formula (I) exhibit a desirable level of 5-$HT_{2A}$ affinity.

Antipsychotics are believed to exert at least part of their therapeutic effects through blockade of the dopamine $D_2$ receptor. The ability of a compound to block dopamine $D_2$ receptors in the rat in vivo was determined by measuring the effect of the compound on the level of DOPAC (3,4-dihydroxyphenylacetic acid), a metabolite of dopamine, in nucleus accumbeus of the rat. Dopamine $D_2$ receptor antagonists increase the release of dopamine into the synapse due to blockade of the dopamine $D_2$ autoreceptor. This increased release of dopamine cannot be directly measured, since the efficiency of the dopamine reuptake system prevents increases in synaptic dopamine concentrations. Instead, increases in the levels of the dopamine metabolites DOPAC (3,4-dihydroxyphenylacetic acid) and HVA (homovanillic acid) reflect increased neuronal dopaminergic activity in vivo. For example, olanzapine and other dopamine $D_2$ receptor antagonists increase concentrations of DOPAC and HVA in striatum and nucleus accumbens without appreciable alteration of dopamine concentrations. The potency of a compound to block dopamine $D_2$ receptors was determined by the dose required to increase DOPAC levels to 200% of control. This value is called the $ED_{200}$.

Antipsychotics are believed to induce at least part of their weight gain effects through blockade of histamine $H_1$ receptors in the hypothalamus.

Their ability of a compound to block histamine $H_1$ receptors can be estimated in vitro by measuring the in vitro histamine $H_1$ receptor affinity. Compounds with decreased affinity for histamine $H_1$ receptors will be less likely to induce weight gain. The ratio of in vitro histamine $H_1$ receptor affinity divided by the in vitro dopamine $D_2$ receptor affinity, both expressed as $K_i$'s, is an estimate of a compound's likelihood to cause weight gain at therapeutic levels. The greater this ratio, the less likely a compound will be to cause weight gain. The ratios of clozapine and olanzapine are 0.01 and 0.3, respectively. Compounds of this invention preferably have $H_1/D_2$ ratios greater than or equal to 1 and more preferably $H_1/D_2$ ratios greater than or equal to 3.

The in vivo potency of a compound to occupy hypothalamic histamine $H_1$ receptors in the rat was determined using a histamine $H_1$ ex vivo binding assay. The $ED_{50}$ is the dose required to occupy 50% of the rat histamine $H_1$ receptors. The greater the $ED_{50}$ the less likely it will be that a compound will cause weight gain. The compounds of this invention preferably have histamine $H_1$ ex vivo binding $ED_{50}$ greater that or equal to 10 mg/kg,po and more preferably have $ED_{50}$'s greater that 30 mg/kg,po.

Histamine $H_1$ Ex Vivo Binding and DOPAC Concentrations

Methods

Male Sprague Dawley rats (Harlan Sprague Dawley, Inc., Indianapolis, Ind.) weighing 110 grams were fasted overnight. Animals were gavaged with clozapine (RBI, Inc.) or with the compound of interest and sacrificed 90 minutes later. Clozapine was administered at 5 ml/kg in 5% acacia suspension. All other compounds were administered at 5 ml/kg in dilute lactic acid. Tissues were dissected, frozen on dry ice and stored at −70° C. prior to analysis.

Histamine $H_1$ Ex Vivo Binding

Ex vivo binding of the histamine $H_1$ antagonist [$^3$H]-pyrilamine (NEN Life Science Products) to rat hypothalamic homogenates was determined. Tissues were homogenized in 600 μl incubation buffer (50 mM sodium phosphate monobasic, pH 7.4) and pre-incubated 10 minutes at 37° C. to remove endogenous histamine. Triplicate tubes, each containing 100 μl homogenate, were combined with 1 ml buffer containing 3 nM [$^3$H]-pyrilamine and incubated 30 minutes at 25° C. Non-specific tissue binding was also measured in duplicate in tubes containing 10 μM clozapine. [$^3$H]-pyrilamine binding was measured after separation filtration using a Brandell cell harvester with GF/C filters which had been soaked in 0.1% polyethylenimine. $ED_{50}$ values were determined using the Allfit statistical program for displacement binding.

DOPAC Concentrations

Rat nucleus accumbens DOPAC (3,4-dihydroxyphenylacetic acid) concentrations were measured using high-pressure liquid chromatography with electrochemical detection (HPLC-EC). Tissues were sonicated in 1 ml 0.1N TCA. After centrifugation, a 25 μl aliquot of supernatant was injected onto a BDS Hypersyl C18 column (150×4.6 mm, Keystone Scientific). The elution buffer contained 75 mM sodium phosphate monobasic, 0.5 mM EDTA, 350 mg/L 1-octanesulfonate sodium, 7% acetonitrile (v/v) and 0.7% tetrahydrofuran (v/v), pH 3.0. The flow rate was 1.2 ml/min at 40° C. Peak heights were measured at 750 mV at 10 nA sensitivity and compared with samples containing known amounts of DOPAC standards. Doses that increased DOPAC levels to 200% of control values ($ED_{200's}$) were calculated using a best-fit linear regression analysis.

TABLE 6

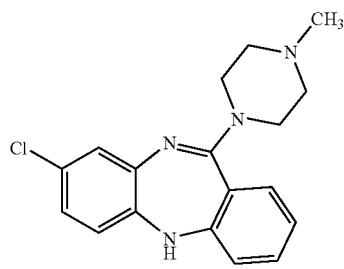

clozapine

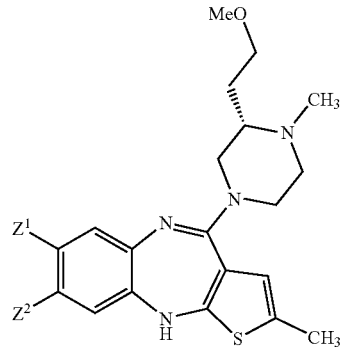

Example 279 $Z^1$ = H; $Z^2$ = F
Example 292 $Z^1$ = Cl; $Z^2$ = H
Example 288 $Z^1$ = F; $Z^2$ = F TABLE 6-continued

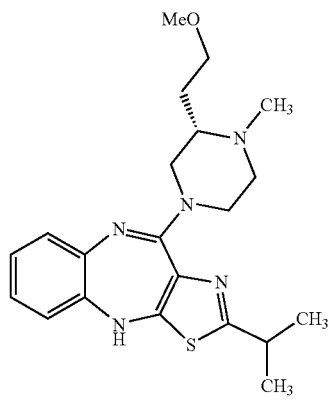

Example 327

| Assay | Clozapine | Example 279 | Example 292 | Example 288 | Example 327 |
|---|---|---|---|---|---|
| Receptor affinity (Ki, nM) | | | | | |
| $D_2$ | 194 | 6 | 13 | 11 | 9 |
| $H_1$ | 2.9 | 24 | 48 | 80 | 91 |
| In vivo activity (mg/kg, po) | | | | | |
| $D_2{}^1$ | 45.6 | 6 | 7.5 | 6.4 | 4 |
| $H_1{}^2$ | 10 | >30 | >30 | >30 | >30 |

[1]DOPAC elevation ($ED_{200}$);
[2]$H_1$ ex vivo binding ($ED_{50}$);

The compounds of formula (I) are useful for treating pathologic psychologic conditions, especially psychosis, with minimal detrimental adverse events. Pathologic psychological conditions which are psychosis or may be associated with psychotic features include, but are not limited to the psychotic disorders which have been characterized in the DSM-IV-TR., *Diagniostic and Statistical Manual of Mental Disorders. Revised*, 4th Ed., Text Revision (2000). See also DSM-IV, *Diagnostic and Statistical Manual of Mental Disorders* 4th Ed., (1994). The DSM-IV and DSM-IV-TR was prepared by the Task Force on Nomenclature and Statistics of the American Psychiatric Association, and provides descriptions of diagnostic categories. The skilled artisan will recognize that there are alternative nomenclatures, nosologies, and classification systems for pathologic psychological conditions and that these systems evolve with medical scientific progress. Examples of pathologic conditions associated with psychosis that may be treated with the compounds of the present invention include, but are not limited to, schizophrenia, schizophreniform disorder, schizoaffective disorder, delusional disorder, brief psychotic disorder, shared psychotic disorder, psychotic disorder due to a general medical condition, substance-induced psychotic disorder, schizotypical, schizoid, paranoid personality disorder, and psychotic disorder—not other specified, see DSM-IV, Section: Schizophrenia and Other Psychotic Disorders, pages 273 to 316.

Compounds of the present invention are useful in treating depression and mood disorders found in the DSM-IV, *Diagnostic and Statistical Manual of Mental Disorders* 4th Ed., (1994) Section: Mood Disorders, pages 317 to 392. Disorders include, but are not limited to, mood disorders such as major depressive episodes, manic episode, mixed episode, hypomanic episode; depressive disorders such as major depressive disorder, dysthymic disorder, depressive disorder not otherwise specificed; Bipolar disorders such as bipolar I disorder, bipolar II disorder, cyclothymic disorder, bipolar disorder not otherwise specified; other mood disorders such as mood disorder due to general medical conditions, substance-induced mood disorder, mood disorder not otherwise specified; and mood disorders with mild, moderate, severe without psychotic features, severe with psychotic features, in partial remission, in full remission, with catatonic features, with melancholic features, with atypical features, with postpartum onset.

One of oridinary skilled in the art would appreciate that the compounds of the present invention would be useful in the treatment of depressive episodes associated with bipolar disorders, treatment of manic episodes associated with bipolar disorders such as, but not limited to, the treatment of the acute manic episodes associated with bipolar I disorder.

Compounds of the present invention are useful in treating cognitive disorders, age-related cognitive disorder, mild cognitive impairment, postconcussional disorder, mild neurocognitive disorder, anxiety (particularly including generalized anxiety disorder, panic disorder, and obsessive compulsive disorder); and migraine (including migraine headache). These compounds are also useful in treating substance withdrawal (including substances such as opiates, nicotine, tobacco products, alcohol, benzodiazepines, cocaine, sedatives, hypnotics, caffeine, etc.). Other conditions that may be treated with the compounds of the present invention include, but are not limited to, dementia, dementia with behavioral disturbances, movement disorders, personality disorders, borderline personality disorder, pervasive development disoders, eating disorders, premenstrual dysphoric disorder, tic disorders, sexual dysfunction, delirium, emesis, substance related disorders, impulse-control disorders, postpsychotic depressive disorder of schizophrenia, simple deteriorative disorder (simple schizophrenia), minor depressive disorder, recurrent brief depressive disorder, and mixed anxiety-depresssive disorder Compounds of the present invention are also useful in treating the cognitive deficients associated with the above listed, but not limited to, psychological conditions such as schizophrenia, mood disorders, and other psychotic disorders.

An effective amount can be readily determined by the attending diagnostician, as one skilled in the art, by the use of known techniques and by observing results obtained under analogous circumstances. In determining the effective amount or dose, a number of factors are considered by the attending diagnostician, including, but not limited to: the species of mammal; its size, age, and general health; the specific disease or disorder involved; the degree of or involvement or the severity of the disease or disorder; the response of the individual patient; the particular compound administered; the mode of administration; the bioavailability characteristics of the preparation administered; the dose regimen selected; the use of concomitant medication; and other relevant circumstances.

The compounds of the present invention are effective over a wide dosage range, but the actual dose administered being dependent on the condition being treated. While the exact dose is administered according to the discretion of the attending health care professional, typically, in the treatment of adult humans, dosages of from 0.1 to 500 mg, preferably from 0.25 mg to 100 mg per day may be used. A once a day dosage is normally sufficient, although divided doses may be administered. For example, for the treatment of psychotic disorders a dose range of from 0.1 mg to 500 mg, preferably 0.25 mg to 100 mg, per day is suitable.

In choosing a suitable regimen for patients suffering from psychotic conditions, compositions containing compounds of formula (I) as an active ingredient may be formulated to provide quick, sustained or delayed release of the active ingredient after administration to the patient. Depending on the method of administration, compositions may be formulated as tablets, capsules, suspensions, or elixirs for oral use, or injection solutions or suppositories for parental use. Preferably the compositions are formulated in a unit dosage form, each dosage containing from 0.1 mg to 500 mg, more usually 0.25 mg to 100 mg, of the active ingredient.

A preferred formulation of the invention is a capsule or tablet comprising 0.1 to 500 mg of active ingredient together with a pharmaceutically acceptable carrier. A further preferred formulation is an injection which in unit dosage form comprises 0.1 mg to 500 mg of active ingredient together with a pharmaceutically acceptable diluent. A sustained release formulation is also a preferred formulation.

Pharmaceutical Formulations

While it is possible to administer a compound of formula (I) with no additional ingredients to a patient in need thereof, it is far more desirable to administer such a compound in the form of a pharmaceutical composition. Pharmaceutical compositions containing a compound of formula (I) as an active ingredient provides control of the dosage and rate of absorption into the body and stability of the product in shipment and storage. Further, pharmaceutical formulations are more acceptable to the patient being treated, and thus increase compliance with a treatment program. Such compositions, comprising at least one pharmaceutically acceptable carrier, are valuable and novel because of the presence of the compounds of formula (I) therein. Formulation of pharmaceutical compositions is an art unto itself, about which much has been published. The compounds of the present invention may be formulated into pharmaceutical compositions by essentially any suitable method of the art including, but not limited to, the methods discussed hereinbelow.

The usual methods of formulation used in pharmaceutical science and the usual types of compositions may be used, including tablets, chewable tablets, capsules, solutions, parenteral solutions, intranasal sprays or powders, troches, suppositories, transdermal patches and suspensions. In general, compositions contain from about 0.5% to about 50% by weight of the compound in total, depending on the desired dose and the type of composition to be used. The amount of the compound, however, is best defined as the effective amount, that is, the amount of each compound which provides the desired dose to the patient in need of such treatment. The compositions may be chosen and formulated for convenience and economy. Any compound may be formulated in any desired form of composition. Some discussion of different compositions will be provided, followed by some typical formulations.

Capsules are prepared by mixing the compound with a suitable diluent and filling the proper amount of the mixture in capsules. The usual diluents include inert powdered substances such as starch of many different kinds, powdered cellulose, especially crystalline and microcrystalline cellulose, sugars such as fructose, mannitol and sucrose, grain flours and similar edible powders.

Tablets are prepared by direct compression, by wet granulation, or by dry granulation. Their formulations usually incorporate diluents, binders, lubricants and disintegrators as well as the compound. Typical diluents include, for example, various types of starch, lactose, mannitol, kaolin, calcium phosphate or sulfate, inorganic salts such as sodium chloride and powdered sugar. Powdered cellulose derivatives are also useful. Typical tablet binders are substances such as starch, gelatin and sugars such as lactose, fructose, glucose and the like. Natural and synthetic gums are also convenient, including acacia, alginates, methylcellulose, polyvinylpyrrolidine and the like. Polyethylene glycol, ethylcellulose and waxes can also serve as binders.

A lubricant is necessary in a tablet formulation to prevent the tablet and punches from sticking in the die. The lubricant is chosen from such slippery solids as talc, magnesium and calcium stearate, stearic acid and hydrogenated vegetable oils.

Tablet disintegrators are substances which swell when wetted to break up the tablet and release the compound. They include starches, clays, celluloses, naphth and gyms. More particularly, corn and potato starches, methylcellulose, agar, bentonite, wood cellulose, powdered natural sponge, cation-exchange resins, alginic acid, guar gum, citrus pulp and carboxymethylcellulose, for example, may be used, as well as sodium lauryl sulfate.

Enteric formulations are often used to protect an active ingredient from the strongly acidic contents of the stomach. Such formulations are created by coating a solid dosage form with a film of a polymer which is insoluble in acidic environments, and soluble in basic environments. Exemplary films are cellulose acetate phthalate, polyvinyl acetate phthalate, hydroxypropyl methylcellulose phthalate and hydroxypropyl methylcellulose acetate succinate.

Tablets are often coated with sugar as a flavor and sealant, or with film-forming protecting agents to modify the dissolution properties of the tablet. The compounds may also be formulated as chewable tablets, by using large amounts of pleasant-tasting substances such as mannitol in the formulation, as is now well-established practice. Instantly dissolving tablet-like formulations are also now frequently used to assure that the patient consumes the dosage form, and to avoid the difficulty in swallowing solid objects that bothers some patients.

When it is desired to administer the combination as a suppository, the usual bases may be used. Cocoa butter is a traditional suppository base, which may be modified by addition of waxes to raise its melting point slightly. Water-miscible suppository bases comprising, particularly, polyethylene glycols of various molecular weights are in wide use, also.

Transdermal patches have become popular in recent years because of technological advances in matrix compositions. Typically they comprise a resinous matrix composition in which the drugs will dissolve, or partially dissolve, which is held in contact with the skin by a film which protects the composition. Many patents have appeared in the field recently. Other, more complicated patch compositions are also in use, particularly those having a membrane pierced with pores through which the drugs are pumped by osmotic action.

EXAMPLES

Example 1

2-Methyl-4,9-dihydro-3-thia-4,9-diazabenzo[f]azulene-10-one

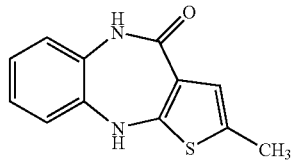

Combine 2-methyl-4H-3-thia-4,9-diazabenzo[f]azulene-10-ylamine hydrochloride (U.S. Pat. No. 5,229,382) (50 g, 0.19 mol) and solid potassium carbonate (182 g, 1.32 mol) in a mixture of water (1 L) and ethanol (450 mL) and heat at 85° C. for 48 h. Cool to room temperature, and place in ice bath for 2 h. The desired material precipitates out as a yellow solid. Collect solid by filtration, wash with cold water, air-dry for a few minutes and place in the vacuum oven at 45° C. for 48 h to obtain 41.9 g of the title compound, which can be used directly on the next step without further purification: mass spectrum (APCI): m/z=231.0 (M+1).

Example 2

2-Methyl-4,9-dihydro-3-thia-4,9-diazabenzo[f]azulene-10-thione

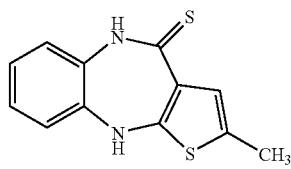

Combine 2-methyl-4,9-dihydro-3-thia-4,9-diazabenzo[f]azulene-10-one (21 g, 0.09 mol) and phosphorus pentasulfide (53 g, 0.12 mol) in pyridine (350 mL) and stir at room temperature overnight, heat at reflux for 5 h. Cool to room temperature to allow precipitate to settle, collect solid by filtration, wash cake with cold ethanol/water and air-dry for a few minutes to obtain 29 g of crude material. Take up solid in a small amount of pyridine, add a like volume of ethanol/water, sonicate for a few minutes and collect again by filtration. Air-dry cake, then place in the vacuum oven at 40° C. for 48 h to obtain 15.9 g of the title compound as an orange solid, which was used directly on the next step without further purification: melting point: 259.0-259.5° C.; Mass spectrum (APCI): m/z=247.0 (M+1).

Example 3

2-Methyl-4,9-dihydro-3-thia-6-fluoro-4,9-diazabenzo[f]azulene-10-thione

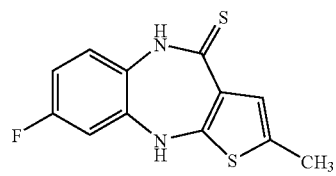

2-Methyl-4,9-dihydro-3-thia-6-fluoro-4,9-diazabenzo[f]azulene-10-one (1.2 g, 4.8 mmol) was suspended in dry toluene with Lawesson's reagent (1.1 g, 2.7 mmol) under nitrogen. The reaction mixture was heated under reflux for one hour and then left to cool overnight. The desired material precipitated and was collected by filtration, air-dried for several minutes to give 529 mg of yellow solid which can be used in the next step without further purification. Mass Spectrum (FIA) 265 (M+1); NMR ($^1$H, 300 MHz, CDCl$_3$): δ 6.98 (s, 1H), 6.75 (t, 1H), 6.6 (t, 1H), 6.43 (d, 1H), 3.29 (s, 1H), 2.21 (s, 3H).

Example 4

2-(5-Fluoro-2-nitro-phenylamino)-5-ethyl-thiophene-3-carbonitrile

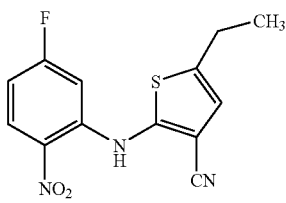

Dissolve 2-amino-5-ethyl-thiophene-3-carbonitrile (8.2 g, 54 mmol) and 2,4-difluoronitrobenzene (8.6 g, 54 mmol) in tetrahydrofuran (20 ml) and add to a stirring solution of sodium hydride (50% dispersion in mineral oil)(4.1 g, 1.4 equiv) in tetrahydrofuran (50 ml) under a nitrogen atmosphere. Maintain the rate of addition to keep the temperature below 45° C. and gas evolution under control. Stir 18 h. Pour the mixture into a mixture of ice and 2NHCl, extract into ethyl acetate, dry (MgSO$_4$) and concentrate under reduced pressure. Dissolve in ethanol (100 ml) and collect 2-(5-fluoro-2-nitro-phenylamino)-5-ethyl-thiophene-3-carbonitrile by filtration as a yellow solid (7.9 g, 50%): mass spectrum (LCMS) 292 (M+1), 314 (M+Na). NMR (1H, 300 MHz, CDCl$_3$): δ 9.7 (1H broad), 8.25 (1H,m), 6.80 (1H, s), 6.75 (1H,dd), 6.65 (1H, s), 2.80 (2H,q), 1.35(3H,t).

Example 5

6-Fluoro-2-ethyl-4H-3-thia-4,9-diaza-benzo[f]azulen-10-ylamine hydrochloride

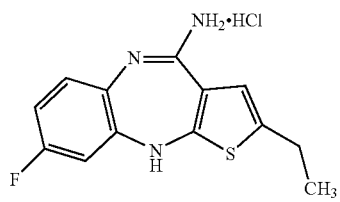

Suspend 2-(5-fluoro-2-nitro-phenylamino)-methyl-thiophene-3-carbonitrile (0.7.9 g, 27 mmol) in ethanol (70 ml), add anhydrous tin(II)chloride(15 g, 79 mmol) in concentrated hydrochloric acid (60 ml) and heat the mixture under reflux for 6 hours. Dilute the mixture with water and allow to cool. Collect the precipitate formed by filtration and dry under high vacuum to give 6-fluoro-2-ethyl-4H-3-thia-4,9-diaza-benzo[f]azulen-10-ylamine hydrochloride as a yellow solid (6.5 g, 82%): mass spectrum (FIA) 262 (M+1).

Example 6

2-(5-Chloro-2-nitro-phenylamino)-5'-methyl-thiophene-3-carbonitrile

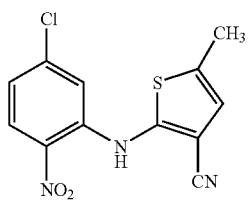

Dissolve 2-amino-5-methyl-thiophene-3-carbonitrile (0.79 g, 5.7 mmol) and 2-fluoro-4-chloronitrobenzene (1 g, 5.7 mmol) in dimethylsulfoxide (15 ml) and stir under nitrogen. Add lithium hydroxide monohydrate (250 mg, 6 mmol) and heat the mixture in an oil bath at 60° C. overnight. Pour the mixture into sat. NH$_4$Cl$_{(aq)}$, extract into ethyl acetate, dry (MgSO$_4$) and concentrate under reduced pressure. Chromatography on silica gel (eluent cyclohexane/ ethylacetate) gives 2-(5-chloro-2-nitro-phenylamino)-5-methyl-thiophene-3-carbonitrile as a yellow solid (0.58 g, 35%): NMR ($^1$H, 300 MHz, CDCl$_3$): δ 9.6 (1H broad), 8.21 (1H,d), 7.09 (1H, s), 6.92 (1H,d), 6.80 (1H, s), 2.49 (3H,s).

Example 7

6-Chloro-2-methyl-4H-3-thia-4,9-diaza-benzo[f]azulen-10-ylamine hydrochloride

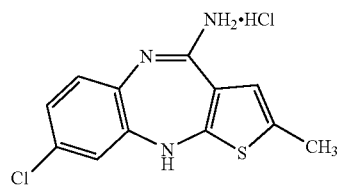

Suspend 2-(5-chloro-2-nitro-phenylamino)-5-methyl-thiophene-3-carbonitrile (0.58 g, 1.98 mmol) in ethanol (20 ml), add anhydrous tin(II)chloride(1.5 g, 6.66 mmol) in concentrated hydrochloric acid (6 ml) and heat the mixture under reflux for 75 minutes. Dilute the mixture with water and allow to cool. Collect the precipitate by filtration and dry under high vacuum to give 6-chloro-2-methyl-4H-3-thia-4, 9-diaza-benzo[f]azulen-10-ylamine hydrochloride as a yellow solid (0.537 g, 90%): Mass Spectrum (FIA) 300/302 (M+1).

Example 8

2-(4-Chloro-2-nitro-phenylamino)-5-methyl-thiophene-3-carbonitrile

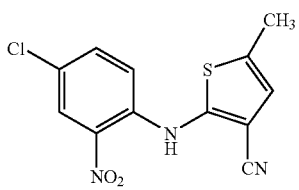

Dissolve 2-amino-5-methyl-thiophene-3-carbonitrile (4.14 g, 30 mmol) and 2,4-dichloronitrobenzene (5.76 g, 30 mmol) in dimethylsulfoxide (70 ml) and stir under nitrogen. Add lithium hydroxide monohydrate (2.0 g, 47.7 mmol) and heat the mixture in an oil bath at room temperature for 18 hours. Pour the mixture into ice water, make acid with 2N HCl, extract into ethyl acetate, dry (MgSO$_4$) and concentrate under reduced pressure. Crystallize from ethanol to give 2-(4-chloro-2-nitro-phenylamino)-5-methyl-thiophene-3-carbonitrile as a yellow solid (2.92 g, 33%): NMR ($^1$H, 300 MHz, CDCl$_3$): δ 9.5 (1H broad), 8.25 (1H,s), 7.45 (1H, d), 7.1 (1H,d), 6.25 (1H, s), 2.5 (3H,s).

Example 9

7-Chloro-2-methyl-4H-3-thia-4,9-diaza-benzo[f]azulen-10-ylamine hydrochloride

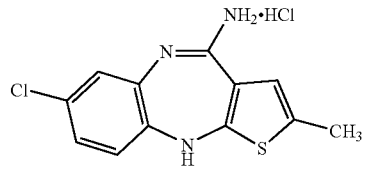

Suspend 2-(4-chloro-2-nitro-phenylamino)-5-methyl-thiophene-3-carbonitrile (2.92 g) in ethanol (40 ml), add anhydrous tin(II)chloride(5 g,) in 1:1 concentrated hydrochloric acid/water (32 ml) and heat the mixture under reflux for 2 hours. Dilute the mixture with water and allow to cool. Collect the precipitate formed by filtration and dry under high vacuum to give 7-chloro-2-methyl-4H-3-thia-4,9-diaza-benzo[f]azulen-10-ylamine hydrochloride as a yellow solid (3.3 g, 90%): mass Spectrum (FIA) 264/266 (M+1).

Example 10

4-Methyl-2-(2-nitro-phenylamino)-benzonitrile

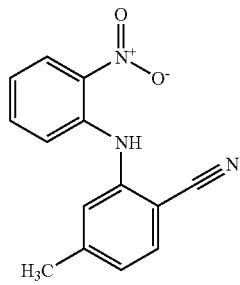

Combine 1-fluoro-2-nitro-benzene (5.34 g, 37.83 mmol), 2-amino-4-methyl-benzonitrile (5.00 g, 37.83 mmol), lithium hydroxide monohydrate (3.17 g, 75.66 mmol) and DMSO (70.0 ml) and stir at 55° C. Afer 16 hours; cool to ambient temperature, pour the mixture onto ice chips and stir. After 1 hour, remove the resulting yellow precipitate by vacuum filtration. Dry the precipitate under vacuum, recrystallize in ethanol to give 5.15 g (54%) of fine, amber colored needles: mp 162-164° C.; mass spectrum (ion spray): m/z 254.0 (M+1).

Example 11

5-Methyl-2-(2-nitro-phenylamino)-benzonitrile

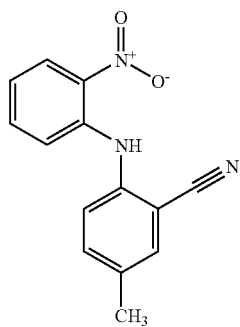

Combine 1-fluoro-2-nitro-benzene (4.34 g, 30.79 mmol), 2-amino-5-methyl-benzonitrile (4.07 g, 30.79 mmol), lithium hydroxide monohydrate (2.58 g, 61.58 mmol) and DMSO (50.0 ml). Stir the mixture at 55° C. for 22 hours, cool to ambient temperature and pour the mixture onto ice chips and stir. After 1 hour, remove the resulting precipitate by vacuum filtration. Dry the precipitate under vacuum, purify on silica gel using dichloromethane/hexanes (75:25) to give 4.45 g (57%) of an orange solid: mp 135-139° C.; mass spectrum (ion spray): m/z=254.0 (M+1).

Example 12

2-Amino-5-methyl-benzonitrile

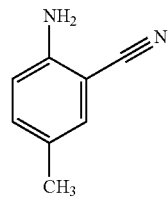

Combine 2-bromo-4-methyl-phenylamine (8.00 g, 43.0 mmol), CuCN (4.62 g, 51.6 mmol), and NMP (30.0 ml) and stir at reflux. After 75 minutes, cool to ambient temperature, pour the mixture onto ice chips and stir for 1 hour. Remove the resulting precipitate by vacuum filtration. Dissolve the precipitate in NH$_4$OH and extract with dichloromethane. Combine, wash (brine), dry (sodium sulfate), and reduce the extracts to residue. Purify the residue on silica gel using dichloromethane/hexanes (75:25) to give 3.39 g (60%) of an orange solid: mass spectrum (ion spray): m/z=133.1 (M+1).

Example 13

2-Methyl-5H-dibenzo[b,e][1,4]diazepin-11-ylamine hydrochloride

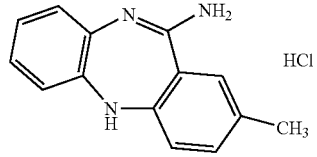

Combine 5-methyl-2-(2-nitro-phenylamino)-benzonitrile (4.03 g, 15.91 mmol), tin(II) chloride dihydrate (10.77 g, 47.74 mmol), 5N HCl (65 ml), and ethanol (40.0 ml) and stir the mixture at reflux. After 7 hours, cool to ambient temperature and chill in the refrigerator overnight. Remove the resulting precipitate by vacuum filtration and place the precipitate in ethanol (100.0 ml) and 5N HCl (20.0 ml) and heat at reflux for 19 hours. Cool the reaction mixture to ambient temperature and chill in the refrigerator. Filter off the resulting precipitate by vacuum filtration and dry it in a vacuum oven to give 2.59 g (63%) of an orange solid: mass spectrum (ion spray): m/z=224.0 (M+1).

Example 14

3-Methyl-5H-dibenzo[b,e][1,4]diazepin-11-ylamine hydrochloride

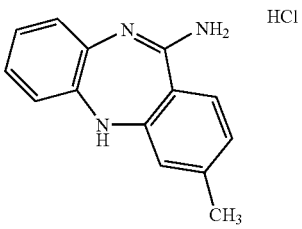

Combine 4-methyl-2-(2-nitro-phenylamino)-benzonitrile (2.46 g, 9.71 mmol), tin(II) chloride dihydrate (6.57 g, 29.71 mmol), 5N HCl (40 ml), and ethanol (40.0 ml). and stir the mixture at reflux. After 8 hours, cool to ambient temperature. Allow the mixture to stand at ambient temperature overnight and chill for an additional 3 hours in the refrigerator. Remove the resulting precipitate by vacuum filtration and dry it under vacuum to give 1.24 g (49%) of the desired compound as a yellow solid: mass spectrum (ion spray): m/z=224.0 (M+1).

Example 15

2-Amino-5-isopropyl-benzonitrile

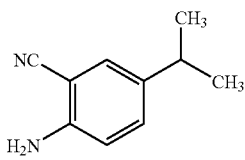

Combine 2-bromo-4-isopropyl aniline (7.5 g, 35 mmol) and copper (I) cyanide (3.76 g, 42 mmol) in NMP (30.0 mL) and heat at 200° C. for 2 hours. Cool to ambient temperature and dilute with water (300 mL). Extract with ethyl acetate to give 4.58 g of the crude product. Silica gel chromatography, eluting with methylene chloride, gives 3.20 g of the title compound as a red oil: mass spectrum (ion spray): m/z=161 (M+1); $^1$H NMR (300 MHz, DMSO-$d_6$): δ 7.21 (m, 2H), 6.73 (d, 1H), 5.79 (s, 2H), 2.73 (quintet, 1H), 1.12 (d, 6H).

Example 16

5-Isopropyl-2-(2-nitro-phenylamino)-benzonitrile

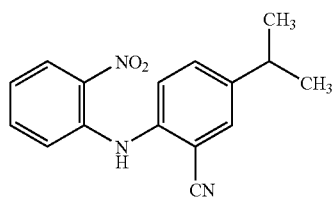

Combine 2-amino-5-isopropyl-benzonitrile (3.19 g, 20 mmol), 1-fluoro-2-nitro benzene (2.1 mL, 20 mmol) and lithium hydroxide (1.68 g, 40 mmol) in DMSO (40.0 mL) and heat at 55° C. for 19 hours. Cool to ambient temperature and dilute with water (200 mL). The title compound precipitates as 4.56 g of an orange solid: mp 91-96° C.; mass spectrum (ion spray): m/z=280 (M+1).

Example 17

2-Isopropyl-5H-dibenzo[b,e][1,4]diazepin-11-ylamine hydrochloride

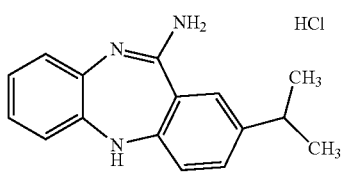

Combine 5-isopropyl-2-(2-nitro-phenylamino)-benzonitrile (4.54 g, 16.1 mmol) and tin (II) chloride (10.92 g, 48.4 mmol) in 65.0 mL of 5N HCl solution and 65.0 mL of ethanol. Heat this mixture at 86° C. for 18 hours. Chilling the mixture precipitates the title compound as 4.22 g of a yellow solid: mp>250° C.; mass spectrum (ion spray): m/z=252 (M+1).

Example 18

2-(2-Nitro-phenylamino)-5-trifluoromethyl-benzonitrile

Add cesium carbonate (1.3 g, 4 mmol) to a solution of 2-nitro-aniline (276 mg, 2 mmol) and 2-fluoro-5-trifluoromethyl-benzonitrile (378 mg, 2 mmol) in DMF (10 mL) at room temperature then stir the resulting dark red solution at room temperature for 16 hours and 2 hours at 50° C. Cool down and pour into a mixture of ice and concentrated hydrochloric acid (50 mL, v/v). Extract the aqueous phase with dichloromethane (3×300 mL), wash with water and brine and dry over $MgSO_4$ to yield the title compound as a yellow solid (480 mg, 80%): mp 160-161° C.; $^1$H NMR ($CDCl_3$) δ 7.14 (ddd, 1H), 7.48 (dd, 1H), 7.58 (dd, 1H), 7.60 (d, 1H), 7.76 (dd, 1H), 7.92 (d, 1H), 8.27 (dd, 1H), 9.63 (bs, 1H). MS (ESI/neg) m/z (rel intensity) 306.1 (100).

Example 19

2-Trifluoromethyl-5H-dibenzo[b,e][1,4]diazepin-11-ylamine hydrochloride

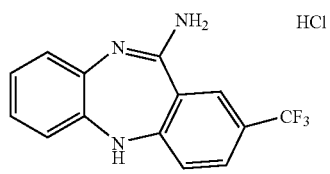

Add a solution of tin(II) chloride (567 mg, 3 mmol) in 12 N hydrochloric acid (1.8 mL) to a solution of 2-(2-nitro-phenylamino)-5-trifluoromethyl-benzonitrile (307 mg, 1 mmol) in ethanol (10 mL). Reflux for 24 hours, then concentrate under vacuum, add water and filter. Wash the resulting solid with water and dichloromethane then dry under vaccum to yield the title compound as a yellow solid (282 mg, 90%): mp 334-336° C.; $^1$H NMR (DMSO-$d_6$) δ 7.05-7.19 (m, 4H), 7.34 (d, 1H), 7.86 (dd, 1H), 7.87 (s, 1H), 8.79 (s, 1H), 9.26 (s, 1H), 9.75 (s, 1H), 12.40 (s, 1H). MS (ESI/neg) m/z (rel intensity) 276.1 (100).

Example 20

2-(4-Fluoro-2-nitro-phenylamino)-5-methyl-benzonitrile

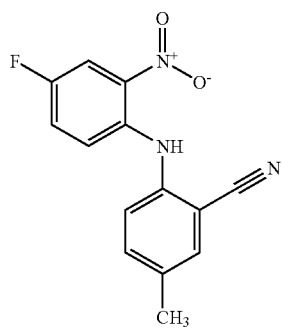

Combine 4-fluoro-2-nitro-phenylamine (2.9 g, 18.50 mmol), 2-fluoro-5-methyl-benzonitrile (2.5 g, 18.50 mmol) and lithium hydroxide monohydrate (2.4 g, 57.20 mmol) in methyl sulfoxide (DMSO, 40 ml). Heat the resulting mixture to 55° C. for 40 hours. Cool the reaction mixture to ambient temperature, then pour into approximately 250 ml of ice water and stir for one hour. Filter the resulting mixture and collect the precipitate. Chromatograph the solid using flash chromatography and elute with mobile phase: 90% hexanes, 5% ethyl acetate, and 5% dichloromethane to obtain 2.267 g of the title compound (8.36 mmol, 45% yield) as an orange amorphous solid: Mass Spectrum (m/e): 272(M+1).

Example 21

8-Fluoro-2-methyl-5H-dibenzo[b,e][1,4]diazepin-11-ylamine hydrochloride

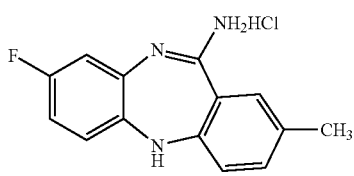

Heat a solution of 2-(4-fluoro-2-nitro-phenylamino)-5-methyl-benzonitrile (1.747 g, 6.44 mmol) in ethanol (35 ml) to 60° C. Add a solution of tin (II) chloride (6.06 g, 31.96 mmol) in 5.0 N hydrochloric acid (35 ml) and heat the resulting mixture to reflux for 40 hours. Cool the reaction to room temperature and place in a freezer for 16 hours. Collect by filtration the product precipitates from the solution to obtain 1.3 g of the title compound (4.68 mmol, 73% yield) as a yellow-green amorphous solid: Mass Spectrum (m/e): 241(M+1).

Example 22

2-Amino-5-isopropyl-benzonitrile

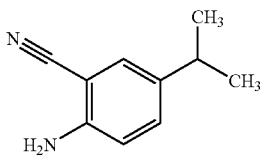

Heat a mixture of copper (I) cyanide (2.5 g, 28.02 mmol), and 2-bromo-4-isopropyl-phenylamine (5.0 g, 23.35 mmol) in 1-methyl-2-pyrrolidinone (20 ml) to 195° C. for four hours. Dilute the reaction mixture with 100 ml of ethyl acetate and the dark solution, wash twice with 28% aqueous ammonium hydroxide, twice with saturated aqueous sodium chloride (brine) and twice with water. Collect the organic layer, dry over sodium sulfate and remove the solvent under reduced pressure. Purify the via flash chromatography eluting with a step gradient starting with hexanes and going to 80% hexanes with 20% ethyl acetate to obtain 3.31 g (20.66 mmol, 88% yield) of the title compound as an orange oil: Mass Spectrum (m/e): 161(M+1).

Example 23

2-(4-Fluoro-2-nitro-phenylamino)-5-isopropyl-benzonitrile

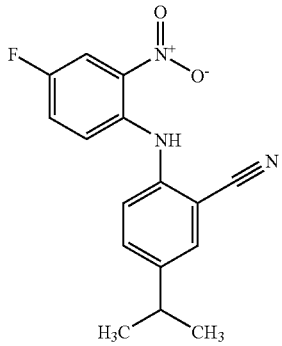

Heat a solution of 2-amino-5-isopropyl-benzonitrile (1.482 g, 9.25 mmol) with 1,4-difluoro-2-nitro-benzene (1.47 g, 9.25 mmol) and lithium hydroxide monohydrate (0.78 g, 18.50 mmol) in DMSO (20 ml) to 70° C. for 38 hours. Cool the reaction to ambient temperature and pour into approximately 200 ml of ice water and stir for one hour. Collect by filtration the title compound which precipitates. No further purification is necessary to obtain 2.236 g (7.47 mmol, 81% yield) of the title compound as an orange amorphous solid: Mass Spectrum (m/e): 300(M+1).

Example 24

8-Fluoro-2-isopropyl-5H-dibenzo[b,e][1,4]diazepin-11-ylamine hydrochloride

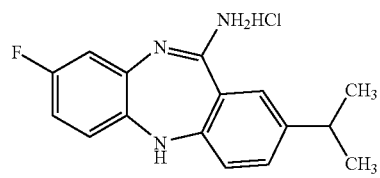

Using a similar procedure as found for 8-fluoro-2-methyl-5H-dibenzo[b,e][1,4]diazepin-11-ylamine hydrochloride, using 2-(4-fluoro-2-nitro-phenylamino)-5-isopropyl-benzonitrile (0.559 g, 1.87 mmol), tin (II) chloride(1.06 g, 5.60 mmol) to obtain the title compound (0.422 g, 1.38 mmol, 74% yield) as a yellow amorphous solid: Mass Spectrum (m/e): 270(M+1).

Example 25

2-(4-Fluoro-2-nitro-phenylamino)-5-trifluoromethyl-benzonitrile

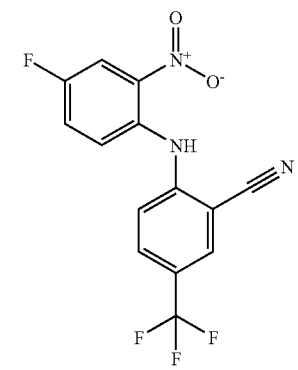

Combine 4-fluoro-2-nitro-phenylamine (5.0 g, 32.03 mmol), 2-fluoro-5-trifluoromethyl-benzonitrile (6.07 g, 32.03 mmol) and lithium hydroxide monohydrate (4.03 g, 96.08 mmol) in methyl sulfoxide (DMSO, 60 ml). Heat the resulting mixture to 70° C. for 16 hours. Cool the reaction mixture to ambient temperature, then pour into approximately 400 ml of ice water and stir for one hour. Filter the resulting mixture and collect the precipitate to obtain 9.995 g of the title compound (30.73 mmol, 96% yield) as an orange amorphous solid. Product used as is with no further purification: Mass Spectrum (m/e): 326(M+1).

Example 26

8-Fluoro-2-trifluoromethyl-5H-dibenzo[b,e][1,4]diazepin-11-ylamine hydrochloride

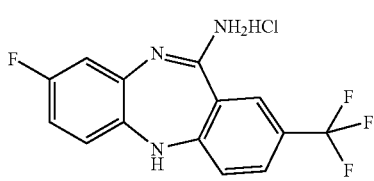

Heat a solution of 2-(4-fluoro-2-nitro-phenylamino)-5-trifluoromethyl-benzonitrile (9.995 g, 30.73 mmol) in ethanol (170 ml) to 60° C. Add to this a solution of tin (II) chloride (29.1 g, 153.67 mmol) in 5.0 N hydrochloric acid (170 ml). Heat the resulting mixture to reflux for 18 hours. Cool the reaction to room temperature and place in a freezer for 24 hours. Precipitate the product from the solution and collect by filtration to btain 2.253 g of the title compound (6.79 mmol, 22% yield) as a yellow amorphous solid: Mass Spectrum (m/e): 296(M+1).

Example 27

2-Amino-5-trifluoromethyl-benzonitrile

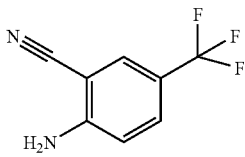

Heat a mixture of copper (I) cyanide (2.24 g, 25.00 mmol) and 2-bromo-4-trifluoromethyl-phenylamine (5.0 g, 20.83 mmol from Avocado) in 1-methyl-2-pyrrolidinone (20 ml) to 195° C. for four hours. Dilute the reaction mixture with 100 ml of ethyl acetate and wash the dark solution twice with 28% aqueous ammonium hydroxide, twice with saturated aqueous sodium chloride (brine) and twice with water. Collect the organic layer, dry over sodium sulfate and remove the solvent under reduced pressure. Purify the residue via flash chromatography eluting with a step gradient starting with hexanes and going to 70% hexanes with 30% ethyl acetate to obtain 1.821 g (9.78 mmol, 47% yield) the title compound as a green amorphous solid: Mass Spectrum (m/e): 187(M+1).

Example 28

2-(5-Fluoro-2-nitro-phenylamino)-5-trifluoromethyl-benzonitrile

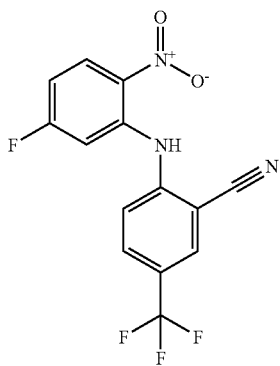

Combine 2,4-difluoro-1-nitro-benzene (5.36 g, 33.69 mmol), 2-amino-5-trifluoromethyl-benzonitrile (5.701 g, 30.63 mmol) and lithium hydroxide monohydrate (2.57 g, 61.25 mmol) in methyl sulfoxide (DMSO, 70 ml). Heat the resulting mixture to 55° C. for 16 hours. Cool the reaction mixture to ambient temperature, then pour into approximately 250 ml of ice water and stir for one hour. Filter the resulting mixture, wash with a large amount of water and collect the precipitate to obtain 9.53 g of the title compound (29.30 mmol, 96% yield) as a yellow amorphous solid: Mass Spectrum (m/e): 324(M−1).

Example 29

7-Fluoro-2-trifluoromethyl-5H-dibenzo[b,e][1,4]diazepin-11-ylamine hydrochloride

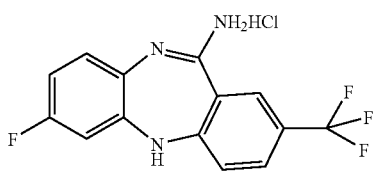

Heat a solution of 2-(5-fluoro-2-nitro-phenylamino)-5-trifluoromethyl-benzonitrile (1.62 g, 4.98 mmol) in ethanol (24 ml) to 60° C. Add to this a solution of tin (II) chloride (2.83 g, 14.94 mmol) in 5.0 N hydrochloric acid (24 ml). Heat the resulting mixture to reflux for 20 hours. Cool the reaction to room temperature, add 30 ml of 5.0 N hydrochloric acid and place the mixture in a freezer for 16 hours. The product precipitates from the solution and is collected by filtration. Wash solid with 5.0 N hydrochloric acid to obtain 1.44 g of the title compound (4.34 mmol, 87% yield) as a yellow amorphous solid: Mass Spectrum (m/e): 295 (M+1).

Example 30

2-(5-Fluoro-2-nitro-phenylamino)-5-isopropyl-benzonitrile

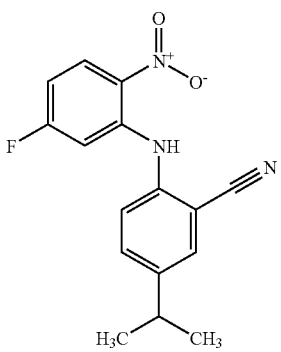

Heat a solution of 2-amino-5-isopropyl-benzonitrile (1.21 g, 7.55 mmol) with 2,4-difluoro-1-nitro-benzene (1.20 g, 7.55 mmol) and lithium hydroxide (0.54 g, 22.66 mmol) in DMSO (15 ml) to 70° C. for 18 hours. Cool the reaction to ambient temperature and then pour into approximately 200 ml of ice water and stir for one hour. The title compound precipitates and is colleted by filtration. Purify the solid via flash chromatography eluting with a 95% hexanes: 5% ethyl acetate mobile phase to obtain 0.372 g (1.24 mmol, 16% yield) of the title compound as an orange amorphous solid: Mass Spectrum (m/e): 298 (M−1).

Example 31

7-Fluoro-2-isopropyl-5H-dibenzo[b,e][1,4]diazepin-11-ylamine hydrochloride

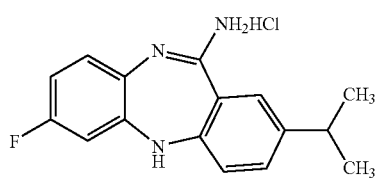

Heat a solution of 2-(5-fluoro-2-nitro-phenylamino)-5-isopropyl-benzonitrile (0.372 g, 1.24 mmol) in ethanol (6 ml) to 60° C. Add a solution of tin (II) chloride (0.707 g, 3.73 mmol) in 5.0 N hydrochloric acid (6 ml) and heat the resulting mixture to reflux for 16 hours. Cool the reaction to room temperature, add 30 ml of 5.0 N hydrochloric acid and place the mixture in a freezer for 16 hours. Precipitate the product from the solution and collect by filtration. Wash solid with 5.0 N hydrochloric acid to obtain 0.365 g of the title compound (1.19 mmol, 96% yield) as a yellow amorphous solid: Mass Spectrum (m/e): 270(M+1).

Example 32

2-Amino-5-cyclopropyl-benzonitrile

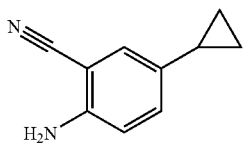

Combine 2-amino-5-bromo-benzonitrile (1.76 g, 8.95 mmol), cyclopropyl boronic acid (1.0 g, 11.64 mmol), tricyclohexylphosphine (0.251 g, 0.89 mmol) and potassium phosphate (6.65 g, 31.26 mmol) in a mixture of toluene (40 ml) and water (2 ml) and stir the mixture for 10 minutes. Add palladium acetate (0.101 g, 0.45 mmol) and heat the mixture to 100° C. After 3 hours add more tricyclohexylphosphine (0.251 g, 0.89 mmol) and palladium acetate (0.101 g, 0.45 mmol). After an additional 3 hours at 100° C., add 20 ml of water and extract the mixture three times with 50 ml of ethyl acetate. Combine the organic layers, dry over sodium sulfate and concentrate. Purify the residue using flash chromatography and eluting with a linear gradient starting with 100% hexanes and going to 70% hexanes: 30% ethyl acetate to obtain 0.988 g of the title compound (6.24 mmol, 70% yield) as a clear yellow oil: Mass spectrum (m/e): 159(M+1).

Example 33

5-Cyclopropyl-2-(5-fluoro-2-nitro-phenylamino)-benzonitrile

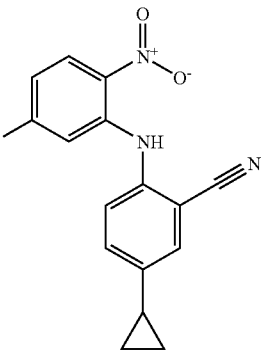

Heat a solution of 2-amino-5-cyclopropyl-benzonitrile (0.980 g, 6.16 mmol) with 2,4-difluoro-1-nitro-benzene (0.676 g, 6.16 mmol) and lithium hydroxide monohydrate (0.517 g, 12.33 mmol) in DMSO (12 ml) to 55° C. for 18 hours. Cool the reaction to ambient temperature and then add approximately 150 ml of ice water and stir the mixture for one hour. Precipitate the title compound and collect by filtration. Purify the solid via flash chromatography eluting with a linear gradient starting with 100% hexanes and going to 70% hexanes: 30% ethyl acetate to obtain 0.452 g (1.52 mmol, 25% yield) of the title compound as a yellow amorphous solid: Mass Spectrum (m/e): 298 (M+1).

Example 34

2-Cyclopropyl-7-fluoro-5H-dibenzo[b,e][1,4]diazepin-11-ylamine hydrochloride

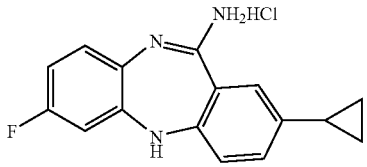

Heat a solution of 5-cyclopropyl-2-(5-fluoro-2-nitro-phenylamino)-benzonitrile (0.447 g, 1.50 mmol) in ethanol (7 ml) to 60° C. Add a solution of tin (II) chloride (0.855 g, 4.51 mmol) in 5.0 N hydrochloric acid (7 ml) and heat the resulting mixture to reflux for 16 hours. Cool the reaction to room temperature, add 25 ml of 5.0 N hydrochloric acid and place the mixture in a freezer for 16 hours. Collect by filtration the precipitated product from the solution. Wash solid with 5.0 N hydrochloric acid to obtain 0.277 g of the title compound (0.91 mmol, 61% yield) as a yellow amorphous solid: Mass Spectrum (m/e): 268(M+1).

Example 35

2-(4,5-Difluoro-2-nitro-phenylamino)-5-trifluoromethyl-benzonitrile

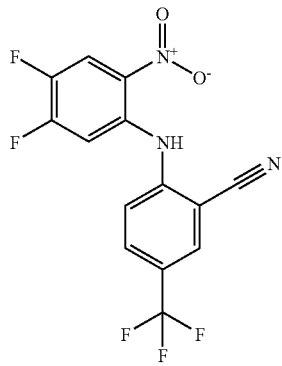

Heat a solution of 2-fluoro-5-trifluoromethyl-benzonitrile (1.0 g, 5.74 mmol) with 4,5-difluoro-2-nitro-phenylamine (1.09 g, 5.74 mmol) and lithium hydroxide monohydrate (0.48 g, 11.49 mmol) in DMSO (12 ml) to 55° C. for 16 hours. Cool the reaction to ambient temperature and then add approximately 150 ml of ice water and stir the mixture for one hour. Extract with three 200 ml portions of dichloromethane. Combine organic layers, dry over sodium sulfate and evaporate solvent. Purify the residue via flash chromatography eluting with a linear gradient starting with 100% hexanes and going to 70% hexanes: 30% ethyl acetate to obtain 0.995 g (2.90 mmol, 50% yield) of the title compound as a yellow amorphous solid: Mass Spectrum (m/e): 344 (M+1).

Example 36

7,8-Difluoro-2-trifluoromethyl-5H-dibenzo[b,e][1,4]diazepin-11-ylamine hydrochloride

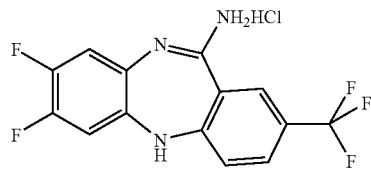

Heat a solution of 2-(4,5-difluoro-2-nitro-phenylamino)-5-trifluoromethyl-benzonitrile (0.995 g, 2.90 mmol) in ethanol (15 ml) to 60° C. Add to this a solution of tin (II) chloride (1.65 g, 8.70 mmol) in 5.0 N hydrochloric acid (15 ml). Heat the resulting mixture to reflux for 18 hours. Cool the reaction to room temperature, add 30 ml of 5.0 N hydrochloric acid and place the mixture in a freezer for 16 hours. Collect by filtration the precipitated product from the solution. Wash solid with 5.0 N hydrochloric acid to obtain 0.648 g of the title compound (1.85 mmol, 64% yield) as a yellow amorphous solid: Mass Spectrum (m/e): 314(M+1).

Example 37

2-(4-Chloro-2-nitro-phenylamino)-5-methyl-benzonitrile

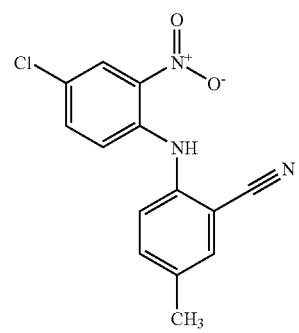

Heat a solution of 2-fluoro-5-methyl-benzonitrile (2.0 g, 14.80 mmol) with 4-chloro-2-nitro-phenylamine (2.5 g, 14.80 mmol) and lithium hydroxide monohydrate (1.24 g, 29.60 mmol) in DMSO (30 ml) to 55° C. for 14 hours. Add an additional 0.61 g (14.80 mmol) of lithium hydroxide monohydrate, and increase heating to 70° C., continue for another 14 hours. Cool the reaction to ambient temperature and pour into a mixture of 100 ml water and 200 ml ethyl acetate. Extract with three 200 ml portions of ethyl acetate. Combine organic layers, dry over sodium sulfate and evaporate solvent. Purify the residue via flash chromatography eluting with a step gradient starting with 90% hexanes: 10% ethyl acetate and going to 40% hexanes: 60% ethyl acetate to obtain 1.63 g (5.67 mmol, 38% yield) of the title compound as a red-orange amorphous solid: Mass Spectrum (m/e): 288 (M+1).

Example 38

8-Chloro-2-methyl-5H-dibenzo[b,e][1,4]diazepin-11-ylamine hydrochloride

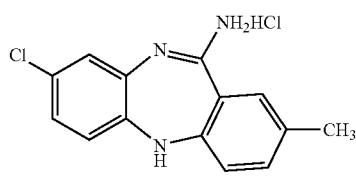

Heat a solution of 2-(4-chloro-2-nitro-phenylamino)-5-methyl-benzonitrile (1.63 g, 6.44 mmol) in ethanol (25 ml) to 60° C. To this add a solution of tin (II) chloride (3.22 g, 17.00 mmol) in 5.0 N hydrochloric acid (25 ml). Heat the resulting mixture to reflux for 16 hours. Cool the reaction to room temperature and place in a freezer for 16 hours. Collect by filtration the precipitated product from the solution and to obtain 1.325 g of the title compound (4.50 mmol, 80% yield) as a yellow amorphous solid: Mass Spectrum (m/e): 258 (M+1).

Example 39

2-(4-Chloro-2-nitro-phenylamino)-5-isopropyl-benzonitrile

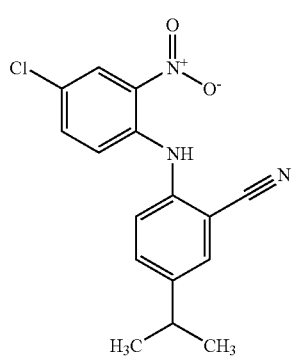

Combine 1,4-dichloro-2-nitro-benzene (0.513 g, 2.67 mmol), 2-amino-5-isopropyl-benzonitrile (0.514 g, 3.21 mmol), potassium carbonate (0.754 g, 5.45 mmol), and fine granular copper (0.031 g, 0.48 mmol) in dimethylformamide (5 ml). Heat the reaction mixture to 160° C. for 16 hours, and cool to ambient temperature. Dilute the reaction mixture with 50 ml of ethyl acetate and wash 3 times with 50 ml water and once with 50 ml of brine. Collect organic layer, dry over sodium sulfate and evaporate solvent. Purify the residue via flash chromatography eluting with a step gradient starting with 90% hexanes: 10% ethyl acetate and going to 85% hexanes: 15% ethyl acetate to obtain 0.316 g (1.00 mmol, 37% yield) of the title compound as an orange amorphous solid: Mass Spectrum (m/e): 316 (M+1).

Example 40

8-Chloro-2-isopropyl-5H-dibenzo[b,e][1,4]diazepin-11-ylamine hydrochloride

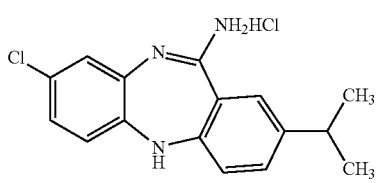

Heat a solution of 2-(4-chloro-2-nitro-phenylamino)-5-isopropyl-benzonitrile (0.313 g, 0.99 mmol) in ethanol (6 ml) to 60° C. To this is add a solution of tin (II) chloride (0.752 g, 3.96 mmol) in 5.0 N hydrochloric acid (6 ml) and heat the resulting mixture to reflux for 16 hours. Cool the reaction to room temperature and place in a freezer for 16 hours. Collect by filtration the precipitated product s from the solution and to obtain 0.316 g of the title compound (0.98 mmol, 99% yield) as a yellow amorphous solid: Mass Spectrum (m/e): 286(M+1).

Example 41

2-(4-Chloro-2-nitro-phenylamino)-5-trifluoromethyl-benzonitrile

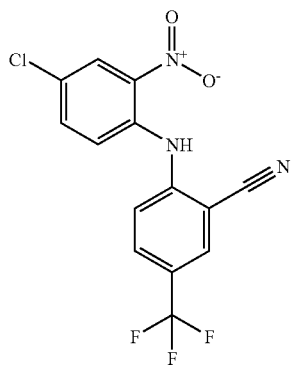

Using a method similar to Example 39, using 4-chloro-2-nitro-phenylamine (6.4 g, 37.3 mmol), 2-fluoro-5-trifluoromethyl-benzonitrile (7.05 g, 37.3 mmol) to obtain 12.03 g of the title compound (95% yield) as an amorphous yellow solid. Product can be used as is with no further purification: Mass Spectrum (m/e): 342(M+1).

Example 42

8-Chloro-2-trifluoromethyl-5H-dibenzo[b,e][1,4]diazepin-11-ylamine hydrochloride

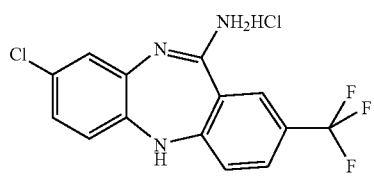

Using a method similar to Example 40 using 2-(4-chloro-2-nitro-phenylamino)-5-trifluoromethyl-benzonitrile (12.03 g, 35.2 mmol) to obtain 8.4 g of the title compound (68% yield) as an amorphous yellow solid: Mass Spectrum (m/e): 313(M+1).

Example 43

2-(5-Fluoro-2-nitro-phenylamino)-5-methyl-thiophene-3-carbonitrile

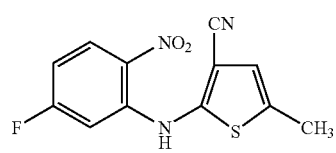

Add 2-amino-5-methyl-thiophene-3-carbonitrile (10.0 g, 72.4 mmol) and 2,4-difluoro-1-nitro-benzene (8.00 mL, 73.0 mmol) to DMSO (130 mL) and stir under nitrogen at ambient temperature. Add lithium hydroxide monohydrate (6.10 g, 145 mmol) in one portion and stir at ambient temperature. After 18 hours, add deionized water (390 mL) dropwise at 10-20° C. Adjust the pH to 7-8 with concentrated HCl (~6 mL) and stir for 4 hours. Filter the crude product and rinse with 3:1/water: DMSO, then water. Dry at 50° C. to constant weight. Purify by flash chromatography, eluting with methylene chloride to give the title compound 10.3 g (62%): $^1$H NMR (400 MHz, DMSO-$d_6$) δ 9.83 (bs, 1H), 8.28 (m, 1H), 7.12 (s, 1H), 6.91 (m, 1H), 6.73 (m, 1H), 2.53 (s, 3H). HRMS (ES) exact mass M+H calcd for $C_{12}H_8FN_3O_2S$ 300.0219; found 300.0219.

Example 44

6-Fluoro-2-methyl-4H-3-thia-4,9-diaza-benzo[f]azulen-10-ylamine hydrochloride

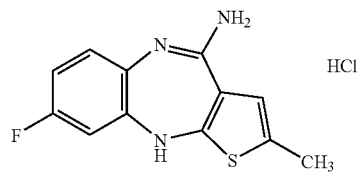

Stir 2-(5-fluoro-2-nitro-phenylamino)-5-methyl-thiophene-3-carbonitrile (113 g, 0.408 mol) as a suspension in EtOH (1.1 L) at ambient temperature. Add aqueous 6N HCl (1.1 L) and tin (II) chloride (232 g, 1.22 mol) with stirring. Heat to gentle reflux (85° C.) for 3-4 hours, and then allow cooling to ambient temperature. Filter the crude product and rinse with 1:1/EtOH:6N HCl, then deionized water, and dry in a vacuum oven at 50° C. to constant weight. Stir the crude product (139 g) as a suspension in aqueous 1N HCl (6 L) at gentle reflux (95° C.) for 2 hours, and then allow cooling to ambient temperature. Filter the product and rinse with 1N HCl and water, then dry at 50° C. to give 101 g (87%) the title compound: $^1$H NMR (400 MHz, DMSO-$d_6$) δ 11.33 (bs, 1H), 9.80 (s, 1H), 9.16 (bs, 1H), 8.88 (bs, 1H), 6.99 (m, 1H), 6.89 (m, 1H), 6.84 (s, 1H), 2.28 (s, 3H). HRMS (ES) exact mass M+H calcd for $C_{12}H_{11}ClFN_3S$ 248.0658; found 248.0657.

Example 45

6-Fluoro-2-methyl-4,9-dihydro-3-thia-4,9-diaza-benzo[f]azulen-10-one

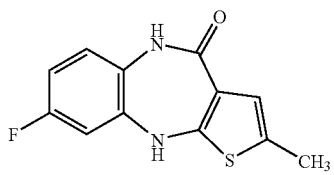

Stir 6-fluoro-2-methyl-4H-3-thia-4,9-diaza-benzo[f]azulen-10-ylamine hydrochloride (82.5 g, 0.291 mol) as a suspension in deionized water (2475 mL) at ambient temperature. Add EtOH (830 mL) and stir for 15 minutes. Add potassium carbonate (301 g, 2.18 mol) with stirring and heat to gentle reflux (80-85° C.) for 3-4 days. Allow cooling to ambient temperature. Filter the product and rinse with 3:1/water:EtOH, then water. Dry the solid at 50-60° C. to give 55.2 g (76%) the title compound: $^1$H NMR (400 MHz, DMSO-$d_6$) δ 9.18 (bs, 1H), 9.00 (bs, 1H), 6.90 (m, 1H), 6.73 (m, 1H), 6.60 (m, 2H), 2.24 (s, 3H). HRMS (ES) exact mass M+H calcd for $C_{12}H_9FN_2OS$ 249.0498; found 249.0488.

Example 46

6-Fluoro-2-methyl-4,9-dihydro-3-thia-4,9-diaza-benzo[f]azulene-10-thione

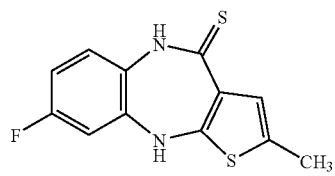

Add 6-fluoro-2-methyl-4,9-dihydro-3-thia-4,9-diaza-benzo[f]azulen-10-one (65.2 g, 0.263 mol) and 2,4-Bis-(4-methoxy-phenyl)-[1,3,2,4]dithiadiphosphetane 2,4-disulfide (Lawesson's Reagent, 63.7 g, 0.157 mol) to 1,2-dichloroethane (DCE, 3500 mL) with stirring. Heat to gentle reflux (80-83° C.) for 30 minutes, and then allow cooling to ambient temperature. Filter the product and rinse with DCE. Dry at 50-60° C. to give 61.9 (89%) the title compound: $^1$H NMR (400 MHz, DMSO-$d_6$) δ 10.98 (bs, 1H), 8.87 (bs, 1H), 7.00 (m, 1H), 6.88 (s, 1H), 6.78(m, 1H), 6.56 (m, 1H), 2.22 (s, 3H). HRMS (ES) exact mass M+H calcd for $C_{12}H_9FN_2S_2$ 265.0269; found 265.0276.

Example 47

6-Fluoro-2-methyl-10-methylsulfanyl-4H-3-thia-4,9-diaza-benzo[f]azulene

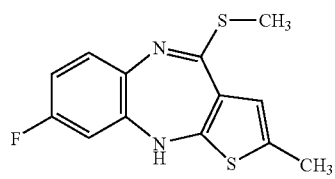

Stir 6-fluoro-2-methyl-4,9-dihydro-3-thia-4,9-diaza-benzo[f]azulene-10-thione (61.5 g, 0.233 mol) and DMF (310 mL) under nitrogen for 15 minutes at ambient temperature. Add powdered potassium carbonate (67.7 g, 0.490 mol); stir 15 minutes at ambient temperature. Add iodomethane (22 mL, 0.35 mol); stir 4 hours at ambient temperature. Cool to 0-5° C. and add deionized water (150 mL) dropwise, keeping the temperature below 15° C. Extract the product with ethyl acetate. Wash the organic solution with brine four times, then dry over magnesium sulfate, filter and concentrate under reduced pressure to give 74.0 g of crude product. Purify by flash chromatography, eluting with 2:1/methylene chloride:heptane, then methylene chloride to give 55.0 g (85%) the title compound: $^1$H NMR (400 MHz, DMSO-$d_6$) δ 8.11 (bs, 1H), 6.87 (m, 1H), 6.73 (m, 1H), 6.50 (s, 1H), 6.44 (m, 1H), 2.41(s, 3H), 2.25 (s, 3H). HRMS (ES) exact mass M+H calcd for $C_{13}H_{11}FN_2S_2$ 279.0426; found 279.0416.

Example 48

5-Amino-2-methyl-thiazole-4-carboxylic acid ethyl ester

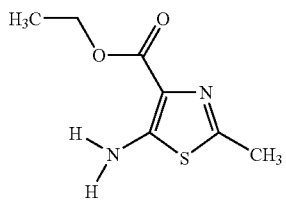

Add acetoamidocyanoacetate (1000 g, 5.88 mol) to a 22 L 3-necked RB flask equipped with reflux condenser, thermometer, mechanical stirrer then add toluene (12L). Add to this suspension at RT Lawesson's reagent (1187 g, 2.93 mol). Stir the resulting yellow slurry at 70° C. for 16 h, cool to RT. Pour the top yellow solution away from the gummy material on the bottom of the flask into a separation funnel. Add 1N HCl solution (2.5L) and TBEA (2.5L) and stir the mixture. After 15 min., combine the bi-phase solution was into the toluene solution in the funnel. Gummy material maybe left in the flask. Repeat the above procedure again. Separate the aqueous and wash the combine organic solution with 1N HCl (2×2.5L). Separate the organic layer and combine the aqueous and basify with 2N KOH solution. Add ethyl acetate (3×4L) and extract the product. Combine the organic layer, dry over anhydrous sodium sulfate, and evaporate to give 552 g as a pale yellow solid. Dissolve the remaining gummy in methanol (1L) and evaporate to dryness. Add MTBE (2.5L) and 1N HCl (4 L) and stir the mixture. After 15 min., separate the organic layer and basify the aqueous with 2N KOH solution Extract the product with ethyl acetate (2×2L). Combine the organic layers and dry over anhydrous sodium sulfate and evaporate to give 165 g as a pale yellow solid. (Total: 717 g, 65%). Mass spectrum (m/e): 187(M+1); $^1$HNMR(300 MHz, DMSO-d$_6$, ppm): δ 1.21(t, 3H), 2.38(s, 3H), 4.21(q, 2H), 7.21(bs, 2H). $^{13}$CNMR (75 MHz, DMSO, ppm): δ 15.1, 19.2, 59.8, 119.3, 145.6, 161.7, 164.1. Formula: $C_7H_{10}N_2O_2S$.

Example 49

2-Methyl-5-(2-nitro-phenylamino)-thiazole-4-carboxylic acid ethyl ester

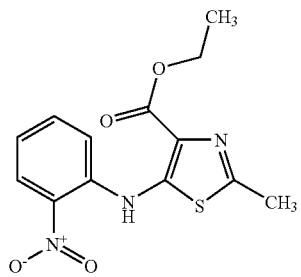

Add a solution of ethyl 5-amino-2-methylthiazole-4-carboxylate (120 g; 645 mmol) and 2-fluoronitrobenzene (68 mL; 645 mmol) in dimethylsulphoxide (1L) to a 2L 3-necked RB flask equipped with reflux condenser, thermometer, mechanical stirrer. Add lithium hydroxide monohydrate (54 g; 1290 mmol) to the solution and heat at 50° C. for 3 hours under nitrogen. Cool the purple solution and pour onto ice/water, allow to stir for one hour, filter and wash with water, dry at 50° C. under reduced pressure to give 190 g (96%) as an orange solid: mass spectrum (m/e): 308(M+1); $^1$HNMR(300 MHz, DMSO-d$_6$, ppm): δ 1.25(tr, 3H), 2.56(s, 3H), 4.25(q, 2H), 7.20(m, 1H), 7.78(m, 2H), 8.20(d, 1H), 11.42(s, 1H, NH). $^{13}$CNMR(75 MHz, DMSO, ppm): δ 24.4, 29.2, 71.2, 127.8, 132.5, 132.8, 137.8, 146.5, 147.0, 147.5, 160.2, 161.5, 173.7. Formula: $C_{13}H_{13}N_3O_4S$.

Example 50

2-Methyl-5-(2-nitrophenylamino)-thiazole-4-carboxylic acid amide

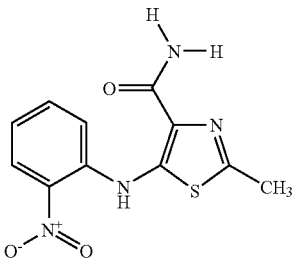

Combine ethyl 2-methyl-5-(2-nitroanilino)thiazole-4-carboxylate (80 g, 260 mmol) and formamide (52 mL, 1.3 mol) in DMF (200 mL) and heat to 105° C. at which time the yellow slurry became a dark solution. Add to this reaction mixture at 105° C. dropwise 25% sodium methoxide in methanol (40 mL, 182.4 mmol) during 45 min period and heat to 115° C. and continue stirring for 60 h. Cool the reaction to RT, pour into a cold saturated NaHCO$_3$ solution. Stir the resulting slurry for 1 h, filter and wash the solid with DMF/H$_2$O (2:1). Dry in a vacuum oven, to obtain a dark brown solid (62 g, 86%). Another batch starting with 100 g of ethyl 2-methyl-5-(2-nitroanilino)thiazole-4-carboxylate gives 82 g (90%) of crude product: mass spectrum (m/e): 279(M+1); $^1$HNMR(300 MHz, DMSO-d$_6$, ppm): δ 2.5(s, 3H), 7.05(m, 1H), 7.51(d, 1H), 7.65(m, 2H), 8.10(d, 1H), 12.18(s, 1H). $^{13}$CNMR(75 MHz, DMSO, ppm): δ 19.4, 116.8, 121.7, 127.3, 129.9, 136.3, 137.0, 137.8, 145.6, 151.2, 166.1. Formula: $C_{11}H_{10}N_4O_3S$.

Example 51

2-Methyl-5-(2-nitro-phenylamino)-thiazole-4-carbonitrile

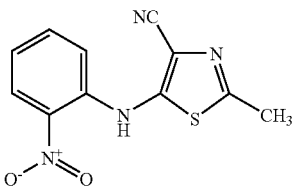

Combine 2-methyl-5-(2-nitroanilino)thiazole-4-carboxylic acid amide (60 g, 215 mmol) and toluene and add POCl$_3$ (40 mL, 430 mmol) and reflux the reaction mixture. After 2.5 h cool to 0° C. Add saturated NaHCO₃ solution to quench the extra POCl₃ (Caution!!) until the aqueous was around pH 8. Add ethyl acetate (2×2 L) to extract the product. Combined organic layer and wash with brine (2×1 L), dry over MgSO₄. and evaporate to give a reddish solid which triturated with 25% ethyl acetate in hexane to give a reddish solid (36 g). Evaporate the filtrate to half volume to give second batch of compound (3.2 g). Total yield (39.2 g, 70%): mass spectrum (m/e): 261(M+1); $^1$HNMR(300 MHz, DMSO-$d_6$, ppm): δ 2.70(s, 1H), 7.02(t, 1H), 7.22(d, 1H), 7.58(t, 1H), 8.25(d, 1H), 9.78(s, 1H): $^{13}$CNMR(75 MHz, DMSO-$d_6$, ppm): δ20.4, 113.1, 116.2, 118.7, 121.2 127.0, 134.9, 136.6, 140.0, 148.6, 161.5. Formula: $C_{11}H_8N_4O_2S$

Example 52

2-Methyl-4H-3-thia-1,4,9-triaza-benzo[f]azulen-10-ylamine hydrochloride

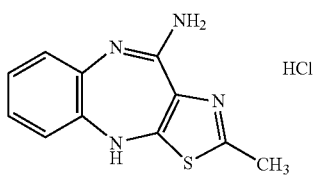

Combine a suspension of 2-methyl-5-(2-nitroanilino)thiazole-4-nitrile (36 g, 138.5 mmol) in isopropanol (400 ml) in a 2.0 liter 3-necked RB flask equipped with a reflux condenser, thermometer, magnetic stirrer bar and heat with stirring to 65° C. (orange solution). Add tin (II) chloride hydrate (78.7 g, 415.4 mmol) in hydrochloric acid (400 ml; 5M) and heat the resulting solution at reflux. After 2.5 h., cool the reaction to 15° C., filter the suspension, wash with isopropanol/water (2:1) and dry at 50° C. under reduced pressure to leave a yellow solid (36.7 g). Evaporate the filtrate to around 200 mL to form a yellow slurry. Filter the slurry again and dry at 50° C. under reduced pressure to leave a yellow solid (10 g). Combine the solid and suspend in 1 N HCl (700 mL) and heat to reflux for 20 min, cool to 15° C. Filter the resulting yellow slurry and dry at 50° C. under reduced pressure to leave a yellow solid (32.4 g, 88%): mass spectrum (m/e): 231 (M+1); $^1$HNMR(300 MHz, DMSO-$d_6$, ppm): δ 2.5(s, 3H), 6.78(dd, 1H), 6.85(dd, 1H), 6.98(t, 1H), 7.02(t, 1H), 8.80(s, 1H), 9.10(s, 1H), 9.98(s, 1H), 10.78(s, 1H). $^{13}$CNMR(75 MHz, DMSO, ppm): δ 19.6, 120.1, 120.8, 123.6, 125.8, 127.8, 129.2, 137.6, 154.4, 159.3, 160.4. Formula $C_{11}H_{11}N_4S$.

Example 53

N-(2,4-Dioxo-2,3,4,5-tetrahydro-1H-benzo[b][1,4]diazapin-3-yl)-propionamide

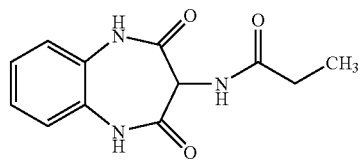

Combine 3-amino-1H-1,5-benzodiazepine-2,4-(3H, 5H)-dione (5.7 g, 30.0 mmol) and triethyl amine(3.33 g, 33.0 mmol) in 120 mL DMF and add propionyl chloride dropwise at RT. After stirrng overnight, remove DMF under reduced pressure, suspend the residue in a mixed solvent (CHCl₃/i-PrOH=3/1, 400 mL). Collect an off-white solid via suction filtration to give the title compound. Wash the filtrate with NaHCO₃ (sat.2×100 mL) and dry with Na₂SO₄. Concentrate the organic solvent down to a residue, treat with ether, collect the solid: mass spectrum (APCI) (m/e): 248.1 (M+1). $^1$H NMR (400 MHz, DMSO-$d_6$): δ 10.70 (s, 2H), 8.19 (d, 1H, J=7.2 Hz), 7.23-7.15 (m, 4H), 4.73 (d, 1H, J=8.0 Hz), 2.27 (q, 2H, J=8.0 Hz), 0.94 (t, 3H, J=8.0 Hz).

Example 54

N-(2,4-Dioxo-2,3,4,5-tetrahydro-1H-benzo[b][1,4]diazapin-3-yl)-butyramide

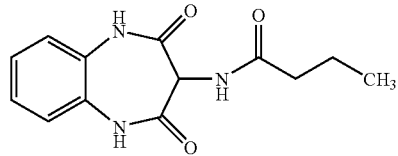

Using the method of Example 53, using 3-amino-1H-1,5-benzodiazepine-2,4-(3H, 5H)-dione (4.0 g, 20.9 mmol), butyryl chloride (2.45 g, 23.0 mmol) and overnight at RT gives the title compound (4.16 g, yield 76%); $^1$H NMR (300 MHz, DMSO-$d_6$): δ 10.70 (s, 2H), 8.21 (d, 1H, J=7.8 Hz), 7.24-7.15 (m, 4H), 4.74 (d, 1H, J=7.5 Hz), 2.24 (t, 2H, J=7.2 Hz), 1.51-1.43 (m, 2H), 0.83 (t, 3H, J=7.5 Hz).

Example 55

N-(2,4-Dioxo-2,3,4,5-tetrahydro-1H-benzo[b][1,4]diazapin-3-yl)-oxalamic acid ethyl ester

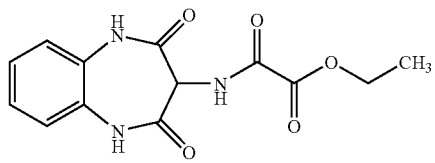

Using the method of Example 53, using 3-amino-1H-1,5-benzodiazepine-2,4-(3H, 5H)-dione (1.91 g, 10.0 mmol)

and ethyl oxalyl chloride (1.50 g, 11.0 mmol) and overnight at RT gives the title compound (1.54 g, 76%) off-white solid: mass spectrum (APCI) (m/e): 292.1.1 (M+1); $^1$H NMR (300 MHz, DMSO-d$_6$): δ 10.95 (s, 2H), 8.32 (d, 1H, J=6.6 Hz), 7.29-7.17 (m, 4H), 4.74 (d, 1H, J=6.6 Hz), 4.27 (q, 2H, J=6.9 Hz), 1.27, (t, 3H, J=7.2 Hz).

Example 56

2-Ethyl-4,9-dihydro-3-thia-1,4,9-triaza-benzo[f]azulene-10-thione

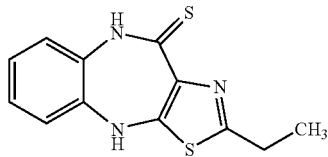

Combine N-(2,4-dioxo-2,3,4,5-tetrahydro-1H-benzo[b][1,4]diazapin-3-yl)-propionamide (3.7 g, 15.0 mmol) and Lawesson's reagent (9.09 g, 22.5 mmol) in 225 mL 1,2-dichloroethane, heat to reflux under N$_2$. After refluxing overnight, cool the reaction to RT, collect the orange solid via suction filtration, and dry under vaccum to obtain 3.3 g crude material. Take crude material (1.0 g), mix with Lawesson's reagent (0.75 g) in 1,2-dichloroethane (30 mL), heat to reflux overnight, cool to RT, collect the orange-red solid via suction filtration to obtain the title compound. Treat the remaining of the intermediate similarly (2.3 g) to obtain additional title compound: mass spectrum (electrospray) (m/e): 261.8 (M+1), 260.0 (M−1); $^1$H NMR (300 MHz, DMSO-d$_6$): δ 10.97 (s, 1H), 9.17 (s, 1H), 7.00-6.91 (m, 3H), 6.79-6.70 (m, 1H), 2.73 (q, 2H, J=7.5 Hz), 1.16 (t, 3H, J=7.5 Hz).

Example 57

2-Propyl-4,9-dihydro-3-thia-1,4,9-triaza-benzo[f]azulene-10-thione

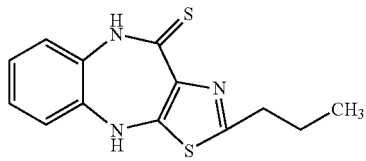

Combine N-(2,4-dioxo-2,3,4,5-tetrahydro-1H-benzo[b][1,4]diazapin-3-yl)-butyramide (2.3 g, 8.80 mmol) and Lawesson's reagent (4.45 g, 11.0 mmol) in 70 mL 1,2-dichloroethane and heat to reflux under N$_2$. After 1.5 hour, cool the reaction to RT, collect the redish solid via suction filtration: $^1$H NMR (300 MHz, DMSO-d$_6$): δ 10.97 (s, 1H), 9.06 (s, 1H), 7.00-6.89 (m, 3H), 6.78-6.75 (m, 1H), 2.68 (t, 2H, J=7.2 Hz), 1.64-1.56 (m, 2H), 0.91 (t, 3H, J=7.2 Hz).

Example 58

10-Thioxo-9,10-dihydro-4H-3-thia-1,4,9-triaza-benzo[f]azulene-2-carboxylic acid ethyl ester

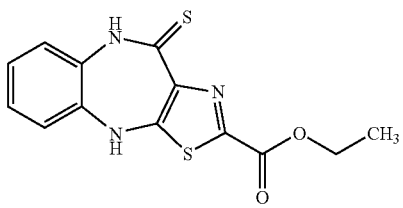

Combine N-(2,4-dioxo-2,3,4,5-tetrahydro-1H-benzo[b][1,4]diazapin-3-yl)-oxalamic acid ethyl ester (0.73 g, 2.5 mmol) and Lawesson's reagent (1.52 g, 3.75 mmol) in 25 mL toluene and heat to reflux under N$_2$. After overnight heating, cool the reaction to RT, collect the orange solid via vacuum filtration to give the crude product, purification by flash chromatography gives the title compound: mass spectrum (APCI) (m/e): 306.0 (M+1); $^1$H NMR (400 MHz, DMSO-d$_6$): δ 11.24 (s, 1H), 9.60 (s, 1H), 7.05-6.96 (m, 3H), 6.78-6.76 (m, 1H), 4.32 (q, 2H, J=6.8 Hz), 1.30 (t, 3H, J=6.8 Hz).

Example 59

Pentanoic acid (2,4-dioxo-2,3,4,5-tetrahydro-1H-benzo[b][1,4]diazepin-3-yl)-amide

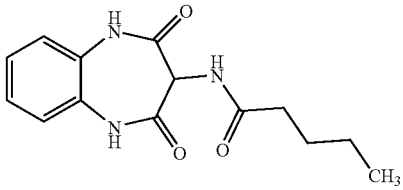

Add valeryl chloride (3.92 mL, 33.0 mmol) dropwise to a solution of 3-amino-1,5-dihydro-benzo[b][1,4]diazepine-2,4-dione (5.74 g, 30.0 mmol) and triethylamine (4.60 mL, 33.0 mmol) in anhydrous dimethylformamide (123 mL) and stir. After 6 hours, concentrate under reduced pressure to a residue and reconstitute the residue in a solution of isopropanol: chloroform (1:3, 500 mL). Stir overnight to give a solid and isolate the solid by suction filtration, washing the solid with dichloromethane. Vacuum dry the solid at ambient temperature 2 hours to afford the title compound. Wash the filtrate with a saturated aqueous solution of sodium bicarbonate (2×200 mL), and filter the extraction mixture to remove salt formed in the wash. Separate the organic phase and wash it with saturated aqueous sodium chloride (150 mL). Back extract the bicarbonate aqueous phase with dichloromethane. Combine all organics, and dry (sodium sulfate), filter, and concentrate under reduced pressure to a residue. Triturate the residue in diethyl ether, filter the resulting solid, and wash it with diethyl ether; repeat 2×. Dry the solid at ambient temperature under vacuum to give the title compound: mass spectrum (APCI, m/e): 276 (M+1); NMR ($^1$H, 300 MHz, DMSO-d): δ 10.68 (s, 2H), 8.23 (d, 1H, J=7.5 Hz), 7.20 (m, 4H), 4.71 (d, 1H, J=7.5 Hz), 2.25 (t, 2H, J=7.5 Hz), 1.43 (m, 2H), 1.25 (m, 2H), 0.83 (t, 3H, J=7.5 Hz).

Example 60

2-Butyl-4,9-dihydro-3-thia-1,4,9-triaza-benzo[f]azulene-10-thione

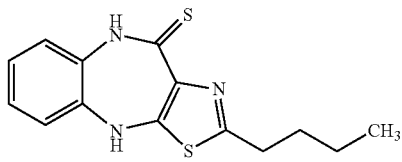

Combine pentanoic acid (2,4-dioxo-2,3,4,5-tetrahydro-1H-benzo[b][1,4]diazepin-3-yl)-amide (4.13 g, 15.0 mmol) and Lawesson's reagent (9.10 g, 22.5 mmol) in anhydrous dichloroethane (250 mL), heat to 85° C., and stir. After 16 hours, cool to ambient temperature, collect the reaction solid by suction filtration, and dry the solid at ambient temperature under vacuum to give the title compound: mass spectrum (APCI, m/e): 290 (M+1); NMR ($^1$H, 300 MHz, DMSO-$d_6$): δ 10.95 (s, 1H), 9.01 (s, 1H), 6.93 (m, 3H), 6.71 (d, 1H, J=7.5 Hz), 2.68 (t, 2H, J=7.5 Hz), 1.53 (m, 2H), 1.30 (m, 2H), 0.85 (t, 3H, J=7.5 Hz).

Example 62

N-(2,4-Dioxo-2,3,4,5-tetrahydro-1H-benzo[b][1,4]diazepin-3-yl)-2,2,2-trifluoro-acetamide

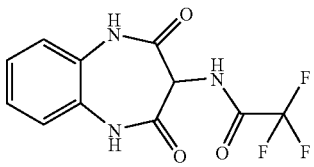

Add 1-(3-dimethylaminopropyl)-3-ethylcarbodiimide hydrochloride (7.67 g, 40.0 mmol), and 4-(dimethylamino)pyridine (0.244 g, 2.00 mmol) to a solution of 3-amino-1,5-dihydro-benzo[b][1,4]diazepine-2,4-dione (7.65 g, 40.0 mmol) in anhydrous N,N-dimethylformamide (50 mL). Rinse solids into reaction with anhydrous N,N-dimethylformamide (50 mL), and cool reaction to 0° C. in an ice/water bath. Add via syringe trifluoroacetic acid (3.08 mL, 40.0 mmol). After 10 minutes, remove cooling, and after 5.5 hours at ambient temperature, add an additional 0.2 equivalents of 1-(3-dimethylaminopropyl)-3-ethylcarbodiimide hydrochloride (1.53 g) and trifluoroacetic acid (0.62 mL) and stir at ambient temperature. After an overnight period, concentrate under reduced pressure to give a residue. Reconstitute the residue in isopropanol: chloroform (1:3, 20 mL) and set 5 minutes. Collect solid formed by suction filtration, wash with isopropanol: chloroform (3:1), and dry at ambient temperature under vacuum to give the title compound. Filter the filtrate, which contained precipitated solid and dry this solid at ambient temperature under vacuum to give a second crop of the title compound: mass spectrum (ES neg., m/e): 286.0 (M−1); NMR ($^1$H, 300 MHz, DMSO-$d_6$): δ 10.93 (s, 2H), 9.42 (d, 1H, J=6.9 Hz), 7.29-7.15 (m, 4H), 4.91 (d, 1H, J=7.2 Hz).

Example 63

2-Trifluoromethyl-4,9-dihydro-3-thia-1,4,9-triaza-benzo[f]azulene-10-thione

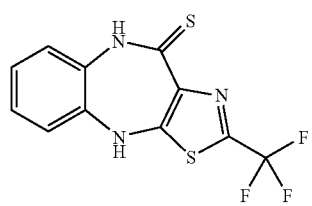

Combine N-(2,4-dioxo-2,3,4,5-tetrahydro-1H-benzo[b][1,4]diazepin-3-yl)-2,2,2-trifluoro-acetamide (3.02 g, 10.5 mmol) with Lawesson's Reagent, [2,4-bis(4-methoxyphenyl)-1,3-dithia-2,4-diphosphetane-2,4-disulfide], (6.38 g, 15.8 mmol) in anhydrous toluene (60 mL), heat to reflux, and stir. After 16 hours, cool and stir for a few hours. Collect the reaction solid by suction filtration, wash with a small amount of toluene, and dry at 40° C. for a few hours to give crude product (3.6 g). Adsorb material on Silica gel 60 and purify by flash chromatography, eluting with a solution of 35% ethyl acetate in hexane. Combine and concentrate the product-containing fractions under reduced pressure, and dry the product at 54° C. under vacuum for 4.5 hours to give the title compound: mass spectrum (APCI, m/e): 302 (M+1); NMR ($^1$H, 300 MHz, DMSO-$d_6$): δ 11.39 (s, 1H), 9.57 (s, 1H), 7.03 (m, 3H), 6.77 (m, 1H).

Example 64

N-(2,4-Dioxo-2,3,4,5-tetrahydro-1H-benzo[b][1,4]diazepin-3-yl)-2,2-difluoro-acetamide Using the method of Example 62, using 3-amino-1,5-dihydro-benzo[b][1,4]diazepine-2,4-dione and difluoroacetic acid, stirring overnight at ambient temperature after the addition of the acid, and washing reaction solid with dichloromethane instead of isopropanol: chloroform (3:1) gives the title compound: mass spectrum (APCI, m/e): 270 (M+1); NMR ($^1$H, 300 MHz, DMSO-$d_6$): δ 10.88 (s, 2H), 9.13 (d, 1H, J=6.9 Hz), 7.29-7.13 (m, 4H), 6.49 (t, 1H, $^2J_{(H,F)}$=53.7 Hz), 4.79 (d, 1H, J=6.9 Hz).

Example 65

2-Difluoromethyl-4,9-dihydro-3-thia-1,4,9-triaza-benzo[f]azulene-10-thione

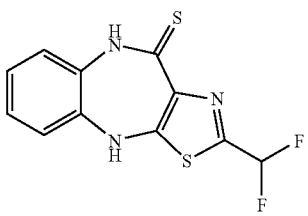

Combine N-(2,4-dioxo-2,3,4,5-tetrahydro-1H-benzo[b][1,4]diazepin-3-yl)-2,2-difluoro-acetamide (3.0 g, 11.1 mmol) with Lawesson's Reagent, [2,4-bis(4-methoxyphenyl)-1,3-dithia-2,4-diphosphetane-2,4-disulfide], (6.8 g, 16.7 mmol) in anhydrous toluene (60 mL), heat to 100° C., and stir. After 20 hours, cool and collect the reaction solid by suction filtration, and wash with a small amount of dichloromethane. Recombine solid with filtrate, containing product, and add methanol and acetonitrile. Filter off insoluble material, adsorb filtrate onto Silica gel 60, and make a pre-column. Purify the material by flash chromatography, eluting with hexane and then with a gradient of hexane:ethyl acetate (0-35% over 55 minutes). Combine fractions containing product to a solid, triturate in hexane, filter, and purify the filtered solid again by flash chromatography, eluting with isopropyl acetate:chloroform. Filter precipitated solid from a mixed fraction to give the title compound. Combine and concentrate pure fractions under reduced pressure to give additional title compound. Purify mixed material by flash chromatography, eluting with a gradient of isopropyl acetate:chloroform (2%-5% isopropyl acetate in chloroform over 61 minutes), and combine and concentrate fractions containing product under reduced pressure to a solid. Triturate and sonicate the solid in hexane and filter. Sonicate the filtered solid in chloroform: hexane (1:3) and filter to give the title compound: mass spectrum (APCI, m/e): 284 (M+1); NMR ($^1$H, 300 MHz, DMSO-d$_6$): δ 11.28 (s, 1H), 9.42 (s, 1H), 7.13 (t, 1H, $^2J_{(H,F)}$=54.3 Hz), 7.07-6.96 (m, 3H), 6.76 (m, 1H).

Example 66

N-(2,4-Dioxo-2,3,4,5-tetrahydro-1H-benzo[b][1,4]diazapin-3-yl)-4,4,4-trifluoro-butyramide

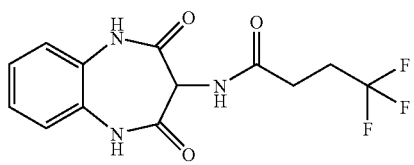

Combine 3-amino-1H-1,5-benzodiazepine-2,4-(3H, 5H)-dione (5.60 g, 29.3 mmol), 1-[3-(dimethylamino)propyl]-3-ethylcarbodiimde hydrochloride (6.75 g, 35.2 mmol) and 4(dimethylamino)pyridine (0.183 g, 1.5 mmol) in 100 mL DMF, add 4,4,4-trifluoro butyric acid dropwise at 0-5° C. After addition, stir the reaction mixture at ice-water. After half an hour, warm to RT. After stirring overnight, remove solvent DMF under reduce pressure and suspend the residue in 200 mL of mixed solvent (CHCl$_3$: i-PrOH=3:1). Collect the solid via vacuum filtration to give the title compound (6.87 g, yield 74%): mass spectrum (APCI) (m/e): 316.1 (M+1); $^1$H NMR (400 MHz, DMSO-d$_6$): δ 10.72 (s, 2H), 8.60 (d, 1H, J=7.2 Hz), 7.24-7.15 (m, 4H), 4.74 (d, 1H, J=7.2 Hz), 2.58 (t, 2H, J=7.2 Hz), 2.39-2.35 (m, 2H).

Example 67

2-(3,3,3-Trifluoro-Propyl)-4,9-dihydro-3-thia-1,4,9-triaza-benzo[f]azulene-10-thione

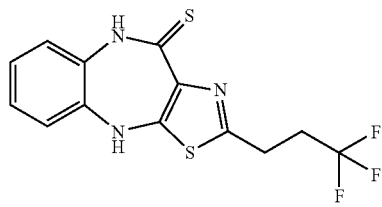

Using the method of Example 57, using N-(2,4-dioxo-2,3,4,5-tetrahydro-1H-benzo[b][1,4]diazapin-3-yl)-4,4,4-trifluoro-butyramide (1.58 g, 5.0 mmol) and Lawesson's reagent (3.04 g, 7.5 mmol) to obtain the title compound: mass spectrum (APCI) (m/e): 330.0 (M+1); NMR (300 MHz, DMSO-d$_6$): δ 11.01 (s, 1H), 9.06 (s, 1H), 7.01-6.92 (m, 3H), 6.77-6.74 (m, 1H), 3.00 (t, 2H, J=7.8 Hz), 2.71-2.61 (m, 2H).

Example 68

Cyclopentanecarboxylic acid (2,4-Dioxo-2,3,4,5-tetrahydro-1H-benzo[b][1,4]diazapin-3-yl)-amide

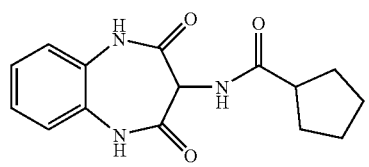

Using the method of Example 53, using 3-amino-1H-1,5-benzodiazepine-2,4-(3H, 5H)-dione (7.0 g, 36.6 mmol), cyclopentanecarbonyl chloride (5.34 g, 40.3 mmol) and triethyl amine (4.07 g, 40.3 mmol), overnight at RT giving the title compound (9.13 g, yield 87%). $^1$H NMR (300 MHz, DMSO-d$_6$): δ 10.70 (s, 2H), 8.11 (d, 1H, J=7.8 Hz), 7.24-7.15 (m, 4H), 4.73 (d, 1H, J=7.5 Hz), 2.96-2.87 (m, 1H), 1.74-1.45 (m, 8H).

Example 69

2-Cyclopentyl-4,9-dihydro-3-thia-1,4,9-triaza-benzo[f]azulene-10-thione

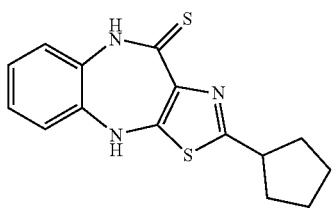

Using the method of Example 57, combine cyclopentanecarboxylic acid (2,4-Dioxo-2,3,4,5-tetrahydro-1H-benzo[b][1,4]diazapin-3-yl)-amide (1.90 g, 6.6 mmol) and Lawesson's reagent (4.01 g, 9.9 mmol) in 120 mL 1,2-dichlorideethane and heat to reflux under $N_2$. The reaction cool to RT, after 4 hour, collect 1.56 g orange solid via suction filtration, yield 78%. $^1$H NMR (400 MHz, DMSO-$d_6$): δ 10.96 (s, 1H), 9.05 (s, 1H), 7.00-6.89 (m, 3H), 6.78-6.76 (m, 1H), 3.21-3.10 (m, 1H), 2.00-1.90(m, 2H), 1.7-1.55 (m, 6H).

Example 70

Cyano-isobutyrylamino-acetic acid ethyl ester

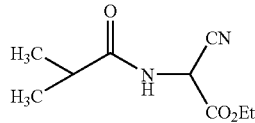

Dilute aqueous saturated sodium bicarbonate (560 mL) with deionized water (700 mL). and stir the solution while addinng ethyl cyanoglyoxylate-2-oxime (70.0 g, 493 mmol), in portions (note: some off-gassing and a gentle endotherm were observed). Add sodium dithionite (238 g, 1.37 mol, 2.8 eq.) in portions and stir at rt. After 2.5-3 hours, during this time the reaction was monitored by TLC (EtOAc, $I_2$ stain), saturate the solution with sodium chloride (400 g), and extract the product $CH_2Cl_2$ (1×500 mL, 3×250 mL), making sure solid NaCl was visible (more added if necessary) during the extractions. Combine the organic layers, dry over ($MgSO_4$), filter, and concentrate the filtrate to dryness in vacuo on a rotovapor at low bath temperature (30-35° C.) to afford 19.6 g (31%) crude amino-cyano-acetic acid ethyl ester which was used immediately in the next reaction.

Cool a solution of amino-cyano-acetic acid ethyl ester (19.0 g, 148 mmol) in $CH_2Cl_2$ (300 mL) to 0-5° C. under $N_2$. Add pyridine (12.0 mL, 148 mmol) followed by isobutyric anhydride (24.6 mL; 148 mmol). Allow the reaction solution to warm to rt overnight until complete by TLC (EtOAc). Wash the solution with aqueous 1N HCl, water, aq. sat'd $NaHCO_3$, then brine (150 mL each). Dry the organic layer over $MgSO_4$, filter, and concentrate the filtrate to dryness in vacuo on a rotovapor to a solid. Triturate the solid with $Et_2O$ (500 mL), filter and dry (50° C. vacuum oven) to afford 22.0 g (75%) of the title compound: $^1$H NMR (300 MHz, DMSO-$d_6$) δ 9.05 (d, 1H, J=7.32 Hz), 5.67 (d, 1H, J=7.32 Hz), 4.25-4.13 (m, 2H), 2.46 (dq, 1H, J=6.95 Hz), 1.21 (t, 3H, J=6.95 Hz), 1.03 (d, 6H, J=6.95 Hz). $^{13}$C NMR (75 MHz, DMSO-$d_6$) δ 176.51, 164.13, 115.60, 62.33, 44.07, 33.29, 18.93, 18.86, 13.74. IR ($CHCl_3$) 3425, 3028, 2975, 2933, 2905, 2874, 1757, 1687, 1492, 1370, 1284, 1189 $cm^{-1}$. HRMS (FAB+) M/z calculated for $C_9H_{15}N_2O_3$ (M+H) 199.1083 found 199.1075.

Example 71

Cyano-isobutyrylamino-acetic acid ethyl ester

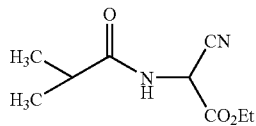

Combine ethyl cyanoglyoxylate-2-oxime (20.0 g, 141 mmol) and 5% Pt/C (2.0 g, 10% wt. load) in acetic acid (120 mL) and EtOAc (60 mL) and hydrogenate under 40 psi $H_2$ overnight until the reaction is complete by TLC (5:1/heptane:EtOAc, $I_2$ stain). Carefully filtered the spent catalyst using partial vacuum through glass fiber paper, and rinse with HOAc/EtOAc without allowing the cake to dry out. Concentrate the filtrate in vacuo on a rotovapor to an oil, leaving 25.5 g (96%) of crude amino-cyano-acetic acid ethyl ester as the HOAc salt. Partition a portion (13.0 g) of the HOAc salt between EtOAc (70 mL) and water (35 mL). Stir the biphasic solution and add dropwise aqueous 5N NaOH (16.5 mL) to adjust the pH to 8.0-8.2. Separate the layers, and extract the aqueous layer with more EtOAc (3×25 mL). Combine the organic layer, dry ($MgSO_4$), filter, and concentrate the filtrate to dryness in vacuo on a rotovapor at low bath temperature (30-35° C.) to afford 5.68 g (65%) crude amino-cyano-acetic acid ethyl ester which was used immediately in the next reaction.

Cool a solution of crude amino-cyano-acetic acid ethyl ester (5.68 g, 44.3 mmol) in $CH_2Cl_2$ (60 mL) to 0-5° C. under $N_2$. Add pyridine (3.60 mL, 44.5 mmol), followed by isobutyric anhydride (7.40 mL, 44.6 mmol). Allow the reaction solution to warm to rt overnight (18 h) until complete by TLC (3:1/EtOAc:heptane, $I_2$ stain, co-spot needed to distinguish between SM and impurity). Wash the solution with aqueous 1N HCl, water, aq. sat'd $NaHCO_3$, then brine (50 mL each). Dry the organic layer ($MgSO_4$), filter, and concentrate the filtrate to dryness in vacuo on a rotovapor to a solid. Triturate the solid with $Et_2O$ (150 mL), filter and dry (50° C. vacuum oven) to afford 4.33 g (49%) of the title compound.

Example 80

5-Amino-2-isopropyl-thiazole-4-carboxylic acid ethyl ester

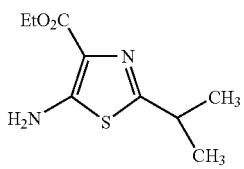

Stir cyano-isobutyrylamino-acetic acid ethyl ester (139 g, 701 mmol) mechanically stir as a slurry in toluene (1.4 L) at rt under $N_2$. Add lawesson's reagent (170 g, 420 mmol, 0.6 eq.) in portions and heat the thick slurry to 70° C. and stir for 12 hours until complete by TLC (2:1/heptane:THF). Cool the mixture and concentrate to dryness in vacuo on a rotovapor to obtain 353 g of thick yellow oil that was partially purified by silica gel plug (1 Kg silica gel 60, 1.5 vol. warm 2:1/THF:heptane as diluent, 2:1/heptane:THF as eluent). Combine the product containing filtrates and concentrate to dryness in vacuo on a rotovapor to obtain 194 g of crude solid. Dissolve the solid in EtOAc (400 mL) at 50-60° C. with stirring, then allow to cool gradually to rt. Precipitate the product and was cool to 0-5° C. with stirring for 30 minutes, isolate by suction filtration, rinse with cold EtOAc (2×50 mL), then dry in a vacuum oven at 50° C. to afford a first crop of 76.3 g (51%) of the title compound. Obtain a second crop of 17.6 g (12%)=from the filtrate after concentration in vacuo and silica gel chromatography (1 Kg silica gel 60, 2:1/heptane:THF). $^1$H NMR (300 MHz, DMSO-$d_6$) δ 7.23 (bs, 2H), 4.21 (q, 2H, J=6.95 Hz), 3.02 (dq, 1H, J=6.95 Hz), 1.27 (t, 3H, J=6.95 Hz), 1.22 (d, 6H, J=6.95 Hz). $^3$C NMR (75 MHz, DMSO-$d_6$) δ 163.72, 160.08, 156.20, 118.08, 58.99, 32.27, 22.35 (2); 14.46. IR (CHCl$_3$) 3483, 3347, 2975, 2933, 2868, 1668, 1582, 1530, 1494, 1464, 1409, 1382 cm$^{-1}$. HRMS (ES) M/z calculated for $C_9H_{14}N_2O_2S$ 215.0854, found 215.0842.

Example 81

2-Isopropyl-5-(2-nitro-phenylamino)-thiazole-4-carboxylic acid ethyl ester

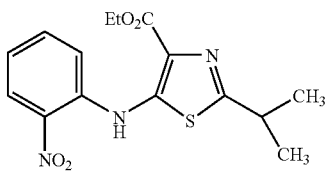

Combine a solution of 5-amino-2-isopropyl-thiazole-4-carboxylic acid ethyl ester (8.71 g, 40.6 mmol) and 2-fluoronitrobenzene (4.28 mL, 40.6 mmol) in DMSO (105 mL) and stir at rt under $N_2$ as LiOH (1.95 g, 81.4 mmol, 2.0 eq.) or LiOH monohydrate (2 eq) is added in one portion. The reaction turns dark. Heat the reaction mixture to 55° C. for 3 h until complete by HPLC (Zorbax SB C18 25 cm, 60:40/ACN:0.1% TFA in water, 233 nm, 1.0 mL/min). Cool to rt overnight, Cool the reaction to 0-5° C. with stirring as deionized water (315 mL) is added at such a rate to maintain the temperature below 20° C. Precipitate the product and the reaction color changes from brown to rust-orange color. Stir the slurry for 3-4 h at rt, filter by vacuum and rinse with minimal 3:1/H$_2$O:DMSO, dry in a vacuum oven at 60° C. to afford 12.4 g (91%) of the title compound as an orange solid: $^1$H NMR (300 MHz, DMSO-$d_6$) δ 11.52 (bs, 1H), 8.23 (d, 1H, J=8.05 Hz), 7.80 (m, 2H), 7.21 (m, 1H), 4.36 (q, 2H, J=7.32 Hz, 6.95 Hz), 3.23 (dq, 1H, J=6.95 Hz), 1.34 (m, 9H); $^{13}$C NMR (75 MHz, DMSO-$d_6$) δ 163.22, 161.85, 149.08, 136.99, 136.37, 136.10, 126.53, 126.48, 121.94, 117.05, 60.45, 32.47, 22.34(2), 14.24; IR (CHCl$_3$) 2976, 2932, 2867, 1709, 1677, 1611, 1580, 1550, 1512, 1415, 1340 cm$^-$; HRMS (ES) M/z calculated for $C_{15}H_{17}N_3O_4S$ 336.1018, found 336.1009.

Example 82

2-Isopropyl-5-(2-nitro-phenylamino)-thiazole-4-carboxylic acid amide

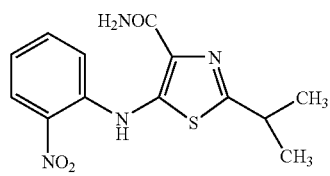

Stir 2-isopropyl-5-(2-nitro-phenylamino)-thiazole-4-carboxylic acid ethyl ester (68.6 g, 204 mmol) at rt under $N_2$ as a slurry in DMF (205 mL). Add formamide (32.4 mL, 816 mmol, 4.0 eq.) in one portion, and heat the thick red slurry to 100° C.; a dark red/purple solution is formed. Add dropwise over 20-30 min, 25% NaOMe in MeOH (32.6 mL, 143 mmol, 0.7 eq.) Increase the temperature 120° C. and stir the dark solution was stirred at 120° C. overnight until complete (<2% Me ester+SM) by HPLC (Zorbax SB C18 25 cm, 60:40/ACN:0.1% TFA in water, 233 nm, 1.0 mL/min). After cooling the reaction to rt, add aqueous 5% NH$_4$Cl (410 mL) at such a rate as to maintain the temperature below 35° C. with no external cooling. Precipitate the product, cool the slurry to 0-5° C., filter by vacuum filtration and dry in a vacuum oven at 60° C. to afford 52.7 g (84% yield) crude title compound as a purple solid that was used without further purification. An aqueous workup may result in bad emulsions/slow separations: $^1$H NMR (300 MHz, DMSO-$d_6$) δ 12.22 (bs, 1H), 8.21 (d, 1H, J=7.69 Hz), 7.78 (m, 2H), 7.59 (bs, 1H), 7.53 (bs, 1H), 7.15 (m, 1H), 3.23 (dq, 1H, J=6.95 Hz), 1.35 (d, 6H, J=6.95 Hz): $^{13}$C NMR (75 MHz, DMSO-$d_6$) δ 165.53, 161.44, 144.58, 137.12, 136.31, 135.72, 128.90, 126.58, 121.08, 116.28, 32.32, 22.35(2): IR (CHCl$_3$) 3520, 3400, 3004, 2967, 2925, 2866, 1658, 1611, 1578, 1513, 1427, 1342 cm$^{-1}$: HRMS (ES) M/z calculated for $C_{13}H_{14}N_4O_3S_1$ 329.0684, found 329.0667.

Example 83

2-Isopropyl-5-(2-nitro-phenylamino)-thiazole-4-carbonitrle

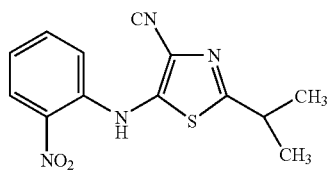

Combine 2-isopropyl-5-(2-nitro-phenylamino)-thiazole-4-carboxylic acid amide (47.5 g, 155 mmol) and 2-dichloroethane (475 mL) and stir at rt under $N_2$ as a dark solution. Pour $POCl_3$ (14.5 mL, 155 mmol) into the solution, and heat the reaction to reflux (80-83° C.) for 2-3 h until complete by HPLC (Zorbax SB C18 25 cm, 60:40/ACN:0.1% TFA in water, 233 nm, 1.0 mL/min). Cool the reaction to rt, cool further to 0-5° C. Adjust the pH to 8-9 by adding aqueous 2N NaOH (275 mL) at such a rate to maintain the temperature below 20° C. Separate the layers, extract the aqueous layer with $CH_2Cl_2$ (2×100 mL). Combine the organic layer, wash with brine (2×100 mL), dry ($MgSO_4$), filter, and concentrate the filtrate in vacuo to a dark oil/solid residue (40 g). Purify the crude product by silica gel chromatography (1200 g silica gel 60, $CH_2Cl_2$) to afford 29.4 g (66%) of the title compound as a red solid: $^1$H NMR (300 MHz, DMSO-$d_6$) δ 9.78 (bs, 1 h), 8.15 (dd, 1H, J=6.95 Hz, 1.46 Hz), 7.67 (dt, 1H, J=7.32 Hz, 1.46 Hz), 7.26 (dd, 1H, J=7.32 Hz, 1.10 Hz), 7.15 (dt, 1H, J=6.95 Hz, 1.10 Hz), 3.26 (dq, 1H, J=6.95 Hz), 1.33 (d, 6H, J=6.95 Hz); $^{13}$C NMR (75 MHz, DMSO-$d_6$) δ 171.85, 150.83, 139.10, 136.22, 136.00, 126.05, 121.41, 118.64, 116.09, 113.73, 33.01, 22.07(2); IR($CHCl_3$) 3311, 3021, 2970, 2928, 2868, 2223, 1613, 1583, 151 g, 1492, 1448, 1403, 1341 cm$^{-1}$; HRMS (ES) M/z calculated for $C_{13}H_{12}N_4O_2S$ 289.0759, found 289.0744.

Example 84

2-Isopropyl-4H-3-thia-1,4,9-triaza-benzo[f]azulen-10-ylamine hydrochloride

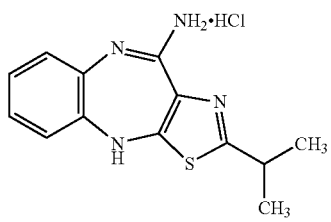

Combine 2-isopropyl-5-(2-nitro-phenylamino)-thiazole-4-carbonitrle (35.1 g, 122 mmol) and IPA (525 mL) stir under $N_2$ and heat to 60° C. to dissolve. Add a solution of $SnCl_2$ (70.0 g, 369 mmol, 3.0 eq.) in aqueous 5M HCl (525 mL) dropwise over 30 min. Heat the reaction mixture at reflux (80-85° C.) for 1 h until complete by HPLC (Zorbax SB C18 25 cm, 60:40/ACN:0.1% TFA in water, 233 nm, 1.0 mL/min). Cooling the reaction to 50° C. Remove most of the solvent in vacuo. Treat the aqueous solid residue (188 g) with IPA (500 mL) and heat to 60-70° C. for a few minutes to form a homogenous slurry. Cool the slurry to rt, then 0-5° C. for 1-2 h. Isolate the product by vacuum filtration and dry in a vacuum oven at 60° C. to afford 45.9 g (128%) of crude product that was heavily contaminated with residual tin. Suspent the crude product in aqueous 1N HCl (2.25 L) and heat to reflux (95° C.) for 1 h, during which time most of the solids dissolve. Cool to rt, isolate the product by vacuum filtration, rinse with aqueous, 1N HCl, and dry in a vacuum oven at 70° C. to afford 34.5 g (97%) of the title compound as a yellow/orange solid. Analytical analysis: Sn (9.0%), $H_2O$ (1.2%); $^1$H NMR (300 MHz, DMSO-$d_6$) δ 10.96 (bs, 1H), 10.15 (bs, 1H), 8.94 (bs, 2H), 7.10-6.95 (m, 2H), 6.93-6.82 (m, 2H), 3.10 (dq, 1H, J=6.95 Hz), 1.28 (s, 3H), 1.26 (s, 3H); $^{13}$CNMR (75 MHz, DMSO-$d_6$) δ 164.42, 159.24, 158.94, 137.01, 128.58, 127.11, 125.09, 122.87, 120.14, 119.23, 32.41, 21.98(2); IR (KBr) 3301, 3249, 2964, 1653, 1614, 1553, 1509 cm$^{-1}$; HRMS (ES) M/z calculated for $C_{13}H_{15}N_4S$ 259.1017 (M$^+$–Cl), found 259.1010.

Example 85

2-Methoxyimino-malonic acid diethyl ester

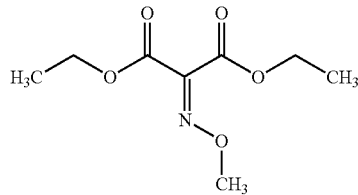

Combine diethylketomalonate (50 g, 0.287 mol) in 3A ethanol (250 mL) and add N-methylhydroxylamine-HCl (23.9 g, 0.287 mol). Add pyridine (22.7 g, 0.287 mol) and heat to reflux (78° C.) the colorless homogeneous solution with stirring under nitrogen for approximately 2.5 hours before cooling to ambient temperature. Stir at ambient temperature for approximately 48 hours monitoring by HPLC analysis (Zorbax RX C18, 55% ACN/45% 0.1% TFA, 1 mL/min, 233 nm). Concentrate the reaction mixture in vacuo to a wet, waxy white solid and partition between 100 mL of EtOAc and 100 mL of $H_2O$. Extract the aqueous layer with 3×100 mL portions of EtOAc. Combine the EtOAc layers, wash with 100 mL of brine, dry over $MgSO_4$, filter, and evaporate down to a yellow oil. Absorb the crude product onto silica gel 60 (Merck, 230-400 mesh) and elute with 4 L of a 9:1 hexanes:EtOAc solution as eluent. Evaporate the eluent in vacuo to afford 56.3 g (96.6% yield) of the title compound as a pale yellow homogeneous oil; $^1$H NMR (300 MHz, CDCl$_3$) δ 4.29 (m, 4H), 4.05 (s, 3H), 1.259 (t, 6H, J=7.32 Hz); $^{13}$C NMR (75 MHz, CDCl$_3$) δ 159.9, 158.9, 143.3, 64.2, 62.3, 62.1, 13.7; IR (CHCl$_3$) 3029, 2986, 2944, 1744, 1605, 1329, 1301, 1264, 1237, 1103, 1043 cm$^{-1}$; UV (EtOH) λmax 231 nm (ε 8582); HRMS (ES) exact mass calc'd for $C_8H_{13}NO_5$ 203.0794, Found 203.0797. Anal. calc'd for $C_8H_{13}NO_5$: C, 47.29; H, 6.45; N, 6.89. Found: C, 46.28; H, 6.36; N, 4.86.

Example 86

1,5-Dihydro-benzo[b][1,4]diazepine-2,3,4-trione 3-(O-methyl-oxime)

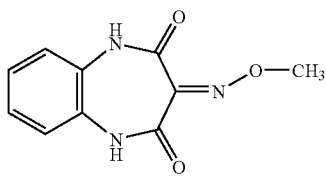

Dissolve 21 wt % NaOEt in EtOH solution (164 g, 0.507 mol) in 2B-3 ethanol (331 mL) and add 1,2-phenylenediamine (27.4 g, 0.253 mol). Stir the resulting mixture allow to stir at ambient temperature for approximately 30 minutes during which time all the solid material dissolves producing a dark amber solution. Add 2-methoxyimino-malonic acid diethyl ester (51.5 g, 0.253 mol). Heat the resulting mixture to 70° C. and stir under nitrogen for approximately 4 hours monitoring by HPLC analysis (Zorbax RX C18, 55% ACN/ 45% 0.1% TFA, 1 mL/min, 233 nm). Allow the reaction mixture to cool to ambient temperature. Lower the pH of the reaction mixture from 11.6 to 1.2 by the addition of 700 mL of aqueous 1N HCl solution. Concentrate the reaction mixture in vacuo to remove the ethanol. Filter the resulting amber slurry through a glass frit. Collect the solid and rinse with aqueous 1N HCl and dry under vacuum at 50° C. to afford 42 g (76% yield) of the title compound as a yellow solid; $^1$H NMR (300 MHz, CDCl$_3$) δ 11.1 (s, 1H), 10.9 (s, 1H), 7.22 (s, 4H), 3.86 (s, 3H); $^{13}$C NMR (75 MHz, CDCl$_3$) δ 161.7; 159.4, 148.1, 128.5, 127.8, 125.8, 125.7, 122.8, 122.7, 63.1; IR (CHCl$_3$) 3062, 2970, 2902, 1704, 1656, 1606, 1505, 1414, 1058, 1043, 754 cm$^{-1}$; UV (EtOH) λmax 278 nm (ε 4623), 276 nm (ε 4618), 216 nm (ε 41495); HRMS (ES+) exact mass calc'd for C$_{10}$H$_9$N$_3$O$_3$ 242.0542, Found 242.0553; Anal. calc'd for C$_{10}$H$_9$N$_3$O$_3$: C, 54.79; H, 4.14; N, 19.17. Found: C, 54.60; H, 4.15; N, 18.94.

Example 87

3-Amino-1,5-dihydro-benzo[b][1,4]diazepine-2,4-dione

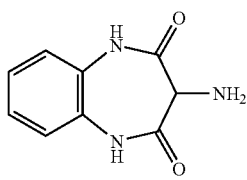

Wet 10% Pd/C (37.5 g) with glacial acetic acid (HOAc, 3.75 L). Add 1,5-dihydro-benzo[b][1,4]diazepine-2,3,4-trione 3-(O-methyl-oxime) (150 g, 0.684 mol), and subject the resulting mixture to catalytic hydrogenation under 50 psi H$_2$ at ambient temperature for ~18 hours until complete by HPLC. Remove the catalyst by filtration over glass fiber paper/Hyflo and rinse with HOAc (2 L). Concentrate the filtrate in vacuo to obtain the crude product as an amber waxy solid. Treat the solid with ethyl acetate (EtOAc, 3 L) and heat to 70° C. with stirring for 1 hour. Allow the slurry to cool to ambient temperature, then force cool to 0° C. Isolate the product by filtration and dry to afford 109.9 g (84%) of the title compound: $^1$H NMR (300 MHz, DMSO-d$_6$) δ 10.48 (bs, 2H), 7.18 (m, 4H), 3.75 (s, 1H), ~3.5 (bs, 2H); $^{13}$C NMR (75 MHz, DMSO-d$_6$) δ 167.9, 164.5, 129.2, 125.1, 122.2, 55.8, 55.7; IR (KBr) 3375, 3306, 3282, 3047, 2750, 1697, 1670, 1559, 1500, 1433, 1411, 1337, 1307, 1258, 1183 cm$^{-1}$; V (EtOH) λmax 217 nm (ε 33772), 285 nm (ε 3210); HRMS (ES+) exact mass calc'd for C$_9$H$_9$N$_3$O$_2$ 192.0773, Found 192.0768.

Example 88

N-(2,4-Dioxo-2,3,4,5-tetrahydro-1H-benzo[b][1,4]diazepin-3-yl)-isobutyramide

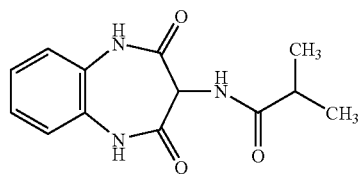

Stir 3-amino-1,5-dihydro-benzo[b][1,4]diazepine-2,4-dione (10.0 g, 52.3 mmol) as a tan colored slurry in THF (300 mL) at 0-3° C. under nitrogen. Add triethylamine (8.00 mL, 57.0 mmol) in one portion. Add dropwise isobutyryl chloride (6.00 mL, 57.0 mmol) keeping the temperature below 3° C. Stir the resulting light yellow colored slurry at 0-3° C. for 3.5 hours until complete reaction by HPLC. Add deionized water (450 mL) over 15-20 minutes, keeping the pot temperature below 10° C. After stirring at 0-10° C. for 1.5 hours, isolate the product by filtration, rinse with cold (0-3° C.) 2:1/Water:THF (50 mL), then water (50 mL). Dry the solid in a vacuum oven at 50° C. to afford 10.5 g (77%) of the title compound: $^1$H NMR (500 MHz, DMSO-d$_6$) δ 10.7 (s, 2H), 8.15 (d, 1H), 7.2 (m, 4H), 4.7 (d, 1H), 2.75 (m, 1H), 1.0 (s, 6H).

Example 89

2-Isopropyl-4,9-dihydro-3-thia-1,49-triaza-benzo[f]azulene-10-thione

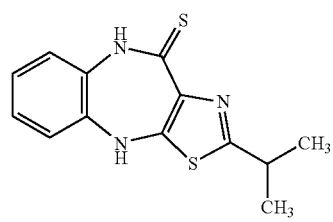

Combine N-(2,4-dioxo-2,3,4,5-tetrahydro-1H-benzo[b][1,4]diazepin-3-yl)-isobutyramide (10.0 g, 38.3 mmol) and Lawesson's Reagent (23.2 g, 57.4 mmol) and stir as a slurry in 1,2-dichloroethane (DCE, 600 mL) under nitrogen at 80° C. for 5 hours until complete reaction by HPLC. Allow the reaction mixture to cool gradually to ambient temperature overnight. Isolate the product by filtration, rinse with DCE (4×40 mL), then dry in a vacuum oven at 50-60° C. overnight to afford 7.96 g (76%) of the title compound (weight and yield corrected for 7.5% wt. residual DCE by proton NMR): $^1$H NMR (300 MHz, DMSO-d$_6$) 510.97 (bs, 1H), 8.93 (bs, 1H), 7.06-6.90 (m, 3H), 6.81-6.74 (m, 1H), 3.11-2.97 (m, 1H), 1.24 (s, 3H), 1.22 (s, 3H); $^{13}$C NMR (75 MHz, DMSO-d$_6$) δ 192.3, 163.0, 150.1, 141.6; 135.0, 131.1, 126.0, 124.1, 123.0, 119.2, 32.6, 22.3; IR (KBr) 3198, 3147, 2965, 1600, 1534, 1505, 1480, 1397, 1306, 1095, 1049 cm$^{-1}$; HRMS (ES+) exact mass calc'd for C$_{13}$H$_{13}$N$_3$S$_2$ 276.0629, Found 276.0613.

Example 90

2-(4-Fluoro-2-nitro-phenylamino)-benzo[b]thiophene-3-carbonitrile

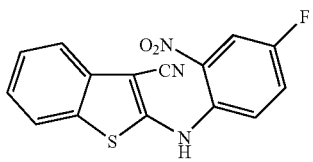

Combine 2-amino-benzo[b]thiophene-3-carbonitrile (3.75 g, 21.5 mmol), 1,4-Difluoro-2-nitro-benzene (2.33 mL, 21.5 mmol), and lithium hydroxide (1.03 g, 43.0 mmol) in anhydrous dimethylsulfoxide (50 mL), and heat at 55° C. for about 5 hours. Cool to ambient temperature, pour into a beaker filled with ice/deionized water (200 mL), and stir for 30 minutes. Isolate the precipitated material by suction filtration, wash the solid with dichloromethane, and dry it under reduced pressure to give the title compound (0.618 g). Add deionized water and ethyl acetate to the filtrate, and then separate the organic layer. Extract the aqueous layer with ethyl acetate many times, and then with dichloromethane many times. Then wash the organics with deionized water (3×). Combine the washes and back extract them with ethyl acetate. Wash the organics with a saturated solution of sodium chloride, and then dry (sodium sulfate), filter, and concentrate the organics under reduced pressure to a dark solid. After triturating with methanol, isolate the resulting solid by suction filtration, wash with methanol, and dry at ambient temperature under reduced pressure to give the title compound (4.422 g). Total solid: 5.04 g (74.8%): Mass spectrum (ES+, m/e): 314 (M+1); NMR ($^1$H, 300 MHz, CDCl$_3$), δ (ppm): 9.96 (s, 1H), 8.06-7.98 (m, 1H), 7.85-7.77 (m, 1H), 7.77-7.69 (m, 1H), 7.68-7.59 (m, 1H), 7.56-7.47 (m, 1H), 7.45-7.34 (m, 2H).

Example 91

8-Fluoro-11H-12-thia-6,11-diaza-dibenzo[a,f]azulen-5-ylamine hydrochloride

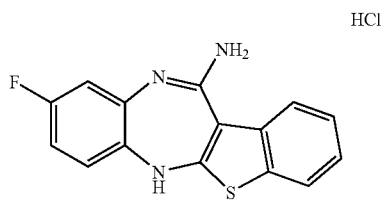

Combine 2-(4-fluoro-2-nitro-phenylamino)-benzo[b]thiophene-3-carbonitrile (5.04 g, 16.1 mmol) and tin(II) chloride (9.15 g, 48.3 mmol) in absolute ethanol and 5N HCl (60 mL each) and reflux the suspension for 4 hours. Cool the reaction to ambient temperature, and collect the reaction solid by suction filtration, washing with cold ethanol, and drying at ambient temperature under reduced pressure to give a solid (6.18 g). Take the solid up in methanol and then deionized water, and isolate the solid by suction filtration. Dry the solid overnight under reduced pressure to give the title compound (5.00 g, 97.3%). Mass spectrum (APCI+, m/e): 284 (M+1-HCl); NMR ($^1$H, 300 MHz, DMSO-d$_6$), δ (ppm): 11.65 (s, 1H), 9.98 (s, 1H), 9.19-9.00 (m, 2H), 7.90-7.82 (m, 1H), 7.72-7.63 (m, 1H), 7.46-7.36 (m, 1H), 7.33-7.24 (m, 1H), 7.11-6.97 (m, 2H), 6.96-6.88 (m, 1H).

Example 92

2-(2-Nitro-4-trifluoromethyl-phenylamino)-benzo[b]thiophene-3-carbonitrile

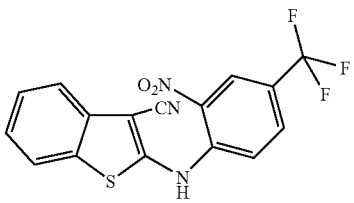

Combine 2-amino-benzo[b]thiophene-3-carbonitrile (3.48 g, 20.0 mmol), 1-Fluoro-2-nitro-4-trifluoromethyl-benzene (4.31 g, 20.0 mmol), and lithium hydroxide (0.958 g, 40.0 mmol) in anhydrous dimethylsulfoxide (50 mL), and heat at 55° C. for 2 hours. Cool to ambient temperature, pour into a beaker filled with ice/deionized water (50 mL), and stir for 30 minutes. Add deionized water and dichloromethane and then separate the organic layer. Extract the aqueous layer with dichloromethane many times. Then wash the organics with deionized water (3×). Combine the washes and back extract them with dichloromethane. Wash the organics with a saturated solution of sodium chloride, and back extract the combined washes with dichloromethane. Dry (sodium sulfate), filter, and concentrate the organics under reduced pressure to a residue. After triturating the residue with methanol, isolate the resulting solid by suction filtration, wash with methanol, and dry at ambient temperature under reduced pressure to give the title compound (4.61 g). Concentrate the filtrate under reduced pressure and purify by flash chromatography, eluting with a gradient of ethyl acetate: dichloromethane: hexane (0.25:5:5, 0-100% in hexane) to give the title compound (0.53 g). Total solid: 5.14 g (70.8%). NMR ($^1$H, 300 MHz, CDCl$_3$), δ (ppm): 10.26 (s, 1H), 8.63-8.56 (m, 1H), 7.93-7.85 (m, 1H), 7.84-7.75 (m, 2H), 7.64-7.45 (m, 3H).

Example 93

8-Trifluoromethyl-11H-12-thia-6,11-diaza-dibenzo[a,f]azulen-5-ylamine hydrochloride

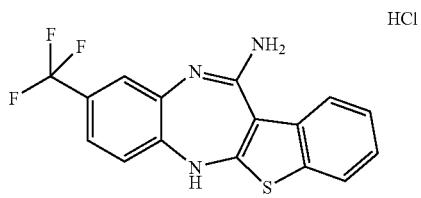

Combine 2-(2-nitro-4-trifluoromethyl-phenylamino)-benzo[b]thiophene-3-carbonitrile (5.14 g, 14.1 mmol) and tin(II) chloride (8.05 g, 42.4 mmol) in absolute ethanol and 5N HCl (60 mL each) and reflux the suspension for 1.5 hours. Cool the reaction to ambient temperature. Collect the reaction solid by suction filtration, wash it with cold ethanol, and dry it at 40° C. under reduced pressure to give the title compound (5.083 g). Isolate a second crop of material from the initial filtrate and dry at 40° C. under reduced pressure to give the title compound (0.482 g). Total solid: 5.20 g (94.6%). Mass spectrum (APCI+, m/e): 334 (M+1-HCl); NMR ($^1$H, 300 MHz, DMSO-$d_6$), δ (ppm): 11.71 (s, 1H), 10.32 (s, 1H), 9.32-9.10 (m, 2H), 7.94-7.85 (m, 1H), 7.74-7.65 (m, 1H), 7.60-7.51 (m, 1H), 7.49-7.40 (m, 1H), 7.39-7.27 (m, 2H), 7.23-7.14 (m, 1H).

Example 94

3-Bromo-2-nitro-benzo[b]thiophene

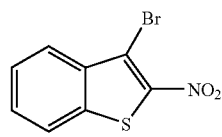

Add dropwise fuming nitric acid (90%, 8.6 mL, 183 mmol) to a mixture of 3-bromo benzo[b]thiophene (39 g, 183 mmol) in TFA (100 mL) and dichloromethane (400 mL) at 0° C. The reaction turn greenish, then yellow precipitates. To this reaction mixture, add dichloromethane (200 mL) and the reaction stir at 0° C. for 30 min. Then pour the reaction into ice-water (2L). Extract with dichloromethane (3×500 mL) and the organic layer dry over MgSO4. Evaporation give a yellow solid. The resulting yellow solid triturate with diethyl ether to give a yellow solid. (Total: 34.8 g, 73%). Mass spectrum (m/e): 259(M+1); $^1$HNMR(300 MHz, DMSO-$d_6$) δ ppm: 7.70(tt, 2H), 8.04(d, 1H), 8.17(d, 1H). $^{13}$CNMR(75 MHz, DMSO-$d_6$) δ ppm: 112.5, 124.8, 126.9, 127.9, 131.3, 137.0, 137.2, 166.1.

Example 95

2-Nitro-Benzo[b]thiophene-3-carbonitrile

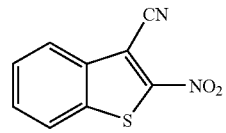

Combine 3-bromo-2-nitro-benzo[b]thiophene (33.0 g, 127.4 mmol), copper cyanide (17.1 g, 191.1 mmol) in DMF (150 mL), heat to 120° C. for three hours. The reaction cool to RT, pour on ice, then filter. The filter cake wash with dichloromethane. The organic layer separate and dry over MgSO$_4$, evaporation to give a DMF solution. Add water (400 mL) and the yellow solid precipitate out. After filtration, obtain a brownish solid (23.5 g, 90%). Mass spectrum (m/e): 205 (M+1); $^1$HNMR (300 MHz, DMSO-$d_6$) δ: 7.78 (m, 2H), 8.04(d, 1H), 8.29(d, 1H). $^3$CNMR(75 MHz, DMSO-$d_6$) δ ppm: 105.9, 112.1, 125.0, 125.2, 128.8, 131.2, 135.9, 137.8, 158.0.

Example 96

2-Amino-benzo[b]thiophene-3-carbonitrile

Combine in a 500 mL schlenk flask, 2-nitro-benzo[b]thiophene-3-carbonitrile (5.8 g, 28.4 mmol) and Pd/C (3.0 g, 10% w/w, 2.84 mmol) in 1,2-dichloroethane (120 ml), the reaction mixture is charged with a balloon of hydrogen. After overnight stirring, release the hydrogen, remove the catalyst by filtration, and wash the catalyst by 1,2-dichloroethane several times. Concentrate down to a residue, which purified by flash chromatography on silica gel, gradient (100% hexane to 100% of Hexane:CH$_2$Cl$_2$:EtOAc=50:50:2.5), afford brownish solid 3.6 g of title compound (yield 73%). Mass spectrum: ES(+)(m/e): 175(M+1); $^1$H NMR (300 MHz, DMSO-$d_6$, ppm): δ 7.81 (br, 2H), 7.65-7.62 (m, 1H), 7.28-7.24 (m, 2H), 7.11-7.01 (m, 1H).

Example 97

2-(5-Fluoro-2-nitro-phenylamino)-benzo[b]thiophene-3-carbonitrile

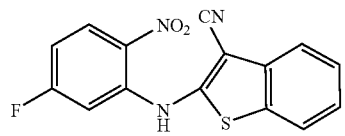

Combine 2-amino-benzo[b]thiophene-3-carbonitrile (2.25 g, 12.5 mmol), 2,4-difluoro-nitrobenzene (1.99 g, 12.5 mmol and Lithium hydroxide (0.58 g, 25 mmol)) in 30 mL of DMSO and heat to 50° C., after 4 hours, cool the reaction to the RT, and pour on ice, stir for 30 min, extract with CH$_2$Cl$_2$, the combined solvent wash with water and brine, dry over Na$_2$SO$_4$. Concentrate down to a residue treat with MeOH, the orange precipitate collect by suction filtration give title compound, 2.15 g. Concentrate the filtrate and purify by flash chromatography to give 0.22 g orange solid.

Total 2.35 g, yield 61%. Mass spectrum: ES(+) (m/e): 314((M+1): $^1$H NMR (300 MHz, DMSO-$d_6$) δ: 10.35 (br, 1H), 8.31-8.25 (m, 1H), 8.00-7.96 (m, 1H), 7.68-7.65 (m, 1H), 7.53-7.37 (m, 3H), 7.13-7.07 9 m, 1H); $^{13}$C NMR (75 MHz, DMSO-$d_6$) δ ppm: 165.5 (d, J=254.5 Hz), 156.2, 139.8 (d, J=12.5 Hz), 135.9, 134.8, 132.2, 129.3 (d, J=11.7 Hz), 126.3, 125.2, 123.0, 120.4, 113.5, 110.4 (d, J=24.0 Hz), 107.6 (d, J=27.4 Hz), 92.9.

Example 98

9-Fluoro-11H-12-thia-6,11-diaza-dibenzo[a,f]azulen-5-ylamine, hydrochloride

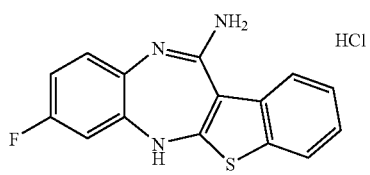

Combine 2-(5-fluoro-2-nitro-phenylamino)-benzo[b]thiophene-3-carbonitrile (2.15 g, 6.87 mmol) and Tin(II) chloride, dihydrate (4.65 g, 20.6 mmol) in a mixed solvent of EtOH (25 mL) and 5.0 N HCl (25 mL), heat the suspension to reflux for 3 hours, cool to RT. Suction filtration obtains the title compound 1.73 g (yield 78%) as a yellow solid by. Mass spectrum: ACPI (m/e): 284((M+1-HCl); $^1$H NMR (300 MHz, DMSO-$d_6$) δ 11.46 (br, 1H), 10.02 (br, 1H), 9.02 (br, 2H), 7.90-7.87 (m, 1H), 7.71-7.68 (m, 1H), 7.46-7.40 (m, 1H), 7.33-7.28 (m, 1H), 7.12-6.94 (m, 2H), 6.85-6.81(m, 1H).

Example 99

2-Amino-5-tert-butyl-thiophene-3-carbonitrile

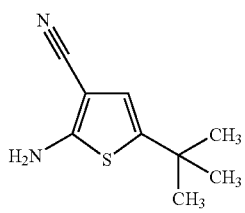

Add a solution of 3,3-dimethyl-butyraldehyde (20 g, 200 mmol) in EtOH (40 mL) dropwise a mixture of sulfur (6.4 g, 200 mmol), malononitrile (13.2 g, 200 mmol) and triethylamine (14.3 mL, 100 mmol) in EtOH (400 mL) at 0° C. Stir the mixture at room temperature for 20 minutes after the addition is complete, then reflux for 2 hours. Cool, concentrate to a paste. Add diethyl ether (200 mL) and 2N HCl (200 mL). Wash the organic layer again with 2N HCl, dry ($Na_2SO_4$), and concentrate. Purify the residue via column chromatography eluting with methylene chloride to afford the title compound as tan crystals (16.9 g, 47%): $^1$H NMR (CDCl$_3$) δ 1.27 (s, 9H), 4.60 (bs, 2H), 6.36 (s, 1H).

Example 100

2-Amino-5-iso-propyl-thiophene-3-carbonitrile

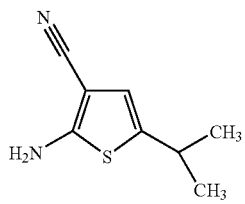

Substitute isovaleraldehyde for 3,3-dimethyl-butyraldehyde and use the method of Example 99 to obtain the title compound as a brown solid: $^1$H NMR (CDCl$_3$) δ 1.24 (d, 6H), 2.93 (septet, 1H), 6.37 (s, 1H).

Example 101

2-Amino-5-cyclopentyl-thiophene-3-carbonitrile

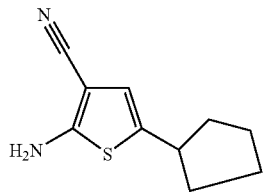

Substitute 2-cyclopentylacetaldehyde for 3,3-dimethyl-butyraldehyde and substitute DMF for EtOH and use the method of Example 99 to obtain the title compound (16.1 g, 57%) as a yellow solid: $^1$H NMR (CDCl$_3$) δ 1.48-1.58 (m, 2H), 1.61-1.69 (m, 2H), 1.72-1.78 (m, 2H), 1.98-2.07 (m, 2H), 3.01 (m, 1H), 4.58 (bs, 2H), 6.38 (s, 1H).

Example 102

5-tert-Butyl-2-(2-nitro-phenylamino)-thiophene-3-carbonitrile

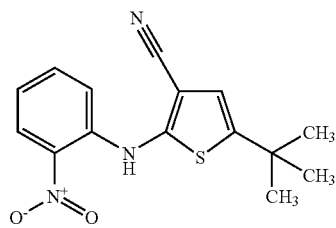

Add a solution of 2-amino-5-tert-butyl-thiophene-3-carbonitrile (16.9 g, 94 mmol) in THF (50 mL) to a mixture of washed NaH (from 6.76 g of 60% mineral oil dispersion) in THF (200 mL) in a water bath at room temperature. Stir 15 minutes, then add a solution of 2-fluoro-nitrobenzene (13.2 g, 94 mmol) in THF (50 mL) dropwise. Stir overnight. Pour the purple reaction mixture unto 6 N HCl (400 mL). Extract the mixture with diethyl ether (400 mL). Wash the ether layer with 2 N HCl (400 mL), brine (250 mL), dry (Na₂SO₄), and concentrate to afford a mixture of crystals in a dark oily residue. Triturate the crystals with hexanes and filter to afford the title compound as a red powder (21.2 g, 75%) mp 85-90° C.: ¹H NMR (CDCl₃) δ 1.39 (s, 9H), 6.81 (s, 1H), 6.97 (t, 1H), 7.23 (d, 1H), 7.53 (t, 1H), 8.25 (d, 1H), 9.66 (bs, 1H).

By the method of Example 102, the following compounds were prepared and isolated as the free base:

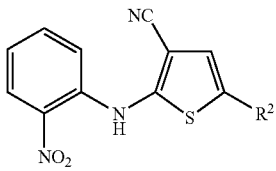

| No: | R² | Data |
|---|---|---|
| 103 | i-Pr | ¹H NMR(CDCl₃)δ 1.35(d, 6H), 3.13(septet, 1H), 6.80(s, 1H), 6.96(t, 1H), 7.22(d, 1H), 7.54(t, 1H), 8.24(d, 1H), 9.65(s, 1H). |
| 104 | c-Pentyl | ¹H NMR(CDCl₃)δ 1.56-1.84(m, 6H), 2.11-2.19(m, 2H), 3.18(pentet, 1H), 6.80(s, 1H), 6.96(t, 1H), 7.21(d, 1H), 7.53(t, 1H), 8.25(d, 1H), 9.64(s, 1H). |

Example 105

2-tert-Butyl-4H-3-thia-4,9-diaza-benzo[f]azulen-10-ylamine hydrochloride

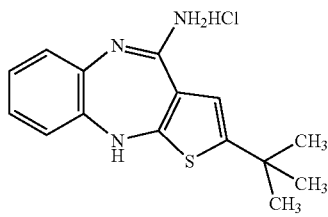

Add 5-tert-butyl-2-(2-nitro-phenylamino)-thiophene-3-carbonitrile (21.2 g, 70 mmol) to a solution of tin(II)chloride dihydrate (46.1 g, 209 mmol) in conc. HCl (200 mL) and ethanol (600 mL). Reflux the mixture for 2 hours. Concentrate the solution to 200 mL and add to water (1 L). Filter and wash with water then hexanes to obtain the title compound as an orange powder (19.4 g): ¹H NMR (DMSO-d₆) δ 1.27 (s, 9H), 6.86 (d, 1H), 6.89 (s, 1H), 6.95 (d, 1H), 7.03 (t, 1H), 7.11 (t, 1H), 8.69 (s, 1H), 9.11 (s, 1H), 9.52 (s, 1H), 10.88 (s, 1H); MS (APCI) m/z (rel intensity) 272 (100).

By the method of Example 105, the following compounds were prepared and isolated as the free base:

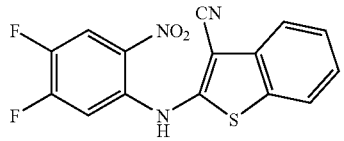

| No. | R | Data |
|---|---|---|
| 106 | i-Pr | ¹H NMR(DMSO-d₆)δ 1.16(d, 6H), 2.88 (septet, 1H), 6.82(s, 1H), 6.83(d, 1H), 6.91(d, 1H), 6.99(t, 1H), 7.07(t, 1H), 8.71(s, 1H), 9.09(s, 1H), 9.54(s, 1H), 10.94(s, 1H). |
| 107 | cyclo-pentyl | ¹H NMR(DMSO-d₆)δ 1.42-1.70(m, 6H), 1.92-2.00(m, 2H), 2.99(pentet, 1H), 6.81(s, 1H), 6.82(d, 1H), 6.91(d, 1H), 6.99(t, 1H), 7.07(t, 1H), 8.63(bs, 1H), 9.05(bs, 1H), 9.50(bs, 1H), 10.79 (bs, 1H). |

Example 108

2-(4,5-Di-fluoro-2-nitro-phenylamino)-benzo[b]thiophene-3-carbonitrile

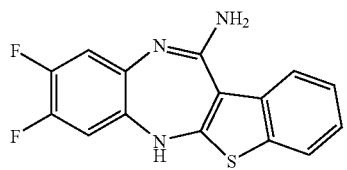

Combine 2-amino-benzo[b]thiophene-3-carbonitrile (3.93 g, 22.6 mmol), 2,4,5-trifluoro-nitrobenzene (4.0 g, 22.6 mmol) in 30 mL of THF, add sodium hydride (3.54 g, 88.5 mmol)) portionwise at 0~5° C., after addition, the reaction stir overnight at RT, Pour the rection on ice water (200 mL), extract with dichloromethane (3×50 mL), the combined organic layer wash with water and brine, dry over Na₂SO₄. Concentrate down to a residue, purify by chromatography, gradient hexanes to hexane:CH₂Cl₂: EtOAc=5:5: 0.5, obtain red orange solid 1.71 g as the title compound. ¹H NMR (300 MHz, DMSO-d₆): δ 10.34 (br, 1H), 8.41-8.35 (m, 1H), 7.96-7.94 (m, 1H), 7.85-7.79 (m, 1H), 7.64-7.61 (m, 1H), 7.52-7.49 (m, 1H), 7.42-7.36 (m, 1H).

Example 109

8,9-Di-fluoro-11H-12-thia-6,11-diaza-dibenzo[a,f]azulen-5-ylamine hydrogenchloride

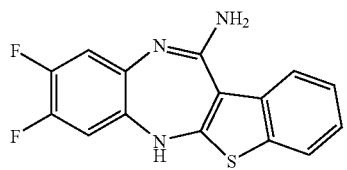

Combine 2-(4,5-difluoro-2-nitro-phenylamino)-benzo[b]thiophene-3-carbonitrile (2.03 g, 6.13 mmol) and Tin(II)

chloride (3.49 g, 18.4 mmol) in a mixed solvent of EtOH (20 mL) and 5.0 N HCl (20 mL), heat the suspension to reflux for overnight, cool to RT. The title compound 2.05 g btaine as a yellow solid by suction filtration. $^1$H NMR (300 MHz, DMSO-d$_6$): δ 11.56 (br, 1H), 10.06 (br, 1H), 9.14 (br, 2H), 7.96-7.85 (m, 1H), 7.71-7.64 (m, 1H), 7.49-7.42 (m, 1H), 7.34-7.29 (m, 1H), 7.22-7.16 (m, 1H), 7.11-7.04 (m, 2H).

Example 110

2-(4-Chloro-2-nitro-phenylamino)-thiophene-3-carbonitrile

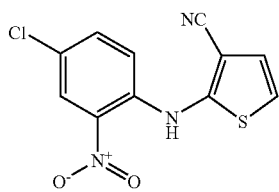

Combine 1,4-dichloro-2-nitro-benzene (3.87 g, 20.13 mmol), 2-aminothiophene-3-carbonitrile (2.50 g, 20.13 mmol), and DMSO (25.0 ml). Add lithium hydroxide monohydrate (1.69 g, 40.27 mmol) all at once and then stir the mixture at ambient temperature for 24 hours. Pour the mixture onto ice chips and stir it for 1.5 hours. Remove the resulting orange precipitate by vacuum filtration and then dry it under vacuum to give 4.85 g (86%) of the title compound: mass spectrum (ion spray): m/z=279.1 (M+1).

Example 111

7-Chloro-4H-3-thia-4,9-diaza-benzo[f]azulen-10-ylamine hydrochloride

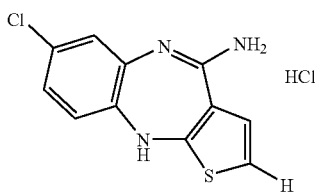

Suspend 2-(4-chloro-2-nitro-phenylamino)-thiophene-3-carbonitrile (4.85 g, 17.35 mmol) in ethanol (40.0 ml). Dissolve tin(II) chloride dihydrate (11.75 g, 52.06 mmol) in 5N HCl (40.0 ml) and then add it to the suspension. Heat the reaction at reflux for 48 hours. Cool the reaction to ambient temperature and then chill it in a refrigerator for 2 hours. Collect the resulting precipitate by vacuum filtration and then dry it under vacuum to give 3.53 g (71%) of the title compound: mass spectrum (ion spray): m/z=250.0 (M+1).

Example 112

2-(5-Fluoro-2-nitro-phenylamino)-thiophene-3-carbonitrile

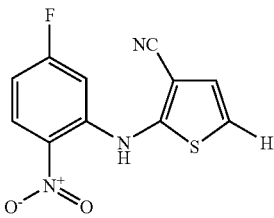

Combine 2,4-difluoro-1-nitro-benzene (5.24 g, 32.94 mmol), 2-aminothiophene-3-carbonitrile (4.09 g, 32.94 mmol), and DMSO (30.0 ml). Add lithium hydroxide monohydrate (2.76 g, 65.88 mmol) all at once and then stir the mixture at 55° for 22 hours. Cool the mixture to ambient temperature and then pour it onto ice chips. Extract with ethyl acetate and then wash (brine), dry (sodium sulfate), and evaporate the organic to residue. Purify the residue on silica gel using hexanes/dichloromethane (35:65) to give 3.89 g (45%) of the title compound as a red solid: mass spectrum (ion spray): m/z=262.0 (M−1).

Example 113

6-Fluoro-4H-3-thia-4,9-diaza-benzo[f]azulen-10-ylamine hydrochloride

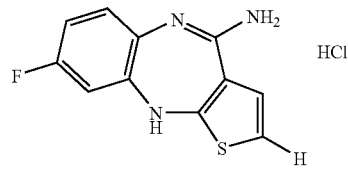

Suspend 2-(5-fluoro-2-nitro-phenylamino)-thiophene-3-carbonitrile (3.89 g, 14.78 mmol) in ethanol (40.0 ml). Dissolve tin(II) chloride dihydrate (10.00 g, 44.33 mmol) in 5N HCl (40.0 ml) and then add it to the suspension. Heat the reaction at reflux for 2.5 hours and then cool it to ambient temperature. Collect the resulting precipitate by vacuum filtration and then dry it under vacuum to give 3.32 g (83%) of the title compound: mass spectrum (ion spray): m/z=234.1 (M+1).

Example 114

2-(2-Nitro-phenylamino)-benzo[b]thiiophene-3-carbonitrile

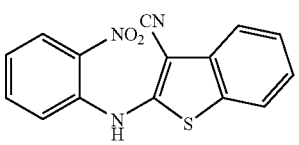

Combine 2-amino-benzo[b]thiophene-3-carbonitrile (3.56 g, 20.5 mmol), 2-fluoro-nitrobenzene (2.88 g, 20.5 mmol) and lithium hydroxide (0.96 g, 41.0 mmol)) in 50 mL of DMSO and heat to 50° C., after over night heating cool the reaction to the RT, and pour on ice, stir for 30 min, extract with $CH_2Cl_2$, the combined solvent wash with water and brine, dry over $Na_2SO_4$. Concentrate down to a residue treat with MeOH, collect the precipitate by suction filtration. Concentrate the filtrate and purify by flash chromatography to give 5.0 g, yield 83%. Mass spectrum: ES(+) (m/e): 296.0 ((M+1); $^1$H NMR (400 MHz, DMSO-$d_6$): δ 10.27 (s, 1H), 8.13 (dd, 1H, J=1.7 Hz, J=8.3 Hz), 7.91-7.89 (m, 1H), 7.76-7.72 (m, 1H), 7.64-7.57 (m, 2H), 7.48-7.44 (m, 1H), 7.36-7.32 (m, 2H).

Example 115

11H-12-Thia-6,11-diaza-dibenzo[a,f]azulen-5-ylamine hydrochloride

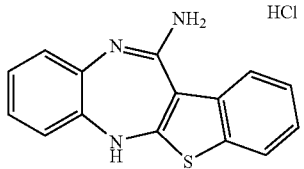

Combine 2-(2-nitro-phenylamino)-benzo[b]thiiophene-3-carbonitrile (5.0 g, 17.0 mmol) and Tin(II) chloride (9.65 g, 51.0 mmol) in a mixed solvent of EtOH (50 mL) and 5.0 N HCl (50 mL), heat the suspension to reflux for 3 hours, cool to RT. Suction filtration obtains the title compound 4.65 g (yield 91%) as a yellow solid by mass spectrum: ACPI (m/e): 266.0 ((M+1-HCl); $^1$H NMR (300 MHz, DMSO-$d_6$): δ 11.7 (br, 1H), 10.00 (br, 1H), 9.10 (br, 2H), 7.90-7.85 (m, 1H), 7.72-7.65 (m, 1H), 7.48-7.38 (m, 1H), 7.35-7.28 (m, 1H), 7.22-6.98 (m, 4H).

Example 116

2-(4,5-Difluoro-2-nitro-phenylamino)-5-methyl-thiophene-3-carbonitrile

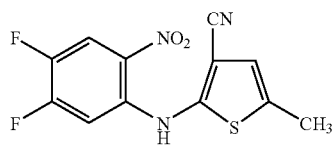

Add sodium hydride, 60% dispersion in mineral oil (55.0 g×60%=33.0 g, 1.38 mol) to THF (950 mL) with stirring at 0-5° C. under nitrogen. Add a solution of 2-amino-5-methyl-thiophene-3-carbonitrile (95.0 g, 0.687 mol) and 1,2,4-trifluoro-5-nitro-benzene (121.7 g, 0.687 mol) in THF (1325 mL) dropwise over ~1 hour, keeping the temperature below 10° C. Allow the reaction to warm to ambient temperature and stir for 8-20 hours. Cool to 10-15° C. and add aqueous 1N HCl (550 mL) dropwise over 10-15 minutes to adjust the pH to 7.0-7.2, keeping the pot temperature below 15° C. Remove most of the organic portion under reduced pressure, and then filter and rinse with water. Dry at 50-60° C. to obtain the crude product. Purify by flash chromatography, eluting with 1:1/methylene chloride:heptane to give 89.1 g (44%) of the title compound. $^1$H NMR (400 MHz, DMSO-$d_6$) δ 9.77 (bs, 1H), 8.33 (m, 1H), 7.09 (s, 1H), 7.07 (m, 1H), 2.47 (s, 3H). HRMS (ES) exact mass M+H calcd for $C_{12}H_7F_2N_3O_2S$ 318.0125; found 318.0133.

Example 117

6,7-Difluoro-2-methyl-4H-3-thia-4,9-diaza-benzo[f]azulen-10-ylamine hydrochloride

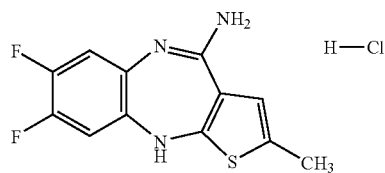

Add 2-(4,5-difluoro-2-nitro-phenylamino)-5-methyl-thiophene-3-carbonitrile (94.0 g, 318 mmol) and tin (II) chloride dihydrate (225 g, 997 mmol) to ethanol (1400 mL) and aqueous 6N HCl (1400 mL) with stirring under nitrogen. Heat at gentle reflux (86-87° C.) for 0.3 hours, and then allow cooling to ambient temperature. Filter, rinse with water (3×250 mL) and dry at 50-60° C. to give 95.7 g (100%) of the title compound. $^1$H NMR (400 MHz, DMSO-$d_6$) δ 11.41 (bs, 1H), 9.84 (bs, 1H), 9.33 (bs, 1H), 8.93 (bs, 1H), 7.00 (m, 2H), 6.85 (s, 1H), 2.28 (s, 3H). HRMS (ES) exact mass M+H calcd for $C_{12}H_9F_2N_3S$ (freebase) 266.0563; found 266.0555.

Example 118

2-(4-Chloro-2-nitro-phenylamino)-5-methyl-thiophene-3-carbonitrile

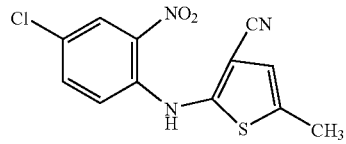

Stir in a 3 neck 500 mL round bottom flask, 2-amino-5-methyl-thiophene-3-carbonitrile (124.11 g, 0.898 mol, 1 eauiv.), 1,4-dichloro-2-nitro-benzene (174.15 g, 0.907 mol, 1.01 equiv), and DMSO (1.6 L, 13 vol)) for 15 min. (dark solution). Charge in one portion, LiOH $H_2O$ (75.37 g, 1.796 mol, 2 equiv). Began to exotherm from 20.4° C. to 25.5° C. over 10 minutes. After 30 minutes temp reaches 28.1° C. and at 1 hour 30.4° C. Place tap water in the bath around the flask to control the exotherm. Check HPLC at 23 h, which shows 81.2% of desired product. Let continue to stir at ambient temperature for greater reaction conversion. Check HPLC at 39 h, which shows 83.5% of one product. Let stir 40 hours total. Cool with ice/water bath to 17° C. Begin pH adjustment by slowly adding 1 N HCl (1020 mL) to reach pH=7.1. Keep exotherm is at 15-22° C. during the addition. Workup includes: pouring reaction mixture into 22 L bottom outlet flask, rinsing in with $CH_2Cl_2$ (5.6 L) and 5% LiCl solution (3.6 L), stirring about 10 min., and allowing layers to separate. The lower layer might be darker than upper layer. Back-extract the aqueous layer with CH$_2$Cl$_2$ (1.5 L). Combine organic layers and wash with 5% LiCl solution (3×1.3 L). Dry organic layer with Na$_2$SO$_4$ (800 g) allowing it to stir 1 hour, filter and evaporate to dryness. Wt.=376 g. Back-extract the combined aqueous layers with CH$_2$Cl$_2$ (0.5 L). Check aq layer by HPLC ~2 mL aq layer in 15 mL of eluent for product in aq layer. Wash the organic phase with brine (2×500 mL) and finally with 5% LiCl (500 mL). Dry over the weekend with NaSO$_4$ (80 g). Filter and add to other organic layer. For Chromatography, dissolve crude material in methylene chloride (950 g) and charge to a silica gel 60 (2.8 kg pre wetted with heptane) bed on fritted funnel. Some product might crash out on top of silica cake. Rinse flask and add to top of cake with CH$_2$Cl$_2$ (0.3 L) until all of the precipitate is dissolve and onto the column. Elute with heptane (~16 L), then 25% CH$_2$Cl$_2$ in heptane (~8 L), then 37.5% CH$_2$Cl$_2$ in heptane (~8 L), follow by 50% CH$_2$Cl$_2$ in heptane and 100% CH$_2$Cl$_2$. Early Fractions might contain no product. Identify mix fractions containing product and rundown separately until virtually all methylene chloride is gone leaving the product in heptane, cool to 0° C. and filter. Filtrate analysis shows 5% product by area % integration. Combine product only fractions and evaporate to dryness. Add cake from mixed fractions. Combined dry weight=197.4 g. HPLC area percent=97.0% NMR is consistent with desired procduct: Yield 74.8%.

Example 119

7-Chloro-2-methyl-4H-3-thia-4,9-diaza-benzo[f]azulen-10-ylamine hydrochloride

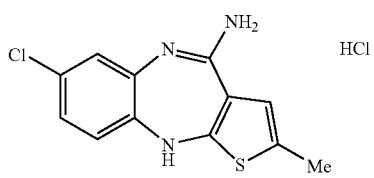

Stir in a 3 neck 12 L round bottom flask, 2-(4-chloro-2-nitro-phenylamino)-5-methyl-thiophene-3-carbonitrile (204.9 g, 0.6976 mol, 1 equiv), 3 A EtOH (2 L), and 6N HCl (2 L) for 10 min. Charge to the slurry in one portion, tin (II) chloride (404.1 g, 2.131 mol, 3.06 equiv) and heat to gentle reflux at 85° C. for 3 hours. HPLC at 3 hours shows <0.4% starting material. Allow mixture to cool and stir overnight. During the workup there is a possibility of tin salts precipitating with the product, did not cool as in lab trial, Workup includes: filtering reaction mixture, rinsing with ambient 1:1 3A EtOH/6N HCl (2×500 mL), rinsing with DI water (2×50 mL), drying in vacuum oven at 60° C. for 2 days. Wt.=231.5 g, and anaylsis. Discard some very small amount of precipitate which appears in the filtrate. Tin Removal in Hot 1 N HCl involves placing 231.5 g of the yellow crude product in 22 L flask, adding 1 N HCl (11.6 L), heating to 95° C. and holding at that temperature for 1 hour, shuting off heat and allowing to cool with heating mantle in place overnight. The next morning the temperature is 29° C. Remove mantle and replace with water bath and cool to 22° C. and filter. Rinse flask and add to cake with 1 N HCl (4 L) and follow by DI water (4 L). Pull air through the cake for 10 minutes, place in vacuum oven at 60° C. for 40 hours (Note: Only 1 gram of weight was lost over the final 16 hours of drying time.)

Dry weight of title compound is 200.4 g (95.7%). Perform tin analysis. NMR is consistent with product. HPLC showed 98.5%.

Example 120

7-Chloro-2-methyl-4,9-dihydro-3-thia-4,9-diaza-benzo[f]azulene-10-thione

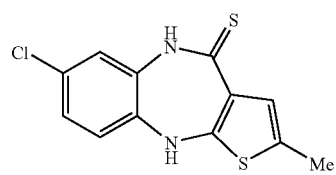

Stir in a 3 neck 22 L round bottom flask, 7-chloro-2-methyl-4H-3-thia-4,9-diaza-benzo[f]azulen-10-ylamine hydrochloride (199 g, 0.6629 mol, 1 equiv.), DI water (6 L), and 3 A EtOH (2 L) for 15 min. Charge to the slurry in one portion, powder potassium carbonate (690.6 g, 4.997 mol, 7.54 equiv.), stir for 10 min, then heat to gentle reflux at 84-85° C. After 3 days, HPLC shows 10.7% starting material. Maintain reaction at reflux for another day. After 4 days, HPLC shows 10.1% starting material remaining. Since, the reaction is not proceeding, allow the mixture to cool to 20-25° C. and filter and rinse with 3:1 3A EtOH/DI water (1.2 L) and follow by DI water (1.2 L). Dry the solid in the vacuum oven for 48 hours at 50° C. After 24 hours the solid is still losing weight. Dry weight=157.6 g. HPLC 85.2% desired amide, 9.8% amidine starting material. NMR shows product and other resonances. Yield of title compound is 157.6 g (89.8%). Appearing in the filtrate is some very small amount of precipitate. Filtering, rinsing with DI water, and drying gives the title compound as a dry weight =1.45 g. HPLC of the mother liquor shows 10.9% desired product left.

Example 120a

7-Chloro-2-methyl-10-methylsulfanyl-4H-3-thia-4,9-diaza-benzo[f]azulene

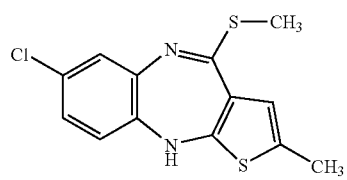

Stir 7-chloro-2-methyl-4,9-dihydro-3-thia-4,9-diaza-benzo[f]azulene-10-thione (59.1 g, 0.210 mol) and DMF (236.4 mL) under nitrogen for 15 minutes at ambient temperature. Add powdered potassium carbonate (61.1 g, 0.442 mol); stir 15 minutes at ambient temperature. Add iodomethane (26.2 mL, 0.421 mol) and stir 2.5 hours at ambient temperature. Add MTBE (591 mL) and stir 15 minutes at ambient temperature. Filter and rinse solids with MTBE (59.1 mL). Wash the organic filtrate with water (3×591 mL), then dry over sodium sulfate, filter and concentrate under reduced pressure to give 60.0 g (96.7%) of crude product. $^1$H NMR (500 MHz, DMSO-$d_6$) δ 2.22 (s, 3H), 2.39 (s, 3H), 6.47 (d, 1H), 6.57 (d, 1H), 6.86 (d, 1H), 6.97(dd, 1H), 8.09 (bs, 1H). $^{13}$C NMR (100 MHz, DMSO-$d_6$) δ 13.24, 14.70, 120.58, 120.62, 121.67, 125.64, 127.51, 127.52, 127.77, 141.65, 142.16, 153.99, 165.48.

Example 121

2-Isopropyl-10-methylsulfanyl-4H-3-thia-1,4,9-triaza-benzo[f]azulene

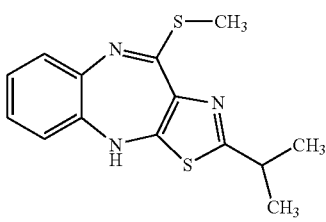

Equip a 750 mL 3-necked Euro-flask with a magnetic stir bar, septum with thermometer lead, addition funnel, nitrogen inlet, and a cooling bath. Charge the flask with compound 2-isopropyl-4,9-dihydro-3-thia-1,4,9-triaza-benzo[f]azulene-10-thione (49.8 g, ~0.181 mol, contained 9.7% (wt. %) of 1,2 dichloroethane, No allowance was made for this fact during the calculations of number of equivalents of the other reagents employed in the reaction) and DMF (249 mL, 5 volumes based on starting material). Allow the resulting mixture to stir at ambient temperature for 5 minutes to dissolve all solids. Add powdered $K_2CO_3$ (325 mesh, 138.2 g, ~0.381 mol, ~2.1 eqs.) to the reaction vessel and stir continuously for 5 minutes. Charge methyl iodide (22.5 mL, ~0.362 mol, ~2.0 eqs.) to the addition funnel, add drop-wise to the above mixture over 20 minutes. Maintain the pot temperature below 28.0° C. via the addition of cool tap water to the cooling bath. Allow the resulting mixture to stir at ambient temperature for an additional hour. Remove a sample of the reaction mixture, and analyze by TLC (60/40 v/v hexanes/acetone, UV). Reaction mixture is found to contain no starting material. Add MTBE (500 mL, 10 vols.) to the reaction mixture, and stir continuously for 20 minutes. Subsequently, filter the mixture and rinse the solids with MTBE (250 mL, 5 vols.). Transfer the filtrate to a separatory funnel and dilute with deionized water (500 mL, 10 vols.). After shaking, separate the layers and re-extract the aqueous layer with MTBE (250 mL, 5 vols.). Combine the organic portions and wash with deionized water (3×500 mL), dry over $Na_2SO_4$, filter, and concentrate in vacuo. Allow the resulting thick orange oil to pull under vacuum overnight at ambient temperature. Crystallization of the material affords 45.17 grams of yellow-orange solids: The crude material was analyzed by HPLC using the following system: Column=Zorbax C-8, Flow=1 mL/min., A=ACN, B=0.1% aqueous TFA, Gradient=95% A/5% B to 5% A/95% B over 10 minutes. Hold at 5/95 A/B for 3 minutes, and return to 95/5 A/B over 2 minutes, Column temperature=30° C., Wavelength=250 nm. Using the above HPLC system, the crude material was assayed and found to be 97.1% pure: $^1$H NMR (500 MHz, DMSO-$d_6$): δ 1.19 (d, 6H), 2.32 (s, 3 H), 2.99-3.02 (m, 1 H), 6.50 (d, 1 H), 6.80 (d, 1 H), 6.82-6.90 (m, 2 H), 8.10 (bs, 1 H). $^{13}$C NMR (100 MHz, DMSO-$d_6$): δ 13.29, 22.88, 32.92, 119.85, 124.88, 127.19, 129.92, 132.94, 140.40, 142.17, 151.59, 164.42, 164.63. MS (80:20 MeOH:$H_2O$ w/6.5 mM $NH_4OAc$). Calculated: 289.07. Found: ES$^+$ 290.0. ES$^-$ 288.0.

Example 122

2-(4,5-Difluoro-2-nitro-phenylamino)-thiophene-3-carbonitrile

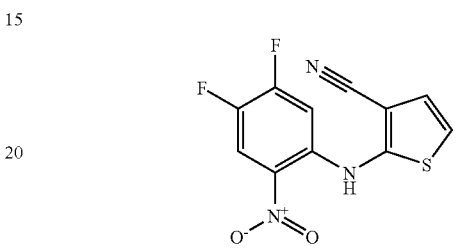

Combine 2,4,5-trifluoro-nitrobenzene (5.00 g, 24.24 mmol), 2-aminothiophene-3-carbonitrile (3.51 g, 28.24 mmol), and anhydrous THF (30.0 ml). Cool the mixture to 10° and then slowly add NaH (2.26 g, 56.47 mmol, 60% dispersion in mineral oil) while keeping the temperature less than 10°. Warm the mixture to ambient temperature after NaH addition is complete. Stir the mixture at ambient temperature for 24 hours and then pour it onto ice chips. Extract the aqueous with ethyl acetate and then wash (brine), dry (sodium sulfate), and reduce the organic to residue. Purify the residue on silica gel using hexanes/dichloromethane (35:65) to give 4.06 g (51%) of the title compound as a red solid: mass spectrum (ion spray): m/z=280.0 (M−1).

Example 123

6,7-Difluoro-4H-3-thia-4,9-diaza-benzo[f]azulen-10-ylamine hydrochloride

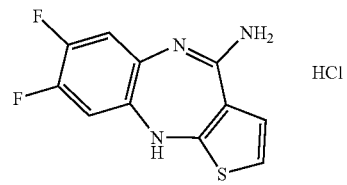

Suspend 2-(4,5-difluoro-2-nitro-phenylamino)-thiophene-3-carbonitrile (4.02 g, 14.30 mmol) in ethanol (40.0 ml). Dissolve tin(II) chloride (8.14 g, 42.91 mmol) in 5N HCl (40.0 ml) and then add it to the suspension. Heat the reaction at reflux for 5.5 hours and then cool it to ambient temperature. Cool the mixture for 16 hours in a refrigerator. Collect the resulting precipitate by vacuum filtration and then dry it by pulling a vacuum on it to give 3.53 g (86%) of the title compound as a yellow solid: mass spectrum (ion spray): m/z =252.1 (M+1).

Example 153

(S)-4-Benzyl-1-methyl-2-(2-methylsulfanyl-ethyl)-piperazine

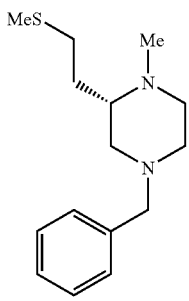

Combine (S)-1-benzyl-3-(2-methylsulfanyl-ethyl)-piperazine (0.900 g, 3.59 mmol) and 37% formaldehyde solution (0.4 mL, 5.39 mmol) in methylene chloride (15 mL). Stir for 10 minutes and add sodium triacetoxy borohydride (3.05 g, 14.4 mmol). Stir an additional 90 minutes and then pour solution onto 1N sodium hydroxide solution. Extract with methylene chloride to give 0.947 g of the crude product. Silica gel chromatography, eluting with methylene chloride:2N ammonia/methanol (100:2), gives 0.906 g of the title compound as a colorless oil; mass spectrum (ion spray): m/z =265 (M+1).

Example 154

(S)-1-Methyl-2-(2-methylsulfanyl-ethyl)-piperazine

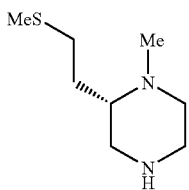

To a cold solution of (S)-4-benzyl-1-methyl-2-(2-methylsulfanyl-ethyl)-piperazine (0.450 g, 1.7 mmol) in 1,2-dichloroethane (5.0 mL) is added dropwise 1-chloroethyl chloroformate (0.24 mL, 2.2 mmol). After stirring at ambient temperature for 18 hours, the 1,2-dichloroethane is evaporated and 40 mL of methanol is added to the residue. This solution is refluxed for 2 hours. Evaporation of the methanol gives the crude product. Silica gel chromatography, eluting with methylene chloride:2N ammonia/methanol (90:10), gives 0.175 g of the title compound as a light yellow oil; mass spectrum (ion spray): m/z=175 (M+1).

Example 155

(S)-1,4-Dibenzyl-2-vinylpiperazine

Example 156

(R)-1,4-Dibenzyl-2-vinylpiperazine

Add anhydrous tetrahydrofuran (4.5 L) to a 10 L flange-neck flask equipped with an air stirrer rod and paddle, thermometer, and nitrogen inlet and outlet tubes. Purge with dry nitrogen gas (inlet tube had a sintered end for maximum gas dispersal) the body of the liquid for 1 h, add tris (dibenzylideneacetone)dipalladium(0) chloroform adduct (36.0 g, 34.8 mmol). Add isopropyl phosphite (67.8 mL, 0.275 mol) in one lot to the mixture still under nitrogen and stir. After 5 minutes, the color lightens from purple to amber. Add dibenzylethylenediamine (322.0 g, 1.34 mol) in one lot, followed by the dropwise addition of cis-1,4-diacetoxy-2-butene (214 mL, 1.34 mol) over 15 minutes stir under nitrogen for 18 hours. Remove the solvent in vacuo at 40° C. and dissolve the residual oil in diethyl ether (2.5 L) and extract with 1N aq. sodium hydroxide (2×2 L). Wash the bulked aqueous extracts with diethyl ether (2×) and basify to pH 14 using 5N aq. sodium hydroxide and extract with diethyl ether (3×). Dry the bulked ethereal extracts over magnesium sulphate, filter and evaporate to dryness in vacuo at 40° C. Purification by chromatography on silica (1.17 kg) using 1% methanol/ether (can also use dichloromethane) gives a pale yellow oil (377.35 g, 96%) 1H NMR and Mass Spec are consistent with product.

Dissolve the mixture of isomers in ethyl acetate (3670 mL) and add portionwise to a hot solution of (S)-(+)-mandelic acid (385 g, 2 eq.) in ethyl acetate (3850 mL), starting at 72° C. Chill the mixture to 0° C. and seed with crystals (obtained from an earlier resolution). Place the mixture in the freezer (−20° C.) overnight. Scrape the crystalline solid away from the sides of the flask and allow the mixture to warm to 0° C. Isolate the solid dry. Further dry the material in vacuo at room temperature. Yield=252.6 g, white, crystalline solid of the S-mandelic acid salt of the (R)-1,4-dibenzyl-2-vinylpiperazine.

Evaporate the filtrate to dryness in vacuo at 40° C. to leave an amber oil. Dissolve the filtrate in dichloromethane (2 L) and wash the solution with 1N aq. sodium hydroxide (2 L+1 L), brine (1 L) and dry over magnesium sulphate. Filter and evaporate to dryness in vacuo at 45° C. to yield the recovered free base. Further dry by vacuum. Extract the aqueous liquors with dichloromethane to further recover any remaining free base (207.6 g). Chiral HPLC showed the material to consist of a 85:15 ratio of isomers in favour of the required isomer.

Add (R)-(−)-mandelic acid (216 g, 1.42 mol) and ethyl acetate (2.5 L) to a 10 liter flange-neck flask equipped with an air stirrer rod and paddle, thermometer and water condenser and warm the suspension to 60° C. Add a solution of free base (207.6 g, 0.71 mol) in ethyl acetate (500 mL) and allow to cool down to room temperature and place in the freezer overnight (at 35° C. solid starts to precipitate). Isolate the crystalline solid by filtration and pull dry. Further dry in vacuo at room temperature (290.34 g).

Recrystallize from hot ethyl acetate (2.3 L) at 70° C. Allow this solution to cool down to room temperature overnight after seeding. Filtration and drying in vacuo at room temperature gives the (R)-mandelic acid salt of the (S)-1,4-dibenzyl-2-vinylpiperazine from which the free base may be prepared (225.44 g). Chiral HPLC showed: 98.74%+ 1.26%: $^1$H NMR, (DMSO-$d_6$): δ 7.20-7.35 (m, 10H); 5.75-5.90 (m, 1H); 5.15-5.30 (q, 2H); 3.85-3.95 (d, 1H); 3.40-3.45 (s, 2H); 3.00-3.10 (d, 1H); 2.80-2.90 (t, 1H); 2.55-2.60 (d, 3H); 1.95-2.10 (m, 3H).

Example 157

(S)-1,4-Dibenzyl-2-Vinyl-piperazine

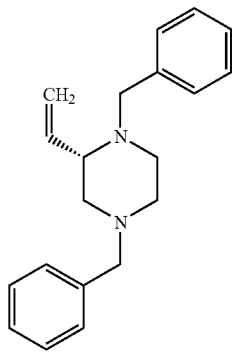

Combine (S)-1,4-dibenzyl-2-vinyl-piperazine mandelic acid salt (200.0 g, 0.450 mol), water (1 L), and 5N sodium hydroxide (112.5 mL, 0.562 mol) and stir at ambient temperature for 15 minutes. Add MTBE (1 L) and stir at ambient temperature for 1 hour. Layer separate and wash the organics with water (2×1 L). Dry the organics over sodium sulfate, filter and concentrate in vacuo to afford 131.2 g of the title compound as an oil (99.7%). $^1$H NMR (500 MHz, DMSO-$d_6$) δ 2.00 (bt, 1H), 2.07 (d, 2H), 2.56 (m, 1H), 2.58 (d, 2H), 2.84 (t, 1H), 3.02 (d, 1H), 3.49 (s, 2H), 3.91 (d, 1H), 5.15 (d, 1H), 5.25 (d, 1H), 5.81 (m, 1H), 7.27 (m, 10H). MS (ES+) M+H calcd for $C_{20}H_{24}N_2$ 292.43; found 293.10.

Example 158

(S)-2-(1,4-Dibenzyl-piperazin-2-yl)-Ethanol

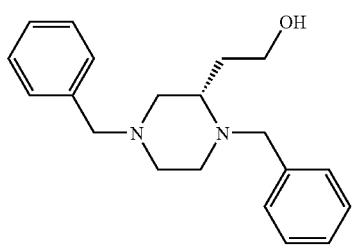

Combine (S)-1,4-dibenzyl-2-vinyl-piperazine (131.0 g, 0.448 mol) and THF (500 mL) at ambient temperature. Add a 0.5M THF solution of 9-borabicyclo[3.3.1] nonane (9-BBN) (985.5 mL, 0.493 mol) over 20 minutes, keeping the pot temperature below 25° C. Stir the resulting mixture at ambient temperature for 16-18 hours. Cool the solution to 0-5° C. and quench with 3N NaOH (164.3 mL, 0.493 mol) over 5-10 minutes. Stir at 0-5° C. for 10-15 minutes and remove cooling bath. Add a 30% aqueous solution of hydrogen peroxide (160.2 mL, 1.57 mol) over 1 hour, maintaining a pot temperature of 30-35° C. Stir the resulting mixture for 1 hour and dilute with water (1.31 L) and MTBE (1.31 L). Layer separate and re-extract the aqueous layer with MTBE (655 mL). Combine organics and wash with water (2×655 mL) and brine (2×655 mL). Dry the MTBE solution over sodium sulfate, filter and concentrate in vacuo to afford 169.1 g of crude oil (theory=139.1 g). Treat the crude with 5N HCl (358 mL, 1.79 moles) and stir 5 minutes. Add water (250 mL) and stir 15-20 minutes. Add heptane (1.31 L) and stir 5 minutes. Layer separate and re-extract the aqueous layer with MTBE (655 mL). Discard these organic extracts and add 5N NaOH (403 mL, 2.02 moles) to the aqueous portion. Stir 5 minutes then dilute with MTBE (1.31 L) and layer separate. Re-extract the aqueous layer with MTBE (655 mL). Combine the MTBE extracts and wash with water (655 mL), then dry over sodium sulfate, filter and concentrate in vacuo to afford 137.8 g (99.0%) of the title compound. $^1$H NMR (500 MHz, DMSO-$d_6$) δ 1.87 (m, 1H), 2.03 (m, 1H), 2.33 (m, 2H), 2.43 (m, 1H), 2.50 (d, 1H), 2.66 (d, 1H), 2.83 (m, 1H), 2.93 (m, 1H), 3.39 (d, 1H), 3.50 (m, 1H), 3.74 (m, 1H), 3.88 (m, 1H), 4.18 (d, 1H), 4.80 (bs, 1H), 7.26 (m, 2H), 7.32 (m, 8H).

Example 159

(S)-1,4-Dibenzyl-2-(2-methoxy-ethyl)-piperazine

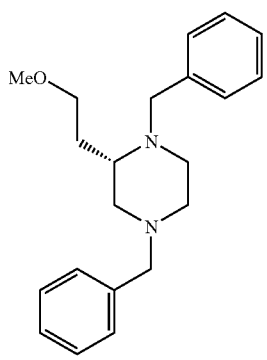

Combine sodium hydride (52.9 g, 1.32 moles) and THF (500 mL) and cool the resulting slurry to 0-5° C. Dissolve (S)-2-(1,4-dibenzyl-piperazin-2-yl)-ethanol (137.0 g, 0.441 mol) in THF (500 mL) and add to the sodium hydride/THF mixture over 30 minutes, maintaining a pot temperature of 0-10° C. Stir the mixture at 0-10° C. for 15-20 minutes, then add dimethyl sulfate (55.6 g, 0.441 mol) over 1 hour, maintaining a pot temperature of 0-10° C. Remove cooling bath and allow reaction mixture to warm to ambient temperature over 1 hour. Stir an additional hour at ambient temperature, re-cool to 0-10° C., then quench with 1N ammonium chloride (863 mL). Extract the mixture with ethyl acetate (2×700 mL). Combine the ethyl acetate extracts and wash with saturated aqueous sodium bicarbonate (2×2 L), dry over magnesium sulfate and concentrate in vacuo to afford 162.1 g of oil. Dissolve the oil in heptane (900 mL) and add water (450 mL). While stirring, add 3N HCl to a pH of 1-2. Layer separate and treat the aqueous layer with 50% caustic to a pH of 13-14. Extract this aqueous solution with methylene chloride (2×1L), combine the organic extracts and dry over magnesium sulfate. Concentrate in vacuo to afford 136.3 g (93.3%) of the title compound. $^1$H NMR (400 MHz, DMSO-$d_6$) δ 1.80 (m, 2H), 2.20 (bm, 2H, 1H), 2.41 (m, 1H), 2.55 (m, 2H), 2.60 (d, 1H), 3.18 (s, 3H), 3.35 (bm, 2H, 1H), 2.40 (d, 1H), 2.52 (d, 1H), 3.90 (d, 1H), MS (ES+) calcd for $C_{21}H_{28}N_2$ 324.47; found 325.2.

Example 160

(S)-2-(2-Methoxy-ethyl)-piperazine

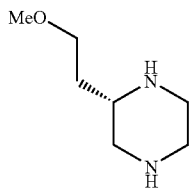

Dissolve (S)-1,4-dibenzyl-2-(2-methoxy-ethyl)-piperazine (2.0 g, 6.2 mmol) in ethanol (15 mL) in a suitable hydrogenation vessel. Add palladium hydroxide (Pearlman's catalyst, 400 mg), purge vessel with nitrogen, then pressure to 60 psi. Heat to 50° C. and stir vigorously for 18-24 hours. Allow the mixture to cool to ambient temperature. Filter off the catalyst and rinse with ethanol (5 mL). Concentrate in vacuo using a 35° C. bath to afford the title compound (0.81 g, 91.1%). $^1$H NMR (500 MHz, DMSO-$d_6$) δ 1.41 (m, 2H), 2.12 (t, 1H), 2.43 (td, 1H), 2.53 (m, 2H, 1H), 2.63 (d, 1H), 2.72 (m, 2H), 3.19. (s, 3H), 3.34 (m, 2H).

Example 161

(S)-(4-Benzyl-3,6-dioxopiperazin-2-yl)acetic acid methyl ester

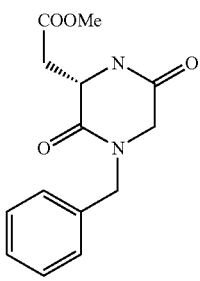

Dissolve commercial N-tBoc-L-aspartic acid β-methyl ester (40 g, 0.16 mol) in dichloromethane (800 mL); cool to 0° C. and add N-benzylglycine methyl ester (28 g, 0.15 mol added as a solution in 100 mL of dichloromethane), followed sequentially by N,N-diisopropylethylamine (28 mL, 0.16 mol), 1-ethyl-3-(3-dimethylaminopropyl) carbodiimide hydrochloride (EDAC, 31 g, 0.16 mol), and 1-hydroxybenzotriazole (22 g, 0.16 mol). Stir at room temperature over the weekend and concentrate in vacuo to an orange oil. Partition oil between 2N hydrochloric acid and ethyl acetate; separate aqueous layer and extract with a second portion of ethyl acetate. Combine organic extracts, concentrate in vacuo, and wash with 10% aqueous potassium carbonate. Dry organic layer over magnesium sulfate, filter and concentrate in vacuo to yield 64 g (95%) of the desired dipeptide as an oily residue.

Dissolve the crude dipeptide in 150 mL of trifluoroacetic acid, stir at room temperature for 1 h; then remove the solvent in vacuo. Take up the resulting residue on 800 mL of commercial 2N ammonia in methanol solution, and stir at room temperature overnight. Heat the mixture at 70° C. for several hours; then cool to room temperature and remove the solvent in vacuo. Redissolve the residue in dichloromethane, filter off the resulting precipitate, and concentrate the filtrate in vacuo. Apply the residue to a silica gel column. Elute with a 2% mixture of 2N ammonia-methanol in dichloromethane to obtain 31.9 g (72%) of the title compound as a yellow oil: mass spectrum (APCI): m/e 277.1 (M+1).

Example 162

(S)-(−)-2-(4-Benzylpiperazin-2-yl)ethanol

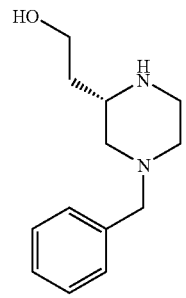

To a 0° C. solution of (S)-(4-benzyl-3,6-dioxopiperazin-2-yl)acetic acid methyl ester (31.9 g, 0.12 mol) in tetrahydrofuran (1 L), add lithium aluminum hydride via slow cannulation (350 mL of a commercial 1.0 M solution in tetrahydrofuran). Stir at room temperature overnight, quench by successive careful addition of 13.3 mL of water, 13.3 mL of 15% aqueous sodium hydroxyde, and 39.9 mL of water, all the while with vigourous stirring to ensure formation of a fine precipitate. Filter through a fritted funnel, washing the solids well with tetrahydrofuran and dichloromethane. Concentrate in vacuo to provide 26.5 g of an oily residue, apply directly to a silica gel column. Elute with a 5% mixture of 7N ammonia-methanol in dichloromethane, to obtain the desired product as an orange oil which solidifies under vacuum. Take up the solid in acetonitrile and sonicate for a few minutes. Filter the resulting precipitate to obtain 7.5 g (25%) of the title compound as an off-white crystalline solid, mp 78.9-80.4° C. Concentrate the mother liquor to obtain 6.8 g (23%) of slightly less pure material as an amorphous solid: mass spectrum (ES): m/e 221.3 (M+1); specific Rotation: −7.84.

Example 163

(S)-4-Benzyl-2-(2-hydroxyethyl)piperazine-1-carboxylic acid tert-butyl ester

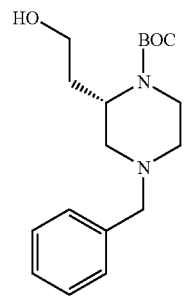

To a solution of (S)-(−)-2-(4-benzylpiperazin-2-yl)ethanol (14.9 g, 67.6 mmol) in dichloromethane (200 mL) add di-tert-butyl dicarbonate (15.5 g, 71 mmol) as a solution in dichloromethane (30 mL). Stir at room temperature 4 h, partition between saturated aqueous bicarbonate and dichloromethane and extract aqueous layer with additional dichloromethane. Combine organic extracts, dry over sodium sulfate, filter and concentrate in vacuo to a residue. Apply residue to silica gel column, eluting with 5% 2N ammonia-methanol in dichloromethane, to obtain title compound as a yellow oil: mass spectrum (APCI): m/e 321.2 (M+1).

Example 164

(R)-2-piperazin-2-yl-ethanol

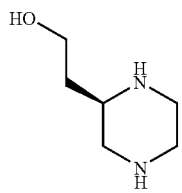

Utilizing a sequence similar to that described in Examples 161 and 162, combine N-tBoc-D-aspartic acid β-benzyl ester with glycine methyl ester to obtain the title compound as a yellow oil: mass spectrum (APCI): m/e 131.1 (M+1).

Example 165

(S)-2-(1,4-Dibenzylpiperazin-2-yl)ethanol

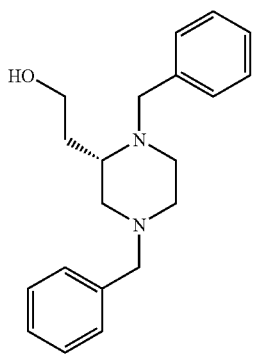

Dissolve (S)-1,4-dibenzyl-2-vinylpiperazine (16.2 g, 55.5 mmol) in tetrahydrofuran (370 mL), add 9-BBN (0.56 L of a 0.5 M solution in tetrahydrofuran) via addition funnel, stir at room temperature overnight. Cool to 0° C. and treat with 30% aqueous hydrogen peroxide (195 mL), followed by 3N aqueous sodium hydroxide (195 mL). Allow to reach room temperature and stir for 24 h. Pour into separatory funnel, separate organic layer and remove solvent in vacuo. Take up residue in dichloromethane, add water and recombine with aqueous layer from before. Pour into separatory funnel, separate organic layer and extract aqueous layer with several portions of dichloromethane. Combine all organic layers, remove solvent in vacuo. Take up residue in 1 L of methanol, add 185 g of SCX resin. Filter slurry through Büchner funnel, washing well with methanol. To elute product, wash cake thoroughly with 50% 7N ammonia-methanol in dichloromethane. Concentrate filtrate in vacuo to obtain the title compound (16.6 g, 96%) as a thick brownish oil: mass spectrum (APCI): m/z=311.2 (M+1).

Example 166

(S)-(1,4-Dibenzyl-piperazin-2-yl)-acetaldehyde

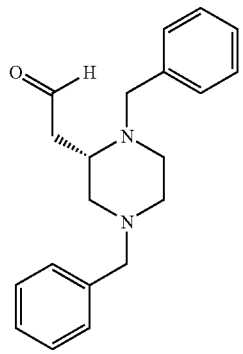

Combine a solution of oxalyl chloride (0.1.83 mL, 21.0 mmol) in dichloromethane (20 mL) with a solution of dimethyl sulfoxide (2.34 mL, 33.0 mmol) in dichloromethane (10 mL) at −78° C. and stir for 15 minutes. Add a solution of (S)-2-(1,4-dibenzylpiperazin-2-yl)ethanol (0.60 g, 1.82 mmol) in dichloromethane (10 mL) at −78° C. via cannula. Stir at −78° C. for one hour, add triethylamine (10.5 mL, 75.0 mmol) and warm to room temperature overnight. Dilute the mixture with saturated aqueous sodium bicarbonate and extract three times with dichloromethane. Combine the organic layers, dry over sodium sulfate and concentrate under reduced pressure. Purify by flash chromatography, eluting with a step gradient starting with dichloromethane going to 6% 2N ammonia-methanol in dichloromethane to obtain the title compound (3.66 g, 11.9 mmol, 79%) as a brown oil: mass spectrum (APCI): m/z=309.4 (M+1).

Example 167

(S)-2-piperazin-2-yl-ethanol

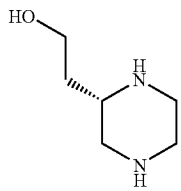

Dissolve (S)-2-(1,4-dibenzylpiperazin-2-yl)ethanol (11.7 g, 0.038 mol) in 380 mL of ethanol, add 10% palladium on carbon (3.7 g of wet reagent, 50% by weight) as a suspension in a few mL of ethanol. Add excess ammonium formate (16.8 g, 0.27 mol) all at once. Heat at reflux for 5 h, cool to room temperature and filter through a celite pad, washing well with ethanol. Concentrate filtrate in vacuo to provide the title compound (5 g, quantitative) as a cloudy residue. Use directly on the next step without further purification: mass spectrum (APCI): m/z=131.1 (M+1).

Example 168

(S)-2-(2-Hydroxyethyl)piperazine-1,4-dicarboxylic acid di-tert-butyl ester

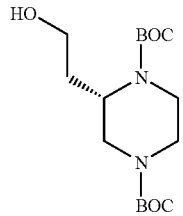

Dissolve (S)-2-piperazin-2-yl-ethanol (4 g, 30.7 mmol) in 150 mL of dichloromethane, add a few mL of ethanol to dissolve material. Add di-tert-butyl dicarbonate (28 g, 0.13 mol) in two portions, at the beginning and again after stirring at room temperature for 4 h. Pour mixture onto saturated aqueous sodium bicarbonate, extract with dichloromethane. Combine organic extracts, dry over sodium sulfate, filter, and concentrate filtrate in vacuo to a residue. Purification via silica gel chromatography eluting with a step gradient of 2% 2N ammonia-methanol in dichloromethane, 4% and 6% to obtain the title compound as a yellow oil which solidifies upon standing: mass spectrum (FAB): m/z=331.20.

Example 169

(S)-2-(2-Oxoethyl)piperazine-1,4-dicarboxylic acid di-tert-butyl ester

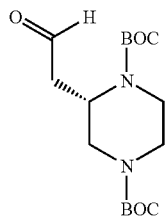

Combine a solution of oxalyl chloride (0.238 mL, 2.72 mmol) in dichloromethane (25 mL) with dimethyl sulfoxide (0.322 mL, 4.54 mmol) at −78° C. and stir. After 15 minutes, add a solution of (S)-2-(2-hydroxyethyl)piperazine-1,4-dicarboxylic acid di-tert-butyl ester (0.60 g, 1.82 mmol) in dichloromethane at −78° C. via cannula and stir at −78° C. After one hour, add triethylamine (1.27 mL, 9.08 mmol) and warm to room temperature overnight. Dilute the mixture with saturated aqueous sodium bicarbonate and extract three times with dichloromethane. Combine the organic layers, dry over sodium sulfate and concentrate under reduced pressure to give the title compound: mass spectrum (APCI): m/z=129.1 (M+1−2BOC).

Example 170

(S)-2-(2-Methoxyethyl)piperazine

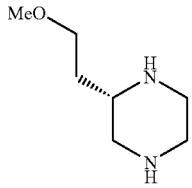

Add sodium hydride (0.675 g, 16.9 mmol) in portions to a 0° C. solution of (S)-2-(2-hydroxyethyl)piperazine-1,4-dicarboxylic acid di-tert-butyl ester (3.72 g, 11.3 mmol) in tetrahydrofuran (50 mL) and stir. After 20 minutes, add methyl iodide (1.4 mL, 22.5 mmol) dropwise. Allow the mixture to reach room temperature overnight, dilute with saturated ammonium chloride and extract three times with ethyl acetate. Combine the organic layers, dry over sodium sulfate and concentrate under reduced pressure. Purify by flash chromatography, eluting with a step gradient starting with dichloromethane up to 7% 2N ammonia-methanol in dichloromethane to obtain 2-(2-methoxyethyl)-piperazine-1,4-dicarboxylic acid di-tert-butyl ester.

To the above material in dichloromethane (50 mL) add trifluoroacetic acid (15 mL) at 0° C. and stir. After 30 minutes, allow the mixture to warm up to room temperature and stir. After 1 h, remove solvent in vacuo to yield a golden yellow oil. Dilute the residue with methanol and apply to a 30 g SCX column. Wash the column with methanol, elute with 2N ammonia in methanol to obtain the title compound as a thick, colorless oil (1.13 g, 7.84 mmol, 89%): mass spectrum (APCI): m/z =145.2 (M+1).

Example 172

(S)-4-Benzyl-2-(2-methanesulfonyloxy-ethyl)piperazine-1-carboxylic acid tert-butyl ester To a solution of (S)-4-benzyl-2-(2-hydroxyethyl)piperazine-1-carboxylic acid tert-butyl ester (4.87 g, 15.2 mmol) in dichloromethane (200 mL), add pyridine (1.84 mL, 22.8 mmol) followed by methanesulfonyl chloride (1.29 mL, 16.7 mmol). Stir at room temperature overnight, then dilute with saturated aqueous sodium bicarbonate. Extract three times with dichloromethane; dry combined organic extracts over sodium sulfate, filter and concentrate in vacuo to give a brown residue. Redissolve residue in dichloromethane and apply to a plug of silica gel. Wash plug with 5% 2N ammonia-methanol in dichloromethane to obtain (S)-4-benzyl-2-(2-methanesulfonyloxy-ethyl)piperazine-1-carboxylic acid tert-butyl ester (3.74 g, 62%) as a yellow-brown thick oil.

Example 173

(S)-2-(2-Phenoxyethyl)piperazine

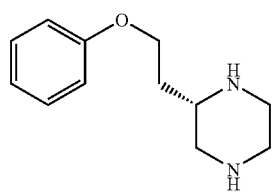

Combine (S)-4-benzyl-2-(2-methanesulfonyloxyethyl)piperazine-1-carboxylic acid tert-butyl ester (2.82 g, 7.08 mmol), sodium iodide (0.106 g, 0.708 mmol), and phenol (3.33 g, 35.4 mmol) in dimethyl formamide (40 mL) and stir at 100° C. for 20 hours. Dilute the mixture with saturated aqueous sodium bicarbonate and extract three times with dichloromethane. Combine the organic layers, dry over sodium sulfate and concentrate under reduced pressure. Purify by flash chromatography, eluting with a step gradient (100% dichloromethane to 5% 2N ammonia-methanol in dichloromethane) to obtain (S)-4-benzyl-2-(2-phenoxyethyl)piperazine-1-carboxylic acid tert-butyl ester (0.703 g, 25%): mass spectrum (APCI): m/z=397.2 (M+1).

Combine the material from above (0.890 g, 2.24 mmol), palladium on carbon (0.090 g, 10%), and ammonium formate (0.707 g, 11.22 mmol) in ethanol (20 mL) and heat at reflux for 8 hours. Cool, filter and evaporate the mixture to give (S)-2-(2-phenoxyethyl)piperazine-1-carboxylic acid tert-butyl ester (0.639 g, 93%): mass spectrum (APCI): m/z=307.2 (M+1).

Add trifluoroacetic acid (3 mL) to the material from above (0.626 g, 2.04 mmol) in dichloromethane (10 mL) at 0° C. and stir. After 1 hour, warm the mixture to room temperature and stir for two hours then evaporate. Dilute the mixture with 1N sodium hydroxide and extract three times with dichloromethane. Combine the organic layers, dry over sodium sulfate and concentrate under reduced pressure gives the title compound (0.334 g, 79%): mass spectrum (APCI): m/z=207.1 (M+1).

Example 174

(S)-2-(2-Ethoxyethyl)piperazine

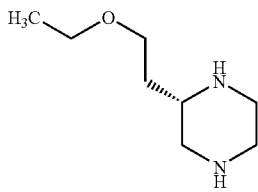

Add sodium hydride (0.558 g, 14.0 mmol) in portions to (S)-2-(2-hydroxyethyl)piperazine-1,4-dicarboxylic acid di-tert-butyl ester (3.075 g, 9.31 mmol) in dimethylformamide (60 mL) and stir for 15 minutes. Cool to 0° C. and add ethyl iodide (1.5 mL, 18.6 mmol) dropwise and stir at 0° C. After 30 minutes warm the mixture to room temperature and stir overnight. Dilute the mixture with ethyl acetate and wash the organics six times with brine. Dry over sodium sulfate and concentrate under reduced pressure to give (S)-2-(2-ethoxyethyl)-piperazine-1,4-dicarboxylic acid di-tert-butyl ester (3.17 g, 95%) as a yellow oil.

Add trifluoroacetic acid (2 mL) to the material from above (0.350 g, 0.976 mmol) in dichloromethane (6 mL) at 0° C. and stir for 30 minutes. Warm the mixture to room temperature and stir for two hours then evaporate to a yellow oil. Dilute the mixture with methanol and apply to a 5 g SCX column. Elute with methanol and then 2N ammonia in methanol to obtain the title compound (144 mg, 94%) as an oil: mass spectrum (APCI): m/z =159.2 (M+1).

Example 175

2(S)-(2(S)-Methoxypropyl)piperazine

2(S)-(2(R)-Methoxypropyl)piperazine

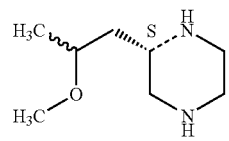

Add methylmagnesium bromide (3.61 mL, 10.8 mmol, 3M solution in diethyl ether) to a solution of 2-(2-oxoethyl)piperazine-1,4-dicarboxylic acid di-tert-butyl ester (3.036 g, 9.84 mmol) in tetrahydrofuran (30 mL) at 0° C. Warm the mixture to room temperature and stir for 5 hours. Dilute the mixture with saturated ammonium chloride and extract three times with ethyl acetate. Combine the organic layers, dry over sodium sulfate and concentrate under reduced pressure to give 2(S)-(2(S)-hydroxypropyl)piperazine-1,4-dicarboxylic acid di-tert-butyl ester and 2(S)-(2(R)-hydroxypropyl)piperazine-1,4-dicarboxylic acid di-tert-butyl ester (3.37 g, 99%) as a yellow oily solid: mass spectrum (APCI): m/z=245.2 (M+1-BOC).

To the material from above (3.35 g, 9.73 mmol) in dimethylformamide (70 mL), add sodium hydride (0.583 g, 14.6 mmol) in portions, stir for 15 minutes and cool to 0° C. Add methyl iodide (1.21 mL, 19.5 mmol) dropwise and stir at 0° C. After 30 minutes, warm the mixture to room temperature and stir overnight. Dilute the mixture with ethyl acetate and wash the organics six times with brine. Dry over sodium sulfate and concentrate under reduced pressure. Purify by flash chromatography, eluting with a step gradient (100% dichloromethane to 3% 2N ammonia-methanol in dichloromethane) to obtain 2(S)-(2(S)-methoxypropyl)piperazine-1,4-dicarboxylic acid di-tert-butyl ester and 2(S)-(2(R)-methoxypropyl)piperazine-1,4-dicarboxylic acid di-tert-butyl ester (mixture of diastereoisomers) (2.67 g, 77%) as a yellow oil.

Add trifluoroacetic acid (15 mL) to the material from above (2.65 g, 7.39 mmol) in dichloromethane (45 mL) at 0° C. and stir for 30 minutes. Warm the mixture to room temperature and stir for six hours then evaporate to a yellow oil. Dilute the mixture with methanol and apply to a 30 g SCX column. Wash with methanol and elute with 2N ammonia in methanol to obtain the title compounds (mixture of diastereoisomers) (1.06 g, 91%) as a thick brown oil: mass spectrum (APCI): m/z =159.2 (M+1).

Example 176

2(S)-(2(S)-Hydroxypropyl)piperazine

2(S)-(2(R)-Hydroxypropyl)piperazine

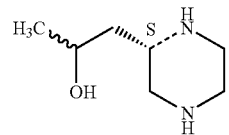

To a solution of 2(S)-(2(S)-hydroxypropyl) piperazine-1,4-dicarboxylic acid di-tert-butyl ester and 2(S)-(2(R)-hydroxypropyl) piperazine-1,4-dicarboxylic acid di-tert-butyl ester (5.11 g, 14.8 mmol) in dichloromethane (100 mL) stirring at 0° C., add trifluoroacetic acid (25 mL). Warm the mixture to room temperature and stir. After 18 hours evaporate to a yellow oil. Dilute the mixture with methanol and apply to a 60 g SCX column. Wash with methanol and elute with 2N ammonia in methanol to obtain the title compound (mixture of diastereoisomers) as an oil (1.932 g, 90%): mass spectrum (APCI): m/z =145.1 (M+1).

Example 177

(S)-2-Methyl-1-piperazin-2-yl-propan-2-ol

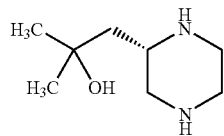

Add oxalyl chloride (2.52 mL, 28.9 mmol) to a solution of dimethyl sulfoxide (3.42 mL, 48.2 mmol) in dichloromethane (130 mL) at −78° C. After 15 minutes at −78° C., add (S)-2-(2-hydroxypropyl)piperazine-1,4-dicarboxylic acid di-tert-butyl ester 6.64 g, 19.3 mmol) in dichloromethane (20 mL). Stir the mixture for 1 hour at −78° C., add triethylamine (13.4 mL, 96.4 mmol) and warm to room temperature overnight. Dilute the mixture with saturated aqueous sodium bicarbonate and extract three times with dichloromethane. Combine the organic layers, dry over sodium sulfate and concentrate under reduced pressure. Purify by flash chromatography, eluting with a step gradient (100% dichloromethane to 5% 2N ammonia-methanol in dichloromethane), to obtain (S)-2-(2-oxo-propyl)-piperazine-1,4-dicarboxylic acid di-tert-butyl ester (5.77 g, 87%): mass spectrum (APCI): m/z=143.1 (M+1-2BOC).

To a solution of the aldehyde from above (0.263 g, 0.768 mmol) in tetrahydrofuran (10 mL) at 0° C., add methylmagnesium bromide (0.28 mL, 0.845 mmol, 3M solution in diethyl ether). Heat the mixture to reflux and stir overnight. Dilute the mixture with saturated ammonium chloride and extract three times with ethyl acetate. Combine the organic layers, dry over sodium sulfate and concentrate under reduced pressure to obtain (S)-2-(2-hydroxy-2-methylpropyl)piperazine-1,4-dicarboxylic acid di-tert-butyl ester (0.258 g, 0.720 mmol, 94%): mass spectrum (APCI): m/z=359.3 (M+1). To the material from above (4.3 g, 12.0 mmol) in dichloromethane (100 mL) at 0° C., add trifluoroacetic acid (25 mL) and stir for 1 hour. Warm the mixture to room temperature, stir overnight, and evaporate to a brown oil. Dilute the mixture with methanol and apply to a 60 g SCX column. Wash with methanol and elute with 2N ammonia in methanol to obtain the title compound (1.9 g, 100%): mass spectrum (APCI): m/z=159.2 (M+1).

Example 178

(S)-2-(2-Phenylsulfanylethyl)piperazine

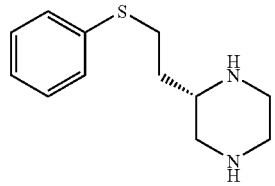

To a solution of (S)-4-benzyl-2-(2-hydroxyethyl)piperazine-1-carboxylic acid tert-butyl ester (4.87 g, 15.2 mmol) in dichloromethane (200 mL), add pyridine (1.84 mL, 22.8 mmol) followed by methanesulfonyl chloride (1.29 mL, 16.7 mmol). Stir at room temperature overnight and dilute with saturated aqueous sodium bicarbonate. Extract three times with dichloromethane, dry combined organic extracts over sodium sulfate, filter and concentrate in vacuo to give a brown residue. Redissolve residue in dichloromethane and apply to a plug of silica gel. Wash plug with 5% 2N ammonia-methanol in dichloromethane to obtain (S)-4-benzyl-2-(2-methanesulfonyloxy-ethyl)piperazine-1-carboxylic acid tert-butyl ester (3.74 g, 62%) as a yellow-brown thick oil.

Combine potassium hydride (9.6 g, 84 mmol, 35%) and thiophenol (9.6 mL, 93.3 mmol) in tetrahydrofuran (250 mL) at 0° C., warm to room temperature over 25 minutes. Cool the mixture again to 0° C. and add the mesylate from above (3.72 g, 9.33 mmol) as a solution in tetrahydrofuran (50 mL); stir the mixture overnight at room temperature. Dilute the mixture with saturated aqueous sodium bicarbonate and extract three times with dichloromethane. Combine the organic layers, dry over sodium sulfate and concentrate under reduced pressure. Purify by flash chromatography, eluting with a step gradient starting with dichloromethane going to 5% 2N ammonia-methanol in dichloromethane, to obtain (S)-4-benzyl-2-(2-phenylsulfanylethyl)piperazine-1-carboxylic acid tert-butyl ester (2.46 g, 64%) as a yellow oil. Mass spectrum (APCI): m/z=413.2 (M+1).

Combine chloroethyl chloroformate (1.16 mL, 10.7 mmol) and the material from above (2.01 g, 4.87 mmol) in dichloroethane (30 mL) at 0° C., and heat at reflux overnight. Evaporate the mixture, dilute with methanol, heat at reflux for 2 hours, and evaporate. Dilute the mixture with methanol and apply to a 10 g SCX column. Wash column with methanol, elute with 2%, 5% 2N and 100% 2N ammonia-methanol in dichloromethane to obtain the title compound (0.470 g, 43%) as an oil: mass spectrum (APCI): m/z=223.1(M+1).

Example 180

(S)-(1,4-Dibenzyl-piperazin-2-yl)-acetaldehyde

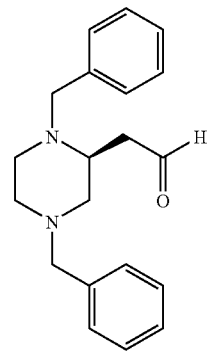

Add anhydrous DMSO (3.57 mL, 50.25 mmol) in anhydrous dichloromethane (68.0 mL). Cool to −78° C. and stir. Add oxalyl chloride (2M in dichloromethane, 12.06 mL, 24.125 mmol) dropwise. Stir at −78° C. for 30 minutes. Add (1,4-dibenzyl-piperazin-2-yl)-ethanol (6.241 g, 20.1 mmol) in dichloromethane (12.0 mL) and stir. After 1 hour, add triethylamine (14.01 mL, 100.5 mmol) and stir for another 1 hour. Allow the reaction mixture gradually warm to ambient temperature. Add saturated ammonium chloride. (200 mL). Exact aqueous portion with ethyl acetate three times. Combine the organic solution, dry over sodium sulfate, filter, and concentrate under reduced pressure to give crude residue. Purify the residue by flash chromatography, eluting with 2M ammonia in methanol:dichloromethane (5:95) to give the title compound: mass spectrum (m/e): 309.03 (M+1).

Example 181

(S)-1,4-Dibenzyl-2-(3-methoxy-allyl)-piperazine

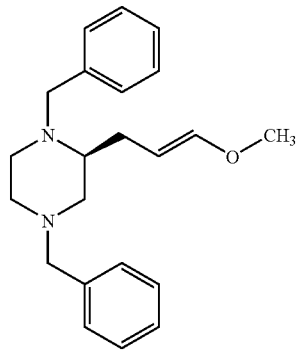

Add LiHMDS (1M in THF, 21.38 mL, 21.38 mmol) to (methoxymethyl)triphenyl-phosphonium chloride (7.329 g, 21.38 mmol) in THF (51.0 mL) via syringe at 0° C. and stir. After 30 minutes, add (S)-(1,4-dibenzyl-piperazin-2-yl)-acetaldehyde (4.71 g, 15.27 mmol) in THF (51.0 mL) via syringe. Remove ice bath and stir at ambient temperature. After 4 hours, add water and extract with ethyl acetate twice. Combine the organic solution, dry over sodium sulfate, filter, and concentrate under reduced pressure to give crude residue. Purify the residue by flash chromatography, eluting with ethyl acetate:hexane (40:60) to give the title compound: mass spectrum (m/e):337.18 (M+1).

Example 182

(S)-2-(3-Methoxy-propyl)-piperazine

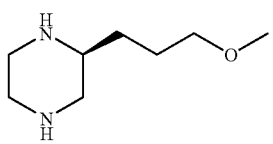

Add 20% Pd(OH)₂/C (2.15 g) to (S)-1,4-dibenzyl-2-(3-methoxy-allyl)-piperazine (3.382 g, 10.05 mmol) in ethanol (100 mL) and under hydrogen atmosphere at 40° C. over night. Filter to give the title compound: mass spectrum (m/e):159.1 (M+1).

Example 183

(S)-2-(3-Ethoxycarbonylallyl)-piperazine-1,4-dicarboxylic acid di-tert-butyl ester

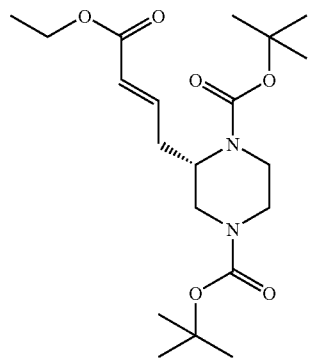

Heat a mixture of (S)-2-(2-oxoethyl)-piperazine-1,4-dicarboxylic acid di-tert-butyl ester (1.38 g, 4.21 mmol) and (carbethoxymethylene)triphenylphosphorane (1.87 g, 5.38 mmol) in THF (17 mL) at reflux for 4 h. Concentrate the mixture under reduced pressure and purify by silica gel chromatography eluting with 20% to 50% EtOAc in hexanes. Combine the purified fractions, concentrate under reduced pressure, azeotrope with CH₂Cl₂/hexanes (1:2) and place under vacuum to give the title compound: yellow tar (0.961 g), mass spectrum (m/e): 416.09(M+NH₄).

Example 184

(S)-2-(3-Ethoxycarbonylpropyl)-piperazine-1,4-dicarboxylic acid di-tert-butyl ester

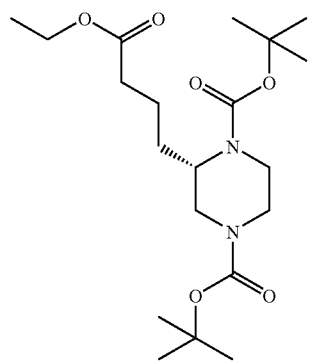

Alternately evacuate and charge with H₂ (3×) a slurry of (S) 2-(3-ethoxycarbonylallyl)-piperazine-1,4-dicarboxylic acid di-tert-butyl ester (0.757 g, 1.89 mmol) and 10% Pd/C (0.198 g) in dichloroethane 2 days. Filter the mixture through a bed of celite washing with CH₂Cl₂ (50 mL), EtOH (50 mL), CH₂Cl₂ (50 mL), EtOH (50 mL). Concentrate the supernat under reduced pressure and place under vacuum to give the title compound: yellow solid (0.747 g), mass spectrum (m/e):401.10 (M+H).

Example 185

(S)-2-(3-Carboxypropyl)-piperazine-1,4-dicarboxylic acid di-tert-butyl ester

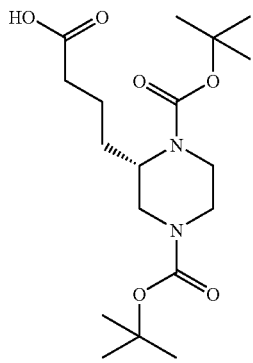

Stir a solution of (S)-2-(3-ethoxycarbonylpropyl)-piperazine-1,4-dicarboxylic acid di-tert-butyl ester (0.739 g, 1.84 mmol) in MeOH add 1.0 N NaOH (2.13 mL) and continue stirring overnight. Concentrate the mixture under reduced pressure, dilute with H$_2$O (40 mL) and wash with Et$_2$O (3×30 mL). Acidify the aqueous layer with 10% NaHSO$_4$ (20 mL) and extract with EtOAc (3×50 mL). Dry the organic layer with Na$_2$SO$_4$ filter, concentrate under reduced pressure and place the residue under vacuum to give the title compound: white solid (0.618 g), mass spectrum (m/e):373.07 (M+H).

Example 186

(S)-2-(4-Hydroxybutyl)-piperazine-1,4-dicarboxylic acid di-tert-butyl ester

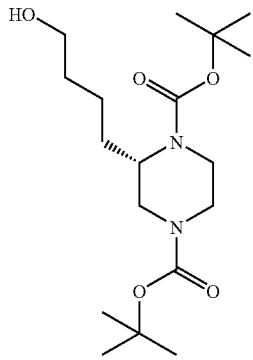

Into a stirred solution of (S)-2-(3-carboxypropyl)-piperazine-1,4-dicarboxylic acid di-tert-butyl ester (0.596 g, 1.60 mmol) in THF add 1.0 M BH$_3$ in THF (3.2 mL, 3.20 mmol) and continue stirring overnight. Concentrate the mixture under reduced pressure, dilute with H$_2$O (30 mL) and extract with EtOAc (3×50 mL). Dry the organic layers with Na$_2$SO$_4$ filter concentrate under reduced pressure, azeotrope the residue with CH$_2$Cl$_2$/hexanes (1:2) and place the residue under vacuum to give the title compound: colorless solid (0.604 g), mass spectrum (m/e):359.12 (M+H).

Example 187

(S)-2-(4-Methoxybutyl)-piperazine-1,4-dicarboxylic acid di-tert-butyl ester

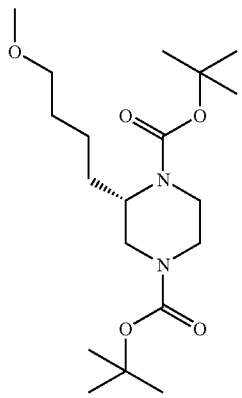

Into a room temperature, stirred solution of (S)-2-(4-hydroxybutyl)-piperazine-1,4-dicarboxylic acid di-tert-butyl ester (0.344 g, 0.95 mmol), and MeI (0.179 mL, 2.87 mmol) in DMF (5 mL) add NaH (0.042 g, 1.05 mmol, 20% in mineral oil). Stir overnight. Dilute the mixture with 75% brine (50 mL) and extract with EtOAc (3×100 mL). Concentrate the organic layers under reduced pressure, dilute with EtOAc (40 mL) and wash with 75% brine (5×25 mL). Dry the organic layer over Na$_2$SO$_4$, and filter. Concentrate the mixture under reduced pressure and purify by silica gel chromatography eluting with 20% to 98% EtOAc in hexanes. Combine the purified fractions, concentrate under reduced pressure and place under vacuum to give the title compound: yellow tar (0.209 g), mass spectrum (m/e): 373.13 (M+H).

Example 188

(S)-2-(4-Methoxybutyl)-piperazine

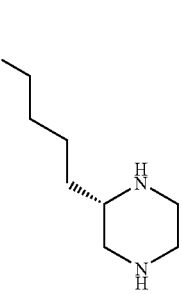

Into a stirred, room temperature solution of (S)-2-(4-methoxybutyl)-piperazine-1,4-dicarboxylic acid di-tert-butyl ester (0.198 g, 0.53 mmol) in CH$_2$Cl$_2$ (2.6 mL), add TFA (2.6 mL) and stir for 2 h. Concentrate the mixture under reduced pressure, dilute with H$_2$O and load onto an SCX column (10 g). Wash the resin with H$_2$O (3×100 mL), MeOH (3×100 mL) and elute the product with 2 M NH$_3$ in MeOH (3×100 mL). Concentrate the purified fractions under reduced pressure and azeotrope the residue with CH$_2$Cl$_2$/ hexanes (1:2). Place the residue under vacuum to give the title compound: orange crystals (0.093 g), mass spectrum (m/e):173.4 (M+H).

Example 190

2-(R)-tert-Butoxycarbonylamino-3-(2-methyl-allyloxy)-propionic acid

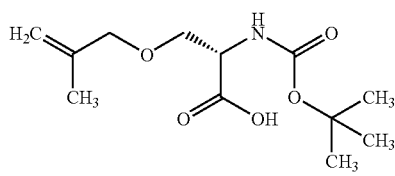

Wash a 60% dispersion of sodium hydride in mineral oil (4.4 g, 115 mmol) with hexanes. Add DMF (30 mL), and cool in an ice bath. Add dropwise a solution N-(tert-butoxycarbonyl)-L-serine (10.0 g, 49 mmol) in DMF (160 mL). Warm to room temperature and stir until hydrogen evolution ceases after one hour. Cool in an ice bath and add 3-bromo-2-methyl-propene (7.40 g, 55 mmol). Stir for 2 hours. Pour mixture onto 5% aqueous sodium bicarbonate (800 mL). Wash twice with ethyl acetate. Add ethyl acetate (200 mL), and acidify the aqueous layer in its presence to pH=3 with concentrated hydrochloric acid. Wash the organic layer with water, dry ($Na_2SO_4$), and concentrate to afford the title compound as a clear oil (12.7 g): $^1$H NMR ($CDCl_3$) δ 1.45 (s, 9H), 1.70 (s, 3H), 3.65 (m, 1H), 3.85 (m, 1H), 3.86-3.94 (m, 2H), 4.44 (m, 1H), 4.89 (s, 1H), 4.93 (s, 1H), 5.43 (d, 1H).

Example 190a 3-(R)-(2-Methyl-allyloxymethyl)-piperazine-2,5-dione

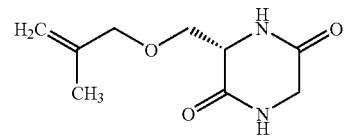

By the cyclization method in Example 161, using 2-(R)-tert-butoxycarbonylamino-3-(2-methyl-allyloxy)-propionic acid (12.7 g) affords the title compound as a white solid (8.95 g): $^1$H NMR (DMSO-$d_6$) δ 1.60 (s, 3H), 3.42 (dd, 1H), 3.57 (d, 1H), 3.66 (d, 1H), 3.75 (d, 1H), 3.80 (m, 1H), 3.81 (s, 2H), 4.82 (s, 1H), 4.86 (s, 1H), 8.03 (s, 1H), 8.11 (s, 1H).

Example b 190b 2-(R)-(2-Methyl-allyloxymethyl)-piperazine

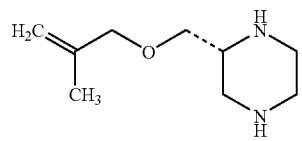

By the reduction method in Example 162, using 3-(R)-(2-methyl-allyloxymethyl)-piperazine-2,5-dione (8.9 g) affords the title compound as a yellow solid (4.6 g): $^1$H NMR ($CDCl_3$) δ 1.73 (s, 3H), 2.48 (t, 1H), 2.72-3.02 (m, 6H), 3.25 (m, 1H), 3.36 (dd, 1H), 3.88 (s, 2H), 4.89 (s, 1H), 4.94 (s, 1H).

Example 191

2-(R)-tert-Butoxycarbonylamino-3-(2-methyl-allyloxy)-propionic acid

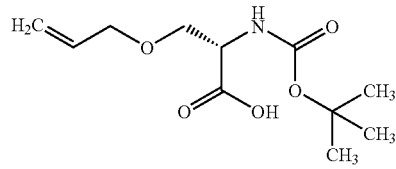

By the allylation method in Example 190, using 2-(R)-tert-butoxycarbonylamino-3-hydroxy-propionic acid (25.0 g, 122 mmol) provides the title compound as a white solid (27.0 g, 90%): $^1$H NMR ($CDCl_3$) δ 1.46 (s, 9H), 2.94 (d, 2H), 3.67 (dd, 1H), 4.00 (d, 2H), 5.23 (ddd, 2H), 5.87 (m, 1H), 10.50 (bs, 1H).

Example 191a 3-(R)-(2-Allyloxymethyl)-piperazine-2,5-dione

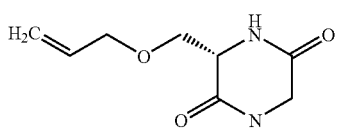

By the cyclization method in Example 161, using 2-(R)-tert-butoxycarbonylamino-3-(2-allyloxy)-propionic acid (27.0 g) affords the title compound as a white solid (8.5 g): $^1$H NMR (DMSO-$d_6$) δ 3.49 (dd, 1H), 3.60 (dd, 1H), 3.73-3.85 (m, 3H), 3.96 (dt, 2H), 5.14 (dq, 1H), 5.23 (dq, 1H), 5.84 (m, 1H), 8.05 (bs, 1H), 8.13 (bs, 1H).

Example 191b 2-(R)-(2-Allyloxymethyl)-piperazine

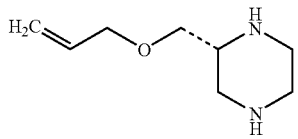

By the reduction method in Example 162, using 3-(R)-(2-allyloxymethyl)-piperazine-2,5-dione (8.5 g, 46.1 mmol) affords the title compound as a white solid (5.0 g, 69%): $^1$H NMR (CDCl$_3$) δ 2.02 (bs, 2H), 2.71-3.69 (m, 9H), 3.98 (dt, 2H), 5.19 (dq, 1H), 5.27 (dq, 1H), 5.90 (m, 1H).

Example 193

2-(R)-tert-butoxycarbonylamino-3-methoxy-propionic acid

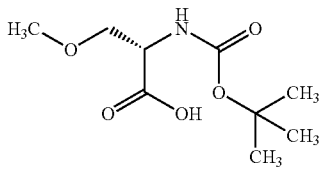

By the alkylation method in Example 190, using 2-(R)-tert-butoxycarbonylamino-3-hydroxy-propionic acid gives the title compound.

Example 194

(R)-3-Methoxymethyl-piperazine-2,5-dione

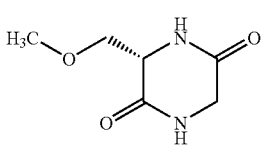

By the cyclization method described for Example 161, using 2-(R)-tert-butoxycarbonylamino-3-methoxy-propionic acid (40 g) affords the title compound as a white powder (20.0 g): $^1$H NMR (DMSO-d$_6$) δ 3.22 (s, 3H), 3.38 (dd, 1H), 3.56 (d, 1H), 3.64 (dd, 1H), 3.72 (d, 1H), 3.79 (m, 1H), 8.00 (bs, 1H), 8.09 (bs, 1H).

Example 194a (R)-2-(Methoxymethyl-piperazine

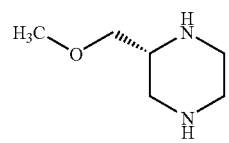

By the reduction method described for Example 162, using (R)-3-(methoxymethyl-piperazine-2,5-dione (4.8 g) affords the title compound as a yellow oil (2.6 g, 67%): $^1$H NMR (CDCl$_3$) δ 2.48 (dd, 1H), 2.72-3.00 (m, 6H), 3.23 (dd, 1H), 3.34 (dd, 1H), 3.35 (s, 3H); MS (APCI) m/z (rel intensity) 131 (100).

Example 195

(R)-2-Phenoxymethyl-piperazine

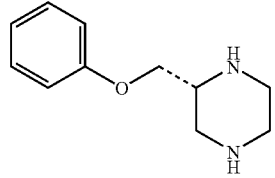

Add a solution of diethyl azodicarboxylate (3.46 mL, 22 mmol) in THF (6 mL) dropwise to a solution of (R)-1,4-dibenzyl-piperazin-2-yl)-methanol (5.92 g, 20 mmol) (J. Med. Chem., 1993, Vol. 36, 2075-2083 and J. Med. Chem., 1993, Vol. 36, 990-1000), phenol (2.07 g, 22 mmol), and triphenyl phosphine (5.78 g, 22 mmol) in THF (100 mL) at 0° C. Stir at room temperature overnight, partition between water and ether and add conc. HCl until the aqueous layer is below pH=2. Separate the aqueous layer and wash with diethyl ether. Add potassium carbonate to the aqueous until pH 10 and extract with ethyl acetate, dry, and concentrate to afford a yellow oil (7.4 g). Add ethanol (200 mL) and conc. HCl (2 mL) to the crude oil and pour the solution in a Parr bottle. Replace the atmosphere twice with nitrogen, and add 10% Pd/C (200 mg). Purge the Parr bottle and replace with hydrogen twice. Heat to 50° C. and shake overnight. Cool, filter through celite, and wash the celite pad three times with water. Remove the ethanol from the combined filtrates via evaporation in vaccuo. Add potassium carbonate to the mixture until pH 10. Extract the mixture three times with 25% iso-propanol in CH$_2$Cl$_2$. Dry and concentrate the combined organic layers to afford the title piperazine as a white solid (3.1 g, 81%): $^1$H NMR (CDCl$_3$) δ 2.57 (dd, 1H), 2.75-3.02 (m, 5H), 3.08 (m, 1H), 3.80 (dd, 1H); 3.86 (dd, 1H), 6.86 (d, 2H), 6.92 (t, 1H), 7.24 (t, 2H); MS (APCI) m/z (rel intensity) 193 (100).

Example 196

2-(R)-tert-Butoxycarbonylamino-3-(2-ethoxy)-propionic acid

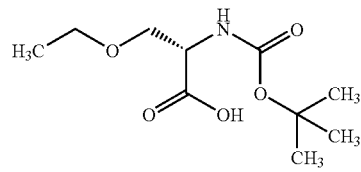

By the alkylation method in Example 190, using 2-(R)-tert-butoxycarbonylamino-3-hydroxy-propionic acid (50.0 g) provides the title compound as a clear oil (41 g): $^1$H NMR (CDCl$_3$) δ1.17 (t, 3H), 1.45 (s, 9H), 3.53 (q, 2H), 3.67 (dd, 1H), 3.90 (dd, 11H), 4.43 (m, 1H), 5.44 (d, 1H).

Example 196a (R)-3-Ethoxymethyl-piperazine-2,5-dione

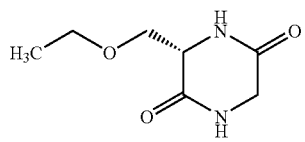

By the cyclization method described for Example 161, using 2-(R)-tert-butoxycarbonylamino-3-methoxy-propionic acid (24 g) affords the title compound as a white powder (6.34 g): $^1$H NMR (DMSO-d$_6$) δ 1.03 (t, 3H), 3.40 (q, 2H), 3.41 (dd, 1H), 3.56 (d, 1H), 3.70-3.80 (m, 3H), 7.99 (bs, 1H), 8.13 (bs, 1H).

Example 196b (R)-2-Ethoxymethyl-piperazine

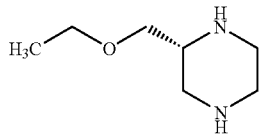

By the reduction method described for Example 162, using (R)-3-ethoxymethyl-piperazine-2,5-dione (6.0 g) affords the title compound as a yellow oil (4.61 g): $^1$H NMR (CDCl$_3$) δ 1.20 (t, 3H), 2.48 (dd, 1H), 2.70-3.40 (m, 8H), 3.42 (q, 2H); MS (APCI) m/z (rel intensity) 145 (100).

Example 197

(R)-3-Benzyloxymethyl-piperazine-2,5-dione

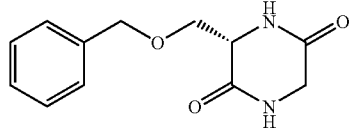

By the cyclization method described for Example 161, using 3-(R)-benzyloxy-2-tert-butoxycarbonylamino-propionic acid (50.0 g) affords the title compound as a white solid (26.4 g, 66%): $^1$H NMR (DMSO-d$_6$) δ 3.52 (dd, 1H), 3.57 (d, 1H), 3.73 (d, 1H), 3.76 (dd, 1H), 3.84 (m, 1H), 4.47 (s, 2H), 7.23-7.35 (m, 5H), 8.02 (s, 1H), 8.12 (s, 1H); MS (APCI) m/z (rel intensity) 235 (100).

Example 197a (R)-2-Benzyloxymethyl-piperazine

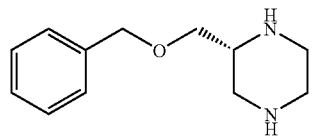

By the reduction method in Example 162, using (R)-3-benzyloxymethyl-piperazine-2,5-dione (16 g) affords the title compound as an orange oil (9.0 g, 64%): $^1$H NMR (CDCl$_3$) δ 2.16 (dd, 1H), 2.45 (ddd, 1H), 2.53 (ddd, 1H), 2.64 (d, 1H), 2.69 (m, 1H), 2.72 (d, 1H), 3.22 (m, 2H), 3.36 (m, 1H), 4.44 (m, 2H), 7.24-7.34 (m, 5H); MS (APCI) m/z (rel intensity) 207 (100).

Example 198

(S)-3-Methyl-11-[3-(2-methoxy-ethyl)-piperazin-1-yl]-5H-dibenzo[b,e][1,4]diazepine

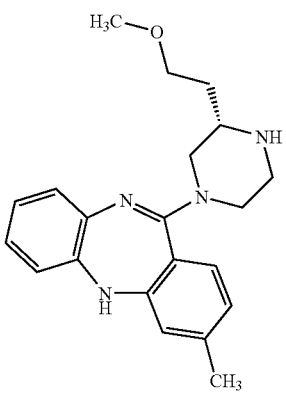

Combine 3-methyl-5H-dibenzo[b,e][1,4]diazepin-1-ylamine hydrochloride (400.0 mg, 1.54 mmol), (S)-2-(2-methoxy-ethyl)-piperazine (444.2 mg, 3.08 mmol), N,N- diisopropylethylamine (199.0 mg, 1.54 mmol), DMSO (0.7 ml), and toluene (2.8 ml) and stir and heat the mixture at 110° C. After 48 hours, cool the mixture to ambient temperature and dilute with ethyl acetate. Wash the organic layer with 0.1N NaOH and brine. Dry (sodium sulfate) and concentrate the organic layer to residue. Purify the residue on silica gel using dichloromethane/methanol (90:10) to give 257.1 mg (48%) of a yellow foam: mp=64° C. dec; mass spectrum (ion spray): m/z =433.1 (M+1).

Example 199

(S)-2-Methyl-11-[3-(2-methoxy-ethyl)-piperazin-1-yl]-5H-dibenzo[b,e][1,4]diazepine

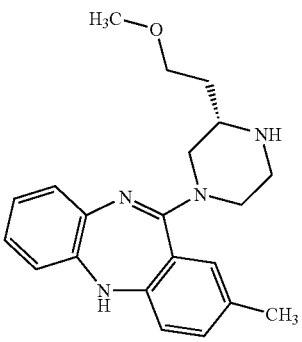

Combine 2-methyl-5H-dibenzo[b,e][1,4]diazepin-11-ylamine hydrochloride (600.0 mg, 2.31 mmol), (S)-2-(2-methoxy-ethyl)-piperazine (666.3 mg, 4.62 mmol), N,N-diisopropylethylamine (298.6 mg, 2.31 mmol), DMSO (1.0 ml), and toluene (4.0 ml) and stir and heat the mixture at 110° C. After 46 hours, cool the mixture to ambient temperature and dilute with ethyl acetate. Wash the organic layer with 0.1N NaOH and brine, dry (sodium sulfate) and concentrate the organic layer to residue. Purify the residue on silica gel using dichloromethane/methanol (90:10) to give 425.5 mg (53%) of a yellow foam: mp 63° C., dec; mass spectrum (ion spray): m/z 351.2 (M+1).

Example 200

(S)-2-Isopropyl-11-[3-(2-methoxy-ethyl)-piperazin-1-yl]-5H-dibenzo[b,e][1,4]diazepine

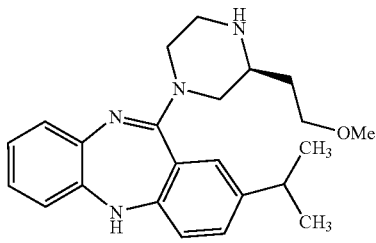

Combine 2-Isopropyl-5H-dibenzo[b,e][1,4]diazepin-11-ylamine (0.969 g, 3.85 mmol) and (S)-2-(2-methoxy-ethyl)-piperazine (0.556 g, 3.85 mmol) in NMP (7.0 mL) and heat at 200° C. for 4 hours. Cool to ambient temperature and dilute with water. Extract with ethyl acetate to give 1.51 g of the crude product. Silica gel chromatography, eluting with methylene chloride: 2N NH$_3$/methanol (100:4), gives 0.560 g of the title compound as a tan solid: mp=158-160° C.; mass spectrum (ion spray): m/z=379 (M+1); Analysis for C$_{23}$H$_{30}$N$_4$O(0.2H$_2$O): calcd: C, 72.29; H, 8.02; N, 14.66; found: C, 72.20; H, 7.70; N, 14.60.

Example 201

(S)-2-Isopropyl-11-[3-(3-methoxy-propyl)-piperazin-1-yl]-5H-dibenzo[b,e][1,4]diazepine,

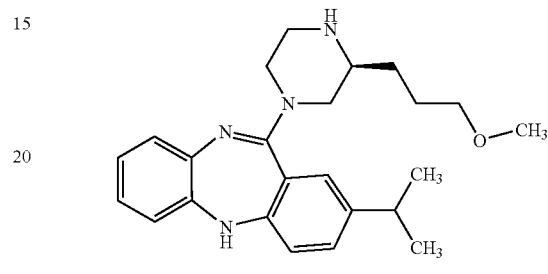

Using a method similar to Example 203 using 2-isopropyl-5H-dibenzo[b,e][1,4]diazepin-11-ylamine gives the title compound: mass spectrum (m/e):393.12 (M+1).

Example 202

(S)-2-Trifluoromethyl-11-[3-(2-methoxy-ethyl)-piperazin-1-yl]-5H-dibenzo[b,e][1,4]diazepine

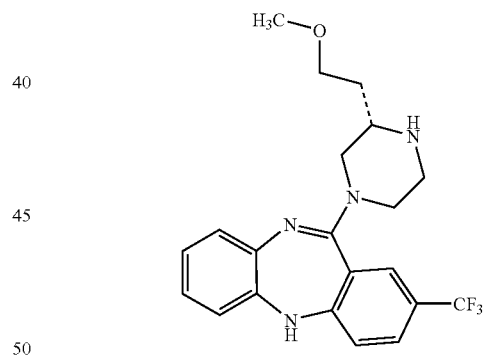

Heat a suspension of 2-trifluoromethyl-5H-dibenzo[b,e][1,4]diazepin-11-ylamine hydrochloride salt (626 mg) and (S)-2-(2-methoxy-ethyl)-piperazine (863 mg) in DMSO (1.42 mL DMSO per mmol of amine) and toluene (5.68 mL per mmol of amine) at reflux for 48 hours. Evaporate the toluene under vaccuo and pour the resulting solution into water (5.71 mL per mmol of amine). Purify the resulting brown solid by flash chromatography (methylene chloride/methanol (95:5) to afford the title compound as a yellow solid (499 mg, 60%): mp 71-82° C.; $^1$HNMR (CDCl$_3$) δ 1.75-1.60 (m, 2H), 2.64 (dd, 1H), 3.07-2.94 (m, 4H), 3.31 (s, 3H), 3.48 (ddd, 2H), 3.78 (bs, 2H), 5.09 (s, 1H), 6.69 (dd, 1H), 6.93-6.88 (m, 2H), 7.00 (dt, 1H), 7.10 (dd, 1H), 7.57-7.50 (m, 2H); MS (ESI/pos) m/z (rel intensity) 405.3 (100).

Example 203

(S)-2-Trifluoromethyl-11-[3-(3-methoxy-propyl)-piperazin-1-yl]-5H-dibenzo[b,e][1,4]diazepine

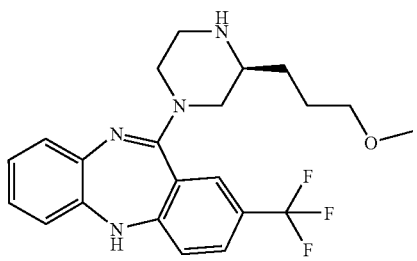

Add 2-trifluoromethyl-5H-dibenzo[b,e][1,4]diazepine-11-ylamine (0.438 g, 1.58 mmol), (S)-2-(3-methoxy-propyl)-piperazine (0.25 g, 1.58 mmol) in NMP (2.8 mL). Heat at 200° C. with stirring. After 2 hours, stop heating and allow the reaction mixture cool down to ambient temperature. Add brine and extract with ethyl acetate. Wash the organic solution with brine three times, dry over sodium sulfate, filter, and concentrate under reduced pressure to give crude residue. Purify the residue by flash chromatography, eluting with 2M ammonia in methanol:dichloromethane (5:95) to give the title compound: mass spectrum (m/e):419.05 (M+1).

Example 204

(S)-8-Chloro-2-methyl-11-[3-(2-methoxy-ethyl)-piperazin-1-yl]-5H-dibenzo[b,e][1,4]diazepine succinate

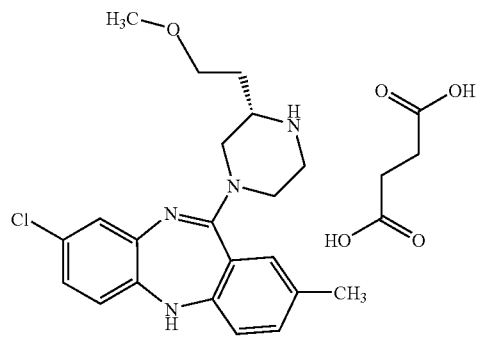

Stir a solution of 8-chloro-2-methyl-5H-dibenzo[b,e][1,4]diazepin-11-ylamine hydrochloride (0.2 g, 0.68 mmol), and diisopropylethylamine (0.264 g, 2.04 mmol) in 1methyl-2-pyrrolidinone (5 mL) for 30 minutes. Add (S)-2-(2-methoxy-ethyl)-piperazine (0.294 g, 2.04 mmol) and heat the resulting mixture to 195° C. for 16 hours. Cool reaction mixture to ambient temperature. Dilute with 50 ml of ethyl acetate and wash twice with brine, twice with water, and once again with brine. Collect the organic layer and dry over sodium sulfate. Remove solvent under reduced pressure. Purification via flash chromatography, eluting with a mixture of 50% hexanes: 50% dichloromethane plus 2% total volume isopropyl amine, gives the free base of the title compound (0.097 g, 0.25 mmol, 37% yield) as a yellow amorphous solid. Convert the product to the succinate salt by dissolving the product in methanol and adding one equivalent of succinic acid, swirl or sonicate the mixture until no solid succinic acid remains, and remove the solvent under reduced pressure to give the title compound: Mass Spectrum (m/e): 385(M+1).

Example 205

(S)-8-Chloro-2-isopropyl-11-[3-(2-methoxy-ethyl)-piperazin-1-yl]-5H-dibenzo[b,e][1,4]diazepine succinate

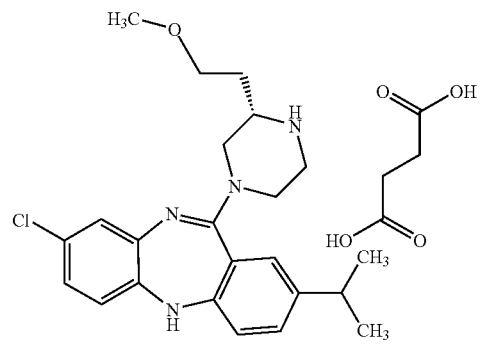

Stir a solution of 8-chloro-2-isopropyl-5H-dibenzo[b,e][1,4]diazepin-11-ylamine hydrochloride (0.285 g, 0.88 mmol), and diisopropylethylamine (0.137 g, 1.06 mmol) in 1-methyl-2-pyrrolidinone (7 mL) for 30 minutes. Add (S)-2-(2-methoxy-ethyl)-piperazine (0.383 g, 2.65 mmol) and heat the resulting mixture to 195° C. for 16 hours. Cool reaction mixture to ambient temperature. Dilute with 50 ml of ethyl acetate and wash twice with brine, twice with water, and once again with brine. Collect the organic layer and dry over sodium sulfate. Remove solvent under reduced pressure. Purification via flash chromatography, eluting with a step gradient starting at 99% dichloromethane: 1% 2M ammonia in methanol and going to 97%: 3%, gives the free base of the title compound (0.132 g, 0.32 mmol, 36% yield) as a light brown amorphous solid. Convert the product to the succinate salt as described previously to give the title compound: Mass Spectrum (m/e): 413(M+1); Exact Mass Spec: Calc. 413.2108; Found 413.2104.

Example 206

(S)-8-Fluoro-2-methyl-11-[3-(2-methoxy-ethyl)-piperazin-1-yl]-5H-dibenzo[b,e][1,4]diazepine succinate

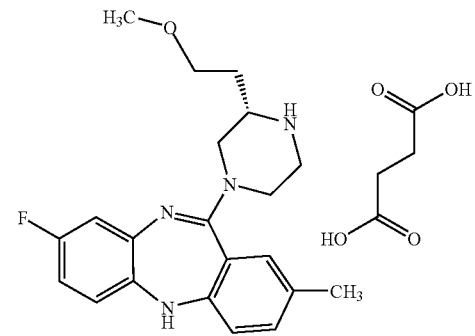

Stir a solution of 8-fluoro-2-methyl-5H-dibenzo[b,e][1,4]diazepin-11-ylamine hydrochloride (0.2 g, 0.72 mmol), and diisopropylethylamine (0.19 g, 1.44 mmol) in 1-methyl-2-pyrrolidinone (5 mL) for 30 minutes. Add (S)-2-(2-methoxy-ethyl)-piperazine (0.31 g, 2.16 mmol) and heat the resulting mixture to 195° C. for 16 hours. Cool reaction mixture to ambient temperature. Dilute with 100 ml of ethyl acetate and wash twice with brine, twice with water, and once again with brine. Collect the organic layer and dry over sodium sulfate. Remove solvent under reduced pressure. Purification via flash chromatography, eluting with a mixture of 50% hexanes: 50% dichloromethane plus 2% total volume isopropyl amine, gives the free base of the title compound (0.073 g, 0.20 mmol, 28% yield) as a yellow amorphous solid. Convert the product to the succinate salt as described previously to give the title compound: Mass Spectrum (m/e): 369(M+1): Exact Mass Spec: Calc. 369.2091; Found 369.2109.

Example 207

(S)-8-Fluoro-2-trifluoromethyl-11-[3-(2-methoxy-ethyl)piperazin-1-yl]-5H-dibenzo[b,e][1,4]diazepine succinate

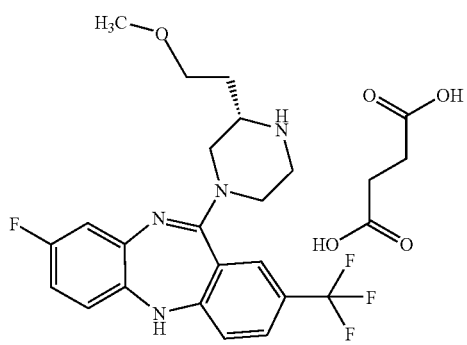

Stir a solution of 8-fluoro-2-trifluoromethyl-5H-dibenzo[b,e][1,4]diazepin-11-ylamine hydrochloride (0.2 g, 0.60 mmol), and diisopropylethylamine (0.078 g, 0.60 mmol) in 1-methyl-2-pyrrolidinone (5 mL) for 30 minutes. Add (S)-2-(2-methoxy-ethyl)-piperazine (0.261 g, 1.81 mmol) and heat the resulting mixture to 195° C. for 16 hours. Cool reaction mixture to ambient temperature. Dilute with 50 ml of ethyl acetate and wash once with brine, twice with water, and once again with brine. Collect the organic layer and dry over sodium sulfate. Remove solvent under reduced pressure. Purification via flash chromatography, eluting with a step gradient starting at 99% dichloromethane: 1% 2M ammonia in methanol and going to 95%: 5%, gives the free base of the title compound (0.061 g, 0.14 mmol, 24% yield) as a yellow-brown amorphous solid. Convert the product to the succinate salt as described previously to give the title compound: Mass Spectrum (m/e): 423(M+1); Exact Mass Spec: Calc. 423.1808; Found 423.1799.

Example 208

(S)-8-Fluoro-2-isopropyl-11-[3-(2-methoxy-ethyl)-piperazin-1-yl]-5H-dibenzo[b,e][1,4]diazepine succinate

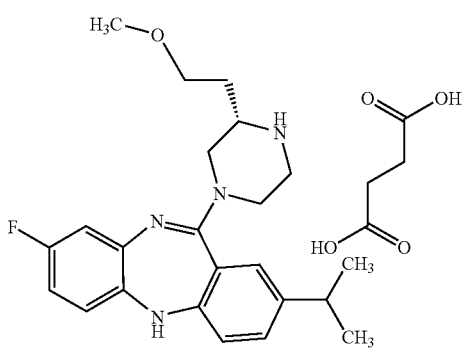

Stir a solution of 8-fluoro-2-isopropyl-5H-dibenzo[b,e][1,4]diazepin-1-ylamine hydrochloride (0.3 g, 0.98 mmol), and diisopropylethylamine (0.139 g. 2.94 mmol) in 1-methyl-2-pyrrolidinone (6 mL) for 30 minutes. Add (S)-2-(2-methoxy-ethyl)-piperazine (0.139 g, 1.08 mmol) and heat the resulting mixture to 195° C. for 16 hours. Cool reaction mixture to ambient temperature. Dilute with 50 ml of ethyl acetate and wash once with brine, twice with water, and once again with brine. Collect the organic layer and dry over sodium sulfate. Remove solvent under reduced pressure. Purification via flash chromatography, eluting with a linear gradient starting at 100% dichloromethane and going to 90% dichloromethane: 10% 2M ammonia in methanol, gives the free base of the title compound (0.094 g, 0.24 mmol, 24% yield) as a yellow-brown amorphous solid. Convert the product to the succinate salt as described previously to give the title compound: Mass Spectrum (m/e): 397(M+1).

Example 209

(S)-7-Fluoro-2-isopropyl-11-[3-(2-methoxy-ethyl-piperazin-1-yl]-5H-dibenzo[b,e][1,4]diazepine succinate

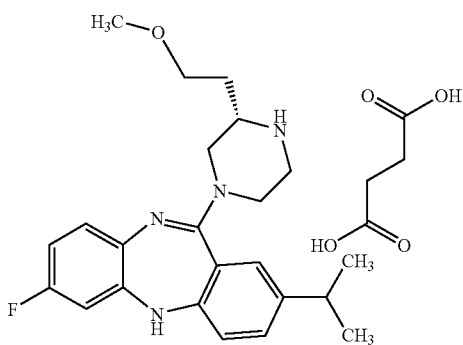

Stir a solution of 7-fluoro-2-isopropyl-5H-dibenzo[b,e][1,4]diazepin-11-ylamine hydrochloride (0.2 g, 0.65 mmol), and diisopropylethylamine (0.093 g, 1.96 mmol) in 1-methyl-2-pyrrolidinone (4 mL) for 30 minutes. Add (S)-2-(2- methoxy-ethyl)-piperazine (0.28 g, 1.96 mmol) and heat the resulting mixture to 195° C. for 16 hours. Cool reaction mixture to ambient temperature. Dilute with 50 ml of ethyl acetate and wash once with brine, twice with water, and once again with brine. Collect the organic layer and dry over sodium sulfate. Remove solvent under reduced pressure. Purification via flash chromatography, eluting with a linear gradient starting at 100% dichloromethane and going to 90% dichloromethane: 10% 2M ammonia in methanol, gives the free base of the title compound (0.085 g, 0.21 mmol, 33% yield) as a yellow-brown amorphous solid. Convert the product to the succinate salt as described previously to give the title compound: Mass Spectrum (m/e): 397(M+1).

Example 210

(S)-7-Fluoro-2-trifluoromethyl-11-[3-(2-methoxy-ethyl)-piperazin-1-yl]-5H-dibenzo[b,e][1,4]diazepine succinate

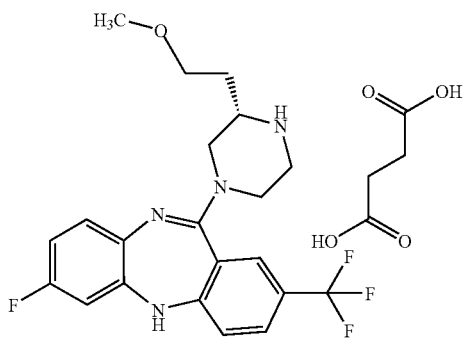

Stir a solution of 7-fluoro-2-trifluoromethyl-5H-dibenzo[b,e][1,4]diazepin-11-ylamine hydrochloride (0.4 g, 1.21 mmol), and diisopropylethylamine (0.171 g, 1.33 mmol) in 1-methyl-2-pyrrolidinone (8 mL) for 30 minutes. Add (S)-2-(2-methoxy-ethyl)-piperazine (0.52 g, 3.62 mmol) and heat the resulting mixture to 195° C. for 16 hours. Cool reaction mixture to ambient temperature. Dilute with 50 ml of ethyl acetate and wash once with brine, twice with water, and once again with brine. Collect the organic layer and dry over sodium sulfate. Remove solvent under reduced pressure. Purification via flash chromatography, eluting with a linear gradient starting at 99% dichloromethane: 1% 2M ammonia in methanol, and going to 90% dichloromethane: 10% 2M ammonia in methanol, gives the free base of the title compound (0.153 g, 0.36 mmol, 30% yield) as a yellow-orange amorphous solid. Convert the product to the succinate salt as described previously to give the title compound: Mass Spectrum (m/e): 423(M+1); Exact Mass Spec: Calc. 423.1808; Found 423.1790.

Example 211

(S)-7-Fluoro-2-trifluoromethyl-11-[3-(3-methoxy-propyl)-piperazin-1-yl]-5H-dibenzo[b,e][1,4]diazepine

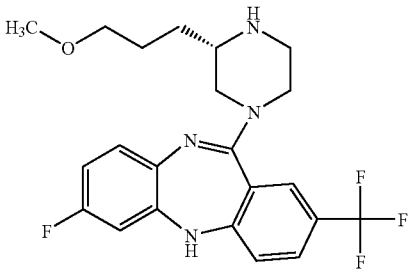

Combine 7-fluoro-2-trifluoromethyl-5H-dibenzo[b,e][1,4]diazepin-11-ylamine hydrochloride (0.399 g, 1.20 mmol), (S)-2-(3-methoxy-propyl)-piperazine (0.381 g, 2.41 mmol), and diisopropylethyl amine (0.21 mL, 1.20 mmol) in a mixture of toluene (4.5 mL) and dimethylsulfoxide (1.5 mL) and stir at 110° C. for 24 hours. Evaporate the mixture then purify by flash chromatography, eluting with a step gradient starting with dichloromethane going to 7% 2N ammonia-methanol in dichloromethane gives (s)-7-fluoro-11-[3-(3-methoxy-propyl)-piperazin-1-yl]-2-trifluoromethyl-5H-dibenzo[b,e][1,4]diazepine (0.268 g, 0.614 mmol, 51%) as a yellow oil. Mass spectrum (APCI): m/z=437.2 (M+1).

Example 212

(S)-8-Fluoro-2-trifluoromethyl-11-[3-(3-methoxy-propyl)-piperazin-1-yl]-5H-dibenzo[b,e][1,4]diazepine

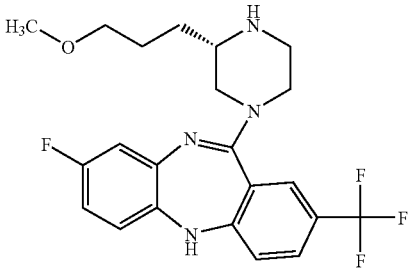

Combine 8-fluoro-2-trifluoromethyl-5H-dibenzo[b,e][1,4]diazepin-11-ylaminehydrochloride (0.201 g, 0.606 mmol), (S)-2-(3-methoxy-propyl)-piperazine (0.192 g, 1.21 mmol), and diisopropylethyl amine (0.106 mL, 0.606 mmol) in a mixture of toluene (3 mL) and dimethylsulfoxide (1 mL) and stir at 110° C. for 24 hours. Evaporate the mixture then purify by flash chromatography, eluting with a step gradient starting with dichloromethane going to 7% 2N ammonia-methanol in dichloromethane gives 8-fluoro-11-[3-(3-methoxy-propyl)-piperazin-1-yl]-2-trifluoromethyl-5H-dibenzo[b,e][1,4]diazepine (0.151 g, 0.346 mmol, 57%) as a yellow oil. Mass spectrum (APCI): m/z=437.2 (M+1).

Example 213

(S)-2-Cyclopropyl-7-fluoro-11-[3-(2-methoxy-ethyl)-piperazin-1-yl]-5H-dibenzo[b,e][1,4]diazepine succinate

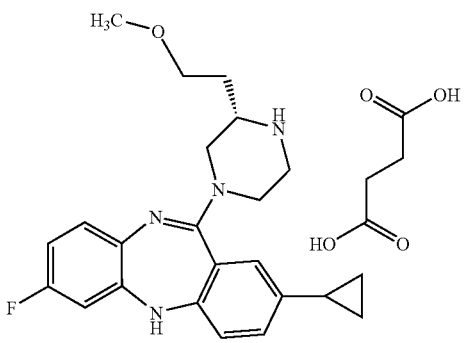

Stir a solution of 2-cyclopropyl-7-fluoro-5H-dibenzo[b,e][1,4]diazepin-11-ylamine hydrochloride (0.120 g, 0.40 mmol), and diisopropylethylamine (0.058 g, 1.22 mmol) in 1-methyl-2-pyrrolidinone (4 mL) for 30 minutes. Add (S)-2-(2-methoxy-ethyl)-piperazine (0.176 g, 1.22 mmol) and heat the resulting mixture to 195° C. for 16 hours. Cool reaction mixture to ambient temperature. Dilute with 50 ml of ethyl acetate and wash once with brine, twice with water, and once again with brine. Collect the organic layer and dry over sodium sulfate. Remove solvent under reduced pressure. Purification via flash chromatography, eluting with a linear gradient starting at 100% dichloromethane and going to 90% dichloromethane: 10% 2M ammonia in methanol, gives the free base of the title compound (0.067 g, 0.17 mmol, 43% yield) as a red amorphous solid. Convert the product to the succinate salt as described previously to give the title compound: Mass Spectrum (m/e): 395(M+1); Exact Mass Spec: Calc. 395.2247; Found 395.2244.

Example 214

(S)-7,8-Difluoro-2-trifluoromethyl-11-[3-(2-methoxy-ethyl)-piperazin-1-yl]-5H-dibenzo[b,e][1,4]diazepine succinate

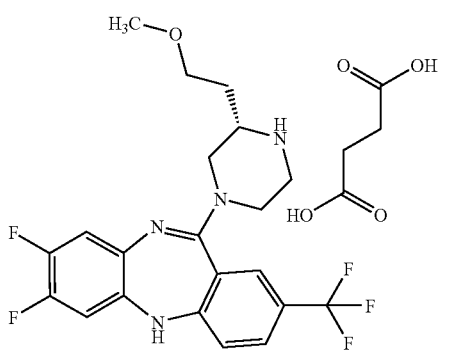

Stir a solution of 7,8-difluoro-2-trifluoromethyl-5H-dibenzo[b,e][1,4]diazepin-11-ylamine hydrochloride (0.2 g, 0.57 mmol), and diisopropylethylamine (0.081 g, 0.63 mmol) in 1-methyl-2-pyrrolidinone (4 mL) for 30 minutes. Add (S)-2-(2-methoxy-ethyl)-piperazine (0.25 g, 1.72 mmol) and heat the resulting mixture to 195° C. for 16 hours. Cool reaction mixture to ambient temperature. Dilute with 40 ml of ethyl acetate and wash once with brine, twice with water, and once again with brine. Collect the organic layer and dry over sodium sulfate. Remove solvent under reduced pressure. Purification via flash chromatography, eluting with a linear gradient starting at 100% dichloromethane and going to 85% dichloromethane: 15% 2M ammonia in methanol, gives the free base of the title compound (0.103 g, 0.23 mmol, 41% yield) as a light brown amorphous solid. Convert the product to the succinate salt as described previously to give the title compound: Mass Spectrum (m/e): 441(M+1); Exact Mass Spec: Calc. 441.1714; Found 441.1718.

Example 215

(S)-8-Chloro-2-trifluoromethyl-11-[3-(2-methoxy-ethyl)-piperazin-1-yl]-5H-dibenzo[b,e][1,4]diazepine succinate

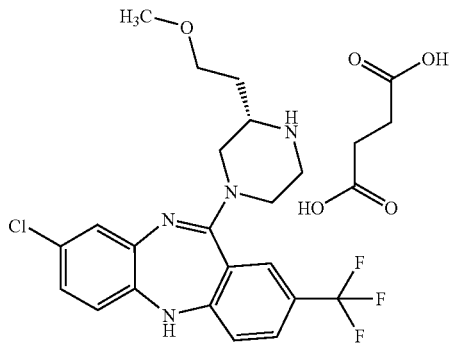

Using a method similar to the method of (S)-8-fluoro-2-trifluoromethyl-1-[3-(2-methoxy-ethyl)-piperazin-1-yl]-5H-dibenzo[b,e][1,4]diazepine succinate, using 8-chloro-2-trifluoromethyl-5H-dibenzo[b,e][1,4]diazepin-11-ylamine hydrochloride (0.706 g, 2.02 mmol) to give 0.081 g (9% yield) of the free base as an yellow solid. Convert the product to the succinate salt as described previously to give the title compound: Mass Spectrum (m/e): 440(M+1).

Example 215a (S)-2-Chloro-11-[3-(2-methoxy-ethyl)-piperazin-1-yl]-5H-dibenzo[b,e][1,4]diazepine

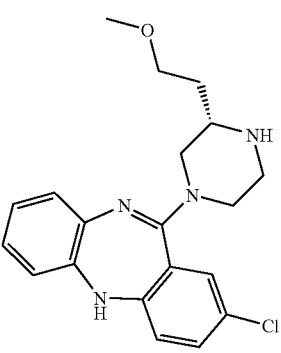

Combine 2-chloro-5H-dibenzo[b,e][1,4]diazepin-11-ylamine hydrochloride (0.840 g, 3.0 mmol), (S)-2-(2-methoxy-ethyl)-piperazine (0.865 g, 6.0 mmol), N,N-diisopropylethylamine (0.53 mL, 3.0 mmol), DMSO (1.25 ml), and toluene (5.0 ml) and stir and heat the mixture at 110° C. After 46 hours, cool the mixture to ambient temperature and dilute with ethyl acetate. Wash the organic layer with 0.1N NaOH and brine, dry (sodium sulfate) and concentrate the organic layer to 0.985 g of the crude product. Silica gel chromatography, eluting with dichloromethane/methanol (90:10) gives 0.501 g of the title compound as a yellow foam: mass spectrum (ion spray): m/z=371 (M+1).

Example 216

(S)-2-Methyl-11-[3-(2-methoxy-ethyl)-4-methyl-piperazin-1-yl]-5H-dibenzo[b,e][1,4]diazepine

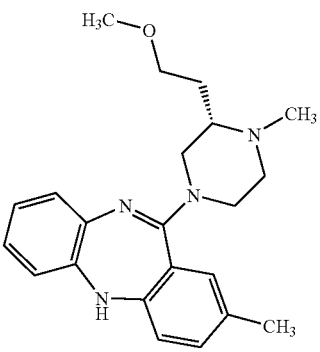

Combine (S)-2-methyl-11-[3-(2-methoxy-ethyl)-piperazin-1-yl]-5H-dibenzo[b,e][1,4]diazepine (300.0 mg, 0.86 mmol), formaldehyde (76.4 µL, 0.94 mmol, 37% in water), and 1,2-dichloroethane (28.0 ml) and stir the mixture at ambient temperature for 5 minutes and add sodium triacetoxyborohydride (272.1 mg, 1.28 mmol). After stirring for 30 minutes at ambient temperature, quench the reaction with saturated sodium bicarbonate. Remove the organic portion, extract the aqueous with dichloromethane and combine, wash (brine), dry (sodium sulfate), and reduce the extracts to residue. Purify the residue on silica gel using dichloromethane/methanol (90:10) to give 260.4 mg (89%) of a yellow foam: mp=60° C., dec; mass spectrum (ion spray): m/z=365.2 (M+1).

Example 217

(S)-3-Methyl-1-[3-(2-methoxy-ethyl)-4-methyl-piperazin-1-yl]-5H-dibenzo[b,e][1,4]diazepine

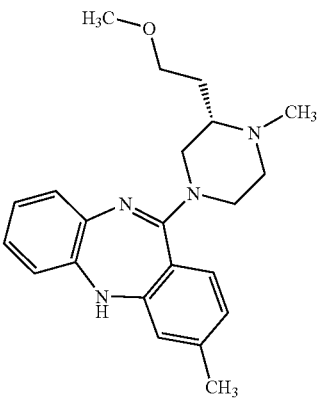

Combine (S)-3-methyl-11-[3-(2-methoxy-ethyl)-piperazin-1-yl]-5H-dibenzo[b,e][1,4]diazepine (215.4 mg, 0.61 mmol), formaldehyde (54.9 µL, 0.68 mmol, 37% in water), and 1,2-dichloroethane (20.0 ml). Stir the mixture at ambient temperature for 5 minutes and then add sodium triacetoxyborohydride (195.4 mg, 0.92 mmol). After stirring for 30 minutes at ambient temperature, quench the reaction with saturated sodium bicarbonate. Remove the organic portion, extract the aqueous with dichloromethane and combine, wash (brine), dry (sodium sulfate), and reduce the extracts to residue. Purify the residue on silica gel using dichloromethane/methanol (90:10) to give 171.1 mg (76%) of a yellow foam: mp=100-108° C.; mass spectrum (ion spray): m/z=365.2 (M+1).

Example 218

(S)-2-Isopropyl-11-[3-(2-methoxy-ethyl)-4-methyl-piperazin-1-yl]-5H-dibenzo[b,e][1,4]diazepine dihydrochloride

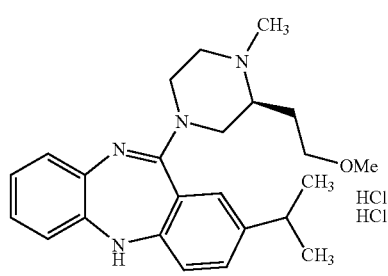

Combine (S)-2-isopropyl-11-[3-(2-methoxy-ethyl)-piperazin-1-yl]-5H-dibenzo[b,e][1,4]diazepine (0.405 g, 1.07 mmol) and 37% formaldehyde solution (0.1 mL, 1.12 mmol) in 1,2-dichloroethane (25 mL). Stir for 10 minutes and add sodium triacetoxy borohydride (0.343 g, 1.60 mmol). Stir an additional 30 minutes and then pour solution onto saturated sodium bicarbonate solution. Extract with methylene chloride to give 0.489 g of the crude product. Silica gel chromatography, eluting with methylene chloride:methanol (100:10), gives 0.354 g of the title compound as the free base. The dihydrochloride salt precipitates in ethyl acetate as a solid: mp=210° C.; mass spectrum (ion spray): m/z=393 (M+1); Analysis for $C_{24}H_{34}Cl_2N_4O$: calcd: C, 61.93; H, 7.36; N, 12.04; found: C, 61.74; H, 7.47; N, 11.86.

Example 219

(S)-2-Isopropyl-11-[3-(3-methoxy-propyl)-4-methyl-piperazin-1-yl]-5H-dibenzo[b,e][1,4]diazepine

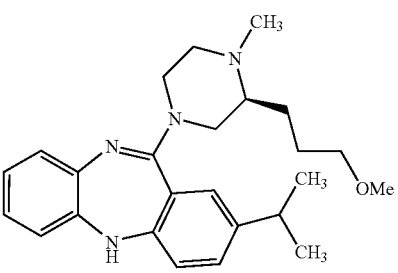

Using a method similar to Example 222 gives the title compound: mass spectrum (m/e):407.15 (M+1).

Example 220

(S)-2-Isopropyl-11-[3-(3-methoxy-propyl)-4-methyl-piperazin-1-yl]-5H-dibenzo[b,e][1.4]diazepine dihydrochloride

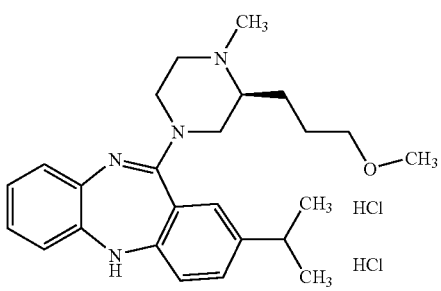

Using a method similar to Example 223 gives the title compound: mass spectrum (m/e):407.15 (M+1).

Example 221

(S)-2-Trifluoromethyl-11-[3-(2-methoxy-ethyl)-4-methyl-piperazin-1-yl]-5H-dibenzo[b,e][1,4]diazepine

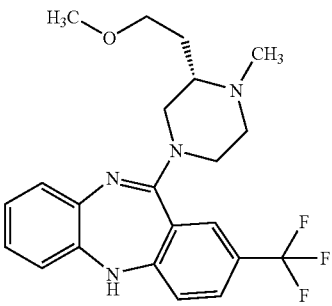

Add aqueous 37% formaldehyde (1.1 equiv.) to a solution of (S)-2-trifluoromethyl-11-[3-(2-methoxy-ethyl)-piperazin-1-yl]-5H-dibenzo[b,e][1,4]diazepine (470 mg) in dichloroethane (0.2M). Stir the mixture 2 minutes and add sodium triacetoxyborohydride (1.5 equiv). Stir the suspension for 30 minutes and quench with a saturated aqueous solution of sodium bicarbonate. Extract the aqueous phase 3 times with dichloromethane and combine the organic phases, dry over magnesium sulfate, filter and concentrate. Purify the residue via chromatography on silica gel (methylene chloride/methanol (90:10) to afford the title compound as a yellow solid (394 mg, 81%): mp 48-56° C.; $^1$H NMR (CDCl$_3$): δ 1.70-1.56 (m, 1H), 2.04-1.92 (m, 1H), 2.31 (m, 1H), 2.37 (s, 3H), 2.43 (dt, 1H), 2.81 (t, 1H), 2.89 (d, 1H), 3.13 (t, 1H), 3.25 (s, 3H), 3.38 (t, 2H), 3.73 (bs, 2H), 5.10 (s, 1H), 6.69 (dd, 1H), 6.93-6.88 (m, 2H), 7.00 (dt, 1H), 7.10 (dd, 1H), 7.56-7.50 (m, 2H); MS (ESI/neg) m/z (rel intensity) 417.4 (100).

Example 222

(S)-2-Trifluoromethyl-11-[3-(3-methoxy-propyl)-4-methyl-piperazin-1-yl]-5H-dibenzo[b,e][1,4]diazepine

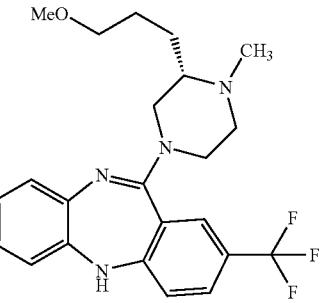

Add (S)-2-trifluoromethyl-11-[3-(3-methoxy-propyl)-piperazin-1-yl]-5H-dibenzo[b,e][1,4]diazepine (0.167 g, 0.399 mmol), formaldehyde (40.8 mg, 0.499 mmol, 37%), and sodium triacetoxyborohydride (0.127 g, 0.598 mmol) in dichloromethane (3 mL). Stir at ambient temperature over night. Dilute the mixture with water and extract with dichloromethane. Wash the organic with brine twice, dry over sodium sulfate, filter, and concentrate under reduced pressure to give crude residue. Purify the residue by flash chromatography, eluting with 2M ammonia in methanol: dichloromethane (5:95) to give the title compound: mass spectrum (m/e):433.08 (M+1).

Example 223

(S)-2-Trifluoromethyl-11-[3-(3-Methoxy-propyl)-4-methyl-piperazin-1-yl]-5H-dibenzo[b,e][1,4]diazepine dihydrochloride

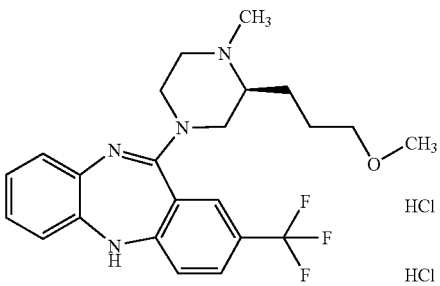

Add 2MHCl in diethyl ether (2.0 mL) to (S)-2-trifluoromethyl-11-[3-(3-methoxy-propyl)-4-methyl-piperazin-1-yl]-5H-dibenzo[b,e][1,4]diazepine (0.112 g, 0.259 mmol) in diethyl ether (1.0 mL), then concentrate under reduced pressure. Add hexane, transfer solid from vaccum filtration to give the title compound: mass spectrum (m/e):433.08, (M+1).

Example 224

(S)-8-Chloro-2-methyl-11-[3-(2-methoxy-ethyl)-4-methyl-piperazin-1-yl]-5H-dibenzo[b,e][1,4]diazepine succinate

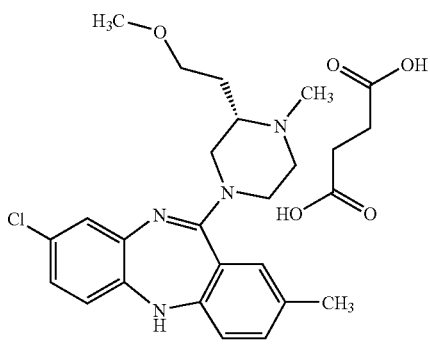

Dissolve (S)-8-chloro-2-methyl-11-[3-(2-methoxy-ethyl)-piperazin-1-yl]-5H-dibenzo[b,e][1,4]diazepine (0.070 g, 0.18 mmol) in dichloromethane (4 ml). Add sodium triacetoxyborohydride (0.116 g, 0.55 mmol) and formaldehyde (0.011 g, 0.36 mmol, 0.030 g of a 37% aqueous solution) and stir the mixture for two hours at ambient temperature. Dilute the mixture with 15 mL of saturated aqueous sodium chloride and extract three times with dichloromethane. Combine the organic layers, dry over sodium sulfate and remove the solvent under reduced pressure. Purification via flash chromatography, eluting with a mixture of 75% hexanes and 25% chloroform with 5% total volume 2M ammonia in methanol, gives the free base of the title compound (0.039 g, 0.10 mmol, 54% yield) as a yellow amorphous solid. It is then converted to the succinate salt as described previously: Mass Spectrum (m/e): 399(M+1).

Example 225

(S)-8-Chloro-2-isopropyl-11-[3-(2-methoxy-ethyl)-4-methyl-piperazin 1-yl]-5H-dibenzo[b,e][1,4]diazepine succinate

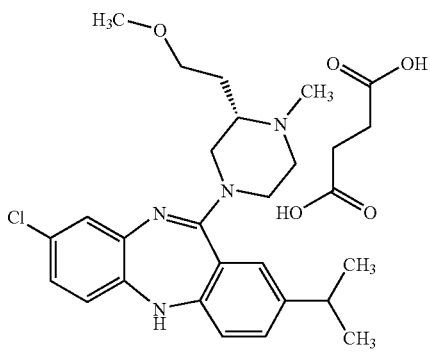

Dissolve (S)-8-chloro-2-isopropyl-11-[3-(2-methoxyethyl) piperazin-1-yl]-5H-dibenzo[b,e][1,4]diazepine succinate (0.089 g, 0.22 mmol) in dichloromethane (12 ml). Add sodium triacetoxyborohydride (0.137 g, 0.65 mmol) and formaldehyde (0.013 g, 0.43 mmol, 0.035 g of a 37% aqueous solution) and stir the mixture for two hours at ambient temperature. Dilute the mixture with 50 mL of saturated aqueous sodium chloride and extract three times with dichloromethane. Combine the organic layers, dry over sodium sulfate and remove the solvent under reduced pressure. Purification via flash chromatography, eluting with a mixture of 75% hexanes and 25% chloroform with 1% total volume isopropylamine, gives the free base of the title compound (0.027 g, 0.06 mmol, 29% yield) as a yellow amorphous solid. Convert to the succinate salt as described previously: Mass Spectrum (m/e): 427(M+1); Exact Mass Spec: Calc. 427.2265; Found 427.2279.

Example 227

(S)-8-Fluoro-2-methyl-11-[3-(2-methoxy-ethyl)-4-methyl-piperazin-1-yl]-5H-dibenzo[b,e][1,4]diazepine succinate

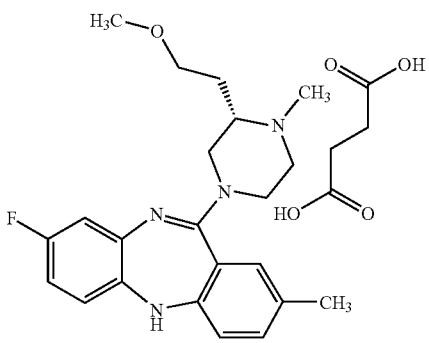

Dissolve (S)-8-fluoro-2-methyl-11-[3-(2-methoxy-ethyl)-piperazin-1-yl]-5H-dibenzo[b,e][1,4]diazepine (0.043 g, 0.12 mmol) in dichloromethane (4 ml). Add sodium triacetoxyborohydride (0.074 g, 0.35 mmol) and formaldehyde, (0.007 g, 0.23 mmol, 0.019 g of a 37% aqueous solution) and stir the mixture for two hours at ambient temperature. Dilute the mixture with 50 mL of saturated aqueous sodium chloride and extract three times with dichloromethane. Combine the organic layers, dry over sodium sulfate and remove the solvent under reduced pressure. Purification via flash chromatography, eluting with a mixture of 75% hexanes and 25% dichloromethane with 3% total volume 2M ammonia in methanol, gives the free base of the title compound (0.032 g, 0.08 mmol, 72% yield) as a yellow amorphous solid. Convert to the succinate salt as described previously: Mass Spectrum (m/e): 383(M+1); Exact Mass Spec: Calc. 383.2247; Found 383.2251.

Example 228

(S)-8-Fluoro-2-trifluoromethyl-11-[3-(2-methoxy-ethyl)-4-methyl-piperazin-1-yl]-5H-dibenzo[b,e][1,4]diazepine succinate

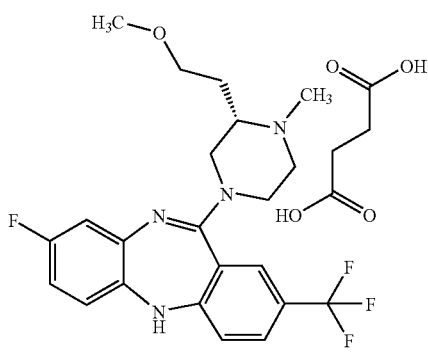

Dissolve (S)-8-fluoro-2-trifluoromethyl-1-[3-(2-methoxy-ethyl)-piperazin-1-yl]-5H-dibenzo[b,e][1,4]diazepine (0.031 g, 0.07 mmol) in dichloromethane (4 ml). Add sodium triacetoxyborohydride (0.047 g, 0.21 mmol) and formaldehyde (0.004 g, 0.14 mmol, 0.012 g of a 37% aqueous solution) stir the mixture for two hours at ambient temperature. Dilute the mixture with 50 mL of saturated aqueous sodium chloride and extract three times with dichloromethane. Combine the organic layers, dry over sodium sulfate and remove the solvent under reduced pressure. Purification via flash chromatography, eluting with a mixture of 75% hexanes and 25% dichloromethane with 5% total volume 2M ammonia in methanol, gives the free base of the title compound (0.021 g, 0.05 mmol, 66% yield) as a yellow amorphous solid. Convert to the succinate salt as described previously: Mass Spectrum (m/e): 437(M+1).

Example 229

(S)-8-Fluoro-2-isopropyl-11-[3-(2-methoxy-ethyl)-4-methyl-piperazin-1-yl]-5H-dibenzo[b,e][1,4]diazepine succinate

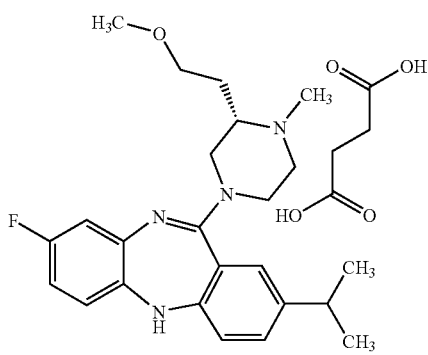

Dissolve (S)-8-fluoro-2-isopropyl-11-[3-(2-methoxy-ethyl)-piperazin-1-yl]-5H-dibenzo[b,e][1,4]diazepine (0.046 g, 0.12 mmol) in dichloromethane (6 ml). Add sodium triacetoxyborohydride (0.049 g, 0.23 mmol) and formaldehyde (0.004 g, 0.14 mmol, 0.011 g of a 37% aqueous solution) and stir the mixture for two hours at ambient temperature. Dilute the mixture with 50 mL of saturated aqueous sodium chloride and extract three times with dichloromethane. Combine the organic layers, dry, over sodium sulfate and remove the solvent under reduced pressure. Purification via flash chromatography, eluting with a mixture of 50% hexanes and 50% dichloromethane with 1% total volume isopropylamine, gives the free base of the title compound (0.030 g, 0.07 mmol, 63% yield) as a yellow amorphous solid. Convert to the succinate salt as described previously: Mass Spectrum (m/e): 411(M+1).

Example 230

(S)-7-Fluoro-2-isopropyl-11-[3-(2-methoxy-ethyl)-4-methyl-piperazin-1-yl]-5H-dibenzo[b,e][1,4]diazepine succinate

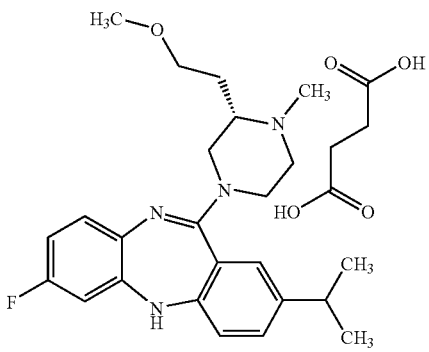

Dissolve (S)-7-fluoro-2-isopropyl-11-[3-(2-methoxy-ethyl)-piperazin-1-yl]-5H-dibenzo[b,e][1,4]diazepine (0.063 g, 0.16 mmol) in dichloromethane (8 ml). Add sodium triacetoxyborohydride (0.067 g, 0.32 mmol) and formaldehyde (0.005 g, 0.16 mmol, 0.013 g of a 37% aqueous solution) and stir the mixture for one hour at ambient temperature. Dilute the mixture with 30 ml of saturated aqueous sodium chloride and extract three times with 50 ml of dichloromethane. Combine the organic layers, dry over sodium sulfate and remove the solvent under reduced pressure. Purification via flash chromatography, eluting with a linear gradient starting at 99% dichloromethane: 1% 2M ammonia in methanol, and going to 90% dichloromethane: 10% 2M ammonia in methanol, gives the free base of the title compound (0.041 g, 0.10 mmol, 63% yield) as a yellow amorphous solid. Convert to the succinate salt as described previously: Mass Spectrum (m/e): 411(M+1); Exact Mass Spec: Calc. 411.2560; Found 411.2557.

Example 231

(S)-7-Fluoro-2-trifluoromethyl-11-[3-(2-methoxy-ethyl)-4-methyl-piperazin-1-yl]-5H-dibenzo[b,e][1,4]diazepine succinate

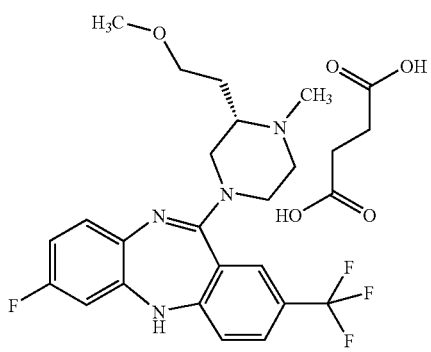

Dissolve (S)-7-fluoro-2-trifluoromethyl-11-[3-(2-methoxy-ethyl)-piperazin-1-yl]-5H-dibenzo[b,e][1,4]diazepine succinate (0.048 g, 0.11 mmol) in dichloromethane (6 ml). Add sodium triacetoxyborohydride (0.048 g, 0.23 mmol) and formaldehyde (0.003 g, 0.11 mmol, 0.009 g of a 37% aqueous solution) and stir the mixture for one hour at ambient temperature. Dilute the mixture with 10 ml of saturated aqueous sodium chloride and extract three times with 20 ml of dichloromethane. Combine the organic layers, dry over sodium sulfate and remove the solvent under reduced pressure. Purification via flash chromatography, eluting with a linear gradient starting at 99% dichloromethane: 1% 2M ammonia in methanol, and going to 90% dichloromethane: 10% 2M ammonia in methanol, gives the free base of the title compound (0.049 g, 0.11 mmol, 98% yield), as a yellow amorphous solid. Convert to the succinate salt as described previously: Mass Spectrum (m/e): 437(M+1); Exact Mass Spec: Calc. 437.1965; Found 437.1948.

Example 232

(S)-7-Fluoro-2-trifluoromethyl-11-[3-(3-methoxy-propyl)-4-methyl-piperazin-1-yl]-5H-dibenzo[b,e][1,4]diazepine dihydrochloride

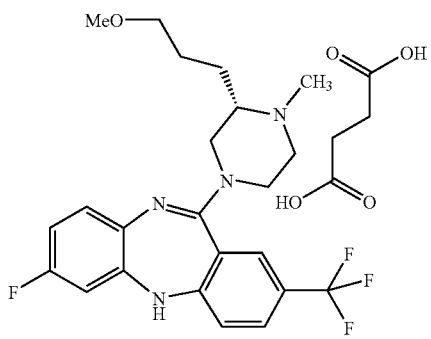

Combine (S)-7-fluoro-2-trifluoromethyl-11-[3-(3-methoxy-propyl)-piperazin 1-yl]-5H-dibenzo[b,e][1,4]diazepine (0.259 g, 0.593 mmol), formaldehyde (67 μL, 0.831 mmol, 37%), and sodium triacetoxyborohydride (0.189 g, 0.890 mmol) in dichloroethane (10 mL) and stir at room temperature overnight. Dilute the mixture with saturated sodium bicarbonate and extract three times with methylene chloride. Combine the organic layers, dry over sodium sulfate and concentrate under reduced pressure to give the crude product. Purification by flash chromatography, eluting with a step gradient starting with dichloromethane going to 5% 2N ammonia-methanol in dichloromethane gives (S)-7-fluoro-2-trifluoromethyl-11-[3-(3-methoxy-propyl)-4-methyl-piperazin-1-yl]-5H-dibenzo[b,e][1,4]diazepine (0.220 g, 0.488 mmol, 82%) as a yellow oil. Mass spectrum (APCI): m/z=451.3 (M+1). Isolate clean product as the corresponding dihydrochloride in the following manner: dissolve the yellow foam in ethanol (5 mL) and add a solution of about 5 equivalents of HCl in ethanol (5 mL). Evaporate the mixture to obtain (S)-7-fluoro-2-trifluoromethyl-11-[3-(3-methoxy-propyl)-4-methyl-piperazin-1-yl]-5H-dibenzo[b,e][1,4]diazepine dihydrochloride.

Example 233

(S)-8-Fluoro-2-trifluoromethyl 11-[3-(3-methoxy-propyl)-4-methyl-piperazin-1-yl]-5H-dibenzo[b,e][1,4]diazepine dihydrochloride Combine (S)-8-fluoro-2-trifluoromethyl-11-[3-(3-methoxy-propyl)-piperazin-1-yl]-5H-dibenzo[b,e][1,4]diazepine (0.144 g, 0.330 mmol), formaldehyde (37 μL, 0.461 mmol, 37%), and sodium triacetoxyborohydride (0.105 g, 0.495 mmol) in dichloroethane (5 mL) and stir at room temperature overnight. Dilute the mixture with saturated sodium bicarbonate and extract three times with methylene chloride. Combine the organic layers, dry over sodium sulfate and concentrate under reduced pressure to give the crude product. Purification by flash chromatography, eluting with a step gradient starting with dichloromethane going to 5% 2N ammonia-methanol in dichloromethane gives (S)-8-fluoro-2-trifluoromethyl-11-[3-(3-methoxy-propyl)-4-methyl-piperazin 1-yl]-5H-dibenzo[b,e][1,4]diazepine (0.115 g, 0.255 mmol, 77%) as a yellow oil. Mass spectrum (APCI): m/z=451.3 (M+1). Isolate clean product as the corresponding dihydrochloride in the following manner: dissolve the yellow foam in ethanol (5 mL) and add a solution of about 5 equivalents of HCl in ethanol (5 mL). Evaporate the mixture to obtain (S)-8-fluoro-2-trifluoromethyl-11-[3-(3-methoxy-propyl)-4-methyl-piperazin-1-yl]-5H-dibenzo[b,e][1,4]diazepine dihydrochloride.

Example 234

(S)-2-Cyclopropyl-7-fluoro-11-[3-(2-methoxy-ethyl)-4-methyl-piperazin-1-yl]-5H-dibenzo[b,e][1,4]diazepine succinate

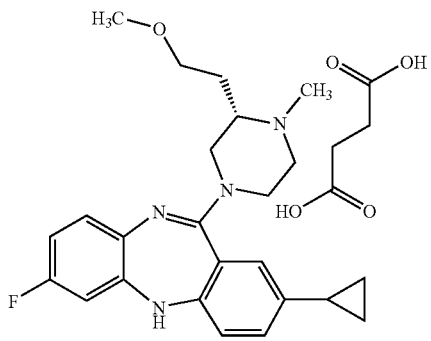

Dissolve (S)-2-cyclopropyl-7-fluoro 11-[3-(2-methoxy-ethyl)-piperazin-1-yl]-5H-dibenzo[b,e][1,4]diazepine (0.039 g, 0.10 mmol) in dichloromethane (5 ml). Add sodium triacetoxyborohydride (0.042 g, 0.20 mmol) and formaldehyde (0.003 g, 0.10 mmol, 0.008 g of a 37% aqueous solution) and stir the mixture for one hour at ambient temperature. Dilute the mixture with 25 ml of saturated aqueous sodium chloride and extract three times with 20 ml of dichloromethane. Combine the organic layers, dry over sodium sulfate and remove the solvent under reduced pressure. Purification via flash chromatography, eluting with a linear gradient starting at 99% dichloromethane: 1% 2M ammonia in methanol, and going to 90% dichloromethane: 10% 2M ammonia in methanol, gives the free base of the title compound (0.034 g, 0.08 mmol, 84% yield) as an orange amorphous solid. Convert to the succinate salt as described previously: Mass Spectrum (m/e): 409(M+1); Exact Mass Spec: Calc. 409.2404; Found 409.2417.

Example 235

(S)-7,8-Difluoro-2-trifluoromethyl-11-[3-(2-methoxy-ethyl)-4-methyl-piperazin-1-yl]-5H-dibenzo[b,e][1,4]diazepine succina

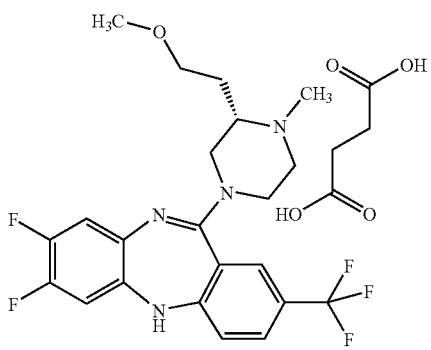

Dissolve (S)-7,8-difluoro-2-trifluoromethyl-11-[3-(2-methoxy-ethyl)-piperazin-1-yl]-5H-dibenzo[b,e][1,4]diazepine (0.067 g, 0.15 mmol) in dichloromethane (7 ml). Add sodium triacetoxyborohydride (0.064 g, 0.30 mmol) and formaldehyde (0.005 g, 0.15 mmol, 0.012 g of a 37% aqueous solution) and stir the mixture for one hour at ambient temperature. Dilute the mixture with 30 ml of saturated aqueous sodium chloride and extract three times with 20 ml of dichloromethane. Combine the organic layers, dry over sodium sulfate and remove the solvent under reduced pressure. Purification via flash chromatography, eluting with a linear gradient starting at 100% dichloromethane, and going to 85% dichloromethane: 15% 2M ammonia in methanol, gives the free base of the title compound (0.055 g, 0.12 mmol, 80% yield) as a yellow amorphous solid. Convert to the succinate salt as described previously: Mass Spectrum (m/e): 455(M+1): Exact Mass Spec: Calc. 455.1870; Found 455.1874.

Example 236

(S)-8-Chloro-2-trifluoromethyl-11-[3-(2-methoxy-ethyl)-4-methyl-piperazin-1-yl]-5H-dibenzo[b,e][1,4]diazepine succinate

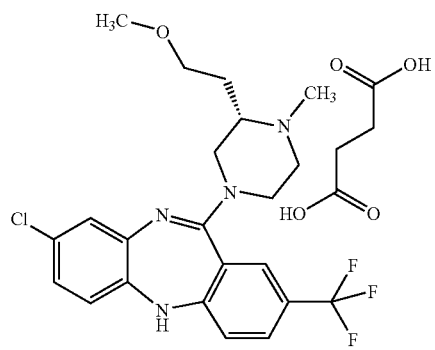

Using a method similar to Example (S)-8-fluoro-2-trifluoromethyl-11-[3-(2-methoxy-ethyl)-4-methyl-piperazin-1-yl]-5H-dibenzo[b,e][1,4]diazepine succinate, using (S)-8-chloro-2-trifluoromethyl-11-[3-(2-methoxy-ethyl)-piperazin-1-yl]-5H-dibenzo[b,e][1,4]diazepine (0.051 g, 0.12 mmol) to give 0.054 g (100% yield) of the free base as a yellow oil which is converted to the succinate salt as described previously: Mass Spectrum (m/e): 454(M+1).

Example 236a (S)-2-Chloro-11-[3-(2-methoxy-ethyl)-4-methyl-piperazin-1-yl]-5H-dibenzo[b,e][1,4]diazepine dihydrochloride

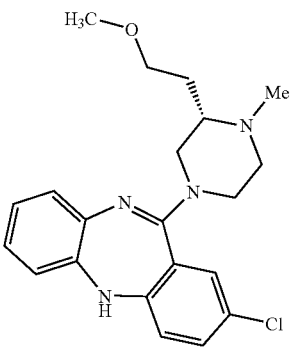

Combine (S)-2-chloro-11-[3-(2-methoxy-ethyl)-piperazin-1-yl]-5H-dibenzo[b,e][1,4]diazepine (0.474 g, 1.27 mmol) and 37% formaldehyde solution (0.1 mL, 1.34 mmol) in 1,2-dichloroethane (20 mL). Stir for 10 minutes and add sodium triacetoxy borohydride (0.542 g, 2.55 mmol). Stir an additional 30 minutes and then pour solution onto saturated sodium bicarbonate solution. Extract with methylene chloride to give 0.555 g of the crude product. Silica gel chromatography, eluting with methylene chloride:methanol (100:5), gives 0.490 g of the title compound as the free base. The dihydrochloride salt precipitates in ethyl acetate as a solid: mp 205° C.; mass spectrum (ion spray): m/z=385 (M+1).

Example 237

(R)-[4-(2-Methyl-4H-3-thia 4,9-diaza-benzo[f]azulen-10-yl)-piperazin-2-yl]-methanol

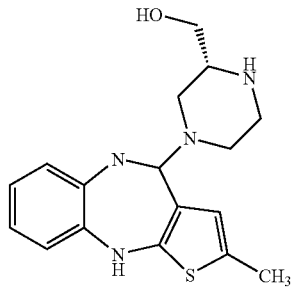

By using a similar coupling method to (S)-2-trifluoromethyl 11-[3-(2-methoxy-ethyl)-piperazin-1-yl]-5H-dibenzo[b,e][1,4]diazepine, using 2-methyl-4H-3-thia-4,9-diaza-benzo[f]-azulen-10-ylamine hydrochloride affords the title compound as a tan powder: mp 90° C.; $^1$H NMR (CDCl$_3$) δ 2.31 (s, 3H), 2.89 (ddd, 1H), 3.00-3.25 (m, 4H), 3.55 (dd, 1H), 3.72 (dd, 1H), 3.72-3.87 (m, 2H), 5.02 (s, 1H), 6.29 (s, 1H), 6.60 (d, 1H), 6.87 (t, 1H), 6.96 (t, 1H), 7.01 (d, 1H); MS (APCI) m/z (rel intensity) 329 (100).

Example 238

(R)-10-(3-Methoxymethyl-piperazin-1-yl)-2-methyl-4H-3-thia-4,9-diaza-benzo[f]azulene

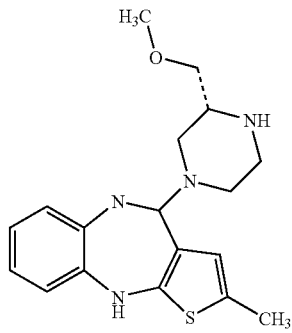

By using a similar coupling method to (S)-2-trifluorom-ethyl-11-[3-(2-methoxy-ethyl)-piperazin-1-yl]-5H-dibenzo[b, e][1,4]diazepine, using 2-methyl-4H-3-thia-4,9-diaza-benzo[f]azulen-10-ylamine hydrochloride (1.9 g) and (R)-2-methoxymethyl-piperazine (2.6 g) affords the title compound as a yellow solid (974 mg, 41%); mp 87-95° C.: $^1$H NMR (CDCl$_3$) δ 2.32 (d, 3H), 2.69 (dd, 1H), 3.10-2.87 (m, 4H), 3.33 (dd, 1H), 3.38 (s, 3H), 3.49-3.43 (m, 1H), 3.94 (d, 1H), 4.02 (d, 1H), 4.98 (s, 1H), 6.30 (s, 1H), 6.61 (dd, 1H), 6.88 (dt, 1H), 6.97 (dt, 1H), 7.03 (dd, 1H); MS (APCI) m/z (rel intensity) 343.3 (100).

Example 239

(R)-10-[3-(2-Methyl-allyloxymethyl)-piperazin-1-yl]-2-methyl-4H-3-thia-4,9-diaza-benzo[f]azulene

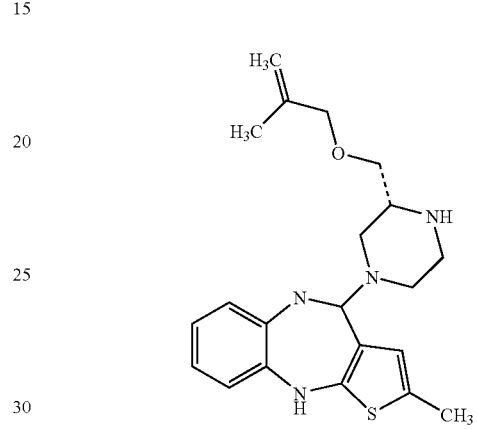

By using a similar coupling method to (S)-2-trifluorom-ethyl-11-[3-(2-methoxy-ethyl)-piperazin-1-yl]-5H-dibenzo[b,e][1,4]diazepine, gives the title compound as a yellow solid: $^1$H NMR (CDCl$_3$) δ 1.74 (s, 3H), 2.31 (s, 3H), 2.68 (dd, 1H), 2.92-2.96 (m, 2H), 3.03-3.10 (m, 2H), 3.35 (dd, 1H), 3.47 (dd, 1H), 3.90 (s, 2H), 3.95-4.04 (m, 2H), 4.90 (s, 1H), 4.96 (s, 2H), 6.30 (s, 1H), 6.60 (d, 1H), 6.87 (t, 1H), 6.97 (t, 1H), 7.02 (d, 1H); MS (es) m/z (rel intensity) 383 (100).

Example 240

(S)-2-[4-(2-Methyl-4H-3-thia-4,9-diazabenzo[f]azulene-10-yl)-piperazin-2-yl]ethanol dihydrochloride

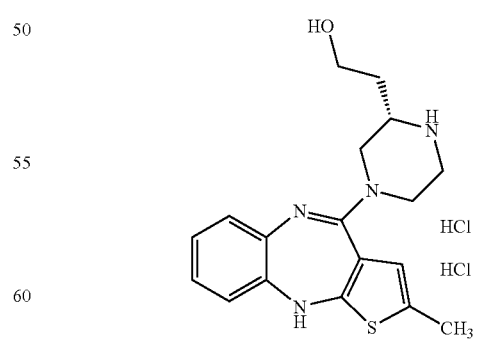

Combine (S)-2-piperazin-2-yl-ethanol (1.48 g, 11.35 mmol) and 2-methyl-4H-3-thia-4,9-diazabenzo[f]azulene-10-ylamine free base (1.3 g, 5.67 mmol) in 9 mL of dimethylsulfoxide and 27 mL of toluene. Fit reaction flask with reflux condenser; heat mixture at 110° C. under gentle positive nitrogen pressure for 3 days. Dilute with methanol and apply directly to a 46 g SCX column. Wash column with methanol, elute with 2N ammonia-methanol. Concentrate eluant in vacuo to obtain a dark brown residue, purify on silica gel. Elute with a gradient of 2.5% 2N ammonia-methanol in dichloromethane, then 5%, then 10% to obtain the crude free base of the title compound (0.48 g, 25%) as a brown oil: mass Spectrum (APCI): m/z=343.1 (M+1).

Isolate clean product as the corresponding dihydrochloride in the following manner: partition 220 mg of the brown oil free base between water and dichloromethane. Separate the organic layer and remove solvent in vacuo; take up residue in methanol and apply to SCX column. Wash column with methanol; elute with hydrochloric acid in ethanol (prepared by adding 20 mL of acetyl chloride to 500 mL of ethanol) and collect the resulting yellow band that slowly travels down the column. Combine yellow fractions and concentrate in vacuo. Redissolve the resulting foamy residue in a 1:1 mixture of water and acetonitrile, and lyophilize overnight to obtain 197 mg (74%) of the dihydrochloride of the title compound as a fluffy orange solid: melting point>250° C. (dec): mass Spectrum (APCI): m/z=343.1 (M+1 of free base).

Example 241

(R)-2-[4-(2-Methyl-4H-3-thia-4,9-diazabenzo[f] azulene-10-yl)-piperazin-2-yl]ethanol dihydrochloride

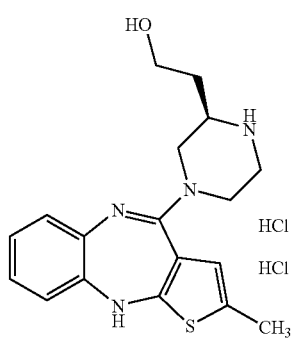

Combine (R)-2-piperazin-2-yl-ethanol (0.92 g, 7 mmol) and 2-methyl-4,9-dihydro-3-thia-4,9-diazabenzo[f]azulene-10-thione (1.7 g, 7 mmol) in pyridine (14 mL). Heat at 120° C. overnight, then remove solvent in vacuo and redissolve in methanol. Purify on 20 g of SCX resin, washing with methanol and eluting first with 5% 2N ammonia-methanol in dichloromethane and then with straight 2N ammonia-methanol. Combine product fractions, then further purify on silica gel utilizing a step gradient from 2.5% to 5% 2N ammonia-methanol in dichloromethane. Isolate as the dihydrochloride salt (243 mg, 8%) by treating an ethanolic solution of the free base with a solution of 5 equivalents of hydrochloric acid in ethanol, then evaporating: melting point>250° C. (dec): mass spectrum (APCI): m/z=343.1 (M+1 of free base).

Example 241a (S)-10-[3-(2-Methoxy-ethyl)-piperazin-1-yl]-4H-3-thia-4,9-diaza-benzo[f]azulene

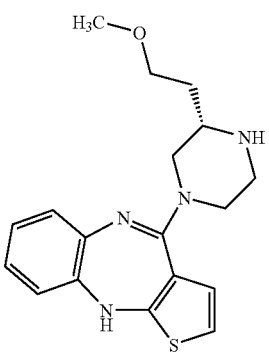

Combine 4H-3-thia-4,9-diaza-benzo[f]azulen-10-ylamine (1.26 g, 5.85 mmol), (S)-2-(2-methoxy-ethyl)-piperazine (2.53 g, 17.56 mmol), DMSO (4.0 ml), and toluene (16.0 ml). Stir and heat the mixture at 105° C. After 24 hours, cool the mixture to ambient temperature. Dilute the mixture with ethyl acetate and wash the organic layer with 0.1N NaOH and brine. Dry (sodium sulfate) and concentrate the organic layer to residue. Purify the residue on silica gel using a gradient of dichloromethane to dichloromethane/methanol (85:15) to give 395.8 mg (20%) of an brown foam: mass spectrum (ion spray): m/z=343.1 (M+1).

Example 242

(S)-10-[3-(2-Methoxyethyl)-piperazin-1-yl]-2-methyl-4H-3-thia-4,9-diazabenzo[f]azulene hydrochloride

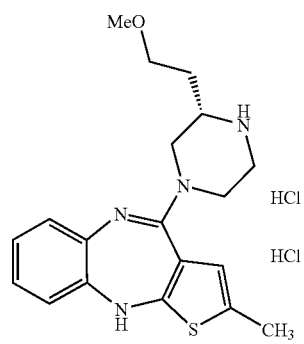

In a manner such as that described in Example 242a, convert (S)-2-(2-methoxyethyl)piperazine (161 mg, 1 mmol) into the title compound: mass spectrum (APCI): m/z=357.2 (M+1).

Example 242a (S)-10-[3-(2-Phenoxy-ethyl)-piperazin-1-yl]-2-methyl-4H-3-thia-4,9-diaza-benzo[f]azulene

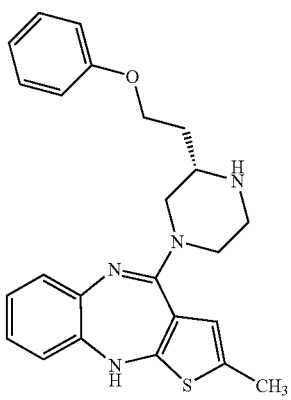

Combine 2-methyl-4,9-dihydro-3-thia-4,9-diazabenzo[f] azulene-10-thione (0.382 g 1.55 mmol), (S)-2-(2-phenoxy-ethyl)piperazine (0.320 g, 1.55 mmol) and pyridine (5 mL) and reflux for 36 hours. Evaporate the mixture and apply the material to 10 g of SCX, then elute with methanol followed by 5% 2N ammonia-methanol in dichloromethane and then 2N ammonia-methanol. Purification by flash chromatography, eluting with a step gradient starting with dichloromethane going to 7% 2N ammonia-methanol in dichloromethane gives the title compound: mass spectrum (APCI): m/z=419.1 (M+1).

Example 243

(S)-10-[3-(2-Ethoxyethyl)-piperazin-1-yl]-2-methyl-4H-3-thia-4,9-diazabenzo[f]azulene

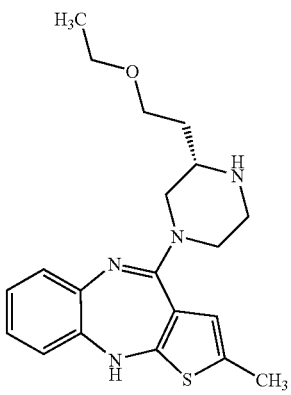

In a manner similar to that described in Example 311, combine 2-methyl-4,9-dihydro-3-thia-4,9-diazabenzo[f] azulene-10-thione (0.487 g, 1.98 mmol) and (S)-2-(2-ethoxyethyl)piperazine (0.313 g, 1.98 mmol) to obtain the title compound: mass spectrum (APCI): m/z=371.2 (M+1).

Example 244

(R)-10-(3-Phenoxymethyl-piperazin-1-yl)-2-methyl-4H-3-thia-4,9-diaza-benzo[f]azulene

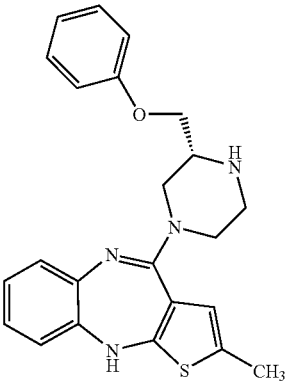

By using a method similr to the coupling method for (S)-2-trifluoromethyl-11-[3-(2-methoxy-ethyl)-piperazin-1-yl]-5H-dibenzo[b,e][1,4]diazepine, 2-methyl-4H-3-thia-4,9-diaza-benzo[f]-azulen-10-ylamine hydrochloride (1.2 g) and (R)-2-phenoxymethyl-piperazine (2.6 g) gives the title compound as a yellow solid (728 mg): mp=64-81° C.: $^1$H NMR (CDCl$_3$) δ 2.32 (s, 3H), 2.86 (dd, 1H), 3.14-2.94 (m, 3H), 3.32-3.24 (m, 1H), 3.98-3.87 (m, 2H), 4.02 (dd, 1H), 4.11 (bd, 1H), 4.96 (bs, 1H), 6.32-6.30 (m, 1H), 6.61 (dd, 1H), 7.00-6.86 (m, 5H), 7.04 (dd, 1H), 7.34-7.25 (m, 2H); MS (APCI) m/z (rel intensity) 405.4 (100).

Example 245

(S)-10-[3-(2-Methoxy-ethyl)-piperazin-1-yl]-2-isopropyl-4H-3-thia-4,9-diaza-benzo[f]azulene

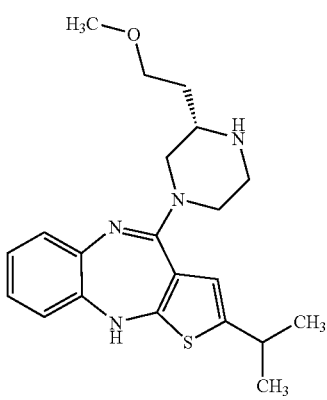

Add 2-isopropyl-4H-3-thia-4,9-diaza-benzo[f]azulene-10-ylamine hydrochloride (0.32 g, 1.07 mmol) to a solution of (S)-2-(2-methoxy-ethyl)-piperazine (0.31 g, 2.15 mmol) in dimethyl sulfoxide: toluene (1:3, 4 mL). Add diisopropylethylamine (0.19 mL, 1.09 mmol), heat to 110° C. and stir. After an overnight period, cool to ambient temperature to give crude title compound.

Example 246

(S)-10-[3-(2-Methoxy-ethyl)-piperazin-1-yl]-2-isopropyl-4H-3-thia-4,9-diaza-benzo[f]azulene

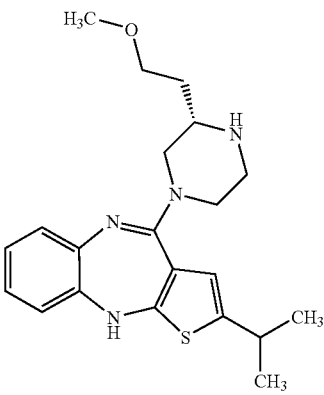

Combine 2-isopropyl-4H-3-thia-4,9-diaza-benzo[f]azulene-10-ylamine hydrochloride (0.31 g, 1.04 mmol) and (S)-2-(2-methoxy-ethyl)-piperazine (0.30 g, 2.08 mmol) with anhydrous pyridine (4 mL), heat to 110° C. and stir overnight. Cool to ambient temperature to give crude material. Purification by cation exchange chromatography, eluting with solutions of 2M ammonia in methanol, in dichloromethane, (2%, 5%, 10%), and 2M ammonia in methanol, followed by flash chromatography, eluting with a gradient of solutions of 2M ammonia in methanol, in dichloromethane (2-4%), to give the title compound: mass spectrum (APCI, m/e): 385 (M+1); NMR ($^1$H, 300 MHz, DMSO-d$_6$),δ (ppm): 7.60 (s, 1H), 6.86-6.73 (m, 3H), 6.67 (m, 1H), 6.30 (s, 1H), 3.78 (m, 2H), 3.38-3.33 (m, 2H), 3.19 (s, 3H), 3.01-2.60 (m, 6H), 2.39 (m, 1H), 1.51 (m, 2H), 1.17 (d, 6H, J=7.5 Hz).

Example 246a (S)-10-[3-(3-Methoxy-propyl)-piperazin-1-yl]-4H-3-thia-4,9-diaza-benzo[f]azulene

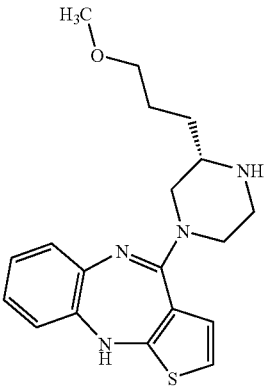

Combine 4H-3-thia-4,9-diaza-benzo[f]azulen-10-ylamine (1.10 g, 5.11 mmol), (S)-2-(3-methoxy-propyl)-piperazine (1.62 g, 10.22 mmol), DMSO (4.0 ml), and toluene (16.0 ml). Stir and heat the mixture at 105° C. After 45 hours, cool the mixture to ambient temperature. Dilute the mixture with ethyl acetate and wash the organic layer with 0.1N NaOH and brine. Dry (sodium sulfate) and concentrate the organic layer to residue. Purify the residue on silica gel using a gradient of dichloromethane to dichloromethane/methanol (85:15) to give 296.0 mg (16%) of the title compound: mass spectrum (ion spray): m/z=357.2 (M+1).

Example 246b (S-10-[3-(3-Methoxy-propyl)-piperazin-1-yl]-2-methyl-4H-3-thia-4,9-diaza-benzo[f]azulene

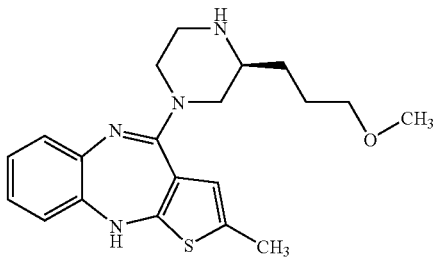

Using a method similar to Example 203 using 2-methyl-4H-3-thia-4,9-diaza-benzo[f]azulen-10-ylamine to give the title compound: mass spectrum (m/e):371.08 (M+1).

Example 247

(S)-10-[3-(4-Methoxybutyl)-piperazin-1-yl]-2-methyl 4H-3-thia-4,9-diaza-benzo[f]azulene

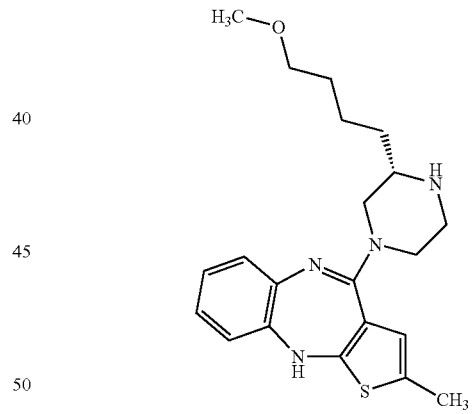

Heat in a 211° C. oil bath, a stirring solution of (S)-2-(4-methoxybutyl)-piperazine 0.086 g, 0.49 mmol), and 2-methyl-4H-3-thia-4,9-diaza-benzo[f]azulen-10-ylamine (0.114 g, 0.49 mmol) in NMP (1 mL) for 4 h. Cool to room temperature, dilute the solution with brine (15 mL) and extract with EtOAc (3×30 mL). Concentrate the organic layers under reduced pressure to a volume of 20 mL and wash with 75% brine (4×20 mL). Dry the organic layer over Na$_2$SO$_4$, and filter. Concentrate the mixture under reduced pressure and purify by silica gel chromatography eluting with 10% (33% 2 M NH$_3$ in MeOH/64% EtOH)/CH$_2$Cl$_2$. Combine the purified fractions, concentrate under reduced pressure, azeotrope with CH$_2$Cl$_2$/hexanes and place under vacuum to give the title compound: brown solid (0.036 g), mass spectrum (m/e):385.08 (M+H).

Example 247a (S)-6-Fluoro-10-[3-(2-methoxy-ethyl)-piperazin-1-yl]-4H-3-thia-4,9-diaza-benzo[f]azulene

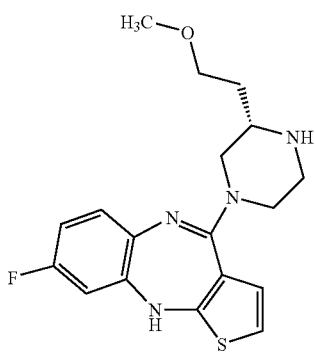

Combine 6-fluoro-4H-3-thia-4,9-diaza-benzo[f]azulen-10-ylamine hydrochloride (1.20 g, 4.45 mmol), (S)-2-(2-methoxy-ethyl)-piperazine (1.60 g, 11.12 mmol), DMSO (4.0 ml), and toluene (16.0 ml). Stir and heat the mixture at 105° C. After 40 hours, cool the mixture to ambient temperature. Dilute the mixture with ethyl acetate and wash the organic layer with 0.1N NaOH and brine. Dry (sodium sulfate) and concentrate the organic layer to residue. Purify the residue on silica gel using a gradient of dichloromethane to dichloromethane/methanol (90:10) to give 400.4 mg (25%) of a tan foam: mass spectrum (ion spray): m/z 361.1 (M+1).

Example 247b (S)-6-Fluoro-10-[3-(3-methoxy-propyl)-piperazin-1-yl]-4H-3-thia-4,9-diaza-benzo[f]azulene

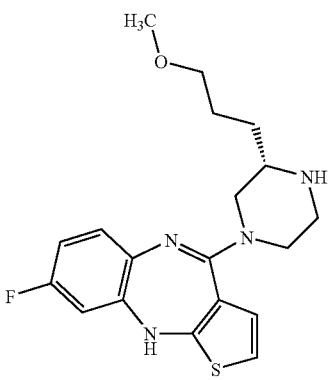

Combine 6-fluoro-4H-3-thia-4,9-diaza-benzo[f]azulen-10-ylamine hydrochloride (742.0 mg, 2.75 mmol), (S)-2-(3-methoxy-propyl)-piperazine (870.7 mg, 5.50 mmol), DMSO (2.0 ml), and toluene (8.0 ml). Stir and heat the mixture at 105° C. After 48 hours, cool the mixture to ambient temperature. Dilute the mixture with ethyl acetate and wash the organic layer with 0.1N NaOH and brine. Dry (sodium sulfate) and concentrate the organic layer to residue. Purify the residue on silica gel using a gradient of dichloromethane to dichloromethane/methanol (85:15) to give 220.1 mg (21%) of the title compound: mass spectrum (ion spray): m/z 375.1 (M+1).

Example 248

(S)-6-Fluoro-10-[3-(2-methoxy-ethyl)-piperazin-1-yl]-2-methyl-4H-3-thia-4,9-diaza-benzo[f]azulene

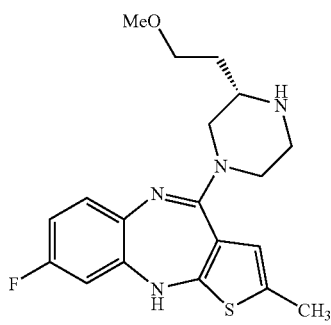

Suspend 6-fluoro-2-methyl-4,9-dihydro-3-thia-4,9-diaza-benzo[f]azulene-10-thione (500 mg, 1.9 mmol) in dichloromethane (30 ml), stir under nitrogen and cool in an ice/water bath. Add methyl trifluoromethanesulfonate (500 μl), and stir overnight. Concentrate the reaction mixture under reduced pressure, take up in pyridine (10 ml) and add (S)-2-(2-methoxyethyl)piperazine (400 mg, 2.78 mmol) and stir the reaction mixture under nitrogen and heat at 90° C. for three days. Concentrate the reaction mixture under reduced pressure and purify by flash column chromatography on silica gel (eluent dichloromethane/methanol) to give the desired as a yellow solid 727 mg: Mass Spectrum (FIA) 375 (M+1).

Example 248a (S)-6-Fluoro-10-[3-(2-methoxy-ethyl)-piperazin-1-yl]-2-methyl-4H-3-thia-4,9-diaza-benzo[f]azulene

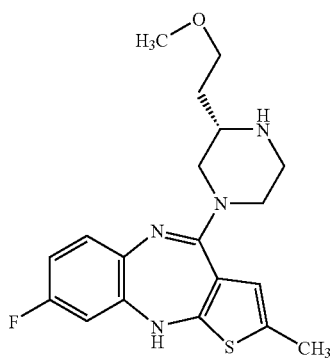

Stir 6-fluoro-2-methyl-10-methylsulfanyl-4H-3-thia-4,9-diaza-benzo[f]azulene (3.40 g, 12.2 mmol) and (S)-2-(2-methoxy-ethyl)-piperazine (2.20 g, 15.3 mmol) in isopropyl alcohol (20 mL) at ambient temperature under nitrogen for 20-30 minutes to dissolve. Heat to reflux (80-83° C.) for 3-4 days, and then allow cooling to ambient temperature. Concentrate the mixture under reduced pressure to give a residue. Purify the residue by flash chromatography, eluting with 90:10:1→80:20:1/EtOAc:MeOH:c. NH₄OH to give 4.06 g (89%) the title compound. ¹H NMR (400 MHz, DMSO-d₆) δ 7.75 (bs, 1H), 6.78 (m, 1H), 6.68 (m, 1H), 6.53 (m, 1H), 6.35 (s, 1H), 3.80 (m, 2H), 3.40 (m, 2H), 3.23 (s, 3H), 2.88 (m, 1H), 2.71 (m, 3H), 2.41 (m, 1H), 2.30 (bs, 1H), (s, 3H), 1.53 (m, 2H). HRMS (ES) exact mass M+H calcd for C₁₉H₂₃FN₄OS 375.1655; found 375.1663.

Example 248b (S)-6-Fluoro-10-[3-(2-methoxy-ethyl)-piperazin-1-yl]-2-methyl-4H-3-thia-4,9-diaza-benzo[f]azulene dihydrochloride

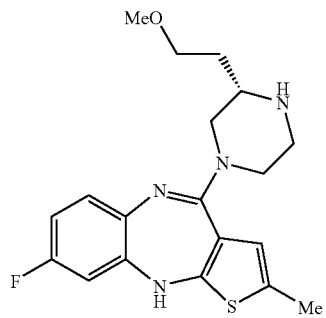

Combine 6-fluoro-2-methyl-4H-3-thia-4,9-diaza-benzo[f]azulen-10-ylamine (2.16 g, 8.7 mmol) and (S)-2-(2-methoxy-ethyl)-piperazine (1.39 g, 9.6 mmol) in NMP (16.0 mL) and heat at 190° C. for 1 hour. Cool to ambient temperature and dilute with water. Extract with ethyl acetate to give 2.25 g of the crude product. Silica gel chromatography, eluting with methylene chloride: 2N NH₃/methanol (100:7), gives 0.616 g of the title compound as an oil. The dihydrochloride salt precipitates in ethyl acetate as a light green solid: mp 90° C.; mass spectrum (ion spray): m/z=375 (M+1); Analysis for C₁₉H₂₅Cl₂FN₄OS(0.8H₂O): calcd: C, 49.41; H, 5.81; N, 12.13; found: C, 49.75; H, 5.74; N, 11.75.

Example 248 c (S)-6-Fluoro-10-[3 (3-methoxy-propyl)-piperazin-1-yl]-2-methyl-4H-3-thia-4,9-diaza-benzo[f]azulene dihydrochloride

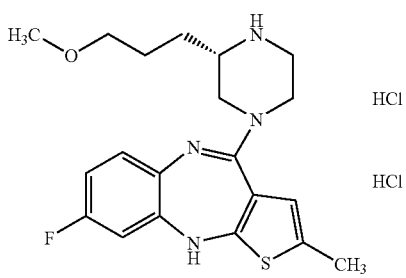

Combine 6-fluoro-2-methyl-4H-3-thia-4,9-diaza-benzo[f]azulen-10-ylamine hydrochloride (0.304 g, 1.07 mmol), (S)-2-(3-methoxy-propyl)-piperazine (0.339 g, 2.14 mmol), and diisopropylethyl amine (0.19 mL, 1.07 mmol) in a mixture of toluene (3 mL) and dimethylsulfoxide (1 mL) and stir at 110° C. for 24 hours. Evaporate the mixture then purify by flash chromatography, eluting with a step gradient starting with dichloromethane going to 5% 2N ammonia-methanol in dichloromethane gives (s)-6-fluoro-10-[3-(3-methoxy-propyl)-piperazin-1-yl]-2-methyl-4H-3-thia-4,9-diaza-benzo[f]azulene (0.110 g, 0.283 mmol, 26%) as a yellow oil. Mass spectrum (APCI): m/z=389.1 (M+1).

Example 249

(S)-7-Fluoro-10-[3-(2-methoxy-ethyl)-piperazin-1-yl]-2-methyl-4H-3-thia-4,9-diaza-benzo[f]azulene

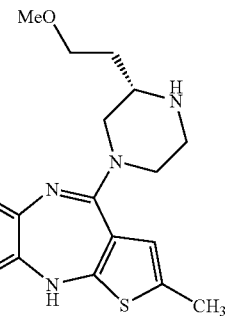

In a similar manner to Example 248, using 7-fluoro-2-methyl-4,9-dihydro-3-thia-4,9-diazabenzo[f]azulene-10-thione (1.25 g, 4.73 mmol) and (S)-2-(3-methoxy-ethyl)-piperazine (800 mg, 5.5 mmol) gives the title compound 1.73 g (4.62 mmol): mass Spectrum (FIA) 375 (M+1); NMR (¹H, 300 MHz, CDCl₃):δ 6.5-6.73 (m, 3H), 6.27 (s, 1H), 5.12 (s, 1H), 4.20 (d, 1H), 4.04 (d, 1H), 3.4-3.65 (m, 5H), 3.34 (s, 3H), 3.13-3.3 (M, 2H), 2.32 (s, 3H), 2.07-2.18 (m, 1H), 1.75 (m, 1H).

Example 249a (S)-7-Fluoro-10-[3-(3-methoxy-propyl)-piperazin-1-yl]-2-methyl-4H-3-thia-4,9-diaza-benzo[f]azulene

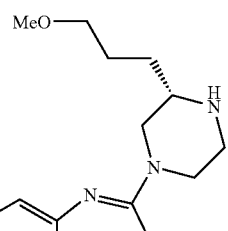

Combine 7-fluoro-2-methyl-4H-3-thia-4,9-diaza-benzo[f]azulen-10-ylamine hydrochloride (270 mg, 0.95 mmol), (S)-2-(3-methoxy-propyl)-piperazine (330 mg, 2 mmol) in a mixture of toluene and dimethylsulfoxide (1:2) and stir at 110° C. for 24 hours. Evaporate the mixture then purify by flash chromatography, eluting with a step gradient starting with dichloromethane going to 5% 2N ammonia-methanol in dichloromethane gives (S)-7-fluoro-10-[3-(3-methoxy-propyl)-piperazin-1-yl]-2-methyl-4H-3-thia-4,9-diaza-benzo[f]azulene (320 mg, 0.82 mmol): mass spectrum (APCI): m/z=389.1 (M+1).

Example 249b (S)-6-Fluoro-10-[3-(2-hydroxy-ethyl)-piperazin-1-yl]-2-methyl-4H-3-thia-4,9-diaza-benzo[f]azulene

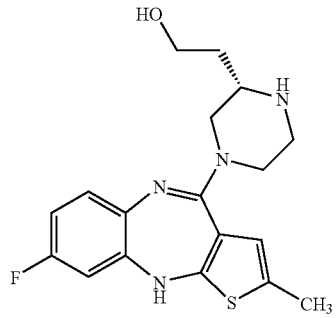

Combine 6-fluoro-2-methyl-4H-3-thia-4,9-diaza-benzo[f]azulen-10-ylamine hydrochloride (2.94 g, 10.35 mmol), (S)-2-piperazin-2-yl-ethanol (2.7 g, 20.7 mmol), diisopropylethylamine (3.6 mL, 20.7 mmol), dimethyl sulfoxide (4.25 mL) and toluene (17 mL) and heat to 110° C. for 42 hours. Cool to ambient temperature and dilute with ethyl acetate (200 mL). Wash with saturated sodium bicarbonate solution, brine and evaporate to give 2.64 g of the crude product. Silica gel chromatography, eluting with methylene chloride: acetonitrile: 7N NH$_3$/methanol (85:10:7), gives 0.523 g of the title compound as a brown solid foam: mass spectrum (ion spray): m/z=361 (M+1).

Example 250

(S)-6-Fluoro-10-r[3-(2-ethoxy-ethyl)-piperazin-1-yl]-2-methyl-4H-3-thia-4,9-diaza-benzo[f]azulene

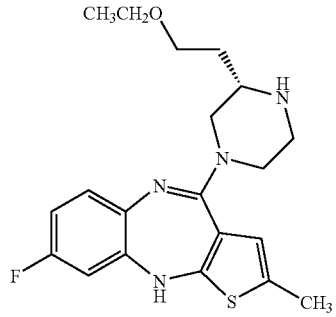

Using a method similar to the method of (S)-6-fluoro-10-[3-(2-methoxy-ethyl)-piperazin-1-yl]-2-methyl 4H-3-thia-4,9-diaza-benzo[f]azulene, using 2-methyl-4,9-dihydro-3-thia-6-fluoro-4,9-diazabenzo[f]azulene-10-thione and (S)-2 (2'-ethoxy)ethylpiperazine gives the title compound: mass spectrum (FIA) 389 (M+1), NMR ($^1$H, 300 MHz, CDCl$_3$): δ 6.93 (m,1H), 6.66 (m,1H), 6.41 (m,1H), 6.26 (s,1H), 4.92 (s,1H), 4.14-4.27 (broad,2H), 3.9-4.1 (m,2H), 3.58 (m,2H), 3.47 (q,2H), 3.0-3.2 (m,3H), 2.80 (m,1H), 2.30 (s,3H), 1.75 (m,1H), 1.17 (t,3H).

Example 251

(S)-7-Fluoro-10-[3-(2-ethoxy-ethyl)-piperazin-1-yl]-2-methyl-4H-3-thia-4,9-diaza-benzo[f]azulene

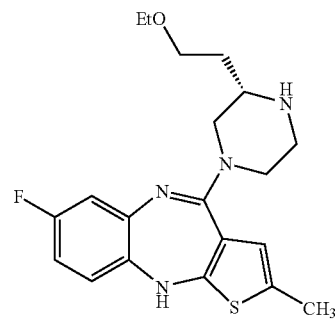

In a similar manner to the method of Example 248, using 7-fluoro-2-methyl-4,9-dihydro-3-thia-4,9-diazabenzo[f]azulene-10-thione (750 mg, 2.84 mmol) and (S)-2-(2-ethoxy)ethylpiperazine (510 mg, 3.3 mmol) gives the title compound (955 mg, 2.46 mmol): mass Spectrum (FIA) 389 (M+1).

Example 252

(S)-6-Fluoro-10-[3-(2-methoxy-ethyl)-piperazin-1-yl]-2-ethyl-4H-3-thia-4,9-diaza-benzo[f]azulene

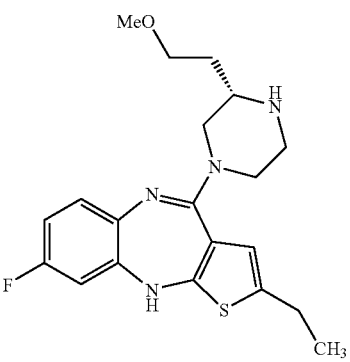

Dissolve 6-fluoro-2-ethyl-4H-3-thia-4,9-diaza-benzo[f]azulen-10-ylamine hydrochloride (0.6 g, 2.0 mmol) and (S)-2-(2-methoxy)ethylpiperazine (0.864 g, 6.0 mmol) in dimethylsulfoxide/toluene (1:2)(15 ml), stir under nitrogen and heat in an oil bath reflux for 18 hours. Pour the mixture into water and extract with ethyl acetate. Dry the organic phase (MgSO$_4$), filter and concentrate under reduced pressure. Chromatography on silica gel (eluent dichloromethane/methanol) gives (S)-6-fluoro-10-[3-(2-methoxy-ethyl)-piperazin-1-yl]-2-ethyl 4H-3-thia-4,9-diaza-benzo[f]azulene (558 mg, 82%): Mass Spectrum (LCMS) 389 (M+1).

Example 253

(S)-6-Fluoro-10-[3-(2-methoxy-ethyl)-piperazin-1-yl-2-isopropyl-4H-3-thia-4,9-diaza-benzo[f]azulene

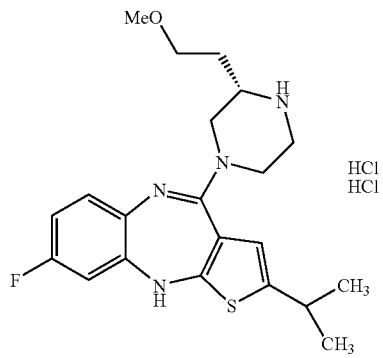

In a similar manner to Example 248, using 6-fluoro-2-isopropyl-4H-3-thia-4,9-diaza-benzo[f]azulen-10-thione (402 mg, 1.34 mmol) and (S)-2-(2-methoxy)ethylpiperazine (350 mg, 2.43 mmol) gives the title compound 410 mg, (1.02 mmol): FIA M+1 403).

Example 253a (S)-6,7-Difluoro-10-[3-(2-methoxy-ethyl)-piperazin-1-yl]-4H-3-thia-4,9-diaza-benzo[f]azulene

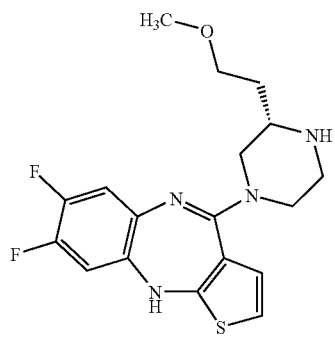

Combine 6,7-difluoro-4H-3-thia-4,9-diaza-benzo[f]azulen-10-ylamine hydrochloride (876.9 mg, 3.05 mmol), (S)-2-(2-methoxy-ethyl)-piperazine (1.32 g, 9.16 mmol), DMSO (3.0 ml), and toluene (12.0 ml). Stir and heat the mixture at 105° C. After 63 hours, cool the mixture to ambient temperature. Dilute the mixture with ethyl acetate and wash the organic layer with 1N NaOH and brine. Dry (sodium sulfate) and concentrate the organic layer to residue. Purify the residue on silica gel using a gradient of dichloromethane to dichloromethane/methanol (85:15) to give 561.6 mg (49%) of the title compound: mass spectrum (ion spray): m/z=379.1 (M+1).

Example 254

(S)-6,7-Difluoro-10-[3-(2-methoxy-ethyl)-piperazin-1-yl]-2-methyl-4H-3-thia-4,9-diaza-benzo[f]azulene Add 6,7-difluoro-2-methyl-4H-3-thia-4,9-diaza-benzo[f]azulen-10-ylamine hydrochloride (65.0 g, 215 mmol) and 2-(2-methoxy-ethyl)-piperazine (96.3 g, 668 mmol) to a solution of DMSO (650 mL) and toluene (1300 mL) with stirring under nitrogen. Heat at gentle reflux (115° C.) for 2 days, and then allow cooling to ambient temperature. Remove most of the organic portion under reduced pressure, and then partition the residue between ethyl acetate (450 mL) and aqueous saturated ammonium chloride solution (450 mL). Separate the layers, and then extract the aqueous layer with ethyl acetate (3×200 mL). Extract the combined organic layers with brine (3×200 mL). Concentrate the organic layer under reduced pressure. Purify the crude product by flash chromatography, eluting with 90:10/methylene chloride:MeOH to give 56 g (66%) of the title compound. $^1$H NMR (400 MHz, DMSO-$d_6$) δ 7.70 (s, 1H), 6.74 (m, 2H), 6.36 (s, 1H), 3.86 (bm, 2H), 3.39 (m, 2H), 3.23 (s, 3H), 2.88 (bd, 1H), 2.72 (bm, 3H), 2.44 (bt, 1H), 2.31 (s, 3H), 2.31 (bm, 1H), 1.53 (m, 2H). HRMS (ES) exact mass M+H calcd for $C_{19}H_{22}F_2N_4OS$ 393.1561; found 393.1554.

Example 254a (S)-6,7-Di-fluoro-10-[3-(2-methoxy-ethyl)-piperazin-1-yl]-2-methyl 4H-3-thia-4,9-diaza-benzo[f]azulene

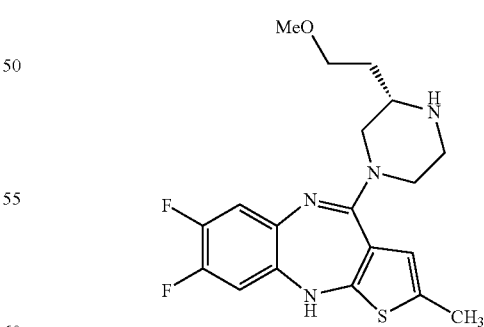

Dissolve 6,7-difluoro-2-methyl-4H-3-thia-4,9-diaza-benzo[f]azulen-10-ylamine hydrochloride (0.90 g, 3 mmol) and (S)-2(2-methoxy)ethylpiperazine (1.34 g, 9.3 mmol) in dimethylsulfoxide/toluene (1:2)(30 ml) and stir under nitrogen and heat in an oil bath at 140° C. for 48 hours. Pour the mixture into water and extract with ethyl acetate. Dry the organic phase (MgSO$_4$), filter and concentrate under reduced pressure to give desired product. Treat the aqueous phase with SCX-2 loose resin. Filter off the resin to obtain more of the desired product by elution with 2N NH$_3$ in MeOH. Purification by chromatography on Florisil (eluent ethyl acetate) of the combined material to give (S)-6,7-difluoro-10-[3-(2-methoxyethyl)piperazin-1-yl]-2-methyl-4H-3-thia-4,9-diaza-benzo[f]-azulene (0.67 g, 57%); mass spectrum (LCMS) 393 (M+1); NMR ($^1$H, 300 MHz, CDCl$_3$) δ 6.80 (m, 1H), 6.45 (m, 1H), 6.30 (s, 1H), 4.82 (s, 1H), 4.00 (bt, 2H), 3.50 (t, 2H), 3.30 (s, 3H), 3.05 (m, 1H), 2.90 (m, 3H), 2.60 (m, 1H), 2.31 (s, 3H), 1.68 (q, 2H).

Example 254b (S)-6,7-Difluoro-10-[3-(2-methoxy-ethyl)-piperazin-1-yl]-2-methyl-4H-3-thia-4,9-diaza-benzo[f]azulene

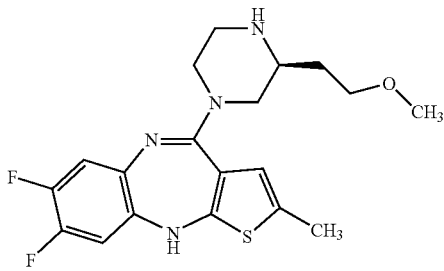

Dissolve 6,7-difluoro-2-methyl-4H-3-thia-4,9-diaza-benzo[f]azulen-10-ylamine hydrochloride (1.7 g, 5.66 mmol) and (S)-2-(2-methoxy-ethyl)-piperazine (2.45 g, 17.0 mmol) in dimethylsulfoxide/toluene (1:2)(21 ml), stir under nitrogen and heat in an oil bath at 130° C. for 43 hours. Cool to ambient temperature. Dilute the mixture with one volume water and two volumes ethyl acetate, separate layers and extract the aqueous layer with ethyl acetate. Basify the aqueous layer with ammonium hydroxide and extract with ethyl acetate. Combine all ethyl acetate extracts and wash with water and brine. Dry the organic phase (Na$_2$SO$_4$), filter and concentrate under reduced pressure. Purify by silica gel chromatography (eluent: 0-10% 2N ammonia in methanol/dichloromethane) to give the title compound (840 mg, 38%): Mass Spectrum (ESMS) 393 (M+1); 391 (M−1).

Example 254c (S)-6,7-Difluoro-10-[3-(2-methoxy-ethyl)-piperazin-1-yl]-2-methyl-4H-3-thia-4,9-diaza-benzo[f]azulene dihydrochloride

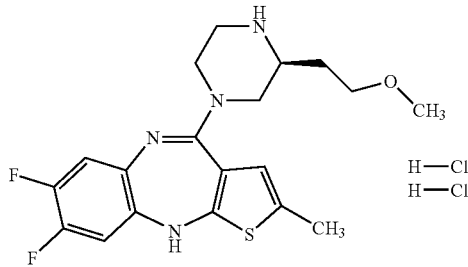

Dissolve (S)-6,7-difluoro-10-[3-(2-methoxy-ethyl)-piperazin-1-yl]-2-methyl-4H-3-thia-4,9-diaza-benzo[f]azulene (730 mg, 1.86 mmol) in ethyl acetate. Add 2.5 equivalents of hydrogen chloride in ethanol. After 3 hours filter the precipitate, wash with ethyl acetate and dry under vacuum to give the title compound (856 mg, 99%): Mass Spectrum (ESMS) 393 (M+1); 391 (M−1), mp 198-202° C. (dec).

Example 254d (S)-2-[4-(6,7-Difluoro-2-methyl-4H-3-thia-4,9-diaza-benzo[f]azulen-10-yl)-piperazin-2-yl]-ethanol

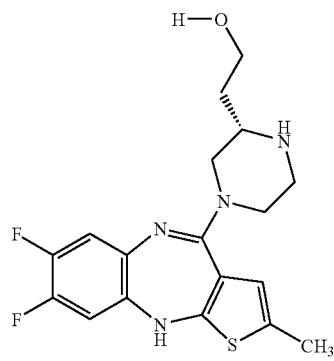

Dissolve 6,7-difluoro-2-methyl-4H-3-thia-4,9-diaza-benzo[f]azulen-10-ylamine hydrochloride (1.51, 4.99 mmol), N,N-diisopropylethylamine (0.91 mL, 5.24 mmol) and (S)-2-piperazin-2-yl-ethanol (1.3 g, 9.99 mmol) in dimethylsulfoxide/toluene (1:2)(18 ml), stir under nitrogen and heat in an oil bath at 120° C. for 72 hours. Dilute the mixture with water (20 mL) and ethyl acetate (40 mL), separate layers and extract the aqueous with ethyl acetate. Combine all ethyl acetate extracts and wash with water and brine. Dry the organic phase (Na$_2$SO$_4$), filter and concentrate under reduced pressure. Purify by silica gel chromatography (eluent: 0-13% 2N ammonia in methanol/dichloromethane) to give 780 mg of impure product. Purify by silica gel chromatography (eluent: 85% dichloromethane/10% acetonitrile/0%2N ammonia in methanol to 80% dichloromethane/10% acetonitrile/10% 2N ammonia in methanol) to give the title compound (516 mg, 27%): Mass Spectrum (ESMS) 379 (M+1); 377 (M−1).

Example 255

(S)-6,7-Difluoro-10-[3-(2-ethoxy-ethyl)-piperazin-1-yl]-2-methyl-4H-3-thia-4,9-diaza-benzo[f]azulene

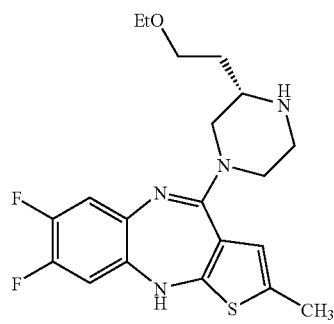

In a similar manner to Example 249a, using 6,7-difluoro-2-methyl-4H-3-thia-4,9-diaza-benzo[f]azulen-10-ylamine hydrochloride (500 mg, 1.66 mmol) and (S)-2(2-ethoxy)

ethylpiperazine (780 mg, 4.93 mmol) gives the title compound 353 mg (0.87 mmol): FIA M+1 407.

Example 256

(S)-6,7-Difluoro-10-[3-(2-methoxy-ethyl)-piperazin-1-yl]-2-ethyl-4H-3-thia-4,9-diaza-benzo[f]azulene

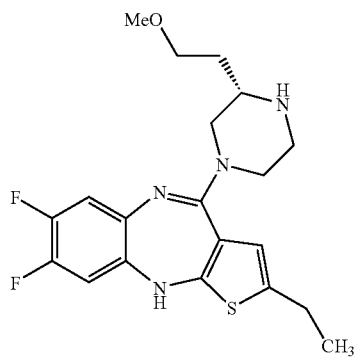

In a similar manner to Example 248, using 6,7-difluoro-2-ethyl-4,9-dihydro-3-thia-4,9-diaza-benzo[f]azulen-10-thione (1.13 g, 3.83 mmol) and (S)-2(2-methoxy)ethylpiperazine (623 mg, 4.33 mmol) gives the title compound 440 mg (1.08 mmol): FIA M+1 407.

Example 257

(S)-6-Chloro-10-[3-(2-methoxy-ethyl)-piperazin-1-yl]-2-methyl-4H-3-thia-4,9-diaza-benzo[f]azulene

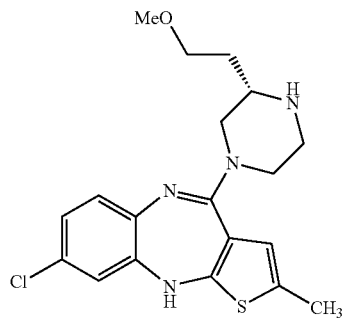

Dissolve 6-chloro-2-methyl-4H-3-thia-4,9-diaza-benzo[t]azulen-10-ylamine hydrochloride (0.537 g, 1.8 mmol) and (S)-2-(2-methoxy)ethylpiperazine (0.8 g, 5.5 mmol) in dimethylsulfoxide/toluene (1:2)(15 ml), stir under nitrogen and heat in an oil bath at 120° C. for 6 days. Pour the mixture into water and extract with ethyl acetate. Dry the organic phase (MgSO$_4$), filter and concentrate under reduced pressure. Chromatography on silica gel (eluent dichloromethane/methanol) gives (S)-6-chloro-10-[3-(2-methoxy-ethyl)-piperazin-1-yl]-2-methyl-4H-3-thia-4,9-diaza-benzo[f]azulene (195 mg, 27%). Mass Spectrum (FIA) 391/393 (M+1).

Example 257a (S)-7-Chloro-10-[3-(2-methoxy-ethyl)-piperazin-1-yl]-4H-3-thia-4,9-diaza-benzo[f]azulene

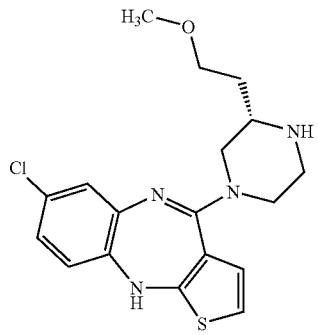

Combine 7-Chloro-4H-3-thia-4,9-diaza-benzo[f]azulen-10-ylamine hydrochloride (1.20 g, 4.19 mmol), (S)-2-(2-methoxy-ethyl)-piperazine (1.51 g, 10.48 mmol), DMSO (4.0 ml), and toluene (16.0 ml). Stir and heat the mixture at 105° C. After 24 hours, cool the mixture to ambient temperature and stir it for 16 hours. Dilute the mixture with ethyl acetate and wash the organic layer with 0.1N NaOH and brine. Dry (sodium sulfate) and concentrate the organic layer to residue. Purify the residue on silica gel using a gradient of dichloromethane to dichloromethane/methanol (90:10) to give 571.5 mg (36%) of an brown solid: mass spectrum (ion spray): m/z=377.1 (M+1).

Example 257b (S)-7-Chloro-10-[3-(3-methoxy-propyl)-piperazin-1-yl]-4H-3-thia-4,9-diaza-benzo[f]azulene

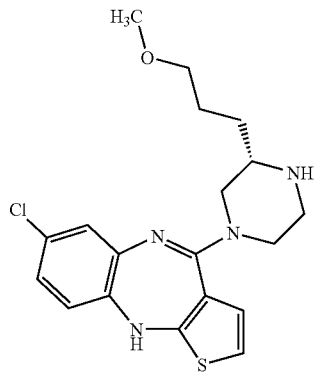

Combine 7-chloro-4H-3-thia-4,9-diaza-benzo[f]azulen-10-ylamine hydrochloride (786.7 mg, 2.75 mmol), (S)-2-(3-methoxy-propyl)-piperazine (870.0 mg, 5.50 mmol), DMSO (2.0 ml), and toluene (8.0 ml). Stir and heat the mixture at 105° C. After 48 hours, cool the mixture to ambient temperature. Dilute the mixture with ethyl acetate and wash the organic layer with 0.1N NaOH and brine. Dry (sodium sulfate) and concentrate the organic layer to residue. Purify the residue on silica gel using a gradient of dichloromethane to dichloromethane/methanol (90:10) to give 280.3 mg (26%) of the title compound: mass spectrum (ion spray): m/z=391.1 (M+1).

Example 258

(S)-7-Chloro-10-[3-(2-methoxy-ethyl)-piperazin-1-yl]-2-methyl-4H-3-thia-4,9-diazabenzo[f]azulene

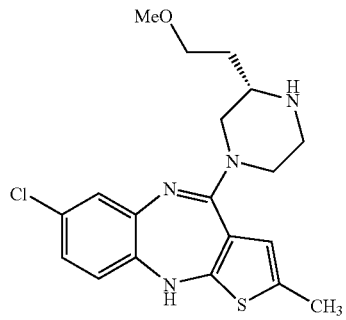

Dissolve 7-chloro-2-methyl-4H-3-thia-4,9-diaza-benzo[f]azulen-10-ylamine hydrochloride (0.60 g, ~2.0 mmol) and (S)-2-(2-methoxy)ethylpiperazine (0.87 g, 5.5 mmol) in dimethylsulfoxide/toluene (1:2)(15 ml), stir under nitrogen and heat in an oil bath at 120° C. for 4 hours. Pour the mixture into water and extract with ethyl acetate. Dry the organic phase (MgSO$_4$), filter and concentrate under reduced pressure. Chromatography on silica gel (eluent dichloromethane/methanol) gives the title compound: mass spectrum (ESMS) 391/393 (M+1); mp 179-183° C. (dec); NMR ($^1$H, 300 MHz, CDCl$_3$) δ 7.0 (d, 1H), 6.8 (1H, dd), 6.5 (d, 1H), 6.28 (s, 1H), 4.6 (s, 1H), 4.02 (m, 2H), 3.5 (m, 2H), 3.35 (s, 3H), 3.05 (m, 1H), 2.4 (m, 3H), 2.6 (m, 1H), 2.3 (s, 3H), 1.7 (m, 2H).

Example 258a (S)-7-Chloro-10-[3-(2-methoxy-ethyl)-piperazin-1-yl]-2-methyl-4H-3-thia-4,9-diaza-benzo[f]azulene

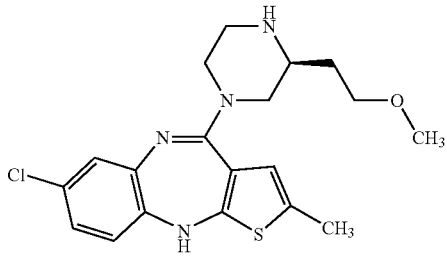

Dissolve 7-chloro-2-methyl-4H-3-thia-4,9-diaza-benzo[f]azulen-10-ylamine hydrochloride (1.46 g, 4.86 mmol) and (S)-2-(2-methoxy-ethyl)-piperazine (2.1 g, 14.6 mmol) in dimethylsulfoxide/toluene (1:2)(18 ml), stir under nitrogen and heat in an oil bath at 130° C. for 28.5 hours. Stir 16 hours at ambient temperature. Dilute the mixture with water and ethyl acetate, and extract with ethyl acetate. Combine the ethyl acetate extracts, wash with water and brine, dry the organic phase (Na$_2$SO$_4$), filter and concentrate under reduced pressure. Chromatograph on silica gel (eluent: 0-10% 2N ammonia in methanol/dichloromethane) to give the title compound (1.14 g, 60%), Mass Spectrum (ESMS) 391/393 (M+1), mp 179-183° C. (dec).

Example 258b (S)-7-Chloro-10-[3-(2-hydroxy-ethyl)-piperazin-1-yl]-2-methyl-4H-3-thia-4,9-diaza-benzo[f]azulene

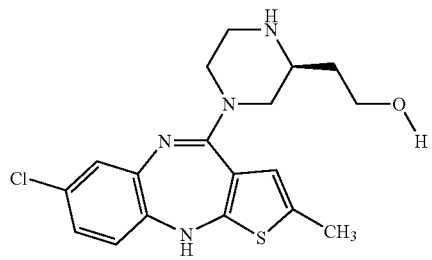

By using a method similar to Example 258, using 7-chloro-2-methyl-4H-3-thia-4,9-diaza-benzo[f]azulen-10-ylamine hydrochloride and (S)-2-(2-hydroxy-ethyl)-piperazine gives the title compound.

Example 258c (S)-7-Chloro-10-[3-(2-methoxy-ethyl)-piperazin-1-yl]-2-methyl-4H-3-thia-4,9-diaza-benzo[f]azulene

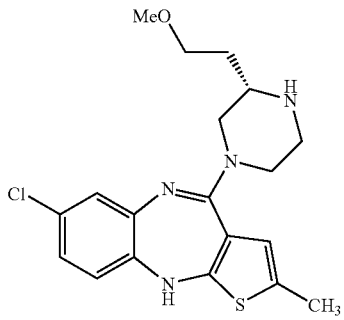

Combine 7-chloro-2-methyl-10-methylsulfanyl-4H-3-thia-4,9-diaza-benzo[f]azulene (42.74 g, 145 mmol) and (s)-2-(2-methoxy-ethyl)-piperazine (26.1 g, 181 mmol) in isopropyl alcohol (190 mL). Heat to 78-81° C. for 3-4 days, and then allow cooling to ambient temperature. Filter the solids and rinse with 1:1 MTBE/Ligroin (2×300 mL). Drying at 30° C. affords 39.1 g (69.5%) of the title compound: $^1$H NMR (500 MHz, DMSO-d$_6$): δ 1.52 (bm, 2H), 2.27 (s, 3H), 2.45 (bt, 1H), 2.65 (bm, 2H), 2.75 (bt, 1H), 2.86 (bd, 1H), 3.20 (s, 3H), 3.38 (m, 2H), 3.80 (m, 1H), 3.90 (m, 1H), 6.33 (s, 1H), 6.67 (d, 1H), 6.75 (d, 1H), 6.82 (dd, 1H), 7.70 (s, 1H). $^{13}$C NMR (100 MHz, DMSO-d$_6$): δ 15.07, 25.49, 33.28, 45.11, 47.36, 52.55, 57.92, 69.18, 118.38, 119.81, 122.29, 122.56, 126.41, 126.99, 128.43, 142.54, 142.90, 152.84, 157.82. MS (ES+) M+H calcd for C$_{19}$H$_{23}$ClN$_4$OS 390.94; found 391.96.

Example 259

(R)-[1-Methyl-4-(2-methyl-4H-3-thia-4,9-diaza-benzo[f]azulen-10-yl)-piperazin-2-yl]-methanol

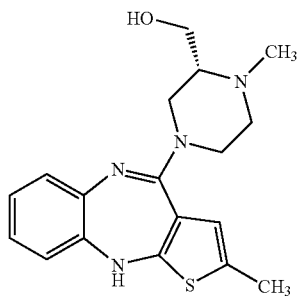

Add aqueous 37% formaldehyde (1.1 eqiv) to a solution of [(R)-4-(2-methyl-4H-3-thia-4,9-diaza-benzo[f]azulen-10-yl)-piperazin-2-yl]-methanol (1 mmol) in dichloroethane (60 mL per 1 mmol non-alkylated starting material). Stir the mixture 2 minutes and add sodium triacetoxyborohydride (1.5 mmol per 1 mmol non-alkylated starting material). Stir the suspension for 30 minutes and quench with a saturated aqueous solution of sodium bicarbonate. Extract the aqueous phase 3 times with dichloromethane and combine the organic phases, dry over magnesium sulfate, filter and concentrate. Purify the residue via chromatography on silica gel (methylene chloride/methanol (90:10) affords the title compound as a yellow powder: mp 118-124° C.; $^1$H NMR (CDCl$_3$) δ 2.31 (s, 3H), 2.43 (s, 3H), 2.45 (m, 1H), 2.59 (m, 1H), 2.82 (m, 1H), 3.31 (m, 1H), 3.58 (dd, 1H) 3.67-3.79 (m, 3H), 3.86 (dd, 1H), 4.96 (s, 1H), 6.30 (s, 1H), 6.60 (d, 1H), 6.87 (t, 1H), 6.96 (t, 1H), 7.01 (d, 1H); MS (APCI) m/z (rel intensity) 343 (100).

Example 260

(R)-10-(3-Methoxymethyl-4-methyl-piperazin-1-yl)-2-methyl-4H-3-thia-4,9-diaza-benzo[f]azulene

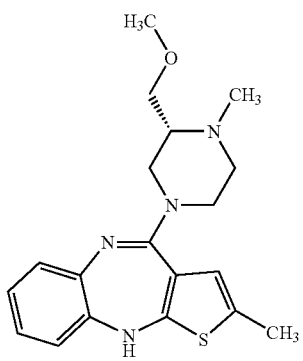

Using a similar method to (R)-[1-methyl-4-(2-methyl-4H-3-thia-4,9-diaza-benzo[f]azulen-10-yl)-piperazin-2-yl]-methanol, using (R)-10-(3-methoxymethyl-piperazin-1-yl)-2-methyl-4H-3-thia-4,9-diaza-benzo[f]azulene (800 mg) affords the title compound as a yellow solid (758 mg): mp 76-80° C.; $^1$H NMR (CDCl$_3$) δ 2.31 (s, 3H), 2.42-2.27 (m, 2H), 2.39 (s, 3H), 2.84 (dt, 1H), 2.99 (dd, 1H), 3.14 (ddd, 1H), 3.36 (s, 3H), 3.46 (dd, 1H), 3.54 (dd, 1H), 3.91 (d, 1H), 4.02 (d, 1H), 4.96 (s, 1H), 6.30 (d, 1H), 6.60 (dd, 1H), 6.87 (dt, 1H), 6.96 (dt, 1H), 7.04 (dd, 1H); MS (APCI) m/z (rel intensity) 357.2 (100).

Example 261

(R)-10-(3-Ethoxymethylpiperazin-1-yl)-2-methyl-4H-3-thia-4,9-diaza-benzo[f]azulene

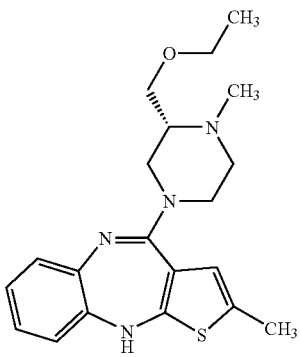

Using a similar method to (R)-[1-methyl-4-(2-methyl-4H-3-thia-4,9-diaza-benzo[f]azulen-10-yl)-piperazin-2-yl]-methanol, using (R)-10-(3-ethoxymethyl-piperazin-1-yl)-2-methyl-4H-3-thia-4,9-diaza-benzo[f]azulene (375 mg, 1 mmol) affords the title compound as a yellow solid (77 mg, 21%): $^1$H NMR (CDCl$_3$) δ 1.08 (t, 3H), 2.30 (s, 3H), 2.31-2.38 (m, 2H), 2.38 (s, 3H), 2.85 (m, 1H), 2.95 (m, 1H), 3.15 (m, 1H), 3.45-3.58 (m, 4H), 3.93 (m, 1H), 4.04 (m, 1H), 5.08 (s, 1H), 6.31 (s, 1H), 6.59 (d, 1H), 6.86 (t, 1H), 6.96 (t, 1H), 7.03 (d, 1H); MS (es) m/z (rel intensity) 371.2 (100).

Example 262

(R)-10-(3-Allyloxymethyl-4-methyl-piperazin-1-yl)-2-methyl-4H-3-thia-4,9-diaza-benzo[f]azulene

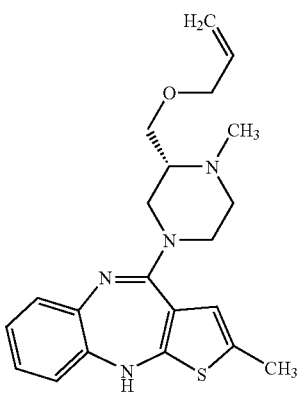

Using a similar method to (R)-[1-methyl-4-(2-methyl-4H-3-thia-4,9-diaza-benzo[f]azulen-10-yl)-piperazin-2-yl]-methanol, gives the title compound as a yellow solid (28 mg); $^1$H NMR (CDCl$_3$) δ 2.30 (s, 3H), 2.35 (m, 2H), 2.39 (s, 3H), 2.85 (d, 1H), 2.97 (t, 1H), 3.15 (t, 1H), 3.53 (m, 2H), 3.92-4.06 (m, 4H), 4.95 (s, 1H), 5.18 (d, 1H), 5.26 (d, 1H), 5.90 (m, 1H), 6.31 (s, 1H), 6.60 (d, 1H), 6.87 (t, 1H), 6.96 (t, 1H), 7.02 (d, 1H); MS (ESI) m/z (rel intensity) 383 (100).

Example 263

(R)-10-(4-Methyl-3-propoxymethyl-piperazin-1-yl)-2-methyl-4H-3-thia-4,9-diaza-benzo[f]azulene

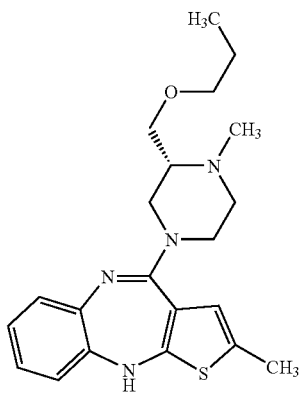

Stir (R)-10-(3-allyloxymethyl-4-methyl-piperazin-1-yl)-2-methyl-4H-3-thia-4,9-diaza-benzo[f]azulene (270 mg), 20% palladium hydroxide (Degaussa type, 15 mg) in ethanol (0.014M)) under hydrogen atmosphere (1 atm) for 4 hours at room temperature. Filter and evaporate the solvent to afford the title compound as a yellow solid (268 mg): $^1$H NMR (CDCl$_3$) δ 0.90 (t, 3H), 1.58 (m, 2H), 2.30 (s, 3H), 2.33 (m, 2H), 2.39 (s, 3H), 2.84 (m, 2H), 3.14 (t, 1H), 3.38 (t, 2H), 3.49 (d, 1H), 3.58 (d, 1H), 3.95 (d, 1H), 4.07 (d, 1H), 4.94 (s, 1H), 6.31 (s, 1H), 6.60 (d, 1H), 6.85 (t, 1H), 6.95 (t, 1H), 7.02 (d, 1H); MS (ESI) m/z (rel intensity) 385 (100).

Example 264

(R)-10-[4-methyl-3-(2-methyl-allyloxymethyl)-piperazin-1-yl]-2-methyl 4H-3-thia-4,9-diaza-benzo[f]azulene

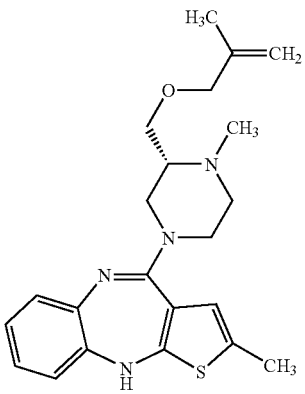

Using a similar method to (R)-[1-methyl-4-(2-methyl-4H-3-thia-4,9-diaza-benzo[I]azulen-10-yl)-piperazin-2-yl]-methanol, gives the title compound as an orange powder: $^1$H NMR (CDCl$_3$) δ 1.73 (s, 3H), 2.30 (s, 3H), 2.31-2.39 (m, 2H), 2.39, (s, 3H), 2.85 (ddd, 1H), 2.93 (dd, 1H), 3.14 (dd, 1H), 3.45 (dd, 1H), 3.56 (dd, 1H), 3.88 (s, 2H), 3.97 (m, 1H), 4.07 (m, 1H) 4.88 (s, 1H), 4.94 (s, 1H), 5.04 (s, 1H), 6.31 (s, 1H), 6.60 (d, 1H), 6.87 (t, 1H), 6.96 (t, 1H), 7.02 (d, 1H); MS (es) m/z (rel intensity) 397 (100).

Example 265

(R)-10-(4-Methyl-3-phenoxymethyl-piperazin-1-yl)-2-methyl-4H-3-thia-4,9-diaza-benzo[f]azulene

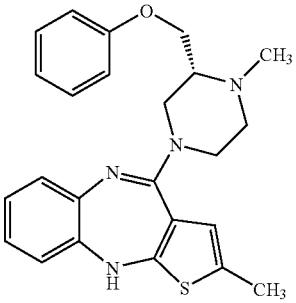

Add aqueous 37% formaldehyde (1.1 eqiv) to a solution of (R)-10-(3-phenoxymethyl-piperazin-1-yl)-2-methyl-4H-3-thia-4,9-diaza-benzo[f]azulene (520 mg) in dichloroethane (60 mL per 1 mmol non-alkylated starting material). Stir the mixture 2 minutes and add sodium triacetoxyborohydride (1.5 mmol per 1 mmol non-alkylated starting material). Stir the suspension for 30 minutes and quench with a saturated aqueous solution of sodium bicarbonate. Extract the aqueous phase 3 times with dichloromethane and combine the organic phases, dry over magnesium sulfate, filter and concentrate. Purify the residue via chromatography on silica gel (methylene chloride/methanol (90:10) to provide the title compound as a yellow solid (265 mg, 49%): mp 74-88° C.; $^1$H NMR (CDCl$_3$) δ 2.28 (s, 3H), 2.47 (s, 3H), 2.50-2.39 (m, 1H), 2.66-2.58 (m, 1H), 2.91 (dt, 1H), 3.11 (dd, 1H), 3.26 (dt, 1H), 3.93 (bd, 1H), 4.14-4.03 (m, 3H), 4.91 (bs, 1H), 6.31-6.29 (m, 1H), 6.59 (dt, 1H), 7.00-6.86 (m, 5H), 7.03 (dd, 1H), 7.32-7.27 (m, 2H); MS (APCI) m/z (rel intensity) 419.3 (100).

Example 266

(S)-2-r 1-Methyl-4-(2-methyl-4H-3-thia-4,9-diaza-benzo[f]azulene-10-yl) piperazin-2-yl]ethanol dihydrochloride

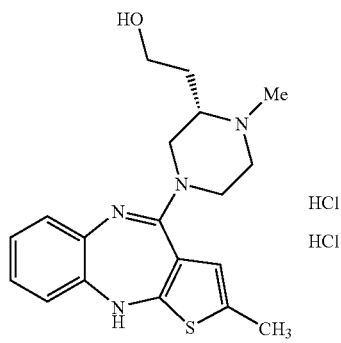

Combine (S)-2-[4-(2-methyl-4H-3-thia-4,9-diazabenzo[f]azulene-10-yl)piperazin-2-yl]ethanol dihydrochloride (110 mg, 0.26 mmol) in dichloromethane (7 mL) and add diisopropyl ethylamine (226 µL, 1.30 mmol). After a few minutes, add 37% aqueous formaldehyde (23 µL, 0.31 mmol) followed by sodium triacetoxyborohydride all at once (83 mg, 0.39 mmol). Stir at room temperature for 30 min. Dilute with methanol and concentrate in vacuo; redissolve in methanol and apply to SCX column. Wash with methanol and elute with 2.5% 7N ammonia-methanol in dichloromethane to give the free base of the title compound as a yellow oil. Isolate as the clean dihydrochloride (39 mg, 35%) in a manner such as that described in Example 319: mass spectrum (APCI): m/z 357.1 (M+1 of free base).

Example 266a (S)-10-[3-(2-Methoxy-ethyl)-4-methyl-piperazin-1-yl]-4H-3-thia-4,9-diaza-benzo[f]azulene

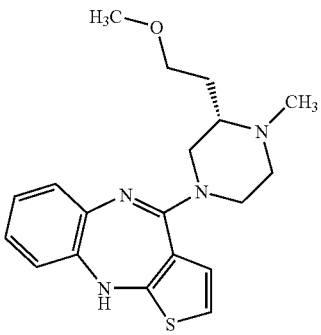

Combine (S)-10-[3-(2-methoxy-ethyl)-piperazin-1-yl]-4H-3-thia-4,9-diaza-benzo[/]azulene (395.8 mg, 1.16 mmol), formaldehyde (103.2 µL, 1.27 mmol, 37% in water), and 1,2-dichloroethane (25.0 ml). Stir the mixture at ambient temperature for 5 minutes and then add sodium triacetoxyborohydride (367.4 mg, 1.73 mmol). After stirring for 30 minutes at ambient temperature, quench the reaction with saturated sodium bicarbonate. Remove the organic portion and wash (brine), dry (sodium sulfate), and reduce the extracts to residue. Purify the residue on silica gel using a gradient of dichloromethane to dichloromethane/methanol (80:20) to give 306.9 mg (75%) of the title compound as a brown foam: mass spectrum (ion spray): m/z=357.1 (M+1).

Example 266b (S)-10-[3-(3-Methoxy-propyl)-4-methyl-piperazin-1-yl]-4H-3-thia-4,9-diaza-benzo[f]azulene

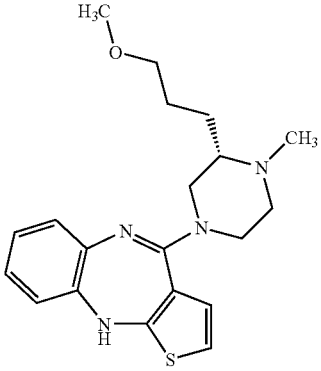

Combine (S)-10-[3-(3-methoxy-propyl)-piperazin-1-yl]-4H-3-thia-4,9-diaza-benzo[/]azulene (296.0 mg, 0.83 mmol), formaldehyde (74.1 µL, 0.91 mmol, 37% in water), and 1,2-dichloroethane (20.0 ml). Stir the mixture at ambient temperature for 5 minutes and then add sodium triacetoxyborohydride (264.0 mg, 1.25 mmol). After stirring for 30 minutes at ambient temperature, quench the reaction with saturated sodium bicarbonate. Remove the organic portion and wash (brine), dry (sodium sulfate), and reduce the extracts to residue. Purify the residue on silica gel using a gradient of dichloromethane to dichloromethane/methanol (90:10) to give 269.6 mg (88%) of the title compound: mass spectrum (ion spray): m/z=371.2 (M+1).

Example 267

(s)-10-[3-(2-Methoxyethyl)-4-methylpiperazin-1-yl]-2-methyl-4H-3-thia-4,9-diazabenzo[f]azulene dihydrochloride

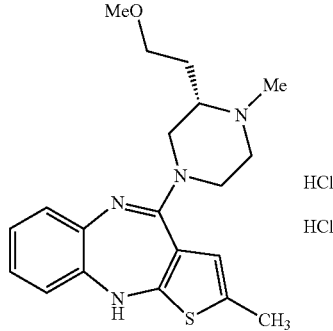

In a manner such as that described in Example 269, using (S)-10-[3-(2-methoxyethyl)-piperazin-1-yl]-2-methyl-4H-3-thia-4,9-diazabenzo[f]azulene dihydrochloride into the dihydrochloride salt of the title compound (102 mg, 22%): mass Spectrum (ES): m/z 371.2 (M+1 of free base).

Example 268

(S)-10-[3-(2-Ethoxyethyl)-4-methyl-piperazin-1-yl]-2-methyl-4H-3-thia-4,9-diazabenzo[f]azulene dihydrochloride

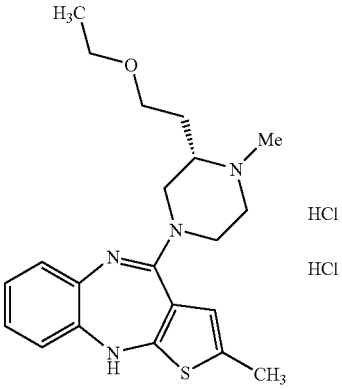

In a manner similar to that described in Example 331, using (S)-10-[3-(2-ethoxyethyl)-piperazin-1-yl]-2-methyl-4H-3-thia-4,9-diazabenzo[f]azulene to obtain the free base of the title compound (0.105 g, 0.273 mmol, 15%) as a yellow oil: mass spectrum (APCI): m/z=385.2 (M+1). Isolate clean product as the corresponding dihydrochloride in the manner described in Example 331. Exact Mass, Calc: 385.2062; Found: 385.2070.

Example 269

(S)-10-[4-Methyl-3-(2-phenoxyethyl)piperazin-1-yl]-2-methyl-4H-3-thia-4,9-diazabenzo[f]azulene dihydrochloride

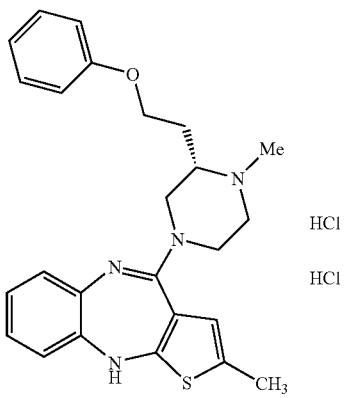

Combine (S)-10-[3-(2-phenoxyethyl)piperazin-1-yl]-2-methyl-4H-3-thia-4,9-diazabenzo[f]azulene, formaldehyde (1.1 equiv, 37% aqueous solution), and sodium triacetoxyborohydride (1.5 equiv.) in dichloroethane (10 mL) and stir at room temperature for 2 hours. Dilute the mixture with saturated aqueous sodium bicarbonate and extract three times with dichloromethane. Combine the organic layers, dry over sodium sulfate and concentrate under reduced pressure. Purification by flash chromatography, eluting with a step gradient starting with dichloromethane going to 6% 2N ammonia-methanol in dichloromethane gives the free base of the title compound. Isolate as the dihydrochloride salt by dissolving the free base in ethanol and adding a solution of 5 equivalents of hydrochloric acid in ethanol. Evaporating the solution and drying the salt provides the title compound (0.059 g, 0.129 mmol, 8%) as an orange-solid. Mass spectrum (APCI): m/z=433.2 (M+1 of free base).

Example 270

(R)-10-(3-Benzyloxymethyl-4-methyl-piperazin-1-yl)-2-methyl-4H-3-thia-4,9-diaza-benzo[f]azulene

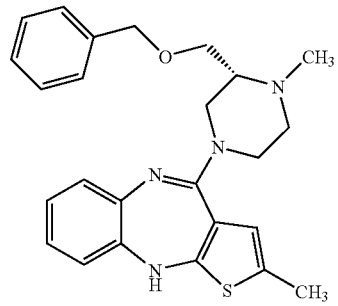

Using a method similar to Example 269, using (R)-10-(3-benzyloxymethyl-piperazin-1-yl)-2-methyl-4H-3-thia-4,9-diaza-benzo[I]azulene gives the title compound as a yellow solid: mp=55-65° C.; $^1$H NMR (DMSO-d$_6$) δ 2.17 (s, 3H), 2.19 (m, 1H), 2.20 (s, 3H), 2.27 (m, 1H), 2.69 (m, 2H), 2.91 (t, 1H), 3.33 (t, 1H), 3.62 (dd, 1H), 3.68 (d, 1H), 3.84 (d, 1H), 4.43. (q, 2H), 6.28 (s, 1H), 6.63 (dd, 1H), 6.77 (m, 3H), 7.27 (m, 5H), 7.55 (s, 1H); MS (ESI) m/z (rel intensity) 433 (100).

Example 271

(R)-10-(4-Methyl-3-phenoxymethyl-piperazin-1-yl)-2-methyl 4H-3-thia-4,9-diaza-benzo[f]azulene

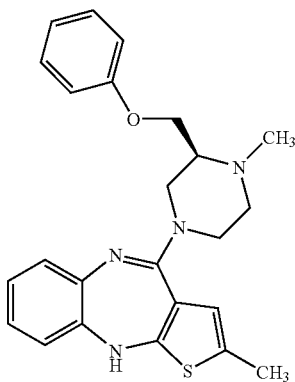

Using a method similar to Example 269, using (R)-10-(3-phenoxymethyl-piperazin-1-yl)-2-methyl-4H-3-thia-4,9-diaza-benzo[f]azulene gives the title compound as as a yellow solid: mp=74-88° C.: $^1$H NMR (CDCl$_3$) δ 2.28 (s, 3H), 2.47 (s, 3H), 2.50-2.39 (m, 1H), 2.66-2.58 (m, 1H), 2.91 (dt, 1H), 3.11 (dd, 1H), 3.26 (dt, 1H), 3.93 (bd, 1H), 4.14-4.03 (m, 3H), 4.91 (bs, 1H), 6.31-6.29 (m, 1H), 6.59 (dt, 1H), 7.00-6.86 (m, 5H), 7.03 (dd, 1H), 7.32-7.27 (m, 2H); MS (APCI) m/z (rel intensity) 419.3 (100). 49%, 520 mg gives 265 mg.

Example 272

(S)-10-[3-(2-Methoxy-ethyl)-4-methyl-piperazin-1-yl]-2-isopropyl-4H-3-thia-4,9-diaza-benzo[f]azulene

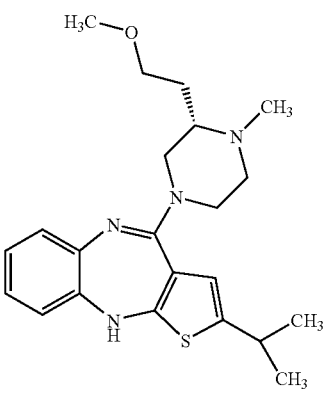

Add sodium triacetoxyborohydride (0.15 g, 0.71 mmol) and aqueous formaldehyde (37% w/w, 0.05 mL, 0.62 mmol) to a solution of (S)-10-[3-(2-methoxy-ethyl)-piperazin-1-yl]-2-isopropyl-4H-3-thia-4,9-diaza-benzo[f]azulene (0.18 g, 0.47 mmol) in dichloroethane (12 mL) and stir. After 5 hours, dilute with a saturated aqueous solution of sodium bicarbonate, and separate the layers. Extract the aqueous layer with dichloromethane (3×), combine organics, and dry (sodium sulfate), filter, and concentrate under reduced pressure to an oil (0.24 g). Purify the oil by flash chromatography, eluting with a gradient of a 5% solution of 2M ammonia in methanol, in dichloromethane (0-100% over 30 minutes), and then with a 5% solution of 2M ammonia in methanol, in dichloromethane to give the title compound (0.14 g, 74%): mass spectrum (APCI, m/e): 399 (M+1); NMR ($^1$H, 300 MHz, DMSO-$d_6$) δ 7.63 (s, 1H), 6.79 (m, 3H), 6.66 (m, 1H), 6.30 (s, 1H), 3.70 (m, 2H), 3.35-3.28 (m, 2H), 3.20 (s, 3H), 2.99-2.88 (m, 2H), 2.80-2.60 (m, 2H), 2.29-2.05 (m, 5H), 1.66 (m, 2H), 1.17 (d, 6H, J=7.5 Hz).

Example 273

(S)-10-[3-(2-Methoxy-ethyl)-4-methyl-piperazin-1-yl]-2-Isopropyl-4H-3-thia-4,9-diaza-benzo[f]azulene dihydrochloride

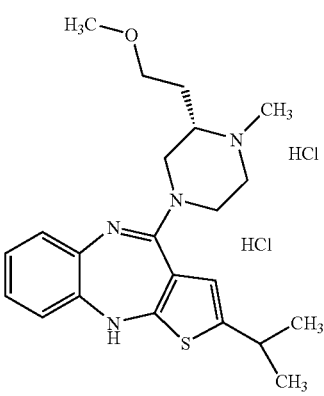

Add a solution of acetyl chloride (0.13 mL, 1.76 mmol) in absolute ethanol to a solution of (S)-10-[3-(2-methoxy-ethyl)-4-methyl-piperazin-1-yl]-2-isopropyl-4H-3-thia-4,9-diaza-benzo[f]azulene (0.14 g, 0.35 mmol) in absolute ethanol and stir. Concentrate under reduced pressure to give the title compound (0.16 g, 94%): mass spectrum (APCI, m/e): 399 (M+1); exact mass spectrum (ES+, m/e, $C_{22}H_{30}N_4OS \cdot 2HCl$): calc. 399.2218 (M+1-2HCl), found 399.2226.

Example 273a (S)-10-[3-(3-Methoxy-propyl)-4-methyl-piperazin-1-yl]-2-methyl-4H-3-thia-4,9-diaza-benzo[f]azulene

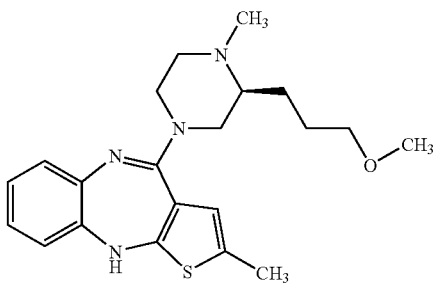

Using the method similar to Example 222 to give the title compound: mass spectrum (m/e):385.12 (M+1).

Example 273b (S)-10-[3-(3-Methoxy-propyl)-4-methyl-piperazin-1-yl]-2-methyl-4H-3-thia-4,9-diaza-benzo[f]azulene hydrochloride

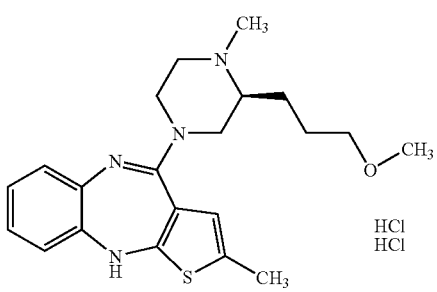

Using the method similar to Example 223 gives the title compound: mass spectrum (m/e):385.12 (M+1).

Example 274

(S)-10-[3-(4-Methoxy-butyl)-4-methyl-piperazin-1-yl]-2-methyl-4H-3-thia-4,9-diaza-benzo[f]azulene

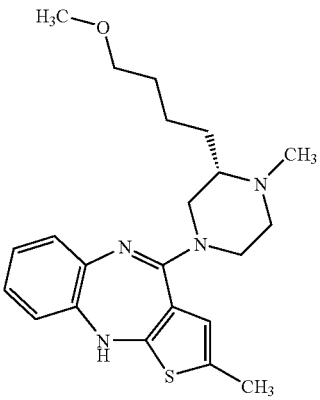

Into a room temperature, stirred solution of (S)-10-[3-(4-methoxybutyl)-piperazin-1-yl]-2-methyl-4H-3-thia-4,9-diaza-benzo[f]azulene (0.031 g, 0.08 mmol), and formaldehyde solution (0.082 mL, 0.10 mmol, 37% in H$_2$O) in dichloroethane (0.5 mL) was added NaHB(OAc)3 (0.026 g, 0.12 mmol) and stirred overnight. Dilute the solution with H$_2$O (20 mL), 1.0 N NaOH (1 mL) and extract with CH$_2$Cl$_2$ (3×40 mL). Dry the combined organic layers over Na$_2$SO$_4$, and filter. Concentrate the mixture under reduced pressure and purify by silica gel chromatography eluting with 10% (33% 2 M NH$_3$ in MeOH/64% EtOH)/CH$_2$Cl$_2$. Combine the purified fractions, concentrate under reduced pressure, and place under vacuum to give the title compound: orange solid (0.014 g), mass spectrum (m/e):399.3 (M+H).

Example 275

(S)-10-[3-(4-Methoxy-butyl)-4-methyl-piperazin-1-yl]-2-methyl-4H-3-thia-4,9-diaza-benzo[f]azulene dihydrochloride

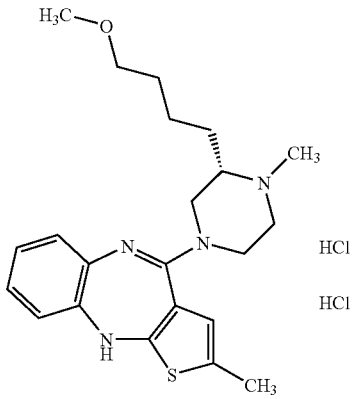

Into a room temperature stirred solution of (S)-10-[3-(4-methoxybutyl)-4-methyl-piperazin-1-yl]-2-methyl-4H-3-thia-4,9-diaza-benzo[f]azulene (0.015 g, 0.038 mmol) in CH$_2$Cl$_2$ add 2.0 N HCl in Et$_2$O (0.038 mL, 0.07 mmol) and stir for 1 h. Concentrate the mixture under reduced pressure and dry in a vacuum oven at 60° C. overnight to give the title compound: brown solid (0.018 g), mass spectrum (m/e): 399.0 (M+1).

Example 276

(S)-10-[3-(2-Methoxy-ethyl)-4-methyl-piperazin-1-yl]-2-trifluoromethyl-4H-3-thia-4,9-diaza-benzo[f]azulene maleate salt

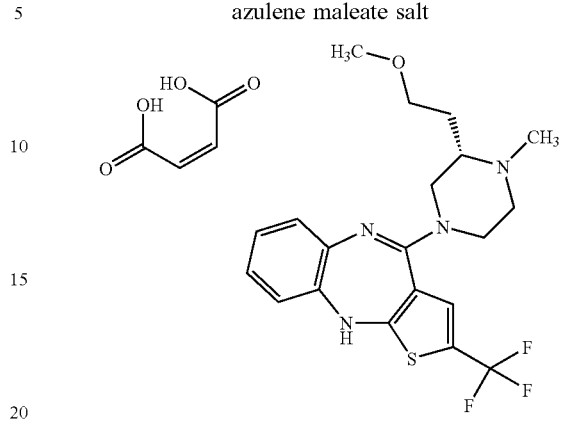

Combine (S)-10-[3-(2-methoxy-ethyl)-4-methyl-piperazin-1-yl]-4H-3-thia-4,9-diaza-benzo[f]azulene (250.0 mg, 0.70 mmol), S-(trifluoromethyl)-3,7-dinitrodibenzothiophenenium trifluoromethanesulfonate (345.2 mg, 0.70 mmol), and DMSO (5 ml). Stir the mixture at ambient temperature for 2 hours. Partition the mixture between 1N NaOH and dichloromethane, remove the organic, wash it with brine, dry the organic over sodium sulfate, and then reduce it to residue. Purify the residue on silica gel using dichloromethane/2N ammonia in methanol (95:5) and reduce the fractions containing the desired product to residue. Purify the residue again using hexanes/THF/ethanol/2N ammonia in methanol (65:30:5:3) to give 53.6 mg (18%) of the desired product as an oil. Prepare the maleate salt of the product in diethyl ether: mass spectrum (ion spray): m/z=425.1 (M+1).

Example 277

(S)-10-[3-(3-Methoxy-propyl)-4-methyl-piperazin-1-yl]-2-trifluoromethyl-4H-3-thia-4,9-diaza-benzo[f]azulene maleate salt

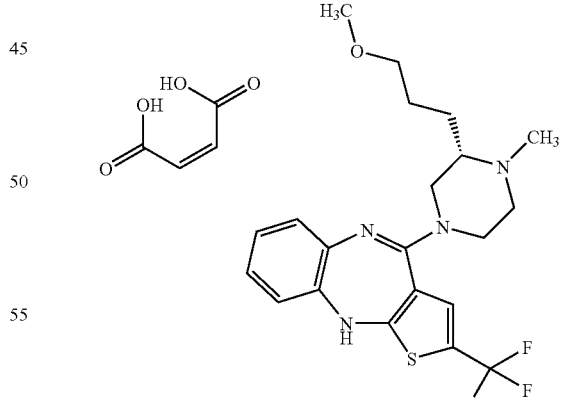

Combine (S)-10-[3-(3-methoxy-propyl)-4-methyl-piperazin-1-yl]-4H-3-thia-4,9-diaza-benzo[f]azulene (235.1 mg, 0.63 mmol), S-(trifluoromethyl)-3,7-dinitrodibenzothiophenenium trifluoromethanesulfonate (343.6 mg, 0.70 mmol), and DMSO (5 ml). Stir the mixture at ambient temperature for 4 hours. Partition the mixture between DI H$_2$O and ethyl acetate, remove the organic, wash it with brine, dry the organic over sodium sulfate, and then reduce it to residue. Purify the residue using hexanes/THP/ethanol/2N ammonia in methanol (65:30:5:3) to give 33.8 mg (122%) of the desired product as a brown oil. Prepare the maleate salt of the product in diethyl ether: mass spectrum (ion spray): m/z=439.0 (M+1).

Example 278a (S)-6-Fluoro-10-r[3-(2-methoxy-ethyl)-4-methyl-piperazin-1-yl]-4H-3-thia-4,9-diaza-benzo[f]azulene

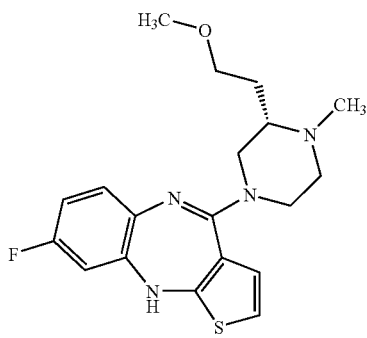

Combine (S)-6-fluoro-10-[3-(2-methoxy-ethyl)-piperazin-1-yl]-4H-3-thia-4,9-diaza-benzo[f]azulene (379.6 mg, 1.05 mmol), formaldehyde (97.7 µL, 1.20 mmol, 37% in water), and dichloromethane (15.0 ml). Stir the mixture at ambient temperature for 5 minutes and then add sodium triacetoxyborohydride (334.8 mg, 1.58 mmol). After stirring for 30 minutes at ambient temperature, quench the reaction with saturated sodium bicarbonate. Remove the organic portion and wash (brine), dry (sodium sulfate), and reduce the extracts to residue. Purify the residue on silica gel using a gradient of dichloromethane to dichloromethane/methanol (90:10) to give 339.8 mg (86%) of the title compound as a tan foam: mass spectrum (ion spray): m/z=375.1 (M+1).

Example 278b (S)-6-Fluoro-10-[3-(3-methoxy-propyl)-4-methyl-piperazin-1-yl]-4H-3-thia-4,9-diaza-benzo[f]azulene

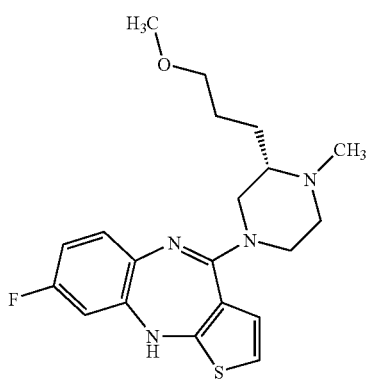

Combine (S)-6-fluoro-10-[3-(3-methoxy-propyl)-piperazin-1-yl]-4H-3-thia-4,9-diaza-benzo[f]azulene (220.1 mg, 0.59 mmol), formaldehyde (52.5 µL, 0.64 mmol, 37% in water), and dichloromethane (8.0 ml). Stir the mixture at ambient temperature for 5 minutes and then add sodium triacetoxyborohydride (186.8 mg, 6.88 mmol). After stirring for 30 minutes at ambient temperature, quench the reaction with saturated sodium bicarbonate. Remove the organic portion and wash (brine), dry (sodium sulfate), and reduce the extracts to residue. Purify the residue on silica gel using a gradient of dichloromethane to dichloromethane/methanol (90:10) to give 195.1 mg (86%) of the title compound: mass spectrum (ion spray): m/z=389.1 (M+1).

Example 278c (S)-6-Fluoro-10-[3-(2-hydroxy-ethyl)-4-methyl-piperazin-1-yl]-2-methyl-4H-3-thia-4,9-diaza-benzo[f]azulene dihydrochloride

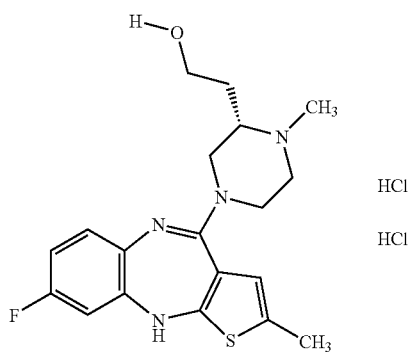

Combine (S)-2-methyl-10-[3-(2-hydroxy-ethyl)-piperazin-1-yl]-4H-3-thia-6-fluoro-4,9-diaza-benzo[f]azulene (0.508 g, 1.40 mmol) and 37% formaldehyde solution (0.11 mL, 1.48 mmol) in 1,2-dichloroethane (20 mL). Stir for 15 minutes and add Sodium triacetoxy borohydride (0.597 g, 2.81 mmol). Stir an additional 60 minutes and then pour solution onto saturated sodium bicarbonate solution. Extract with methylene chloride to give 0.521 g of the crude product. Silica gel chromatography, eluting with methylene chloride: 2N NH$_3$/methanol (100:7.5), gives 0.271 g of the title compound as the free base. The dihydrochloride salt precipitates in ethyl acetate as a yellow solid: mp=230° C.; mass spectrum (ion spray): m/z=375 (M+1).

Example 279

(S)-6-Fluoro-10-[3-(2-methoxy-ethyl)-4-methyl-piperazin-1-yl]-2-methyl-4H-3-thia-4,9-diaza-benzo[f]azulene hydrochloride

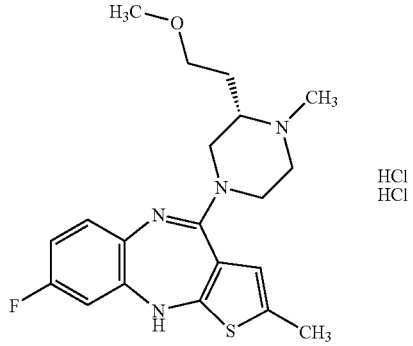

Stir (S)-6-fluoro-10-[3-(2-methoxy-ethyl)-piperazin-1-yl]-2-methyl-4H-3-thia-4,9-diaza-benzo[f]azulene (5.00 g, 13.4 mmol) under nitrogen to dissolve in 1,2-dichloroethane (DCE, 55 mL). Cool to 15-20° C. and add formaldehyde (37% wt. in water, 1.03 g solution, 0.38 g, 12.7 mmol) in one portion. Add sodium triacetoxyborohydride (3.41 g, 16.1 mmol) in portions over 5-10 minutes, keeping the pot temperature below 20° C. Stir at 15-20° C. for 15 minutes, and then allow warming to ambient temperature. Stir for 2 hours, and then add aqueous saturated sodium bicarbonate (50 mL). Stir for 15 minutes, and then separate layers. Extract the product with methylene chloride. Extract the combined organic layers with brine, dry over magnesium sulfate, and then concentrate under reduced pressure to a residue. Add methylene chloride to the residue and concentrate under reduced pressure to give 4.94 g (100%) of the free base of the title compound. $^1$H NMR (400 MHz, DMSO-$d_6$) δ7.78 (bs, 1H), 6.79 (m, 1H), 6.68 (m, 1H), 6.53 (m, 1H), 6.34 (s, 1H), 3.74 (m, 2H), 3.36 (m, 3H), 3.22 (s, 3H), 2.95 (m, 1H), 2.77 (m, 1H), 2.69 (m, 1H), 2.30 (s, 3H), 2.23 (s, 3H), 2.17 (bs, 1H), 1.84 (m, 1H), 1.52 (m, 1H). HRMS (ES) exact mass M+H calcd for $C_{20}H_{25}FN_4OS$ 389.1811; found 389.1802.

Preparation of Crystalline Form I
(Dihydrochloride-Hydrated State)

Add (S)-6-fluoro-10-[3-(2-methoxy-ethyl)-4-methyl-piperazin-1-yl]-2-methyl-4H-3-thia-4,9-diaza-benzo[f]azulene free base (100 mg) into a scintillation vial. Add IPA (5 mL). Heat to approximately 60° C. on a stir plate. Add 2 molar equivalents of HCl (1N HCl). Evaporate to dryness. Back add IPA (5 mL) to the slurry/suspension. Isolate the solid by vacuum filtration. Allow air-drying overnight to obtain crystalline form I. Decomposes after 194.08° C. (TGA-DTA).

Preparation of Crystalline Form II
(Dihydrochloride-Hydrated State)

Saturate 400 microliters of water with (S)-6-fluoro-10-[3-(2-methoxy-ethyl)-4-methyl-piperazin-1-yl]-2-methyl-4H-3-thia-4,9-diaza-benzo[f]azulene dihydrochloride anhydrate. Seed with Form I and mix at room temperature overnight. Filter solid and characterize as crystalline form II: Melting point (onset): 195.92° C. (DSC).

Confirmation of Crystalline Form II

Add (S)-6-fluoro-10-[3-(2-methoxy-ethyl)-4-methyl-piperazin-1-yl]-2-methyl-4H-3-thia-4,9-diaza-benzo[f]azulene dihydrochloride anhydrate (60 mg) to water (1 mL). Seed with the material obtained from the initial preparation of crystalline form II (dihydrochloride hydrated state). Allow to stir overnight. Filter solid and characterize.

Preparation of Crystalline Form III
(Dihydrochloride-Anhydrate)

Stir (S)-6-fluoro-10-[3-(2-methoxy-ethyl)-4-methyl-piperazin-1-yl]-2-methyl-4H-3-thia-4,9-diaza-benzo[f]azulene (38.2 g, 98.3 mmol) under nitrogen to dissolve in 2-propanol (IPA, 380 mL) at ambient temperature. Heat to 70-75° C. Add a solution of concentrated HCl (19.0 mL, 228 mmol) in IPA (190 mL) at such a rate as to maintain the temperature above 70° C.; the product should crystallize within a few minutes. Heat the product slurry for 10-15 minutes at 70-75° C., then allow cooling to ambient temperature. Cool to 0-5° C. and stir for 1-2 hours. Filter and rinse with cold IPA. Dry at 50° C. to give 41.9 g (92%) of crystalline form III (dihydrochloride anhydrate). Analysis for $C_{20}H_{26}Cl_2FN_4OS$: calcd: C, 52.06; H, 5.90; N, 12.14; found: C, 51.75; H, 5.82; N, 11.95. HRMS (ES) exact mass M+H calcd for $C_{20}H_{25}FN_4OS$ (free base) 389.1811; found 389.1805.

Example 279a (S)-6-Fluoro 10-[3-(2-methoxy-ethyl)-4-methyl-piperazin-1-yl]-2-methyl-4H-3-thia-4,9-diaza-benzo[f]azulene dihydrochloride

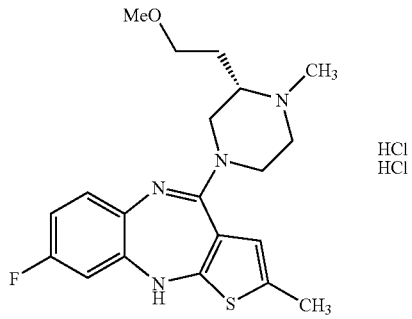

Dissolve (S)-6-fluoro-10-[3-(2-methoxy-ethyl)-piperazin-1-yl]-2-methyl-4H-3-thia-4,9-diaza-benzo[f]azulene (1.08 g, 2.88 mmol) in 1,2-dichloroethane (30 ml) and stir at room temperature. Add 37% aqueous formaldehyde solution (2 ml) followed by sodium triacetoxyborohydride (0.65 g, 3.06 mmol). Stir the reaction mixture at room temperature overnight. Add saturated aqueous sodium and collect the organic phase, dry and concentrate to 1.2 g dark oil. Take up in methanol (20 ml), add 2N hydrochloric acid (5 ml) and stir the mixture at room temperature for 2 hours. Concentrate the reaction mixture partition between dichloromethane and 2N sodium hydroxide solution. Collect the organic phase, dry and concentrate to 1 g dark oil. Purify this material by flash column chromatography on florisil (eluent dichloromethane/methanol) to give 0.6 g yellow oil. Dissolve this material in ethanol (20 ml), add 2N hydrochloric acid (2 ml) and concentrate the mixture and dry under high vacuum to give the desired as an orange solid (610 mg): mp. 190-192° C.; Mass Spectrum (FIA) 389 (M+1); NMR ($^1$H, 300 MHz, CDCl$_3$)(on free base) δ 6.93 (m, 1H), 6.68 (m, 1H), 6.37 (d,1H), 4.90 (s, 1H), 3.88 (m, 2H), 3.43 (m, 2H), 3.32 (s, 3H), 3.10 (m, 1H), 2.72 (m, 2H), 2.32 (s, 3H), 2.30 (s, 3H) 2.2-2.3 (m, 2H), 1.98 (m, 1H), 1.65 (m, 1H).

Example 280

(S)-6-Fluoro-10-[3-(2-methoxy-ethyl)-4-methyl-piperazin-1-yl]-2-ethyl-4H-3-thia-4,9-diaza-benzo[f]azulene dihydrochloride

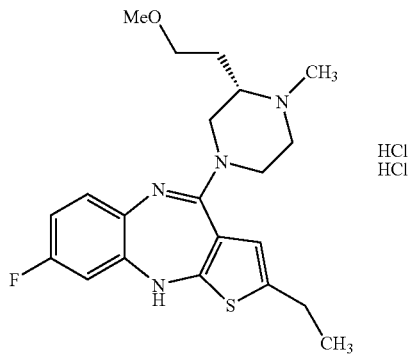

Dissolve (S)-6-fluoro-10-[3-(2-methoxy-ethyl)-piperazin-1-yl]-2-ethyl-4H-3-thia-4,9-diaza-benzo[f]azulene (558 mg, 1.44 mmol) in 1,2-dichloroethane (8 ml) and stir at room temperature. Add 37% Aqueous formaldehyde solution (200 μl) followed by sodium triacetoxyborohydride (370 mg, 1.73 mmol). Stir the reaction mixture for 2 hours. Add saturated aqueous sodium carbonate and collect the organic phase, dry and concentrate to a dark oil. Purify this material by flash column chromatography on florisil (eluent dichloromethane/methanol) to give 340 mg yellow oil. Dissolve this material in ethyl acetate and add 2N hydrochloric acid in ether and concentrate the mixture and dry under high vacuum to give the desired product as an orange solid 350 mg. Mass Spectrum (FIA) 403 (M+1). Mpt 186-188° C.

Example 281

(S)-6-Fluoro-10-[3-(2-ethoxy-ethyl)-4-methyl-piperazin-1-yl]-2-methyl-4H-3-thia-4,9-diaza-benzo[f]azulene hydrochloride

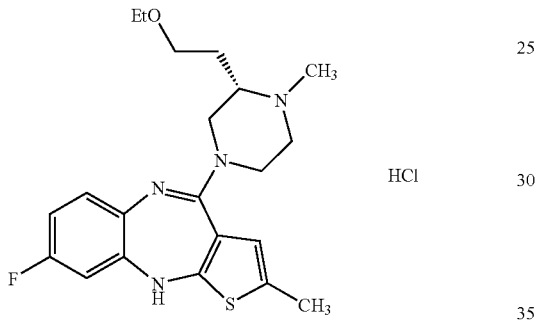

In a similar manner to Example 280, using (S)-6-fluoro-10-[3-(2-ethoxy-ethyl)-piperazin-1-yl]-2-methyl-4H-3-thia-4,9-diaza-benzo[f]azulene (285 mg, 0.73 mmol) gives the title compound 142 mg (0.32 mmol): mass Spectrum (FIA) 403 (M+1); mp 180-182° C.

Example 282

(S)-6-Fluoro-10-[3-(2-methoxy-ethyl)-4-methylpiperazin-1-yl]-2-isopropyl-4H-3-thia-4,9-diaza-benzo[f]azulene dihydrochloride

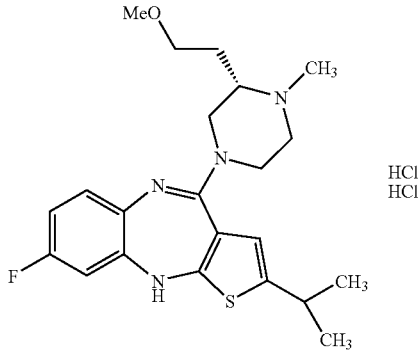

In a similar manner to Example 280, using (S)-6-fluoro-10-[3-(2-methoxy-ethyl)-piperazin-1-yl]-2-isopropyl-4H-3-thia-4,9-diaza-benzo[f]azulene (384 mg, 0.96 mmol) gives the title compound 274 mg (0.56 mmol): NMR ($^1$H) (DMSO-$d_6$): δ 11.6961(2H, bs), 9.6123 (1H, bs), 7.3012 (1H, bs), 7.0050 (1H, bt), 6.8960 (1H, bd), 6.6748 (1H, s), 4.4881 (1H, bs), 4.0587 (1H, bs), 3.8868 (2H, bs), 3.6106 (2H+ H2O, bs), 3.4060 (3H, bs), 3.1656 (3H, bd), 3.0294 (1H, m), 2.8423 (3H, bs), 2.2724 (1H, bs), 1.8456 (1H, bs), 1.2292 (6H, d); Mass Spectrum M+H=417.1.

Example 283

(S)-6-Fluoro-10-[3-(3-methoxy-propyl)-4-methyl-piperazin-1-yl]-2-methyl 4H-3-thia-4,9-diaza-benzo[f]azulene dihydrochloride

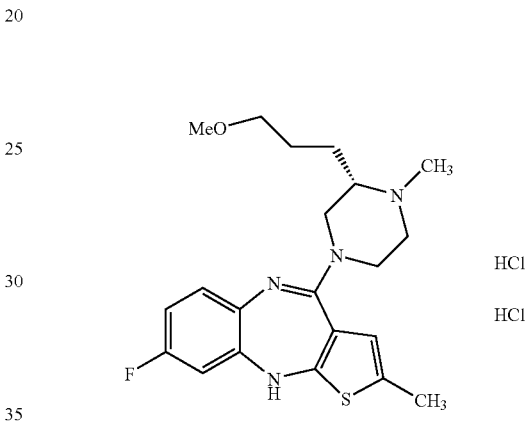

Combine (S)-6-fluoro-10-[3-(3-methoxy-propyl)-piperazin-1-yl]-2-methyl-4H-3-thia-4,9-diaza-benzo[f]azulene (0.105 g, 0.270 mmol), formaldehyde (31 μL, 0.378 mmol, 37%), and sodium triacetoxyborohydride (0.086 g, 0.405 mmol) in dichloroethane (6 mL) and stir at room temperature overnight. Dilute the mixture with saturated sodium bicarbonate and extract three times with methylene chloride. Combine the organic layers, dry over sodium sulfate and concentrate under reduced pressure to give the crude product. Purification by flash chromatography, eluting with a step gradient starting with dichloromethane going to 5% 2N ammonia-methanol in dichloromethane gives (S)-6-fluoro-10-[3-(3-methoxy-propyl)-4-methyl-piperazin-1-yl]-2-methyl-4H-3-thia-4,9-diaza-benzo[f]azulene (0.097 g, 0.240 mmol, 89%) as a yellow oil. Mass spectrum (APCI): m/z=403.1 (M+1). Isolate clean product as the corresponding dihydrochloride in the following manner: dissolve the yellow foam in ethanol (5 mL) and add a solution of about 5 equivalents of HCl in ethanol (5 mL). Evaporate the mixture to obtain (S)-6-fluoro-10-[3-(3-methoxy-propyl)-4-methyl-piperazin-1-yl]-2-methyl-4H-3-thia-4,9-diaza-benzo[f]azulene dihydrochloride.

Example 283a (S)-7-Fluoro-10-[3-(3-methoxy-propyl)-4-methyl-piperazin-1-yl]-2-methyl-4H-3-thia-4,9-diaza-benzo[f]azulene dihydrochloride

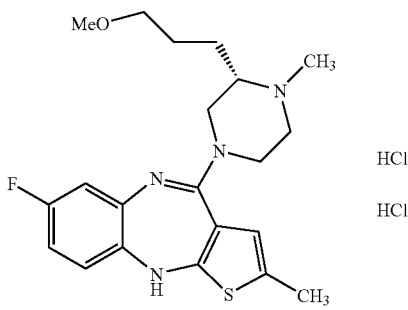

In a similar manner to Example 280, using (S)-7-fluoro-10-[3-(3-methoxy-propyl)-piperazin-1-yl]-2-methyl-4H-3-thia-4,9-diaza-benzo[f]azulene (320 mg, 0.825 mmol) gives the title compound 210 mg (0.48 mmol: Mass spectrum (APCI): m/z=403.1 (M+1).

Example 284

(S)-6-Fluoro-10-[3-(2-methoxy-ethyl)-4-methyl-piperazin-1-yl]-2-trifluoromethyl-4H-3-thia-4,9-diaza-benzo[f]azulene dihydrochloride

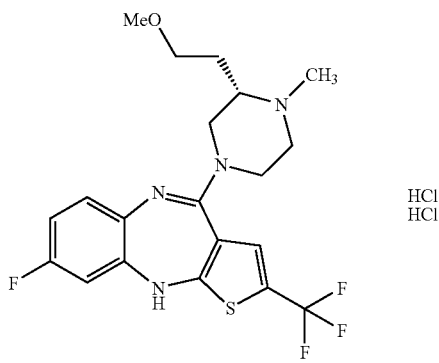

Combine (S)-6-fluoro-10-[3-(2-methoxy-ethyl)-4-methyl-piperazin-1-yl]-4 H-3-thia-4,9-diaza-benzo[f]azulene (309.0 mg, 0.83 mmol), S-(trifluoromethyl)-3,7-dinitrodibenzothiophenenium trifluoromethanesulfonate (406.2 mg, 0.83 mmol), and DMSO (7.0 ml). Stir the mixture at ambient temperature for 24 hours. Dilute the mixture with DI H₂O and remove the precipitate by vacuum filtration. Basify the filtrate by the addition of 0.1 N NaOH. Extract the aqueous with ethyl acetate, wash it with brine, dry the organic over sodium sulfate, and then reduce it to residue. Purify the residue using hexanes/THF/ethanol/2N ammonia in methanol (65:30:5:3) to give 60.2 mg (17%) of the desired product. Prepare the dihydrochloride salt of the product in diethyl ether: mass spectrum (ion spray): m/z=443.1 (M+1).

Example 285

(S)-6-Fluoro-10-[3-(2-methoxy-propyl)-4-methyl-piperazin-1-yl]-2-trifluoromethyl-4H-3-thia-4,9-diaza-benzo[f]azulene dihydrochloride

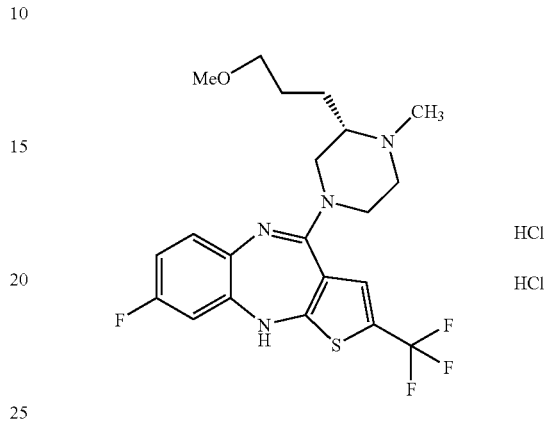

Combine (S)-6-fluoro-10-[3-(3-methoxy-propyl)-4-methyl-piperazin-1-yl]-4H-3-thia-4,9-diaza-benzo[f]azulene (170.6 mg, 0.44 mmol), S-(trifluoromethyl)-3,7-dinitrodibenzothiophenenium trifluoromethanesulfonate (216.2 mg, 0.44 mmol), and DMSO (5 ml). Stir the mixture at ambient temperature for 24 hours. Dilute the mixture with DI H₂O and remove the precipitate by vacuum filtration. Basify the filtrate by the addition of 0.1 N NaOH. Extract the aqueous with ethyl acetate, wash it with brine, dry the organic over sodium sulfate, and then reduce it to residue. Purify the residue using hexanes/THF/ethanol/2N ammonia in methanol (65:30:5:3) to give 21.8 mg (11%) of the desired product. Prepare the dihydrochloride salt of the product in diethyl ether: mass spectrum (ion spray): m/z 457.1 (M+1).

Example 286

(S)-7-Fluoro-10-[3-(2-methoxy-ethyl)-4-methyl-piperazin-1-yl]-2-methyl-4H-3-thia-4,9-diaza-benzo[f]azulene hydrochloride

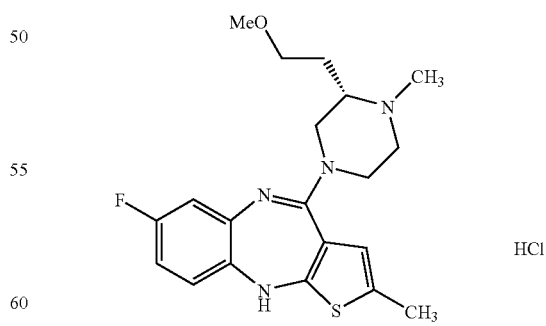

In a similar manner to Example 280, (S)-7-fluoro-10-[3-(2-ethoxy-ethyl)-piperazin-1-yl]-2-methyl-4H-3-thia-4,9-diaza-benzo[f]azulene (1.73 g, 4.62 mmol) gives the title compound 965 mg (2.09 mmol): Mass Spectrum (FIA) 389 (M+1); Mp 192-194° C.

Example 287

(S)-7-Fluoro-10-[3-(2-ethoxy-ethyl)-4-methyl-piperazin-1-yl]-2-methyl-4H-3-thia-4,9-diaza-benzo[f]azulene dihydrochloride

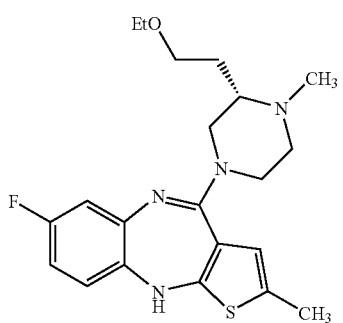

In a similar manner to Example 280, using (S)-7-fluoro-10-[3-(2-ethoxy-ethyl)-piperazin-1-yl]-2-methyl-4H-3-thia-4,9-diaza-benzo[f]azulene (734 mg, 1.89 mmol) gives the title compound 312 mg (0.66 mmol): Mass Spectrum (FIA) 403 (M+1); mp 193-195° C.

Example 287a (S)-2-[4-(6,7-Difluoro-2-methyl-4H-3-thia-4,9-diaza-benzo[f]azulen-10-yl)-1-methyl-piperazin-2-yl]-ethanol

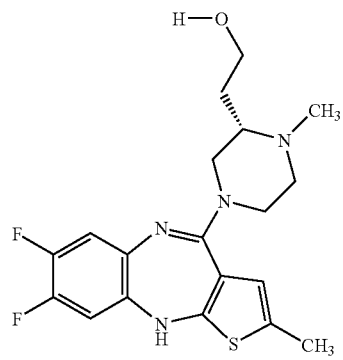

Dissolve (S)-2-[4-(6,7-difluoro-2-methyl-4H-3-thia-4,9-diaza-benzo[f]azulen-10-yl)-piperazin-2yl]-ethanol (436 mg, 1.15 mmol) in 1,2 dichloroethane (5 ml), add formaldehyde (91 µL, 1.15 mmol, 37% in water) and stir under nitrogen for 10 min. Add sodium triacetoxyborohydride (452 mg, 2.13 mmol) and stir 1 hour at ambient temperature. Dilute the mixture with saturated sodium bicarbonate solution and extract with dichloromethane. Wash the extracts with brine and dry the organic phase ($Na_2SO_4$), filter and concentrate under reduced pressure. Purify by silica gel chromatography (eluent: 0-5% 2N ammonia in methanol/dichloromethane) to give 255 mg of impure product. Purify by silica gel chromatography (eluent: 0-10% 2N ammonia in methanol/dichloromethane) to give 120 mg of impure product and 113 mg of pure product. Purify by radial silica gel chromatography using a 2 mm plate (eluent: 1-2% 2N ammonia in methanol/dichloromethane) to give 76 mg of pure product. Combine both lots of pure product to give 189 mg (42%) of the title compound: Mass Spectrum (ESMS) 393 (M+1); 391 (M−1).

Example 287b (S)-2-[4-(6,7-Difluoro-2-methyl-4H-3-thia-4,9-diaza-benzo[f]azulen-10-yl)-1-methyl-piperazin-2-yl]-ethanol dihydrochloride

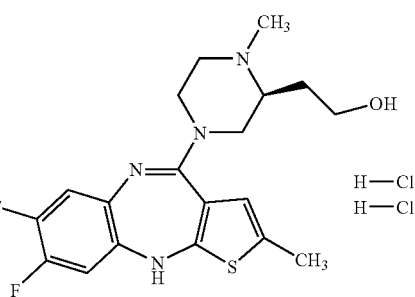

Dissolve (S)-2-[4-(6,7-difluoro-2-methyl-4H-3-thia-4,9-diaza-benzo[f]azulen-10-yl)-1-methyl-piperazin-2-yl]-ethanol (171 mg, 0.44 mmol) in ethyl acetate. Add 3 equivlents of hydrogen chloride in ethanol. After 18 hours filter the precipitate under a nitrogen atmosphere, wash with ethyl acetate and dry under vacuum to give the title compound (198 mg, 98%): Mass Spectrum (LCMS) 393 (M+1); 391 (M−1).

Example 288

(S)-6,7-Difluoro-10-[3-(2-methoxy-ethyl)-4-methyl-piperazin-1-yl]-2-methyl-4H-3-thia-4,9-diaza-benzo[f]azulene hydrochloride

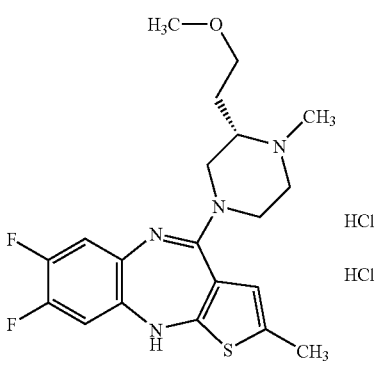

Dissolve (S)-6,7-difluoro-10-[3-(2-methoxy-ethyl)-piperazin-1-yl]-2-methyl-4H-3-thia-4,9-diaza-benzo[f]azulene (26.1 g, 66.5 mmol) in 1,2-dichloroethane (DCE, 260 mL) with stirring at ambient temperature under nitrogen; cool to 10-15° C. Add aqueous 37% wt. formaldehyde (5.40 g×37%=2.00 g, 66.6 mmol) in one portion. Add powdered sodium triacetoxyborohydride (19.8 g, 93.4 mmol) in a few portions over 10-15 minutes, keeping the temperature below 20° C. Rinse in the residue with DCE (26 mL). Stir the reaction solution at ambient temperature for 1-2 hours. Add aqueous saturated sodium bicarbonate (260 mL) dropwise, and then stir at ambient temperature for 20-30 minutes. Separate the layers, and then extract the aqueous layer with methylene chloride (50 mL). Extract the combined organic layers with water (100 mL) then brine (100 mL). Dry the organic solution over magnesium sulfate with stirring, filter, and then concentrate under reduced pressure to an oily foam residue. Dissolve in methylene chloride and concentrate under reduced pressure to give 26.0 g (96%) of the free base of the title compound as a foam. $^1$H NMR (400 MHz, DMSO-$d_6$) δ 7.70 (s, 1H), 6.74 (m, 2H), 6.36 (s, 1H), 3.75 (bm, 2H), 3.35 (m, 2H), 3.20 (s, 3H), 2.95 (bt, 1H), 2.75 (m, 2H), 2.30 (s, 3H), 2.22 (s, 3H), 2.15 (bm, 2H), 1.82 (m, 1H), 1.50 (m, 1H). HRMS (ES) exact mass M+H calcd for $C_{20}H_{24}F_2N_4OS$ 407.1717; found 407.1716.

Preparation of Crystalline Form I
(Dihydrochloride-Hydrated State)

Weigh (S)-6,7-difluoro-10-[3-(2-methoxy-ethyl)-4-methyl-piperazin-1-yl]-2-methyl-4H-3-thia-4,9-diaza-benzo[f]azulene (123 mg) into a scintillation vial. Add acetone (4 mL). Heat to approximately 60° C. Add 2 molar equivalence of HCl (1N HCl stock). Stir at temperature for a few minutes. Observe a suspension. Cool to room temperature overnight. Filter by vacuum filtration to isolate the solid. Allow to air dry and characterize as crystalline form I.

Preparation of Crystalline Form II (Dihydrochloride Hydrated State)

Dissolve (S)-6,7-difluoro-10-[3-(2-methoxy-ethyl)-4-methyl-piperazin-1-yl]-2-methyl-4H-3-thia-4,9-diaza-benzo[f]azulene (3.00 g, 7.38 mmol) in acetone (98 mL) with stirring at ambient temperature under nitrogen; heat to 50-55° C. Add aqueous 1N HCl (15.5 mL, 15.5 mmol) containing suspended product seed crystals (30 mg) in one portion. Heat at 50-55° C. for 20-30 minutes to allow the product to precipitate, and then allow cooling to ambient temperature. Cool to 0-5° C. and stir for 1-2 hours. Filter and rinse with cold acetone (2×20 mL); dry at 45-50° C. Allow standing at ambient temperature until constant weight is achieved to give 3.40 g (96%) of crystalline form II dihydrochloride hydrated state). HRMS (ES) exact mass M+H calcd for $C_{20}H_{24}F_2N_4OS$ (as the freebase) 407.1717; found 407.1721.

Example 288a (S)-6,7-Difluoro 10-[3-(2-methoxy-ethyl)-4-methyl-piperazin-1-yl]-2-methyl-4H-3-thia-4,9-diaza-benzo[f]azulene dihydrochloride

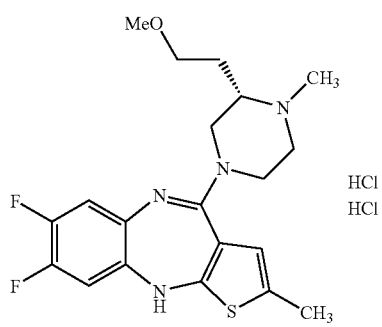

Using a method similar to the example (S)-6-fluoro 10-[3-(2-methoxy-ethyl)-4-methyl-piperazin-1-yl]-2-ethyl-4H-3-thia-4,9-diaza-benzo[f]azulene dihydrochloride, using 6,7-difluoro-2-methyl-4H-3-thia-4,9-diaza-benzo[f]azulen-10-ylamine hydrochloride and (S)-2-(2-methoxy)ethylpiperazine: $^1$H NMR (DMSO-$d_6$): δ 11.7110 (2H, bs), 9.3793 (1H, bs), 7.3795 (1H, bs), 7.0701 (1H, bt), 6.6326 (1H, bs), 4.1000 (3H, bm), 3.6041 (3H, bs), 3.4347 (3H, bs), 3.2081 (3H, bs), 2.8371 (3H, bs), 2.3319 (3H, bs), 2.2842 (1H, bm), 1.8410 (1H, bs); Mass Spectrum M+H=407.1.

Example 289

(S)-6,7-Difluoro-10-[3-(2-ethoxy-ethyl)-4-methyl-piperazin-1-yl]-2-methyl-4H-3-thia-4,9-diaza-benzo[f]azulene dihydrochloride

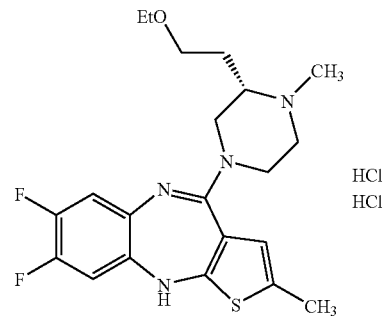

In a similar manner to Example 280, using (S)-7,8-difluoro-10-[3-(2-ethoxy-ethyl)-piperazin-1-yl]-2-methyl-4H-3-thia-4,9-diaza-benzo[f]azulene (353 mg, 0.868 mmol) gives the title compound 172 mg (0.35 mmol): $^1$H NMR (DMSO-$d_6$): δ 11.6927 (2H, bs), 9.3610 (1H, bs), 7.3801 (1H, bs), 7.0656 (1H, bt), 6.6658 (1H, bs), 4.2374 (2H, bs), 4.0610 (1H, bs), 3.6059 (2H, bs), 3.4634 (3H, bs), 3.3831 (3H, bs), 2.8383 (3H, bs), 2.3242 (3H, bs), 2.2500 (1H, bd), 1.8171 (1H, bs), 1.0375 (3H, bs); Mass Spectrum M+H=421.1.

Example 290

(S)-6,7-Difluoro-10-[3-(2-methoxy-ethyl)-4-methyl-piperazin-1-yl]-2-ethyl-4H-3-thia-4,9-diaza-benzo[f]azulene succinate

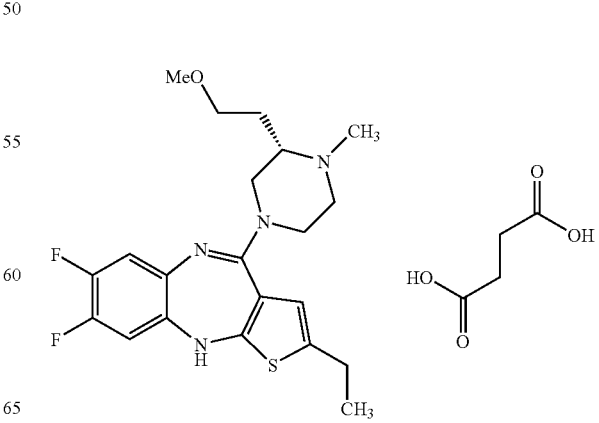

In a similar manner to Example 280, (S)-6,7-difluoro-10-[3-(2-methoxy-ethyl)-piperazin-1-yl]-2-ethyl-4H-3-thia-4,9-diaza-benzo[f]azulene succinate (440 mg, 1.08 mmol) gives the free base of the titled comound (236 mg, 1.78 mmol). This was dissolved in DCM and treated with a solution of succinic acid (66.4 mg, 0.57 mmol) in ethanol to give after evaporation the title compound 300 mg (0.56 mmol):$^1$H NMR (DMSO-d$_6$): δ 12.14 (2H, bs), 7.73 (1H, s), 6.72 (2H, m), 6.35 (1H, s), 3.76 (2H, bm), 3.33 (4H, m), 2.99 (1H, m), 2.77 (2H, m), 2.65 (2H, m), 2.41 (5H, m), 2.25 (5H, m), 1.85 (1H, m), 1.51 (1H, m), 1.16 (3H, m); Mass Spectrum M+H=421.1.

Example 290a (S)-6,7-Difluoro-10-[3-(2-methoxy-ethyl)-4-methyl-piperazin-1-yl]-4H-3-thia-4,9-diaza-benzo[f]azulene

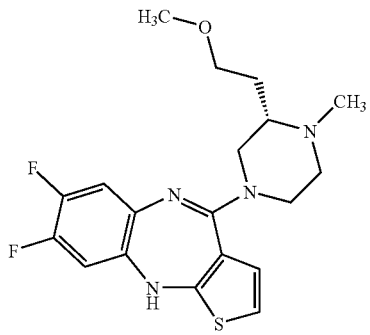

Combine (S)-6,7-difluoro-10-[3-(2-methoxy-ethyl)-piperazin-1-yl]-4H-3-thia-4,9-diaza-benzo[f]azulene (207.2 mg, 0.55 mmol), formaldehyde (48.9 μL, 0.60 mmol, 37% in water), and dichloromethane (8.0 ml). Stir the mixture at ambient temperature for 5 minutes and then add sodium triacetoxyborohydride (174.0 mg, 0.82 mmol). After stirring for 30 minutes at ambient temperature, quench the reaction with saturated sodium bicarbonate. Remove the organic portion and wash (brine), dry (sodium sulfate), and reduce the extracts to residue. Purify the residue on silica gel using a gradient of dichloromethane to dichloromethane/methanol (90:10) to give 176.2 mg (82%) of the title compound: mass spectrum (ion spray): m/z=393.2 (M+1).

Example 290b (S)-6,7-Difluoro-10-[3-(2-methoxy-ethyl)-4-methyl-piperazin-1-yl]-2-trifluormethyl-4H-3-thia-4,9-diaza-benzo[f]azulene dihydrochloride

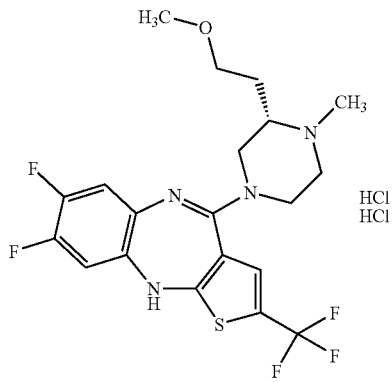

Combine (S)-6,7-difluoro-10-[3-(2-methoxy-ethyl)-4-methyl-piperazin-1-yl]-4H-3-thia-4,9-diaza-benzo[f]azu-lene (381.9 mg, 0.97 mmol), S-(trifluoromethyl)-3,7-dinitrodibenzothiophenenium trifluoromethanesulfonate (479.0 mg, 0.97 mmol), and DMSO (10.0 ml). Stir the mixture at ambient temperature for 24 hours. Dilute the mixture with DI H$_2$O and remove the precipitate by vacuum filtration. Basify the filtrate by the addition of 0.1 N NaOH. Extract the aqueous with ethyl acetate, wash it with brine, dry the organic over sodium sulfate, and then reduce it to residue. Purify the residue using hexanes/THF/ethanol/2N ammonia in methanol (65:30:5:3) to give 58.7 mg. (13%) of the desired product. Prepare the dihydrochloride salt of the product in diethyl ether: mass spectrum (ion spray): m/z=461.2 (M+1).

Example 291

(S)-6-Chloro-10-[3-(2-methoxy-ethyl)-4-methyl-piperazin-1-yl]-2-methyl-4H-3-thia-4,9-diaza-benzo[f]azulene dihydrochloride

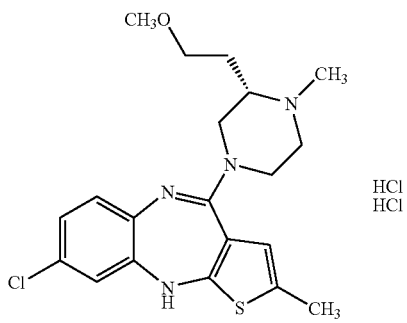

Dissolve (S)-6-chloro-10-[3-(2-methoxy-ethyl)-piperazin-1-yl]-2-methyl-4H-3-thia-4,9-diaza-benzo[f]azulene 195 mg, 0.5 mmol) in 1,2-dichloroethane (3 ml) and stir at room temperature. Add 37% aqueous formaldehyde solution (50 μl) followed by sodium triacetoxyborohydride (140 mg). Stir the reaction mixture at room temperature overnight. Add saturated aqueous sodium carbonate and collect the organic phase, dried and concentrate to a dark oil. Purify this material by flash column chromatography on florisil (eluent dichloromethane/methanol) to give 71 mg yellow oil. Dissolve this material in ethyl acetate and add 2N hydrochloric acid in ether and concentrate the mixture and dry under high vacuum to give (S)-6-chloro-10-[3-(2-methoxy-ethyl)-4-methyl-piperazin 1-yl]-2-methyl-4H-3-thia-4,9-diaza-benzo [f]azulene dihydrochloride as the desired product as an orange solid 76 mg. Mass Spectrum (FIA) 405/407 (M+1); mp=174-176° C.

Example 291a (S)-7-Chloro-10-[3-(2-methoxy-ethyl)-4-methyl-piperazin-1-yl]-4H-3-thia-4,9-diaza-benzo[f]azulene

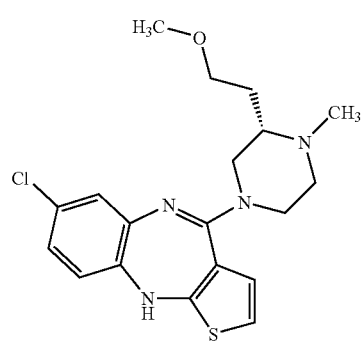

Combine (S)-7-chloro-10-[3-(2-methoxy-ethyl)-piperazin-1-yl]-4H-3-thia-4,9-diaza-benzo[f]azulene (571.5 mg, 1.52 mmol), formaldehyde (135.4 µL, 1.67 mmol, 37% in water), and dichloromethane (20.0 ml). Stir the mixture at ambient temperature for 5 minutes and then add sodium triacetoxyborohydride (482.0 mg, 2.27 mmol). After stirring for 30 minutes at ambient temperature, quench the reaction with saturated sodium bicarbonate. Remove the organic portion and wash (brine), dry (sodium sulfate), and reduce the extracts to residue. Purify the residue on silica gel using a gradient of dichloromethane to dichloromethane/methanol (90:10) to give 418.3 mg (71%) of the title compound as a brown foam: mass spectrum (ion spray): m/z=391.1 (M+1).

Example 291b (S)-7-Chloro-10-[3-(3-methoxy-propyl)-4-methyl-piperazin-1-yl]-4H-3-thia-4,9-diaza-benzo[f]azulene

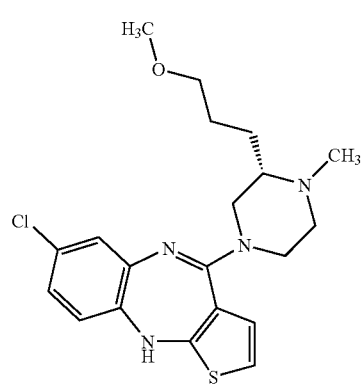

Combine (S)-7-chloro-10-[3-(3-methoxy-propyl)-piperazin-1-yl]-4H-3-thia-4,9-diaza-benzo[f]azulene (280.3 mg, 0.72 mmol), formaldehyde (64.0 µL, 0.79 mmol, 37% in water), and dichloromethane (10.0 ml). Stir the mixture at ambient temperature for 5 minutes and then add sodium triacetoxyborohydride (227.9 mg, 1.08 mmol). After stirring for 30 minutes at ambient temperature, quench the reaction with saturated sodium bicarbonate. Remove the organic portion and wash (brine), dry (sodium sulfate), and reduce the extracts to residue. Purify the residue on silica gel using a gradient of dichloromethane to dichloromethane/methanol (90:10) to give 223.0 mg (77%) of the title compound: mass spectrum (ion spray): m/z=405.1 (M+1).

Example 291c (S)-7-Chloro 10-[3-(2-hydroxy-ethyl)-4-methyl-piperazin-1-yl]-2-methyl-4H-3-thia-4,9-diaza-benzo[f]azulene dihydrochloride

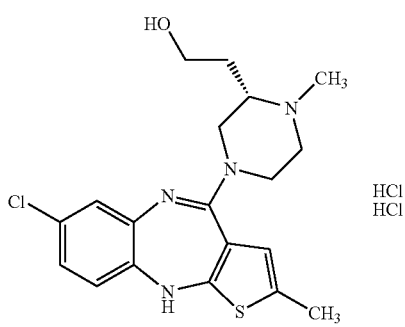

Using a method similar to Example 287a, using (S)-7-chloro-10-[3-(2-hydroxy-ethyl)-piperazin-1-yl]-2-methyl-4H-3-thia-4,9-diaza-benzo[f]azulene dihydrochloride gives the title compound.

Example 292

(S)-7-Chloro-10-[3-(2-methoxy-ethyl)-4-methyl-piperazin-1-yl]-2-methyl-4H-3-thia-4,9-diaza-benzo[f]azulene dihydrochloride

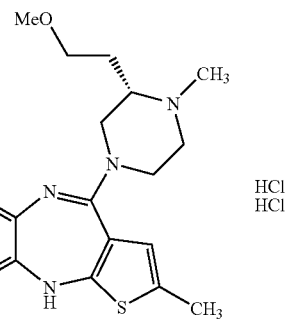

Dissolve (S)-7-chloro-10-[3-(2-methoxy-ethyl)-piperazin-1-yl]-2-methyl-4H-3-thia-4,9-diaza-benzo[f]azulene dihydrochloride (1.15 g) in 1,2-dichloroethane (150 ml) and stir at room temperature. Add 37% aqueous formaldehyde solution (0.18 ml) followed by sodium triacetoxyborohydride (940 mg). Stir the reaction mixture at room temperature overnight. Add saturated aqueous sodium carbonate and collect the organic phase, dry and concentrate to a dark oil. Purify this material by flash column chromatography on florisil (eluent dichloromethane/methanol) to give 400 mg yellow oil. Dissolve this material in ethyl acetate and add 2N hydrochloric acid in ether and concentrate the mixture and dry under high vacuum to give the desired product as an orange solid 224 mg. Mass Spectrum (LCMS) 405/407 (M+1). Mpt 200-202° C.

Example 292a (S)-7-Chloro-10-[3-(2-methoxy-ethyl)-4-methyl-piperazin-1-yl]-2-methyl-4H-3-thia-4,9-diaza-benzo[f]azulene

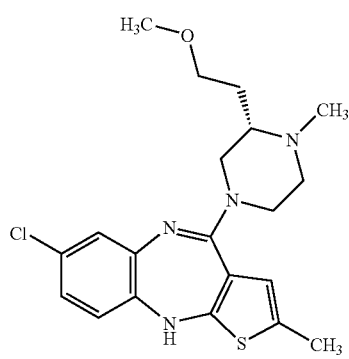

Combine (S)-7-chloro-10-[3-(2-methoxy-ethyl)-piperazin-1-yl]-2-methyl-4H-3-thia-4,9-diaza-benzo[f]azulene (33.3 g, 85.2 mmol) and 1,2-dichloroethane (DCE, 500 mL). Add formaldehyde (37% wt. in water, 6.91 g solution, 2.56 g, 85.2 mmol) in one portion and stir at ambient temperature for 5 minutes. Add sodium triacetoxyborohydride (3.41 g, 16.1 mmol) in portions over 5-10 minutes, keeping the pot temperature below 25° C. Stir at ambient temperature overnight. Add saturated aqueous sodium bicarbonate (333 mL). Stir for 15 minutes, and then separate layers. Extract the aqueous layer with methylene chloride (250 mL). Wash the combined organic layers with water (3×333 mL), dry over sodium sulfate, and then concentrate ins vacuo to a residue (>100% recovery). Purify the residue by flash column chromatography, eluting with (100% $CH_2Cl_2$ to 93/7 $CH_2Cl_2$/MeOH) 91.2% recovery of the title compound. $^1$H NMR (500 MHz, DMSO-$d_6$) δ 1.49 (m, 1H), 1.82 (m, 1H), 2.13 (m, 2H), 2.20 (s, 3H), 2.27 (s, 3H), 2.74 (m, 2H), 2.98 (bt, 1H), 3.19 (s, 3H), 3.32 (m, 2H), 3.77 (bm, 2H).

Example 292b (S)-7-Chloro-10-[3-(2-methoxy-ethyl)-4-methyl-piperazin-1-yl]-2-methyl-4H-3-thia-4,9-diaza-benzo[f]azulene dihydrochloride

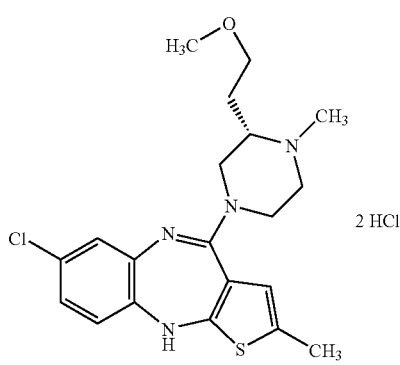

Combine (S)-7-chloro-10-[3-(2-methoxy-ethyl)-4-methyl-piperazin-1-yl]-2-methyl-4H-3-thia-4,9-diaza-benzo[f] azulene (39.7 g, 97.6 mmol) and 2-propanol (IPA, 397 mL) at ambient temperature and hear to 80-81° C. Add a solution of concentrated HCl (17.1 mL, 206 mmol) in IPA (79 mL) over 20-30 minutes. Maintain the temperature of the resulting mixture at 79-80° C. for 1.5 hours. Shut heat source and allow the mixture to cool slowly to 30° C. over 3 hours. Cool to 0-5° C. and stir for an additional hour. Filter the solids and rinse with ice cold IPA (3×50 mL). Dry at 50° C. to afford 46.5 g (99.3%) of the title compound. KF analysis gives 5.47% $H_2O$, Chloride analysis affords a value of 12.8%.

Example 293

(S)-7-Chloro-10-[3-(2-methoxy-ethyl)-4-methyl-piperazin-1-yl]-2-trifluoromethyl-4H-3-thia-4,9-diaza-benzo[f]azulene dihydrochloride

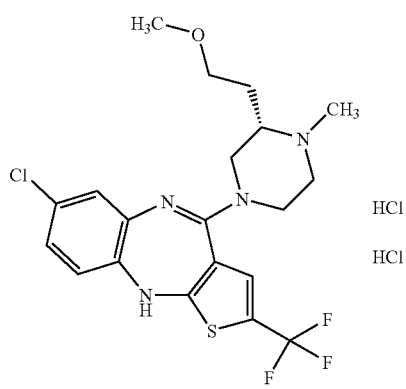

Combine (S)-7-chloro-10-[3-(2-methoxy-ethyl)-4-methyl-piperazin-1-yl]-4H-3-thia-4,9-diaza-benzo[f]azulene (381.2 mg, 0.98 mmol), S-(trifluoromethyl)-3,7-dinitrodibenzothiophenenium trifluoromethanesulfonate (480.0 mg, 0.98 mmol), and DMSO (8.0 ml). Stir the mixture at ambient temperature for 24 hours. Dilute the mixture with DI $H_2O$ and remove the precipitate by vacuum filtration. Basify the filtrate by the addition of 0.1 N NaOH. Extract the aqueous with ethyl acetate, wash it with brine, dry the organic over sodium sulfate, and then reduce it to residue. Purify the residue using hexanes/THF/ethanol/2N ammonia in methanol (65:30:5:3) to give 78.3 mg (18%) of the desired product. Prepare the dihydrochloride salt of the product in ethyl acetate: mass spectrum (ion spray): m/z=459.1 (M+1).

Example 294

(S)-7-Chloro-10-[3-(3-methoxy-propyl)-4-methyl-piperazin-1-yl]-2-trifluormethyl-4H-3-thia-4,9-diaza-benzo[f]azulene dihydrochloride

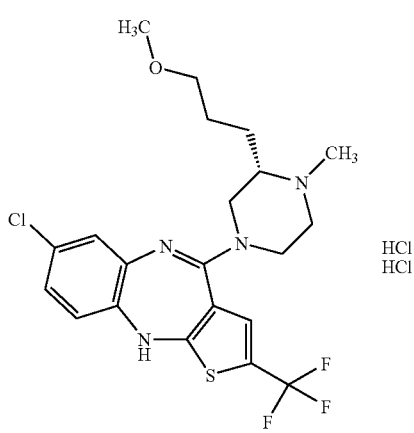

Combine (S)-7-chloro-10-[3-(3-methoxy-propyl)-4-methyl-piperazin-1-yl]-4H-3-thia-4,9-diaza-benzo[f]azulene (196.8 mg, 0.49 mmol), S-(trifluoromethyl)-3,7-dinitrodibenzothiophenenium trifluoromethanesulfonate (239.2 mg, 0.49 mmol), and DMSO (5 ml). Stir the mixture at ambient temperature for 24 hours. Dilute the mixture with DI H$_2$O and remove the precipitate by vacuum filtration. Basify the filtrate by the addition of 0.1 N NaOH. Extract the aqueous with ethyl acetate, wash it with brine, dry the organic over sodium sulfate, and then reduce it to residue. Purify the residue using hexanes/THF/ethanol/2N ammonia in methanol (65:30:5:3) to give 34.5 mg (15%) of the desired product. Prepare the dihydrochloride salt of the product in diethyl ether: mass spectrum (ion spray): m/z=473.0 (M+1).

Example 295

(S)-10-[3-(2-phenylsulfanyl-ethyl)piperazin-1-yl]-2-methyl-4H-3-thia-4,9-diazabenzo[f]azulene

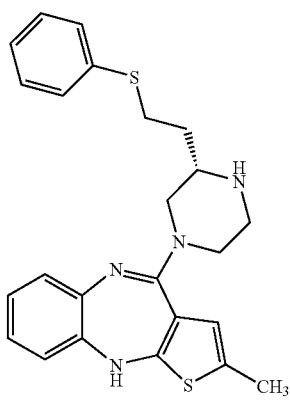

Combine 2-methyl-4,9-dihydro-3-thia-4,9-diazabenzo[f]azulene-10-thione (0.455 g, 1.85 mmol), (S)-2-(2-phenylsulfanyl-ethyl)-piperazine (0.411, 1.85 mmol) and pyridine (5 mL) and reflux for 36 hours. Evaporate the mixture and apply the material to 10 g of SCX, then elute with methanol followed by 5% 2N ammonia-methanol in dichloromethane and then 2N ammonia-methanol. Purification by flash chromatography, eluting with a step gradient starting with dichloromethane going to 7% 2N ammonia-methanol in dichloromethane gives (S)-10-[3-(2-phenylsulfanyl-ethyl)-piperazin-1-yl]-2-methyl 4H-3-thia-4,9-diazabenzo[f]azulene (0.126 g, 0.290 mmol, 16%). Mass spectrum (APCI): m/z=435.1 (M+1).

Example 296

(S)-10-[4-Methyl-3-(2-phenylsulfanylethyl)piperazin-1-yl]-2-methyl-4H-3-thia-4,9-diazabenzo[f]azulene dihydrochloride

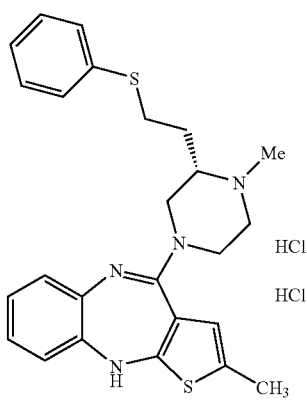

Combine (S)-10-[3-(2-phenylsulfanyl-ethyl)piperazin-1-yl]-2-methyl-4H-3-thia-4,9-diazabenzo[f]azulene (0.118 g, 0.271 mmol), formaldehyde (24 μL, 0.299 mmol, 37% aqueous solution), and sodium triacetoxyborohydride (86 mg, 0.407 mmol) in dichloroethane (10 mL) and stir at room temperature for 2 hours. Dilute the mixture with saturated aqueous sodium bicarbonate and extract three times with dichloromethane. Combine the organic layers, dry over sodium sulfate and concentrate under reduced pressure. Purification by flash chromatography, eluting with a step gradient starting with dichloromethane going to 6% 2N ammonia-methanol in dichloromethane gives the free base of the title compound. Isolate clean product as the corresponding dihydrochloride by dissolving the free base in ethanol and adding a solution of 5 equivalents of hydrochloric acid in ethanol. Evaporating the solution and drying the salt provides the title compound (0.089 g, 0.189 mmol, 70%) as a brown solid. Mass spectrum (APCI): m/z=449.1 (M+1 of free base).

Example 297

(S)-6-Fluoro-10-[4-methyl-3-(2-methylsulfanyl-ethyl)-piperazin-1-yl]-2-methyl-4H-3-thia-4,9-diazabenzo[f]azulene dihydrochloride

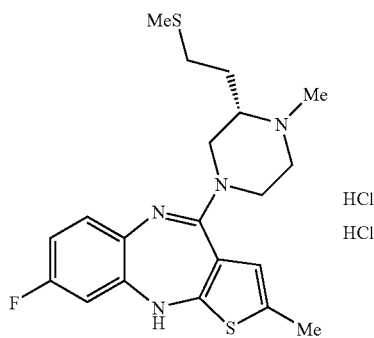

Heat a mixture of 6-fluoro-2-methyl-4H-3-thia-4,9-diazabenzo[f]azulen-10-ylamine hydrochloride salt (0.135 g, 0.476 mmol), (S)-1-methyl-2-(2-methylsulfanyl-ethyl)-piperazine (0.166 g, 0.95 mmol) and diisopropyl ethylamine (0.083 mL, 0.476 mmol) in DMSO (0.2 mL) and toluene (0.8 mL) at 110° C. for 46 hours. Dilute the reaction mixture with ethyl acetate and 0.1N sodium hydroxide solution. The ethyl acetate extract gives 0.196 g. of the crude product. Silica gel chromatography, eluting with methylene chloride: methanol (100:5), gives 0.081 g of the title compound as an orange oil. The dihydrochloride salt precipitates in ethyl acetate as an orange solid: mp 194° C.; mass spectrum (ion spray): m/z=405 (M+1).

Example 300

(S)-2-[4-(2-Methyl-4H-3-thia-1,4,9-triazabenzo[f]azulene-10-yl)-piperazin-2-yl]-ethanol

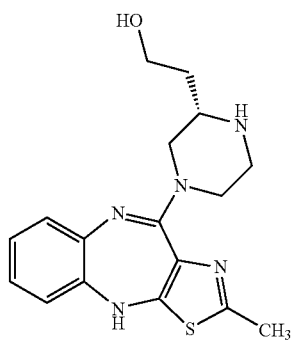

Combine 2-methyl-4H-3-thia-1,4,9-triazabenzo[f]azulene-10-ylamine hydrochloride (0.458 g, 1.72 mmol), (S)-2-piperazin-2-yl-ethanol (0.518, 3.98 mmol), diisopropyl-ethylamine (0.346 mL, 1.99 mmol), dimethyl sulfoxide (1.5 mL) and toluene (4.5 mL) and heat to 110° C. for 48 hours. Evaporate the mixture and apply the material to 20 g of SCX, elute with methanol followed by 5% 2N ammonia-methanol in dichloromethane and finally 100% 2N ammonia-methanol. Purify by flash chromatography, eluting with a step gradient starting with dichloromethane going to 10% 2N ammonia-methanol in dichloromethane, to obtain (S)-2-[4-(2-methyl-4H-3-thia-1,4,9-triazabenzo[f]azulene-10-yl)-piperazin-2-yl]-ethanol (0.082 g, 0.239 mmol, 14%): mass spectrum (APCI): m/z=344.4 (M+1).

Example 301

(S)-10-[3-(2-Methoxyethyl)piperazin-1-yl]-2-methyl-4H-3-thia-1,4,9-triazabenzo[f]azulene

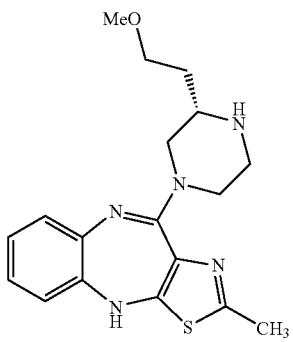

In a manner such as that described in Example 300, combine 2-methyl-4H-3-thia-1,4,9-triazabenzo[f]azulene-10-ylamine hydrochloride (0.437 g, 1.64 mmol) and (S)-2-(2-methoxyethyl)piperazine (0.474 g, 3.29 mmol) to obtain the title compound: mass spectrum (APCI): m/z=358.0 (M+1).

Example 302

(S)-10-[3-(2-Ethoxyethyl)-piperazin-1-yl]-2-methyl-4H-3-thia-1,4,9-triazabenzo[f]azulene

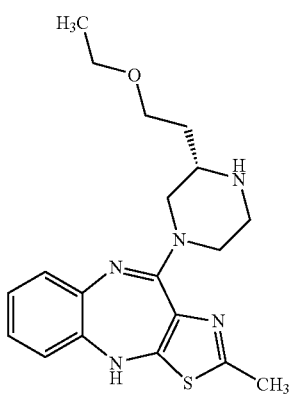

In a manner similar to that described in Example 300, combine 2-methyl-4H-3-thia-1,4,9-triazabenzo[f]azulene-10-ylamine (0.534 g, 2.01 mmol) and (S)-2-(2-ethoxyethyl)piperazine (0.635 g, 4.01 mmol) to obtain the title compound: Exact Mass, Calc: 372.1858; Found: 372.1867.

Example 303

(S)-10-[3-(2-Methoxy-ethyl)-piperazin-1-yl]-2-ethyl-4H-3-thia-1,4,9-triaza-benzo[f]azulene

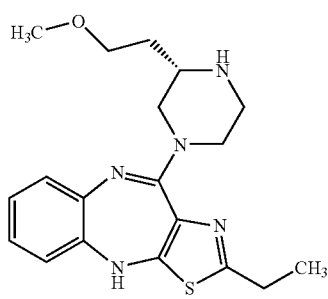

Combine 2-ethyl-4,9-dihydro-3-thia-1,4,9-triaza-benzo{f}azulene-10-thione (1.05 g, 4.0 mmol) in 8 mL CH₂Cl₂, add methyl trifluoromethanesulfonate (0.98 g, 0.68 mL 6.0 mmol) and stir overnight. If reaction is not complete, add additional methyl trifluoromethanesulfonate. Concentrate the reaction mixture under reduced pressure to give a red-brown solid (1.62 g). Take half of the material (0.81 g, ~1.9 mmol), mix with 2(S)-(2-methoxy-ethyl)-piperazine (0.27 g, 1.9 mmol) in 5 mL pyridine and heat the reaction to 100° C. Cool the reaction after overnight heating and concentrate to a residue. Purification by flash chromatography on silica gel (35 g) (gradient 100% CH₂Cl₂ to 100% mixed solvent of (CH₂Cl₂: 2N NH₃/MeOH=15:1) over 55 min. give 265 mg of the title compound: mass spectrum (electrospray) (m/e): $C_{19}H_{25}N_5OS2HCl$, Calc. Mass (M+1-2HCl): 372.1658, Found: 372.1876; ¹H NMR (300 MHz, CDCl₃): δ 7.05-6.96 (m, 2H), 6.89-6.84 (m, 1H), 6.64-6.61 (m, 1H), 4.99 (s, 1H), 4.20 (br, 1H), 3.51 (t, 2H, J=6.3 Hz), 3.32 (s, 3H), 3.01-2.97 (m, 4H), 2.85 (q, 2H, J=6.9 Hz), 2.71-2.63 (m, 1H), 1.87-1.63 (m, 4H), 1.30 (t, 3H, J=7.2 Hz).

Example 304

(S)-10-[3-(2-Methoxy-ethyl)-piperazin-1-yl]-2-propyl-4H-3-thia-1,4,9-triaza-benzo[f]azulene

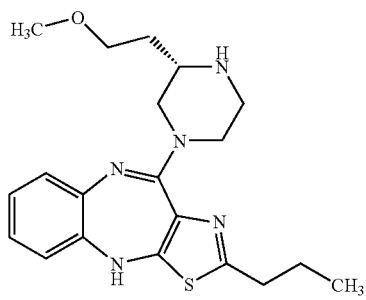

Using the method of Example 303 gives the title compound (S)-10-[3-(2-methoxy-ethyl)-piperazin-1-yl]-2-propyl-4H-3-thia-1,4,9-triaza-benzo[f]azulene as light yellow solid: ¹H NMR (400 MHz, CDCl₃): δ 7.05-6.98 (m, 2H), 6.92-6.89 (m, 1H), 6.67-6.50 (m, 1H), 5.40 (br, 1H), 4.20 (br, 1H), 3.54 (m, 2H), 3.34 (s, 3H), 3.25-2.95 (m, 7H), 2.78 (t, 2H, J=7.6 Hz), 1.84-1.80 (m, 2H), 178-1.63 (m, 2H), 0.98 (t, 3H, J=7.6 Hz)

Example 305

(S)-10-[3-(2-Methoxy-ethyl)-piperazin-1-yl]-2-butyl-4H-3-thia-1,4,9-triaza-benzo[f]azulene

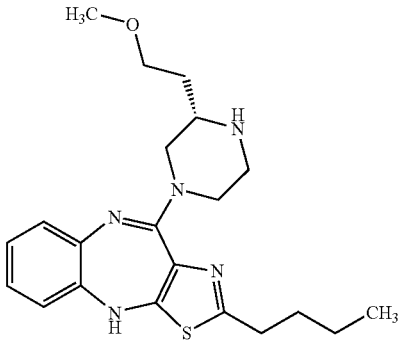

Add methyl trifluoromethanesulfonate (0.51 mL, 4.5 mmol) to a 0° C. solution of 2-butyl-4,9-dihydro-3-thia-1,4,9-triaza-benzo[f]azulene-10-thione (0.87 g, 3.0 mmol) in anhydrous dichloromethane (4 mL). Rinse solids into reaction with dichloromethane (3 mL) and stir allowing reaction to slowly reach-ambient temperature. After an overnight period, concentrate under reduced pressure to afford crude methylated intermediate (1.30 g). Combine the intermediate (1.30 g, 2.87 mmol) and 2-(S)-(2-methoxy-ethyl)-piperazine (0.41 g, 2.87 mmol) with anhydrous pyridine (10 mL), heat to 100° C. and stir. After an overnight period, cool to ambient temperature and concentrate under reduced pressure to an oil (2.16 g). Purify the oil by flash chromatography, eluting with a gradient of a 7% solution of 2M ammonia in methanol, in dichloromethane, (0-100% over 55 minutes) to give the title compound (0.37 g, 32%): mass spectrum (APCI, m/e): 400 (M+1); NMR (¹H, 300 MHz, DMSO-d₆): δ 7.88 (s, 1H), 6.82 (m, 3H), 6.67 (m, 1H), 4.07 (m, 2H), 3.45-3.27 (m, 3H), 3.20 (s, 3H), 3.15-2.82 (m, 4H), 2.82-2.68 (m, 3H), 1.76-1.53 (m, 4H), 1.30 (m, 2H), 0.86 (t, 3H, J=7.2 Hz).

Example 306

(S)-10-[3-(2-Methoxy-ethyl)-piperazin-1-yl]-2-butyl 4H-3-thia-1,4,9-triaza-benzo[f]azulene dihydrochloride

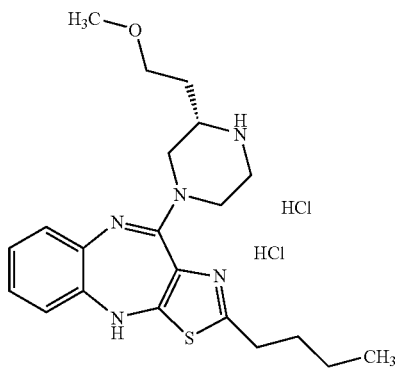

Using the method of Example 273 using (S)-2-butyl-10-[3-(2-methoxy-ethyl)-piperazin-1-yl]-4H-3-thia-1,4,9-triaza-benzo[f]azulene and a solution of acetyl chloride in absolute ethanol at ambient temperature gives the title compound: mass spectrum (APCI, m/e): 400 (M+1); exact mass spectrum (ES+, m/e, $C_{21}H_{29}N_5OS.2HCl$): calc. 400.2171 (M+1-2HCl), found 400.2193.

Example 307

(S)-2-[4-(2-Isopropyl-4H-3-thia-1,4,9-triazabenzo[f]azulene-10-yl)-piperazin-2-yl]ethanol

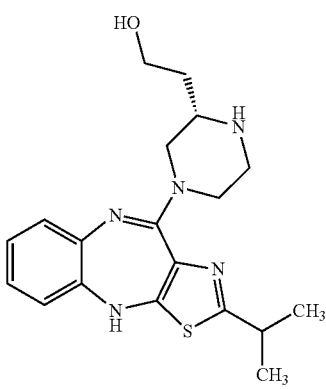

In a manner such as that described in Example 300, combine 2-isopropyl-4H-3-thia-1,4,9-triazabenzo[f]azulene-10-ylamine hydrochloride (0.558 g, 1.89 mmol) and (S)-2-piperazin-2-yl-ethanol (0.493 g, 3.79 mmol) to obtain the title compound: mass spectrum (APCI): m/z=372.4 (M+1).

Example 308

(S)-10-[3-(2-Methoxyethyl)-piperazin-1-yl]-2-isopropyl-4H-3-thia-1,49-triazabenzo[f]azulene

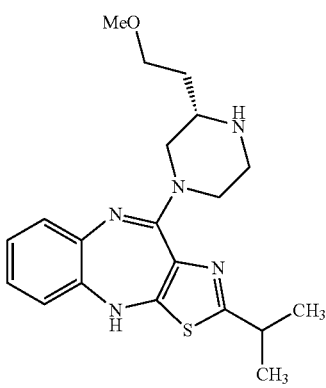

Combine 2-isopropyl-4H-3-thia-1,4,9-triaza-benzo[f]azulen-10-ylamine hydrochloride (0.481 g, 1.63 mmol), (S)-2-(2-methoxyethyl)piperazine (0.471 g, 3.27 mmol), and diisopropylethyl amine (0.284 mL, 1.63 mmol) in a mixture of toluene (4.5 mL) and dimethylsulfoxide (1.5 mL) and stir at 110° C. for 24 hours. Evaporate the mixture then dilute with methanol and apply to two 10 g SCX columns. Eluting with methanol and then a step gradient starting with dichloromethane going to 10% 2N ammonia-methanol in dichloromethane followed by 2N ammonia-methanol gives the desired material in a crude state. Purification by flash chromatography, eluting with a step gradient starting with dichloromethane going to 9% 2N ammonia-methanol in dichloromethane gives the title compound (0.186 g, 0.482 mmol, 30%) as a yellow oil: mass spectrum (APCI): m/z=386.2 (M+1).

Example 308a (S)-10-[3-(2-Methoxyethyl)piperazin-1-yl]-2-isopropyl-4H-3-thia-1,4,9-triazabenzo[f]azulene

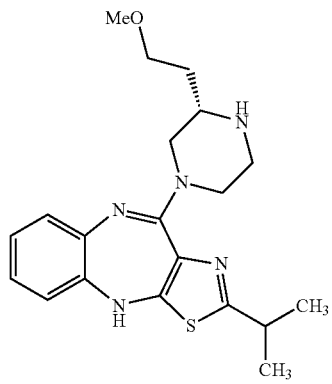

Combine 2-isopropyl-4,9-dihydro-3-thia-1,4,9-triazabenzo[f]azulene-10-thione (2.61 g, 9.48 mmoles) with trifluoromethanesulfonic acid methyl ester (1.61 mL, 14.2 mmoles) in dichloromethane (20 mL). Stir at room temperature for 2 h, then remove solvent in vacuo. Suspend residue in pyridine (20 mL) and add (S)-2-(2-methoxyethyl)piperazine (1.37 g, 9.48 mmoles). Heat at 115° C. for 8 h, then remove solvent in vacuo and apply residue to silica gel column. Elute column with dichloromethane followed by 5% 2N ammonia-methanol in dichloromethane to obtain the title compound (2.11 g, 58%) as a yellow oil: mass spectrum (APCI): m/z=386.2 (M+1).

Example 308b (S)-10-[3-(2-Methoxyethyl)piperazin-1-yl]-2-isopropyl 4H-3-thia-1,4,9-triazabenzo[f]azulene

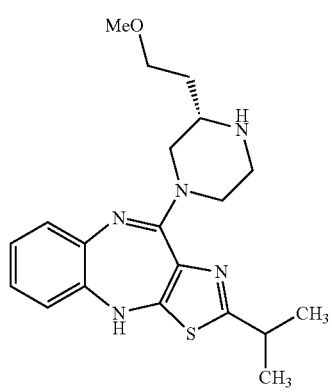

Equip a 1 liter single necked round bottom flask with a condenser, magnetic stir bar, heating mantle, and nitrogen inlet. Charge the flask with 2-isopropyl-10-methylsulfanyl-4H-3-thia-1,4,9-triaza-benzo[f]azulene (44.9 g, 0.155 mol), (S)-2-(2-methoxyethyl)piperazine (27.98 g, 0.194 mol, 1.25 eqs.), and IPA (270 mL, 6 vols.). Heat the resulting slurry to reflux and monitor by HPLC: Column=Zorbax C-8, Flow=1 mL/min., A=ACN, B=0.1% aqueous TFA, Gradient=95% A/5% B to 5% A/95% B over 10 minutes, Hold at 5/95 A/B for 3 minutes, and return to 95/5 A/B over 2 minutes, Column temperature=30° C., Wavelength=250 nm. After 3 hours at reflux, HPLC analysis indicates a product to starting material ratio (p/sm) of 2.9/1.0. Allow the reaction mixture to reflux overnight under a nitrogen purge. After 19.75 hours at reflux, HPLC analysis indicates a p/sm ratio of 16.1/1.0. Allow the mixture to reflux 2 hours longer and assay again by HPLC. Indications of this analysis show no change in the p/sm. ratio. Charge additional (S)-2-(2-methoxyethyl)piperazine (2.24 g, 0.0155 mol, 0.1 eq.) to the reaction vessel and continue to reflux for 5 hours. Indications of HPLC analysis shows 3% remaining starting material, 2-Isopropyl-10-methylsulfanyl-4H-3-thia-1,4,9-triaza-benzo[f]azulene. Methyl mercaptan is evolved during the reaction. On this scale, the odors associated with that chemical were controlled by a nitrogen purge exhausted to the far back of the hood. For future, larger scale operations, a bleach scrubber should be considered. Stop the heating and allow the reaction mixture to cool to 40-50° C. Transfer the flask to the roto-vap and strip the IPA using a 40-50° C. bath. Dissolve the resulting thick, orange oil in ethyl acetate (1000 mL), transfer to a separatory funnel, and wash with deionized water (2×250 mL). After a brine wash (250 mL), dry the solution over $Na_2SO_4$, filter, and concentrate in vacuo. Allow the resulting oil to pull under vacuum overnight at ambient temperature. Solidification of the material overnight into a yellow mass (74.1 g, theory=59.84 g). HPLC analysis indicates 2.1% remaining 2-Isopropyl-10-methylsulfanyl-4H-3-thia-1,4,9-triaza-benzo[f]azulene. Treat these solids with ligroin (500 mL) and ethyl acetate (50 mL). Place a magnetic stir bar in the flask and the mixture vigorously at ambient temperature until all of the solids were broken into small particles (6 hrs.). Filter the mixture and rinse the solids with 100/5 ligroin/ethyl acetate (105 mL), then ligroin (2×200 mL). Transfer the yellow solids to a tared dish and dry under vacuum at ambient temperature. Recover 53.67 grams of title compound (89.7%): $^1$H NMR (500 MHz, DMSO-$d_6$): δ 1.23 (d, 6H), 1.49-1.53 (m, 2H), 2.20-2.39 (bm, 1H), 2.43-2.49 (m, 1H), 2.62-2.74 (m, 2H), 2.70-2.83 (m, 1H), 2.85-2.90 (m, 1H), 3.04-3.08 (m, 1H), 3.19 (s, 3H), 3.30-3.41 (m, 2H), 3.90-4.09 (bm, 2H), 6.67 (m, 1H), 6.69-6.79 (m, 2H), 6.79-6.86 (m, 1H). $^{13}$C NMR (100 MHz, DMSO-$d_6$): δ 22.88, 22.91, 33.13, 33.85, 39.36, 40.61, 45.54, 52.88, 58.36, 69.67, 119.25, 123.43, 124.33, 127.96, 131.74, 141.41, 143.52, 151.04, 155.97, 165.59. MS (80:20 MeOH:$H_2O$ w/6.5 mM $NH_4OAc$). Calculated: 385.53. Found: $ES^+$ 386.2. $ES^-$ 384.2.

Example 309

(S)-10-[3-(2-Ethoxyethyl)-piperazin-1-yl]-2-isopropyl-4H-3-thia-1,4,9-triazabenzo[f]azulene

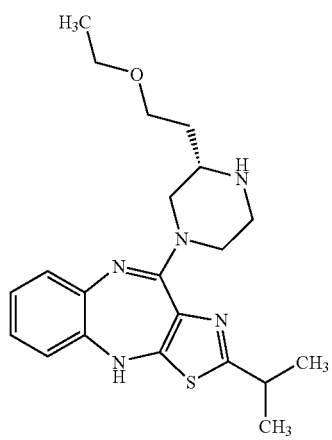

In a manner similar to that described in Example 300, combine 2-isopropyl-4H-3-thia-1,4,9-triazabenzo[f]azulene-10-ylamine hydrochloride (0.523 g, 1.77 mmol) and (S)-2-(2-ethoxyethyl)piperazine (0.561 g, 3.54 mmol) to obtain the title compound: mass spectrum (APCI): m/z = 400.2 (M+1).

Example 310

(S)-10-[3-(3-Methoxy-propyl)-piperazin-1-yl]-2-isopropyl-4H-3-thia-1,4,9-triaza-benzo[f]azulene

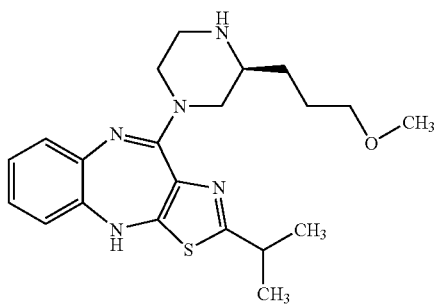

Combine 2-isopropyl-4,9-dihydro-3-thia-1,4,9-triazabenzo[f]azulene-10-thione (0.5 g, 1.816 mmol), methyl triflate (0.306 mL, 2.723 mmol) in dichloromethane (4 mL) and stir at ambient temperature for 2 hours. Evaporate the mixture uner reduced pressure and then combine the residue with (S)-2-(3-methoxy-propyl)-piperazine (0.287 g, 1.816 mmol) and pyridine (4 mL) and reflux for 8 hours. Concentrate the reaction mixture under reduced pressure and dilute the residue with ethyl acetata. Wash the organic with brine twice, dry over sodium sulfate, filter and concentrate under reduced pressure to give a residue. Purify the residue by flash chromatography, eluting with 2M ammonia in methanol:dichloromethane (5:95) to give the title compound: mass spectrum (m/e):400.03 (M+1).

Example 311

(S)-10-[3-(2-Methoxyethyl)-piperazin-1-yl]-2-cyclopentyl-4H-3-thia-1,4,9-triazabenzo[f]azulene

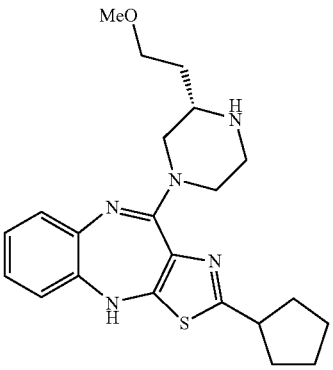

Combine 2-cyclopentyl-4,9-dihydro-3-thia-1,4,9-triazabenzo[f]azulene-10-thione (0.529 g, 1.75 mmol) and methyl triflate (0.24 mL, 2.11 mmol) in dichloromethane (3 mL) at 0° C. Stir the mixture at 0° C. for 15 minutes and warm to room temperature overnight. Evaporate the mixture, combine the residue with (S)-2-(2-methoxyethyl)piperazine (0.253 g, 1.75 mmol) and pyridine (3 mL) and heat at reflux overnight. Evaporate the mixture, then dilute with methanol and apply to a 10 g SCX column. Wash with methanol, then elute with a step gradient starting with dichloromethane going to 10% 2N ammonia-methanol in dichloromethane followed by 100% 2N ammonia-methanol to obtain the desired coupled product. Purify by flash chromatography, eluting with a step gradient starting with dichloromethane going to 6% 2N ammonia-methanol in dichloromethane, to give (S)-10-[3-(2-methoxy-ethyl)-piperazin-1-yl]-2-cyclopentyl 4H-3-thia-1,4,9-triazabenzo[f]azulene (0.378 g, 0.918 mmol, 52%) as a yellow amorphous solid: mass spectrum (APCI): m/z=412.2 (M+1).

Example 312

(S)-10-[3-(2-Methoxy-ethyl)-piperazin-1-yl]-4H-3-thia-1,4,9-triaza-benzo[f]azulene-2-yl-methanol

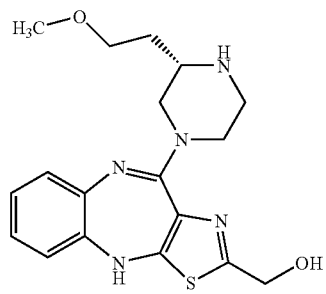

Combine (S)-10-[3-(2-methoxy-ethyl)-4-methyl-piperazin-1-yl]-4H-3-thia-1,4,9-triaza-benzo[f]azulene-2-carboxylic acid ethyl ester (0.49 g, 1.18 mmol) in 5.0 mL THF, add 2.95 mL of LiAlH$_4$ (1.0 M THF) dropwise at ice-water bath. After addition, remove the ice bath, stir the reaction mixture at RT. After half hour, quench the reaction by adding 1.0 N NaOH cautiously until no gas evolves. Pass the suspension through celite plug, wash repeatedly with ether, and concentrate the organic solution to a residue. Purify by flash chromatography affords 0.22 g of the title compound: mass spectrum (electrospray) (m/e): 374.0 (M+1), 372.1 (M−1); $^1$H NMR (400 MHz, DMSO-d$_6$): 7.79 (s, 1H), 6.86-6.75 (m, 3H), 6.69-6.66 (m, 1H), 5.89 (br, 1H), 4.50 (d, 2H, J=4.4 Hz), 4.04-3.93 (m, 2H), 3.38-3.33 (m, 2H), 3.30 (s, 3H), 2.84-2.60 (m, 4H), 2.46-2.41 (m, 1H), 1.49 (q, 2H, J=6.6 Hz).

Example 313

(S)-10-[3-(2-Methoxy-ethyl)-piperazin-1-yl]-4H-3-thia-1,4,9-triaza-benzo[f]azulene-2-carboxylic acid ethyl ester

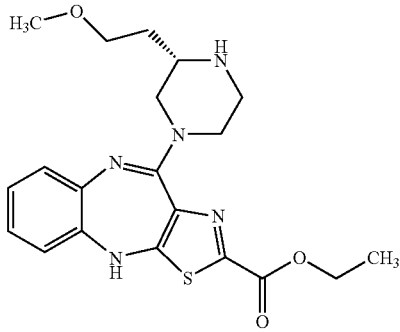

Combine 10-thioxo-9,10-dihydro-4H-3-thia-1,4,9-triazabenzo[f]azulene-2-carboxylic acid ethyl ester (3.59 g, 11.76 mmol) in 25 mL CH$_2$Cl$_2$ and add methyl trifluoromethanesulfonate (2.41 g, 14.7 mmol) dropwise at 0° C., stir at 0° C. for half hour, and warm to RT. After 2 h, concentrate the reaction mixture under reduced pressure, mix with (S)-2-(2-methoxy-ethyl)-piperazine (0.1.47 g, 10.2 mmol) in 20 mL pyridine and heat to 100° C. After 4 hours, cool the reaction to RT, and concentrate to a residue. Purification by flash chromatography (twice) on silica gel using a gradient (100% CH$_2$Cl$_2$ to 100% mixed solvent of (CH$_2$Cl$_2$: 2N NH$_3$/MeOH=20:1)) over 55 min. gives the title compound: mass spectrum (electrospray) (m/e): C$_{20}$H$_{25}$N$_5$O$_3$S, Calc. Mass (M+1): 416.1756, Found: 416.1748. $^1$H NMR (400 MHz, CDCl$_3$): δ 7.05-6.98 (m, 2H), 6.91-6.85 (m, 1H), 6.65-6.62 (m, 1H), 5.51 (br, 1H), 4.40 (q, 2H, J=7.5 Hz). 4.10 (br, 2H), 3.51 (t, 2H, J=6.0 Hz), 3.32 (s, 3H), 3.30-3.00 (m, 4H), 2.79-2.72 (m, 1H), 1.79-1.66 (m, 2H), 1.38 (t, 3H, J=7.5 Hz).

Example 314

(S)-10-[3-(2-Methoxy-ethyl)-piperazin-1-yl]-2-trifluoromethyl-4H-3-thia-1,4,9-triaza-benzo[f]azulene

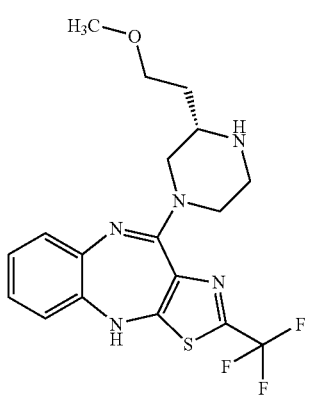

Using the method of Example 305, using 2-trifluoromethyl-4,9-dihydro-3-thia-1,4,9-triaza-benzo[f]azulene-10-thione and methyl trifluoromethanesulfonate, and 2-(S)-(2-methoxy-ethyl)-piperazine, followed by purification, eluting with a gradient of a 7% solution of 2M ammonia in methanol, in dichloromethane (0-100%), gives the title compound: mass spectrum (APCI, m/e): 412 (M+1); NMR (1H, 300 MHz, DMSO-d$_6$): δ 8.71 (br. s, 1H), 8.60 (s, 1H), 6.93 (m, 3H), 6.71 (m, 1H), 4.07 (br. m, 2H), 3.46-3.29 (m, 4H), 3.29-3.06 (m, 5H), 2.99 (m, 1H), 2.48 (m, 2H).

Example 315

(S)-10-[3-(2-Methoxy-ethyl)-piperazin-1-yl]-2-trifluoromethyl-4H-3-thia-1,4,9-triaza-benzo[f]azulene dihydrochloride

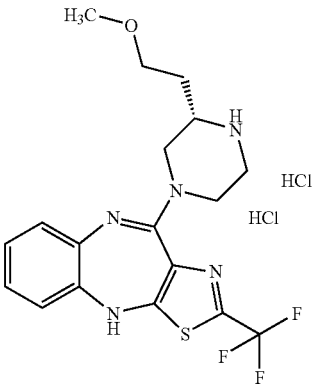

Using the method of Example 273, using (S)-10-[3-(2-methoxy-ethyl)-piperazin-1-yl]-2-trifluoromethyl-4H-3-thia-1,4,9-triaza-benzo[f]azulene and a solution of acetyl chloride in absolute ethanol at ambient temperature, reconstitution of the product in deionized water: acetone (1:1), and lyophilization gives the title compound: mass spectrum (APCI, m/e): 412 (M+1); exact mass spectrum (ES+, m/e, $C_{18}H_{20}F_3N_5OS \cdot 2HCl$): calc. 412.1419 (M+1-2HCl), found 412.1429.

Example 316

(S)-10-[3-(2-Methoxy-ethyl)-piperazin-1-yl]-2-difluoromethyl-4H-3-thia-1,49-triaza-benzo[f]azulene

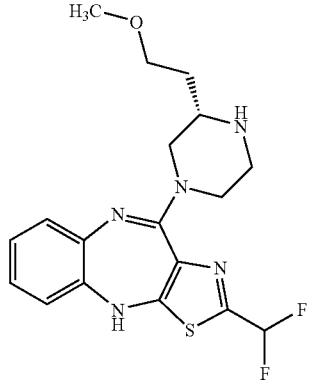

Using the method of Example 305, using 2-difluoromethyl-4,9-dihydro-3-thia-1,4,9-triaza-benzo[f]azulene-10-thione and methyl trifluoromethanesulfonate, and (S)-2-(2-methoxy-ethyl)-piperazine and 20 hours at 100° C., followed by two purifications: the first, eluting with a gradient of a 4% solution of 2M ammonia in methanol, in dichloromethane (0-100%); and the second, eluting with a gradient of solutions of 2M ammonia in methanol, in dichloromethane (2%-4%), gives the title compound: mass spectrum (APCI, m/e): 394 (M+1); NMR ($^1$H, 300 MHz, DMSO-d$_6$): δ 8.27 (s, 1H), 7.13 (t, 1H, $^2J_{(H,F)}$=54.3 Hz), 6.93-6.78 (m, 3H), 6.70 (m, 1H), 3.92 (br. m, 2H), 3.41-3.15 (m, 4H), 2.82 (m, 2H), 2.67 (m, 2H), 2.53-2.41 (m, 2H), 2.31 (br. s, 1H), 1.50 (m, 2H).

Example 317

(S)-10-[3-(2-Methoxy-ethyl)-piperazin-1-yl]-2-difluoromethyl-4H-3-thia-1,4,9-triaza-benzo[f]azulene dihydrochloride

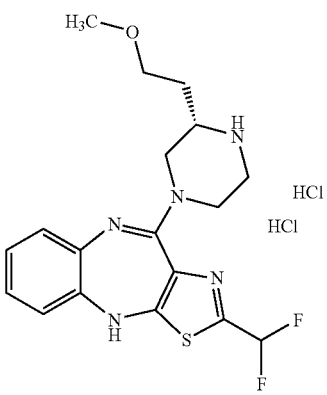

Using the method of Example 273, using (S)-10-[3-(2-methoxy-ethyl)-piperazin-1-yl]-2-difluoromethyl-4H-3-thia-1,4,9-triaza-benzo[f]azulene and a solution of acetyl chloride in absolute ethanol at ambient temperature gives the title compound: mass spectrum (APCI, m/e): 394 (M+1); exact mass spectrum (ES+, m/e, $C_{18}H_{21}F_2N_5OS \cdot 2HCl$): calc, 394.1513 (M+1-2HCl), found 394.1490.

Example 318

(S)-10-[3-(2-Methoxy-ethyl)-piperazin-1-yl]-2-(3,3,3-trifluoro-propyl)-4H-3-thia-1,4,9-triaza-benzo[f]azulene dihydrochloride

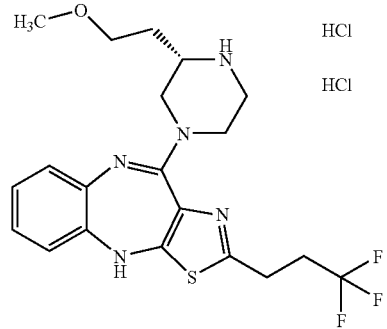

Combine 2-(3,3,3-trifluoro-propyl)-4,9-dihydro-3-thia-1,4,9-triaza-benzo[f]azulene-10-thione (1.11 g, 3.37 mmol) and 7 mL CH$_2$Cl$_2$, add methyl trifluoromethanesulfonate (0.69 g, 4.22 mmol) dropwise at 0° C., stir at 0° C. for half hour, and warm to RT. 4.5 h. Concentrate the reaction mixture under reduced pressure to give 1.58 g of orange solid. Take 1.18 g of that material (1.18 g, 2.4 mmol), mix with (S)-2-(2-methoxy-ethyl)-piperazine (0.346 g, 2.4 mmol) in 10 mL pyridine and heat to 100° C. Cool the reaction to RT after 3 hours and concentrate to a residue. Purification by flash chromatography on silica gel, using a gradient (100% CH$_2$Cl$_2$ to 100% mixed solvent of (CH$_2$Cl$_2$: 2N NH$_3$/MeOH=25:1)) over 55 min. gives 0.56 g of (S)-10-[3-(2-methoxy-ethyl)-piperazin-1-yl]-2-(3,3,3-trifluoro-propyl)-4H-3-thia-1,4,9-triaza-benzo[f]azulene, yield 53%. The dihydrochloric salt is form by adding 5 eq of acetyl chloride (156 mg, 1.99 mmol) to the free base (175 mg, 0.55 mmol) in ethanol (5 mL). Remove the solvent, dissolve in 12 mL mix solvent of CH$_3$CN/H$_2$O=50/50, lyophilize overnight to afford 186 mg of orange solid as the title compound: mass spectrum (electrospray) (m/e): C$_{20}$H$_{24}$F$_3$N$_5$OS.2HCl, Calc. Mass (M+1-2HCl): 440.1732, Found: 440.1716.

Example 319

(S)-2-[1-Methyl-4-(2-methyl-4H-3-thia-1,4,9-triaza-benzo[f]azulene-10-yl)piperazin-2-yl]ethanol dihydrochloride

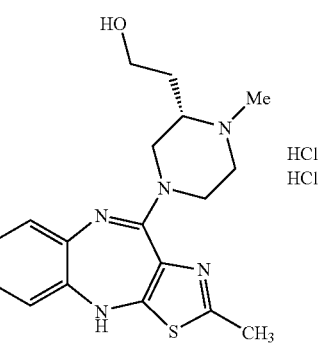

Combine material from Example 300 (0.080 g, 0.233 mmol), formaldehyde (25 μL, 0.303 mmol, 37% aqueous solution), and sodium triacetoxyborohydride (74 mg, 0.349 mmol) in dichloroethane (8 mL) and stir at room temperature overnight. Dilute the mixture with saturated aqueous sodium bicarbonate and extract three times with dichloromethane. Combine the organic layers, dry over sodium sulfate and concentrate under reduced pressure. Purify by flash chromatography, eluting with a step gradient starting with dichloromethane going to 6% 2N ammonia-methanol in dichloromethane, to obtain the free base of the title compound (0.038 g, 0.106 mmol, 46%). Isolate as the dihydrochloride salt by dissolving the free base in ethanol and adding a solution of 5 equivalents of hydrochloric acid in ethanol. Evaporating the solution and drying the salt provides the title compound as a brown solid: mass spectrum (APCI): m/z=358.3 (M+1 of free base).

Example 320

(S)-10-[3-(2-Methoxyethyl)-4-methylpiperazin-1-yl]-2-methyl-4H-3-thia-1,4,9-triazabenzo[f]azulene dihydrochloride

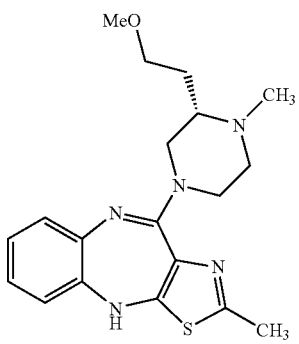

In a manner such as that described in Example 319, using (S)-10-[3-(2-methoxyethyl)-piperazin-1-yl]-2-methyl-4H-3-thia-1,4,9-triazabenzo[f]azulene to obtain the dihydrochloride salt as a yellow foam (0.125 g, 19%): Exact mass, Calc: 372.1858; Found: 372.1866.

Example 321

(S)-10-[3-(2-Ethoxyethyl)-4-methyl-piperazin-1-yl]-2-methyl-4H-3-thia-1,4,9-triazabenzo[f]azulene dihydrochloride

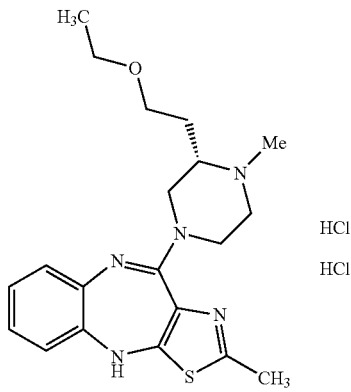

In a manner similar to that described in Example 319, using (S)-10-[3-(2-ethoxyethyl)-piperazin-1-yl]-2-methyl-4H-3-thia-1,4,9-triazabenzo[f]azulene to obtain the free base of the title compound (0.207 g, 0.537 mmol, 33%) as a yellow oil: mass spectrum (APCI): m/z=414.2 (M+1). Isolate clean product as the corresponding dihydrochloride in the manner described in Example 319. Exact Mass, Calc: 386.2015; Found: 386.2033.

Example 322

(S)-10-[3-(2-Methoxy-ethyl)-4-methyl-piperazin-1-yl]-2-ethyl-4H-3-thia-1,49-triaza-benzo[f]azulene dihydrochloride

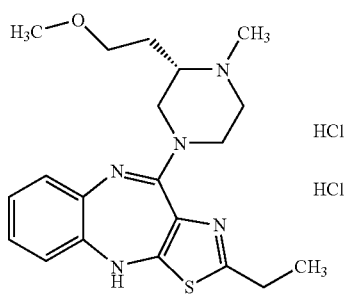

Combine (S)-10-[3-(2-methoxy-ethyl)-piperazin-1-yl]-2-ethyl-4H-3-thia-1,4,9-triaza-benzo[f]azulene (180 mg, 0.48 mmol), formaldehyde (37%, w/w, aq) (49 mg, 0.6 mmol) and sodium triacetoxyborohydride (152.6 mg, 0.72 mmol) in 5 mL 1,2-dichloroethane and stir at RT. After 18 h, quench the reaction by adding water, extract with $CH_2Cl_2$, and dry the combined organic solvents over $Na_2SO_4$. Purification by flash chromatography on silica gel using a gradient (100% $CH_2Cl_2$ to 100% mixed solvent of ($CH_2Cl_2$: 2N $NH_3$/MeOH=15:1) over 55 min) gives 85 mg light brown foam of the free base: $^1$H NMR (300 MHz, $CDCl_3$): δ 6.98-6.89 (m, 2H), 6.82-6.77 (m, 1H), 6.56-6.53 (m, 1H), 4.99 (s, 1H), 4.00 (br, 2H), 3.38 (t, 2H, J=6.9 Hz), 3.26 (s, 3H), 3.20-3.12 (m, 1H), 2.89-2.75 (m, 4H), 2.42-2.31 (m, 2H), 2.28 (s, 3H), 1.92-1.83 (m,1H), 1.69-1.60 (m, 1H), 1.23 (t, 3H, J=7.2 Hz). The dihydrochloride salt is form by adding 4 eq of acetyl chloride (69.3 mg, 0.88 mmol) to the free base (85 mg, 0.22 mmol) in ethanol (5 mL). Remove the solvent, dissolve the residue in 15 ml mix solvent of $CH_3CN/H_2O$=50/50 and lyophilize overnight to afford 90 mg of orange solid of the title compound: mass spectrum (electrospray) (m/e): $C_{20}H_{27}N_5OS.2HCl$, Calc. Mass (M+1-2HCl): 386.2028, Found: 386.2015.

Example 323

(S)-10-[3-(2-Methoxy-ethyl)-4-methyl-piperazin-1-yl]-2-propyl 4H-3-thia-1,4,9-triaza-benzo[f]azulene dihydrochloride

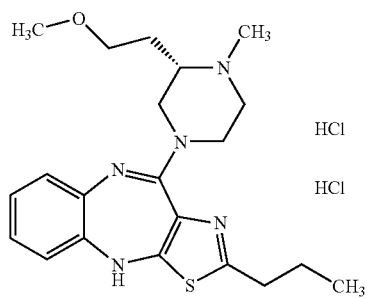

Using method of Example 322, using (S)-10-[3-(2-methoxy-ethyl)-piperazin-1-yl]-2-propyl-4H-3-thia-1,4,9-triaza-benzo[f]azulene (390 mg, 1.01 mmol), formaldehyde (37%, w/w, aq) (102.2 mg, 1.26 mmol) and sodium triacetoxyborohydride (321.0 mg, 1.55 mmol) gives 200 mg yellow foam, (S)-10-[3-(2-methoxy-ethyl)$_4$-methyl-piperazin-1-yl]-2-propyl-4H-3-thia-1,4,9-triaza-benzo[f]azulene: mass spectrum (electrospray) (m/e): 399.9 (M+1), 398.1 (M-1); $^1$H NMR (400 MHz, DMSO-$d_6$): 7.04-6.97 (m, 2H), 6.89-6.85 (m, 1H), 6.63-6.61 (m, 1H), 5.29 (s, 1H), 4.10 (br, 1H), 3.45 (m, 2H), 3.31 (s, 3H), 3.26-3.23 (m, 1H), 3.01-2.77 (m, 4H), 2.49-2.43 (m, 1H), 2.36 (s, 3H), 2.02-1.93 (m, 1H), 1.77-1.60 (m, 5H), 0.99 (t, 3H, J=6.8 Hz). The dihydrochloride salt is form by adding 4 eq of acetyl chloride (157 mg, 2.0 mmol) to the free base (200 mg, 0.50 mmol) in ethanol (8.0 mL). Remove the solvent, dissolve the residue in 15 ml mix solvent of $CH_3CN/H_2O$=50/50 and lyophilize overnight to afford 213 mg the title compound: mass spectrum (electrospray) (m/e): $C_{21}H_{29}N_5OS.2HCl$, Calc. Mass (M+1-2HCl): 400.2171, Found: 400.2191.

Example 324

(S)-10-[3-(2-Methoxy-ethyl)-4-methyl-piperazin-1-yl]-2-butyl 4H-3-thia-1,4,9-triaza-benzo[f]azulene

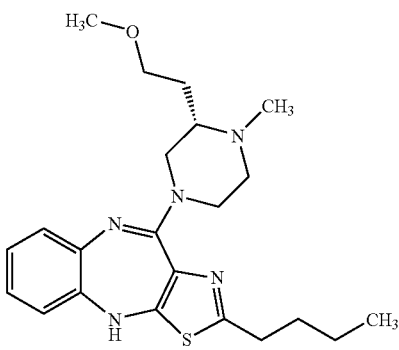

Using the method of Example 272, using (S)-10-[3-(2-methoxy-ethyl)-piperazin-1-yl]-2-butyl-4H-3-thia-1,4,9-triaza-benzo[f]azulene and 2 hours at ambient temperature, and employing a saturated aqueous sodium chloride wash of the organics after the saturated aqueous sodium bicarbonate wash gives the title compound: mass spectrum (APCI, m/e): 414 (M+1); NMR (1H, 300 MHz, $CDCl_3$): δ 7.00 (m, 2H), 6.87 (dt, 1H, $J_o$=7.2 Hz, $J_m$=1.5 Hz), 6.62 (dd, 1H, $J_o$=7.8 Hz, $J_m$=0.9 Hz), 5.00 (s, 11H), 4.05 (br. m, 2H), 3.45 (br. m, 2H), 3.32 (s, 3H), 3.23 (m, 1H), 2.94 (m, 1H), 2.82 (m, 3H), 2.45 (m, 1H), 2.35 (m, 4H), 1.95 (m, 1H), 1.69 (m, 3H), 1.39 (m, 2H), 0.93 (t, 3H, J=7.5 Hz).

Example 325

(S)-10-[3-(2-Methoxy-ethyl)-4-methyl-piperazin-1-yl]-2-butyl-4H-3-thia-1,4,9-triaza-benzo[f]azulene dihydrochloride

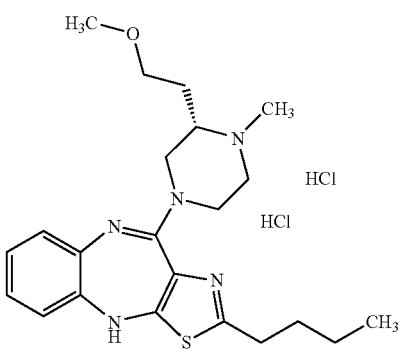

Using the method of Example 273, using (S)-10-[3-(2-methoxy-ethyl)-4-methyl-piperazin-1-yl]- -butyl-4H-3-thia-1,4,9-triaza-benzo[f]azulene in absolute ethanol, with added drops of methanol to solubilize the freebase, and a solution of acetyl chloride in absolute ethanol at ambient temperature gives the title compound: mass spectrum (APCI, m/e): 414 (M+1); exact mass spectrum (ES+, m/e, $C_{22}H_{31}N_5OS \cdot 2HCl$): calc. 414.2328 (M+1-2HCl), found 414.2350.

Example 326

(S)-2-[4-(2-Isopropyl-4H-3-thia-1,49-triazabenzo[f]azulene-10-yl)-1-methylpiperazin-2-yl]ethanol

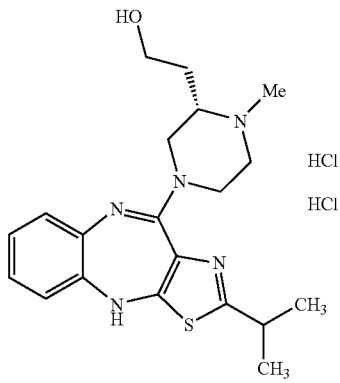

Combine 2-[4-(2-Isopropyl-4H-3-thia-1,4,9-triaza-benzo[f]azulen-10-yl)-piperazin-2-yl]-ethanol (0.161 g, 0.433 mmol), formaldehyde (46 μL, 0.563 mmol, 37%), and sodium triacetoxyborohydride (0.138 g, 0.650 mmol) in dichloroethane (15 mL) and stir at room temperature overnight. Dilute the mixture with saturated sodium bicarbonate and extract three times with methylene chloride. Combine the organic layers, dry over sodium sulfate and concentrate under reduced pressure to give the crude product. Purification by flash chromatography, eluting with a step gradient starting with dichloromethane going to 8% 2N ammonia-methanol in dichloromethane gives (S)-2-[4(2-isopropyl-4H-3-thia-1,4,9-triazabenzo[f]azulen-10-yl)-1-methylpiperazin-2-yl]ethanol (0.059 g, 0.153 mmol, 35%) as a yellow oil. Mass spectrum (APCI): m/z=386.4 (M+1). Isolate clean product as the corresponding dihydrochloride in the following manner: dissolve the yellow oil in ethanol (5 mL) and add a solution of about 5 equivalents of HCl in ethanol (5 mL). Evaporate the mixture to obtain (S)-2-[4-(2-isopropyl-4H-3-thia-1,4,9-triazabenzo[f]azulen-10-yl)-1-methylpiperazin-2-yl]ethanol dihydrochloride.

Example 327

(S)-10-[3-(2-Methoxyethyl)-4-methylpiperazin-1-yl]-2-isopropyl-4H-3-thia-1,4,9-triazabenzo[f]azulene dihydrochloride

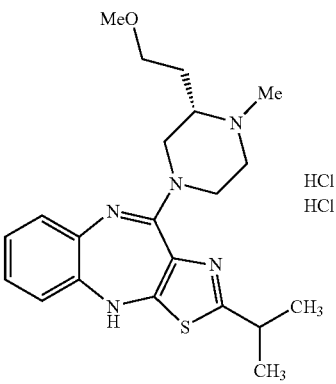

Combine (S)-10-[3-(2-methoxy-ethyl)-piperazin-1-yl]-2-isopropyl-4H-3-thia-1,4,9-triaza-benzo[f]azulene (0.181 g, 0.469 mmol), formaldehyde (50 μL, 0.610 mmol, 37%), and sodium triacetoxyborohydride (0.149 g, 0.704 mmol) in dichloroethane (12 mL) and stir at room temperature for 2 hours. Dilute the mixture with saturated sodium bicarbonate and extract three times with methylene chloride. Combine the organic layers, dry over sodium sulfate and concentrate under reduced pressure to give the crude product. Purification by flash chromatography, eluting with a step gradient starting with dichloromethane going to 5% 2N ammonia-methanol in dichloromethane gives (S)-10-[3-(2-methoxy-ethyl)-4-methyl-piperazin-1-yl]-2 isopropyl-4H-3-thia-1,4,9-triaza-benzo[f]azulene (0.168 g, 0.420 mmol, 90%) as a yellow oil: mass spectrum (APCI): m/z=400.3 (M+1). Isolate clean product as the corresponding dihydrochloride in the following manner: dissolve the yellow foam in ethanol (5 mL) and add a solution of about 5 equivalents of HCl in ethanol (5 mL). Evaporate the mixture to obtain the title compound as a brown foam. Exact Mass, Calc: 400.2171; Found: 400.2171.

Example 327a

(S)-10-[3-(2-Methoxyethyl)-4-methylpiperazin-1-yl]-2-isopropyl-4H-3-thia-1,4,9-triazabenzo[f]azulene dihydrochloride

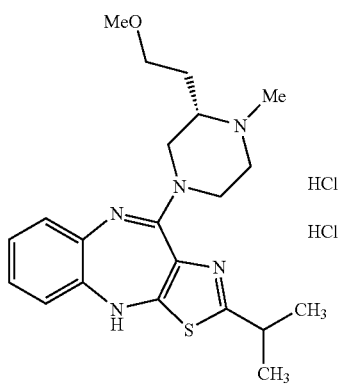

In the manner already described in Example 327, convert (S)-10-[3-(2-methoxyethyl)piperazin-1-yl]-2-isopropyl-4H-3-thia-1,4,9-triazabenzo[f]azulene (1.44 g, 3.73 mmoles) into (S)-10-[3-(2-methoxyethyl)-4-methylpiperazin-1-yl]-2-isopropyl-4H-3-thia-1,4,9-triazabenzo[f]azulene (1.22 g, 82%). Follow standard methods to isolate as the title hydrochloride (1.43 g, 100%). Exact Mass, Calc: 400.2171; Found: 400.2171.

Example 327b

(S)-10-[3-(2-Methoxyethyl)-4-methylpiperazin-1-yl]-2-isopropyl-4H-3-thia-1,4,9-triazabenzo[f]azulene

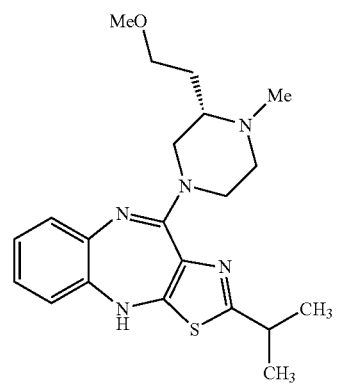

Equip a 1 L 3-necked round bottom flask with an overhead air stirrer apparatus, addition funnel, septum, thermometer lead and cooling bath. Charge the flask with convert (S)-10-[3-(2-methoxyethyl)piperazin-1-yl]-2-isopropyl-4H-3-thia-1,4,9-triazabenzo[f]azulene (50.0 g, 0.129 mol) and DCE (500 mL, 10 vols). Allow the resulting mixture to stir at ambient temperature for 20 minutes and to allow all solids to dissolve. Charge 37% aqueous formalin (9.7 mL, 0.129 mol, 1.0 eq.) to the addition funnel and add drop-wise to the above mixture over 4 minutes. Add sodium triacetoxy borohydride (31.6 g, 0.149 mol, 1.15 eq.) in portions over 10 minutes, keeping the pot temperature below 25° C. Stir the reaction mixture overnight at ambient temperature. Quench after 21 hours, a small sample (4 drops) of the reaction mixture into 0.4 mL of saturated $NaHCO_3$. Dilute the sample with 0.25 mL EtOAC, shake and allow to separate. Analysis of a sample of the organic phase by TLC (100% acetone+2.5% v/v 2M $NH_3$ in MeOH, UV) indicates no starting material remained. Quench the reaction mixture with saturated $NaHCO_3$ (500 mL) and stir at ambient temperature for 20 minutes. After transfer to a separatory funnel and layer separation, extract the aqueous layer with methylene chloride (500 mL). Combine the organic phases and wash with saturated $NaHCO_3$ (2×500 mL), and deionized water (500 mL). Dry the solution over $Na_2SO_4$ (50 g) in the presence of Darco (1 T), and filter across a pad of Hi-Flo topped with a ⅛" layer of Kieselgel-60 silica. Concentrate the filtrate in vacuo to afford 58.6 grams of orange-yellow oil (theory 51.82 g). Treat the crude, overweight oil with ligroin (500 mL) and EtOAc (50 mL) and allow to stir at ambient temperature for 6 hours. Filter the resulting solids, rinse with ligroin (2×150 mL), and dry by vacuum to afford 43.6 grams of the free base as a pale yellow solid (84.2%): $^1$H NMR (500 MHz, DMSO-$d_6$): δ 124 (d, 6H), 1.50-1.59 (m, 1H), 1.75-1.84 (m, 1H), 2.12-2.24 (m, 2H), 2.20 (s, 3H), 2.71-2.77 9 m, 1H), 2.79-2.82 (m, 1H), 3.02-3.10 (m, 2H), 3.19 (s, 3H), 3.27-3.32 (m, 2H), 3.80-3.92 (bm, 2H), 6.67 (m, 1H), 6.77-6.81 (m, 2H), 6.84-6.87 (m, 1H), 7.82 (s, 1H). Crystallization of Free Base: Equip a 750 mL 3-necked Euro-flask with a magnetic stir bar, condenser, heating mantle, and septum with thermometer lead. Charge the flask with the re-slurried, amorphous (S)-10-[3-(2-methoxyethyl)-4-methylpiperazinyl]-2-isopropyl-4H-3-thia-1,4,9-triazabenzo[f]azulene (30.0 g, 0.075 mol), heptane (300 mL, 10 vols.), and toluene (60 mL, 2 vols.). Allow the resulting mixture to stir at ambient temperature for 10 minutes, and heat to reflux (99.8° C.). Dissolve all solids were by the time the pot temperature reaches 97.1° C. Reflux the clear yellow solution for 5 minutes. Shut the heat source while keeping the mantle in place, thus allowing the pot temperature to drift slowly downward. Slow stirring to a minimum. Observe at 70.1° C., the first signs of haziness in the mixture. Formation at a pot temperature of 69.3° C. of solids. Allow the mixture to cool to a temperature of 25.7° C. over 3.25 hours. Remove the heating mantle and stir the mixture for an additional 50 minutes while reaching a final temperature of 22.1° C. Vacuum filter the material onto a sintered glass funnel and rinse the solids with ligroin (2×100 mL). Pull dry on the funnel for 15 minutes, transfer the filter cake to a tared glass dish and further dry under vacuum at 30° C. Recover 27.9 grams of yellow solids (92.9%). $^1$H NMR (500 MHz, DMSO-$d_6$): δ 124 (d, 6H), 1.50-1.59 (m, 1H), 1.75-1.84 (m, 1H), 2.12-2.24 (m, 2H), 2.20 (s, 3H), 2.71-2.77 9 m, 1H), 2.79-2.82 (m, 1H), 3.02-3.10 (m, 2H), 3.19 (s, 3H), 3.27-3.32 (m, 2H), 3.80-3.92 (bm, 2H), 6.67 (m, 1H), 6.77-6.81 (m, 2H), 6.84-6.87 (m, 1H), 7.82 (s, 1H). A small sample of the material was observed under a microscope and found to exhibit birefringence. Alternately, diffuse amorphous (S)-10-[3-(2-methoxyethyl)-4-methylpiperazinyl]-2-isopropyl-4H-3-thia-1,4,9-triazabenzo[f]azulene (65 ng) in n-pentane (200 uL) into amorphous (S)-10-[3-(2-methoxyethyl)-4-methylpiperazinyl]-2-isopropyl-4H-3-thia-1,4,9-triazabenzo[f]azulene (65 mg) in ethyl acetate (210 uL). Crystals form and isolate.

Example 328

(S)-10-[3-(2-Ethoxyethyl)-4-methylpiperazin-1-yl]-2-isopropyl-4H-3-thia-1,4,9-triazabenzo[f]azulene dihydrochloride

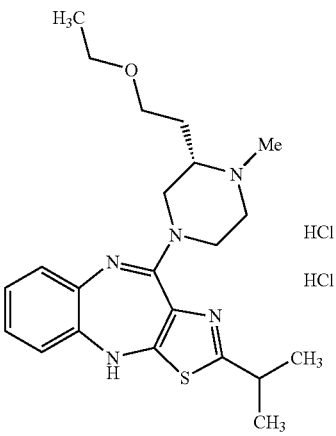

In a manner similar to that described in Example 319, using (S)-10-[3-(2-ethoxyethyl)-piperazin-1-yl]-2-isopropyl-4H-3-thia-1,4,9-triazabenzo[f]azulene to obtain the title hydrochloride (0.215 g, 0.491 mmol, 34%) as an orange solid: Exact Mass, Calc: 414.2328; Found: 414.2341.

Example 329

(S)-10-[3-(3-Methoxy-propyl)-4-methyl-piperazin-1-yl]-2-isopropyl-4H-3-thia-1,4,9-triaza-benzo[f]azulene

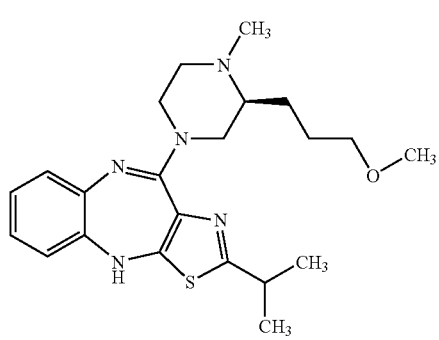

Using the method of Example 222 to give the title compound: mass spectrum (m/e):414.08 (M+1).

Example 330

(S)-10-[3-(3-Methoxy-propyl)-4-methyl-piperazin-1-yl]-2-isopropyl 4H-3-thia-1,4,9-triaza-benzo[f]azulene hydrochloride

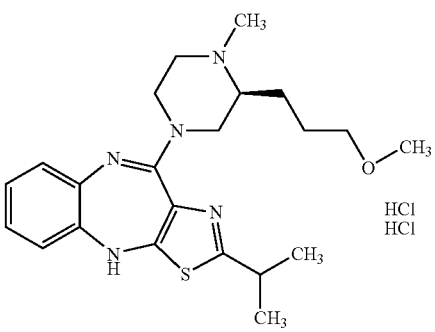

Using the method of Example 223 to give the title compound: mass spectrum (m/e):414.08 (M+1).

Example 331

(S)-10-[3-(2-Methoxyethyl)-4-methylpiperazin-1-yl]-2-cyclopentyl 4H-3-thia-1,4,9-triazabenzo[f]azulene dihydrochloride

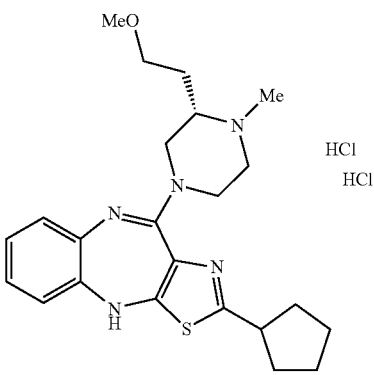

Combine (S)-10-[3-(2-methoxyethyl)-piperazin-1-yl]-2-cyclopentyl-4H-3-thia-1,4,9-triazabenzo[f]azulene (0.364 g, 0.884 mmol), formaldehyde (93 μL, 1.15 mmol, 37%), and sodium triacetoxyborohydride (0.281 g, 1.33 mmol) in dichloroethane (15 mL) and stir at room temperature for 4 hours. Dilute the mixture with saturated aqueous sodium bicarbonate and extract three times with dichloromethane. Combine the organic layers, dry over sodium sulfate and concentrate under reduced pressure to give a solid residue. Purify by flash chromatography, eluting with a step gradient starting with dichloromethane going to 6% 2N ammonia-methanol in dichloromethane, to obtain the free base of the title compound (0.342 g; 0.804 mmol, 91%) as a yellow oil: mass spectrum (APCI): m/z=386.4 (M+1). Isolate the clean product as the corresponding dihydrochloride in the following manner: dissolve the yellow foam in ethanol (5 mL) and add a solution of about 5 equivalents of hydrochloric acid in ethanol (5 mL); then remove the solvent under vacuum: Exact Mass, Calc: 426.2328; Found: 426.2329.

Example 332

(S)-10-[3-(2-Methoxy-ethyl)-4-methyl-piperazin-1-yl]-4H-3-thia-1,4,9-triaza-benzo[f]azulene-2-yl-methanol dihydrochloride

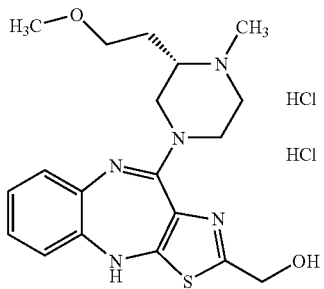

Using the method of Example 322, using (S)-10-[3-(2-methoxy-ethyl)-piperazin-1-yl]-4H-3-thia-1,4,9-triaza-benzo[f]azulene-2-yl-methanol (210 mg, 0.564 mmol), formaldehyde (37% aq. w/w) (57.2 mg, 0.706 mmol) and sodium triacetoxyborohydride (179.2 mg, 0.846 mmol) gives 150 mg yellow solid of the free base: mass spectrum (electrospray) (m/e): 388.0 (M+1), 386.1 (M−1); $^1$H NMR (400 MHz, DMSO-$d_6$): 7.83 (s, 1H), 6.86-6.75 (m, 3H), 6.69-6.66 (m, 1H), 5.90 (t, 1H, J=6.0 Hz), 4.51 (d, 2H, J=6.0 Hz), 3.83 (m, 2H), 3.33-3.31 (m, 2H), 3.29 (s, 3H), 3.06 (t, 1H, J=10.4 Hz), 2.81-2.68 (m, 2H), 2.18 (s, 3H), 2.19-2.11 (m, 2H), 1.81-1.75 (m, 1H), 1.54-1.48 (m, 1H). The dihydrochloride salt is form by adding 5 eq of acetyl chloride (49.5 mg, 1.90 mmol) to the free base (147 mg, 0.38 mmol) in ethanol (5.0 mL). Remove the solvent, dissolve the residue in 15 ml mix solvent of CH$_3$CN/H$_2$O=50/50 and lyophilize overnight to afford 170 mg of (S)-10-[3-(2-methoxy-ethyl)-4-methyl-piperazin-1-yl]A4H-3-thia-1,4,9-triaza-benzo[f]azulene-2-yl-methanol dihydrochloride: mass spectrum (electrospray) (m/e): C$_{19}$H$_{25}$N$_5$O$_2$S.2HCl, Calc. Mass (M+1-2HCl): 388.1807, Found: 388.1794.

Example 333

(S)-10-[3-(2-Methoxy-ethyl)-4-methyl-piperazin-1-yl]-4H-3-thia-1,4,9-triaza-benzo[f]azulene-2-carboxylic acid ethyl ester dihydrochloride

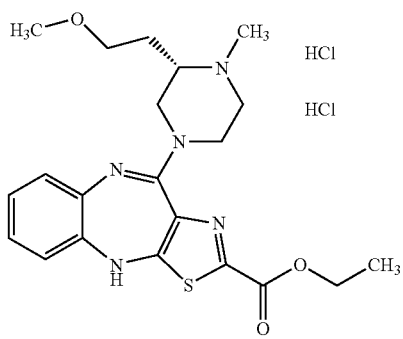

Using the method of Example 322, using (S)-10-[3-(2-methoxy-ethyl)-piperazin-1-yl]-4H-3-thia-1,4,9-triaza-benzo[f]azulene-2-carboxylic acid ethyl ester (300 mg, 0.72 mmol), formaldehyde (37%, w/w, aq) (72.9 mg, 0.90 mmol) and sodium triacetoxyborohydride (228.9 mg, 1.08 mmol) gives 280 mg (yield 90%) of (5)-10-[3-(2-methoxy-ethyl)-4-methyl-piperazin-1-yl]-4H-3-thia-1,4,9-triaza-benzo[f]azulene-2-carboxylic acid ethyl ester: mass spectrum (electrospray) (m/e): 430.0 (M+1), 428.1 (M−1); $^1$H NMR (400 MHz, DMSO-$d_6$): 8.50 (s, 1H), 6.91-6.80 (m, 3H), 6.69-6.67 (m, 1H), 4.30 (q, 2H, J=6.8 Hz), 3.83-3.81 (m, 2H), 3.32-3.30 (m, 2H), 3.13 (s, 3H), 3.12-3.06 (m, 1H), 2.81-2.70 (m, 2H), 2.22-2.13 (m, 5H), 1.83-1.75 (m, 1H), 1.53-1.46 (m,1H), 1.27 (t, 3H, J=7.2 Hz). The dihydrochloride is form by adding 5 eq of acetyl chloride (256.2 mg, 3.26 mmol) to the free base (280 mg, 0.65 mmol) in ethanol. Collect the precipitates via vacuum filtration to afford 300 mg of yellow solid of the title compound: mass spectrum (electrospray) (m/e): C$_{21}$H$_{27}$N$_5$O$_3$S.2HCl, Calc. Mass (M+1): 430.1913, Found: 430.1890.

Example 334

(S)-10-[3-(2-Methoxy-ethyl)-4-methyl-piperazin-1-yl]-2-trifluoromethyl-4H-3-thia-1,4,9-triaza-benzo[f]azulene

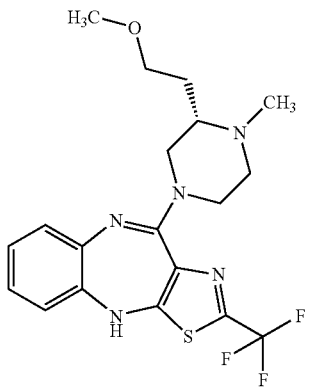

Using the method of Example 272, using (S)-10-[3-(2-methoxy-ethyl)-piperazin-1-yl]-2-trifluoromethyl-4H-3-thia-1,4,9-triaza-benzo[f]azulene and 6.75 hours at ambient temperature, and employing a saturated aqueous sodium chloride wash of the organics after the saturated aqueous sodium bicarbonate wash gives the title compound. Mass spectrum (APCI, m/e): 426 (M+1); NMR ($^1$H, 300 MHz, DMSO-$d_6$): δ 8.47 (s, 1H), 6.97-6.82 (m, 3H), 6.71 (m, 1H), 3.79 (br. m, 2H), 3.36-3.24 (m, 2H), 3.15 (s, 3H), 3.09 (m, 1H), 2.85-2.69 (m, 2H), 2.28-2.08 (m, 5H), 1.65 (m, 2H).

Example 335

(S)-10-[3-(2-Methoxy-ethyl)-4-methyl-piperazin-1-yl]-2-trifluoromethyl-4H-3-thia-1,4,9-triaza-benzo[f]azulene dihydrochloride

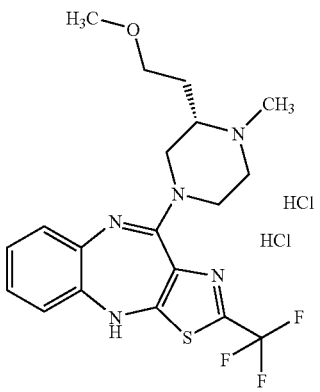

Using the method of Example 273, using (S)-10-[3-(2-methoxy-ethyl)-4-methyl-piperazin-1-yl]-2-trifluoromethyl-4H-3-thia-1,4,9-triaza-benzo[f]azulene and a solution of acetyl chloride in absolute ethanol at ambient temperature, reconstitution of the product in deionized water: acetone (1:1), and lyophilization gives the title compound: mass spectrum (APCI, m/e): 426 (M+1); exact mass spectrum (ES+, m/e, $C_{19}H_{22}F_3N_5OS\cdot2HCl$): calc. 426.1575 (M+1-2HCl), found 426.1565.

Example 336

(S)-10-[3-(2-Methoxy-ethyl)-4-methyl-piperazin-1-yl]-2-difluoromethyl 4H-3-thia-1,4,9-triaza-benzo[f]azulene

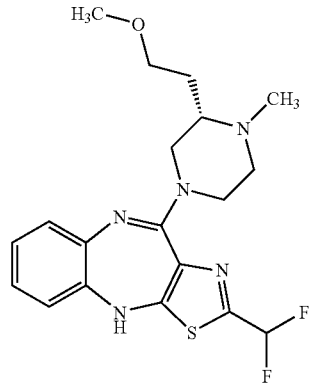

Using the method of Example 272, using (S)--10-[3-(2-methoxy-ethyl)-piperazin-1-yl]-2-difluoromethyl 4H-3-thia-1,4,9-triaza-benzo[f]azulene and 24 hours at ambient temperature, and purification by flash chromatography, eluting with a gradient of solutions of 2M ammonia in methanol, in dichloromethane (2%-6%) gives the title compound: mass spectrum (APCI, m/e): 408 (M+1); NMR ($^1$H, 300 MHz, DMSO-$d_6$): δ 8.29 (s, 1H), 7.13 (t, 1H, F=54.3 Hz), 6.97-6.79 (m, 3H), 6.70 (m, 1H), 3.80 (br. m, 2H), 3.40-3.22 (m, 1H), 3.22-3.02 (m, 5H), 2.77 (m, 2H), 2.27-2.08 (m, 5H), 1.65 (m, 2H).

Example 337

(S)-10-[3-(2-Methoxy-ethyl)-4-methyl-piperazin-1-yl]-2-difluoromethyl 4H-3-thia-1,4,9-triaza-benzo[f]azulene dihydrochloride

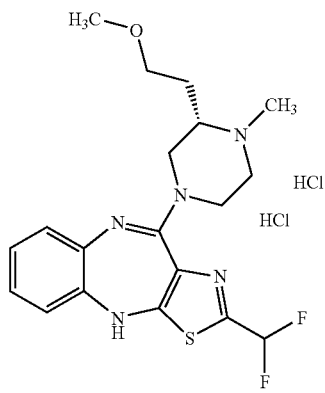

Using the method of Example 273, using (S)-10-[3-(2-methoxy-ethyl)-4-methyl-piperazin-1-yl]-2-difluoromethyl-4H-3-thia-1,4,9-triaza-benzo[f]azulene and a solution of acetyl chloride in absolute ethanol at ambient temperature gives the title compound: mass spectrum (APCI, m/e): 408 (M+1); exact mass spectrum (ES+, m/e, $C_{19}H_{23}F_2N_5OS\cdot2HCl$): calc. 408.1670 (M+1-2HCl), found 408.1652.

Example 338

(S)-10-[3-(2-Methoxy-ethyl)-4-methyl-piperazin-1-yl]-2-(3,3,3-trifluoro-propyl)-4H-3-thia-1,4,9-triaza-benzo[f]azulene dihydrochloride

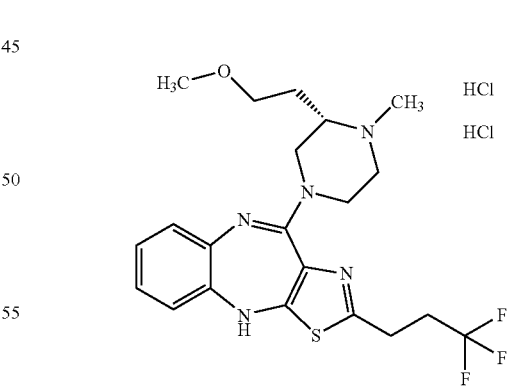

Using the method of Example 322, using (S)-10-[3-(2-methoxy-ethyl)-piperazin-1-yl]-2-(3,3,3-trifluoro-propyl)-4H-3-thia-1,4,9-triaza-benzo[f]azulene (385 mg, 0.876 mmol), formaldehyde (37% aq, w/w) (88.8 mg, 1.09 mmol) and sodium triacetoxyborohydride (278.0 mg, 1.31 mmol) gives 203 mg foam of the free base: $^1$H NMR (300 MHz, CDCl$_3$): δ 7.05-6.84 (m, 3H), 6.62-6.59 (m, 1H), 5.24 (s, 1H), 4.02 (br, m, 2H), 3.44 (t, 2H, J=6.9 Hz), 3.31 (s, 3H), 3.26-3.03 (m, 1H), 2.97-2.81 (m, 4H), 2.65-2.37 (m, 4H), 2.34 (s, 3H), 1.97-1.92 (m, 1H), 1.73-1.66 (m, 1H). The dihydrochloride salt is form by adding 5 eq of acetyl chloride (173 mg, 2.2 mmol) to the free base (200 mg, 0.44 mmol) in ethanol (10.0 mL). Remove the solvent, dissolve the residue in 15 ml mix solvent of $CH_3CN/H_2O=50/50$, and lyophilize overnight to afford 224 mg of the title compound: mass spectrum (electrospray) (m/e): $C_{21}H_{26}F_3N_5OS \cdot 2HCl$, Calc. Mass (M+1-2HCl): 454.1888, Found: 454.1871.

Example 339

(S)-10-[4-Cyclopropyl-3-(2-methoxyethyl)piperazin-1-yl]-2-isopropyl-4H-3-thia-1,4,9-triazabenzo[f]azulene dihydrochloride

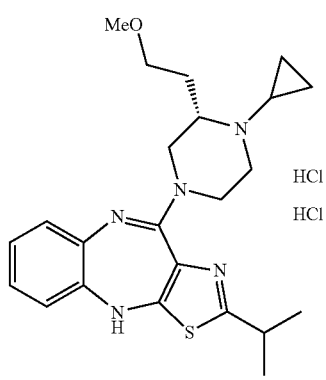

Combine (S)-10-[3-(2-methoxyethyl)piperazin-1-yl]-2-isopropyl-4H-3-thia-1,4,9-triazabenzo[f]azulene (0.100 g, 0.259 mmol) with commercial (1-ethoxycyclopropoxy)trimethylsilane (261 µL, 1.3 mmol), sodium cyanoborohydride (0.065 g, 1.04 mmol), and acetic acid (0.148 mL, 2.59 mmol) in methanol (3 mL) and heat at reflux for 2 hours. Evaporate the mixture; then dilute the residue with saturated aqueous sodium bicarbonate and extract three times with dichloromethane. Combine the organic layers, dry over sodium sulfate and concentrate under reduced pressure to give the crude product. Purification by flash chromatography, eluting with a step gradient starting with dichloromethane going to 5% 2N ammonia-methanol in dichloromethane, gives the free base of the title compound (0.045 g, 41%) as a yellow oil. Mass spectrum (APCI): m/z=426.2 (M+1). Isolate clean product as the corresponding dihydrochloride in the manner described in Example 319. Exact Mass, Calc: 426.2328; Found: 426.2346.

Example 340

(S)-10-[4-Ethyl-3-(2-methoxyethyl)piperazin-1-yl]-2-isopropyl-4H-3-thia-1,4,9-triazabenzo[f]azulene dihydrochloride

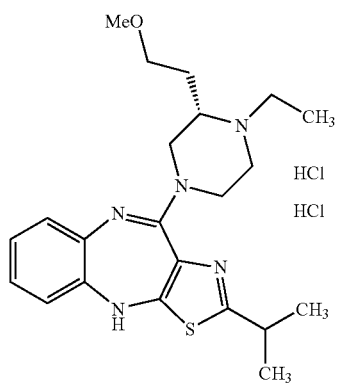

Combine (S)-10-[3-(2-methoxyethyl)piperazin-1-yl]-2-isopropyl 4H-3-thia-1,4,9-triazabenzo[f]azulene (0.103 g, 0.267 mmol), acetaldehyde (30 µL, 0.534 mmol), and sodium triacetoxyborohydride (0.085 g, 0.401 mmol) in dichloroethane (7 mL) and stir, at room temperature for 6 hours. Dilute the mixture with saturated aqueous sodium bicarbonate and extract three times with dichloromethane. Combine the organic layers, dry over sodium sulfate and concentrate under reduced pressure to give the crude product. Purification by flash chromatography, eluting with a step gradient starting with dichloromethane going to 5% 2N ammonia-methanol in dichloromethane, gives the free base of the title compound (0.79 g, 71%) as a yellow foam: mass spectrum (APCI): m/z=414.2 (M+1). Isolate clean product as the corresponding dihydrochloride in the manner described in Example 319. Exact Mass, Calc: 414.2328; Found: 414.2326.

Example 341

(S)-10-[3-(2-Methoxyethyl)-4-propylpiperazin-1-yl]-2-isopropyl-4H-3-thia-1,4,9-triazabenzo[f]azulene dihydrochloride

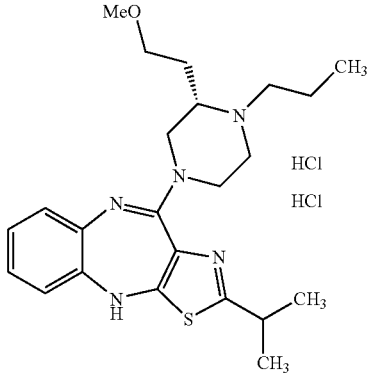

In a manner similar to that described in example 340 but using propionaldehyde, convert (S)-10-[3-(2-methoxyethyl)piperazin-1-yl]-2-isopropyl 4H-3-thia-1,4,9-triazabenzo[f]

azulene (0.295 g, 0.765 mmol) into the free base of the title compound (0.208 g, 64%): mass spectrum (APCI): m/z=428.2 (M+1). Isolate clean product as the corresponding dihydrochloride in the manner described in Example 319.

Example 342

(S)-2-[4-(2-Isopropyl-4H-3-thia-1,4,9-triazabenzo[f]azulene-10-yl)-2-(2-methoxyethyl)piperazin-1-yl]ethanol dihydrochloride

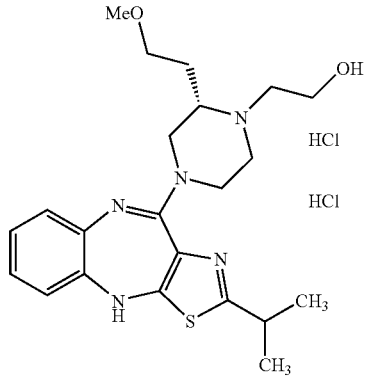

Combine (S)-10-[3-(2-methoxyethyl)piperazin-1-yl]-2-isopropyl-4H-3-thia-4,9-diazabenzo[f]azulene (0.0972 g, 0.252 mmol), potassium carbonate (0.348 g, 2.52 mmol), potassium iodide (0.209 g, 1.26 mmol) and 2-bromoethanol (72 µL, 1.08 mmol) in acetonitrile (5 mL) and heat at reflux for 7 hours. Evaporate the mixture. Purification by silica gel chromatography, eluting with a gradient starting with dichloromethane going to 5% 2N ammonia-methanol in dichloromethane gives the free base of the title compound (0.042 g, 39%) as a yellow foam: mass spectrum (APCI): m/z=430.2 (M+1). Isolate clean product as the corresponding dihydrochloride in the manner described in Example 319. Exact Mass, Calc: 430.2277; Found: 430.2277.

Example 343

(S)-10-[3,4-Bis(2-methoxyethyl)piperazin-11-yl]-2-isopropyl-4H-3-thia-1,4,9-triazabenzo[f]azulene dihydrochloride

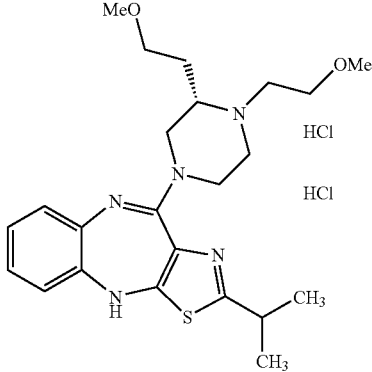

In a manner similar to that described in Example 340 but using methoxyacetaldehyde, convert (S)-10-[3-(2-methoxyethyl)piperazin-1-yl]-2-isopropyl-4H-3-thia-1,4,9-triazabenzo[f]azulene (0.331 g, 0.859 mmol) into the free base of the title compound (0.266 g, 70%):. mass spectrum (APCI): m/z=444.2 (M+1). Isolate clean product as the corresponding dihydrochloride in the manner described in Example 319: Exact Mass, Calc: 444.2433; Found: 444.2414.

Example 344

(S)-10-[4-Ethyl-3-(2-methoxy-ethyl)-piperazin-1-yl]-2-trifluoromethyl-4H-3-thia-1,4,9-triaza-benzo[f]azulene

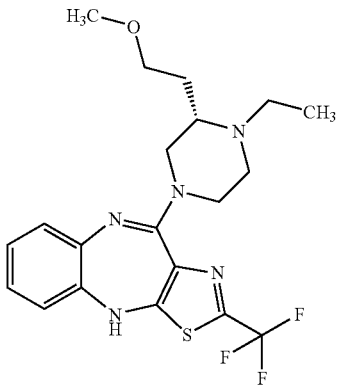

Using the method of Example 346 using (5)-10-[3-(2-methoxy-ethyl)-piperazin-1-yl]-2-trifluoromethyl-4H-3-thia-1,4,9-triaza-benzo[f]azulene and acetaldehyde at ambient temperature, and purification by flash chromatography, eluting with a gradient of a 5% solution of 2M ammonia in methanol, in dichloromethane, (0-50% over 25 minutes, 50% for 10 minutes, 50-100% over 23 minutes, 100% for 5 minutes) gives the title compound: mass spectrum (APCI, m/e): 440 (M+1); NMR ($^1$H, 300 MHz, DMSO-$d_6$), δ (ppm): δ 8.47 (s, 1H), 6.96-6.81 (m, 3H), 6.71 (m, 1H), 3.50 (br. m, 3H), 3.35-3.21 (m, 2H), 3.21-3.07 (m, 4H), 2.76-2.51 (m, 3H), 2.37 (m, 2H), 1.67 (m, 2H), 0.96 (t, 3H, J=6.9 Hz).

Example 345

(S)-10-[4-Ethyl-3-(2-methoxy-ethyl)-piperazin-1-yl]-2-trifluoromethyl-4H-3-thia-1,4,9-triaza-benzo[f]azulene dihydrochloride

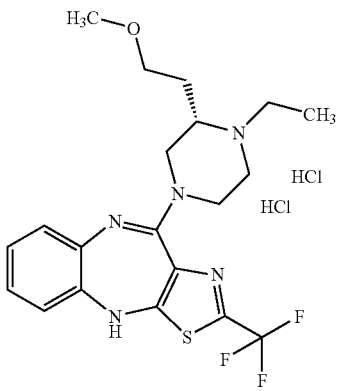

Using the method of Example 273, using (S)-10-[4-ethyl-3-(2-methoxy-ethyl)-piperazin-1-yl]-2-trifluoromethyl-4H-3-thia-1,4,9-triaza-benzo[f]azulene and a solution of acetyl chloride in absolute ethanol at ambient temperature gives the title compound: mass spectrum (APCI, m/e): 440 (M+1); exact mass spectrum (ES+, m/e, $C_{20}H_{24}F_3N_5OS \cdot 2HCl$): calc. 440.1732 (M+1-2HCl), found 440.1716.

Example 346

(S)-10-[3-(2-Methoxy-ethyl)-4-propyl-piperazin-1-yl]-2-trifluoromethyl-4H-3-thia-1,4,9-triaza-benzo[f]azulene

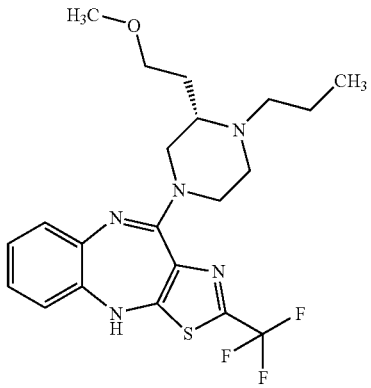

Add sodium triacetoxyborohydride (0.273 g, 1.29 mmol), and then propionaldehyde (0.083 mL, 1.15 mmol) to (S)-10-[3-(2-methoxy-ethyl)-piperazin-1-yl]-2-trifluoromethyl-4H-3-thia-1,4,9-triaza-benzo[f]azulene (0.353 g, 0.858 mmol) in anhydrous dichloroethane (15 mL) and stir at ambient temperature overnight. Add saturated aqueous sodium bicarbonate and extract aqueous phase with dichloromethane. Wash organics with saturated aqueous sodium chloride, and dry (sodium sulfate), filter, and concentrate under reduced pressure to a residue (0.29 g). Purify the residue by flash chromatography, eluting with a gradient of a 3% solution of 2M ammonia in methanol, in dichloromethane, (0-100%) to give the title compound (0.287 g, 74%): mass spectrum (APCI, m/e): 454 (M+1); NMR ($^1$H, 300 MHz, DMSO-$d_6$): δ 8.46 (s, 1H), 6.96-6.82 (m, 3H), 6.71 (m, 1H), 3.46 (br. m, 3H), 3.31-3.17 (m, 3H), 3.15 (s, 3H), 2.73 (m, 1H), 2.58-2.44 (m, 2H), 2.31 (m, 2H), 1.67 (m, 2H), 1.40 (m, 2H), 0.83 (t, 3H, J=7.5 Hz).

Example 347

(S)-10-[3-(2-Methoxyethyl)-4-propyl-piperazin-1-yl]-2-trifluoromethyl-4H-3-thia-1,4,9-triaza-benzo[f]azulene dihydrochloride

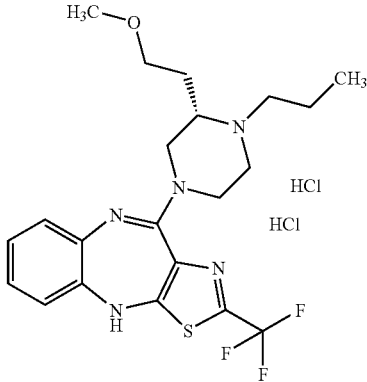

Using the method of Example 273, using (S)-10-[3-(2-methoxy-ethyl)-4-propyl-piperazin-1-yl]-2-trifluoromethyl-4H-3-thia-1,4,9-triaza-benzo[f]azulene and a solution of acetyl chloride in absolute ethanol at ambient temperature gives the title compound: mass spectrum (APCI, m/e): 454 (M+1); exact mass spectrum (ES+, m/e, $C_{21}H_{26}F_3N_5OS·2HCl$): calc. 454.1888 (M+1-2HCl), found 454.1893.

Example 348

(S)-2-Fluoro-1-[2-(2-methoxy-ethyl)-4-(2-trifluoromethyl-4H-3-thia-1,4,9-triaza-benzo[f]azulen-10-yl)-piperazin-1-yl]-ethanone

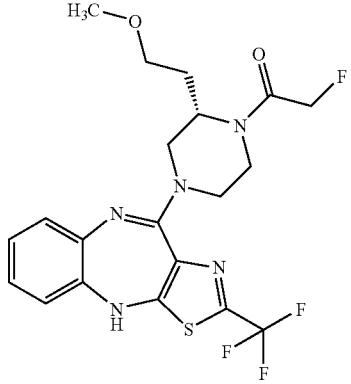

Add a solution of fluoroacetyl chloride (0.133 g, 1.38 mmol) in anhydrous dichloromethane (1-2 mL) dropwise to a 0° C. solution of (S)-10-[3-(2-Methoxy-ethyl)-piperazin-1-yl]-2-trifluoromethyl-4H-3-thia-1,4,9-triaza-benzo[f]azulene (0.283 g, 0.688 mmol) and diisopropylethylamine (0.240 mL, 1.38 mmol) in anhydrous dichloromethane, and stir at 0° C. for 3 hours. Concentrate the reaction under reduced pressure to afford an oil. Purify the oil by flash chromatography, eluting with a gradient of a solution of 2% 2M ammonia in methanol, in dichloromethane (0-100% in dichloromethane over 30 minutes, then 100% for 28 minutes) to give the title compound: 0.18 g (56%). Mass spectrum (APCI+, m/e): 472 (M+1).

Example 349

(S)-10-[4-(2-Fluoro-ethyl)-3-(2-methoxy-ethyl)-piperazin-1-yl]-2-trifluoromethyl-4H-3-thia-1,4,9-triaza-benzo[f]azulene

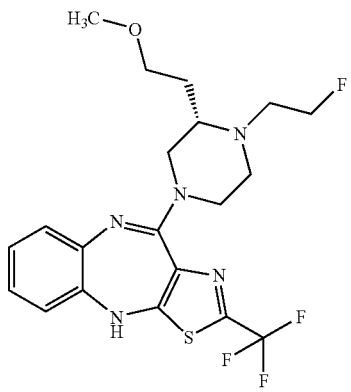

Add a solution of borane-tetrahydrofuran complex (1.0 M in tetrahydrofuran; 3.8 mL, 3.8 mmol) to a 0° C. solution of (S)-2-fluoro-1-[2-(2-methoxy-ethyl)-4-(2-trifluoromethyl-4H-3-thia-1,4,9-triaza-benzo[f]azulen-10-yl)-piperazin-1- yl]-ethanone (0.18 g, 0.38 mmol) in anhydrous tetrahydrofuran (3 mL) and stir at 0° C. for 3 hours. Quench the reaction, in an ice/water bath, slowly with methanol. Concentrate the reaction under reduced pressure and reconstitute in anhydrous dichloroethane (6 mL). Add ethylenediamine (0.23 mL, 3.4 mmol) and reflux for 45 minutes. Cool the reaction to ambient temperature and dilute with deionized water and dichloromethane (20 mL each). Separate the organic layer and extract the aqueous layer with dichloromethane (2×). Wash the combined organics with deionized water and then a saturated solution of sodium chloride, and then dry (sodium sulfate), filter, and concentrate under reduced pressure to an orange oil (0.19 g). Purify the oil by flash chromatography, eluting with a gradient of a solution of ethyl acetate:hexane (1:1, 0-50% in hexane over 45 minutes, then 100% for 13 minutes) to give the title compound: 0.050 g (29%). Mass spectrum (APCI+, m/e): 458 (M+1).

Example 350

(S)-10-[4-(2-Fluoro-ethyl)-3-(2-methoxy-ethyl)-piperazin-1-yl]-2-trifluoromethyl-4H-3-thia-1,4,9-triaza-benzo[f]azulene dihydrochloride

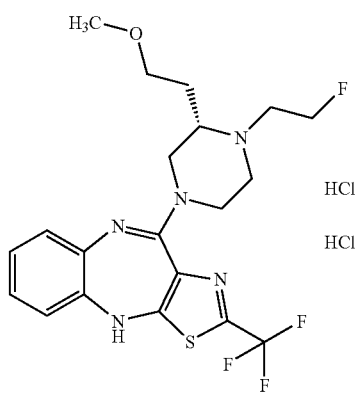

Using the method of Example 273, using (S)-10-[4-(2-fluoro-ethyl)-3-(2-methoxy-ethyl)-piperazin-1-yl]-2-trifluoromethyl-4H-3-thia-1,4,9-triaza-benzo[f]azulene (0.050 g, 0.11 mmol) and a solution of acetyl chloride (0.039 mL, 0.55 mmol) in absolute ethanol at ambient temperature gives the title compound. Mass spectrum (APCI+, m/e): 458 (M+1-2HCl); exact mass spectrum (ES+, m/e, $C_{20}H_{23}F_4N_5OS \cdot 2HCl$): calc. 458.1638 (M+1-2HCl), found 458.1627.

Example 351

(S)-10-[4-(3-Fluoro-propyl)-3-(2-methoxy-ethyl)-piperazin-1-yl]-2-trifluoromethyl-4H-3-thia-1,4,9-triaza-benzo[f]azulene

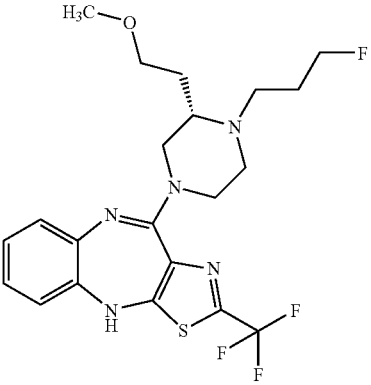

Add 1-bromo-3-fluoropropane (0.14 mL, 1.52 mmol) to a slurry of (S)-10-[3-(2-methoxy-ethyl)-piperazin-1-yl]-2-trifluoromethyl-4H-3-thia-1,4,9-triaza-benzo[f]azulene (0.52 g, 1.26 mmol), powdered potassium carbonate (0.87 g, 6.32 mmol), and sodium iodide (0.95 g, 6.32 mmol) in absolute ethanol (7.8 mL) and heat to reflux. After an overnight period, cool, add saturated aqueous sodium chloride and ethyl acetate, and add deionized water to dissolve precipitated salt that formed during the extraction. Extract aqueous phase with ethyl acetate (2×), and dry (sodium sulfate), filter, and concentrate organics under reduced pressure to an oil (0.564 g). Purify the oil by flash chromatography, eluting with a gradient of a 2% solution of 2M ammonia in methanol, in dichloromethane, (0-100%) to give the title compound: mass spectrum (APCI, m/e): 472 (M+1); NMR ($^1$H, 300 MHz, DMSO-$d_6$): δ 8.47 (s, 1H), 6.96-6.82 (m, 3H), 6.71 (m, 1H), 4.55 (td, 2H, $^2J_{(H,F)}$=48 Hz, $^3J_{(H,H)}$=5.7 Hz), 3.47 (br. m, 3H), 3.31-3.18 (m, 3H), 3.15 (s, 3H), 2.70 (m, 2H), 2.55 (br. m, 1H), 2.38 (m, 2H), 1.86-1.67 (in, 3H), 1.61 (m, 1H).

Example 352

(S)-10-[4-(3-Fluoro-propyl)-3-(2-methoxy-ethyl)-piperazin-1-yl]-2-trifluoromethyl-4H-3-thia-1,4,9-triaza-benzo[f]azulene dihydrochloride

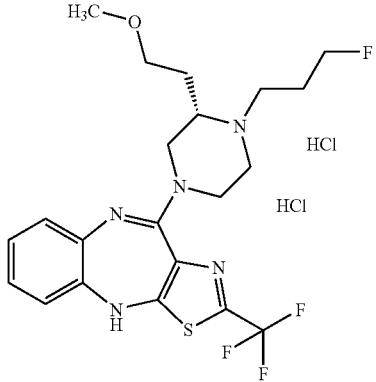

Using the method of Example 273, using (S)-10-[4-(3-fluoro-propyl)-3-(2-methoxy-ethyl)-piperazin-1-yl]-2-trifluoromethyl-4H-3-thia-1,4,9-triaza-benzo[f]azulene and a solution of acetyl chloride in absolute ethanol at ambient temperature gives the title compound: mass spectrum (APCI, m/e): 472 (M+1); exact mass spectrum (ES+, m/e, $C_{21}H_{25}F_4N_5OS.2HCl$): calc. 472.1794 (M+1-2HCl), found 472.1771.

Example 353

(S)-(2-[2-(2-Methoxy-ethyl)-4-(2-trifluoromethyl-4H-3-thia-1,4,9-triaza-benzo[f]azulene-10-yl)-piperazin-1-yl]-ethanol

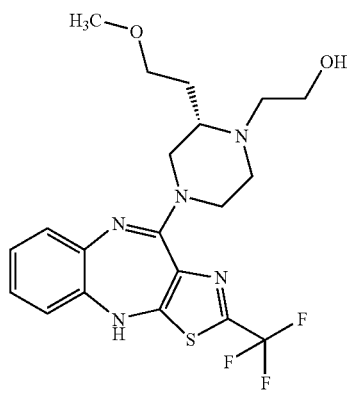

Add 2-iodo-ethanol (0.44 mL, 2.55 mmol) to a slurry of (S)-10-[3-(2-methoxy-ethyl)-piperazin-1-yl]-2-trifluoromethyl-4H-3-thia-1,4,9-triaza-benzo[f]azulene (0.75 g, 1.82 mmol), and powdered potassium carbonate (1.26 g, 9.11 mmol) in absolute ethanol (7.5 mL) and heat to reflux. After an overnight period, cool, add saturated aqueous sodium chloride and ethyl acetate, and add deionized water to dissolve precipitated salt formed during the extraction. Extract aqueous phase with ethyl acetate (2×), and dry (sodium sulfate), filter, and concentrate organics under reduced pressure to an oil (0.564 g). Add absolute ethanol (8 mL), powdered potassium carbonate (0.62 g, 4.50 mmol), followed by 2-iodo-ethanol (0.098 mL, 1.26 mmol), and stir 15.5 hours at reflux. Add additional 2-iodo-ethanol (0.010 mL, 0.13 mmol), and stir at reflux. After 4 hours, cool to ambient temperature and add deionized water and ethyl acetate. Extract separated aqueous phase with ethyl acetate, and combine, dry (sodium sulfate), filter, and concentrate organics under reduced pressure to a residue (0.86 g). Purify the residue by flash chromatography, eluting with a gradient of solutions of 2M ammonia in methanol: ethyl acetate (1%-5% 2M ammonia in methanol in ethyl acetate) to give the title compound (0.213 g, 26%): mass spectrum (APCI, m/e): 456 (M+1); NMR ($^1$H, 300 MHz, DMSO-$d_6$) δ 8.45 (s, 1H), 6.96-6.81 (m, 3H), 6.71 (m, 1H), 4.38 (t, 1H, J=5.4 Hz), 3.54-3.06 (m, 11H), 2.71 (m, 2H), 2.55 (m, 1H), 2.41 (m, 2H), 1.68 (m, 2H).

Example 354

(S)-(2-[2-(2-Methoxy-ethyl)-4-(2-trifluoromethyl-4H-3-thia-1,4,9-triaza-benzo[f]azulene-10-yl)-piperazin-1-yl]-ethanol dihydro chloride

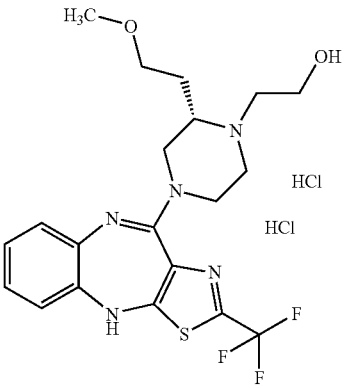

Add a solution of acetyl chloride (0.194 mL, 2.47 mmol) in absolute ethanol to a solution of freebase (S)-2-[2-(2-methoxy-ethyl)-4-(2-trifluoromethyl-4H-3-thia-1,4,9-triaza-benzo[f]azulene-10-yl)-piperazin-1-yl]-ethanol (0.213 g, 0.468 mmol) in absolute ethanol and stir. Isolate the precipitated solid by suction filtration, washing with diethyl ether, and dry the solid at ambient temperature under reduced pressure overnight to give the title compound (0.197 g, 79.8%): mass spectrum (APCI, m/e): 456 (M+1); exact mass spectrum (ES+, m/e, $C_{20}H_{24}F_3N_5O_2S.2HCl$): calc. 456.1681 (M+1-2HCl), found 456.1668.

Example 355

(S)-3-[2-(2-Methoxy-ethyl)-4-(2-trifluoromethyl-4H-3-thia-1,4,9-triaza-benzo[f]azulene-10-yl)-piperazin-1-yl]-propan-1-ol

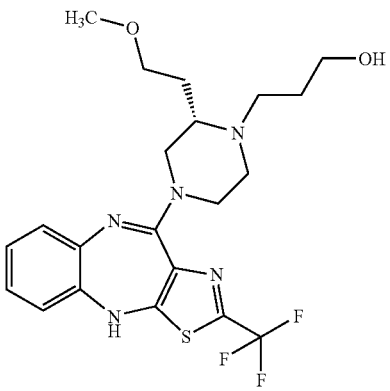

Using the method of Example 351, using (S)-10-[3-(2-methoxy-ethyl)-piperazin-1-yl]-2-trifluoromethyl-4H-3-thia-1,4,9-triaza-benzo[f]azulene and 3-bromo-propan-1-ol, 15 hours at reflux after the addition of alcohol, and two purifications by flash chromatography: the first, eluting with a gradient of a 3% solution of methanol in ethyl acetate (0-100%), and then with a gradient of methanol: ethyl acetate (3%-5% methanol in ethyl acetate); and the second, eluting with a gradient of solutions of 2M ammonia in methanol, in ethyl acetate (4%-5% over 40 minutes), gives the title compound: mass spectrum (APCI, m/e): 470 (M+1); NMR ($^1$H, 300 MHz, DMSO-$d_6$): δ 8.47 (s, 1H), 6.96-6.81 (m, 3H), 6.70 (m, 1H), 4.42 (m, 1H), 3.54-3.37 (m, 6H), 3.37-3.18 (m, 2H), 3.15 (s, 3H), 2.68 (m, 2H), 2.58-2.45 (m, 1H), 2.35 (m, 2H), 1.68 (m, 2H), 1.55 (m, 2H).

Example 356

(S)-3-[2-(2-Methoxy-ethyl)-4-(2-trifluoromethyl-4H-3-thia-1,4,9-triaza-benzo[f]azulene-10-yl)-piperazin-1-yl]-propan-1-ol dihydrochloride

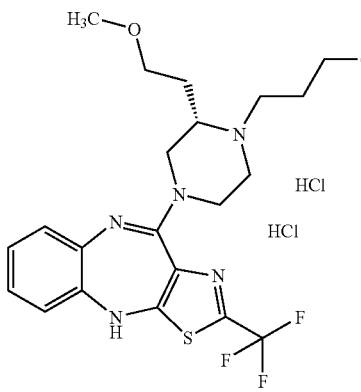

Using the method of Example 273, using (S-)3-[2-(2-methoxy-ethyl)-4-(2-trifluoromethyl-4H-3-thia-1,4,9-triaza-benzo[f]azulene-10-yl)-piperazin-1-yl]-propan-1-ol and a solution of acetyl chloride in absolute ethanol at ambient temperature gives the title compound: mass spectrum (APCI, m/e): 470 (M+1); exact mass spectrum (ES+, m/e, $C_{21}H_{26}F_3N_5O_2S$·2HCl): calc. 470.1837 (M+1-2HCl), found 470.1833.

Example 357

(S)-(2-[2-(2-(2-Methoxy-ethyl)-4-(2-trifluoromethyl-4H-3-thia-1,4,9-triaza-benzo[f]azulene-10-yl)-piperazin-1-yl)-ethoxy]-ethanol

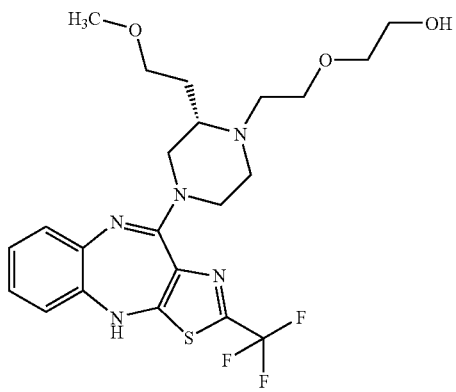

Add (S)2-(2-chloro-ethoxy)-ethanol (0.267 mL, 2.53 mmol) to a slurry of (S)-10-[3-(2-methoxy-ethyl)-piperazin-1-yl]-2-trifluoromethyl-4H-3-thia-1,4,9-triaza-benzo[f]azulene (0.52 g, 1.26 mmol), powdered potassium carbonate (0.87 g, 6.32 mmol), and sodium iodide (0.95 g, 6.32 mmol) in absolute ethanol (5.2 mL), and heat to reflux. After 22 hours, cool and add powdered potassium carbonate (0.09 g, 0.65 mmol), sodium iodide (0.09 g, 0.60 mmol), and (S)-(2-2-chloro-ethoxy)-ethanol (0.100 mL, 0.938 mmol); rinse in solids with absolute ethanol, and reflux. After 4 hours, add (S)-2-(2-chloro-ethoxy)-ethanol (0.307 mL, 2.88 mmol) and reflux. After 17.5 hours, cool and add deionized water and ethyl acetate. After separation of layers, extract aqueous layer with ethyl acetate (2×), and combine, dry (sodium sulfate), filter, and concentrate organics under reduced pressure to a solid (1.54 g). Purify the solid by flash chromatography, eluting with a gradient of solutions of 2M ammonia in methanol: ethyl acetate (1%-5% 2M ammonia in methanol in ethyl acetate over 61 minutes), and then with a 5% solution of 2M ammonia in methanol, in ethyl acetate for 30 minutes to give the title compound (0.146 g, 23%): mass spectrum (APCI, m/e): 500 (M+1); NMR ($^1$H, 300 MHz, DMSO-$d_6$) δ 8.47 (s, 1H), 6.96-6.81 (m, 3H), 6.71 (m, 1H), 4.60 (t, 1H, J=5.1 Hz), 3.56-3.10 (m, 15H), 2.76 (m, 2H), 2.61-2.41 (m, 3H), 1.68 (m, 2H).

Example 358

(S)-2-[2-(2-(2-Methoxy-ethyl)-4-(2-trifluoromethyl-4H-3-thia-1,4,9-triaza-benzo[f]azulene-10-yl)-piperazin-1-yl)-ethoxy]-ethanol dihydrochloride

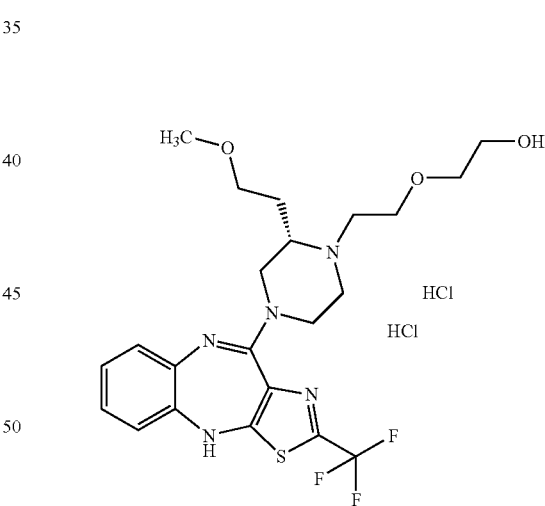

Using the method of Example 273, using (S)-(2-[2-(2-(2-methoxy-ethyl)-4-(2-trifluoromethyl-4H-3-thia-1,4,9-triaza-benzo[f]azulene-10-yl)-piperazin-1-yl)-ethoxy]-ethanol and a solution of acetyl chloride in absolute ethanol at ambient temperature gives the title compound: mass spectrum (APCI, m/e): 500 (M+1); exact mass spectrum (ES+, m/e, $C_{22}H_{28}F_3N_5O_3S$·2HCl): calc. 500.1943 (M+1-2HCl), found 500.1943.

Example 359

10-[3(S)-(2(S)-Methoxypropyl)-piperazin-1-yl]-2-methyl-4H-3-thia-4,9-diazabenzo[f]azulene 10-[3(S)-(2(R)-Methoxypropyl)-piperazin-1-yl]-2-methyl-4H-3-thia-4,9-diazabenzo[f]azulene

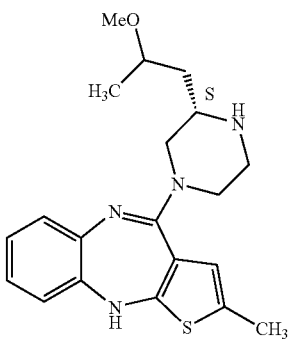

In a manner similar to that described in Example 311, combine 2-methyl-4,9-dihydro-3-thia-4,9-diazabenzo[f]azulene-10-thione (0.711 g, 2.89 mmol) and the mixture of isomers of 2(S)-(2(S)-methoxypropyl)piperazine and 2(S)-(2(R)-methoxypropyl)piperazine (0.456 g, 2.89 mmol) to obtain the mixture of isomers: 10-[3(S)-(2(S)-methoxypropyl)piperazin-1-yl]-2-methyl-4H-3-thia-4,9-diazabenzo[f]azulene and 10-[3(S)-(2(R)-methoxypropyl)piperazin-1-yl]-2-methyl-4H-3-thia-4,9diazabenzo[f]azulene (0.54 g, 50%) as a brown amorphous solid (mixture of isomers): Mass spectrum (APCI): m/z 371.2 (M+1).

Example 360

10-[3(S)-(2(S)-Methoxypropyl)-4-methylpiperazin-1-yl]-2-methyl-4H-3-thia-4,9-diazabenzo[f]azulene dihydrochloride 10-[3(S)-(2(R)-Methoxypropyl)-4-methylpiperazin-1-yl]-2-methyl-4H-3-thia-4,9-diazabenzo[f]azulene dihydrochloride

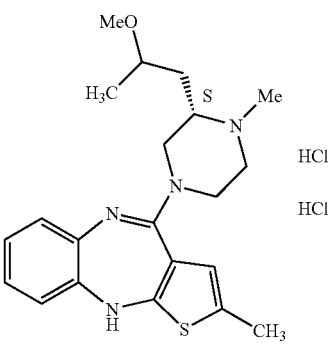

Combine the material from Example 359 (0.235 g, 0.634 mmol), formaldehyde (67 µL, 0.825 mmol, 37%), and sodium triacetoxyborohydride (0.202 g, 0.951 mmol) in dichloroethane (15 mL) and stir at room temperature for 6 hours. Dilute the mixture with saturated aqueous sodium bicarbonate and extract three times with dichloromethane. Combine the organic layers, dry over sodium sulfate and concentrate under reduced pressure to give the crude product. Purification by flash chromatography, eluting with a step gradient starting with dichloromethane going to 5% 2N ammonia-methanol in dichloromethane, gives the free base of the title compounds: 10-[3(S)-(2(S)-methoxypropyl)-4-methylpiperazin-1-yl]-2-methyl-4H-3-thia-4,9-diazabenzo[f]azulene dihydrochloride and 10-[3(S)-(2(R)-methoxypropyl)-4-methylpiperazin-1-yl]-2-methyl-4H-3-thia-4,9-diazabenzo[f]azulene dihydrochloride (0.188 g 77%) as a yellow foam (mixture of isomers): mass spectrum (APCI): m/z=385.2 (M+1). Isolate clean product as the corresponding dihydrochloride in the manner described in Example 319: exact mass, calc: 385.2062; found: 385.2085.

Example 361

10-[3(S)-(2(S)-Methoxy-propyl)-piperazin-1-yl]-2-isopropyl-4H-3-thia-1,4,9-triazabenzo[f]azulene 10-[3(S)-(2(R)-Methoxy-propyl)-piperazin-1-yl]-2-isopropyl-4H-3-thia-1,4,9-triazabenzo[f]azulene

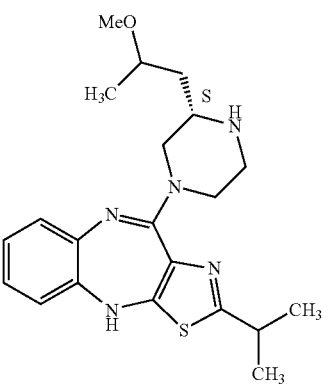

In a manner similar to that described in Example 359, combine 2-isopropyl-4,9-dihydro-3-thia-1,4,9-triazabenzo[f]azulene-10-thione (0.865 g, 3.14 mmol) and the isomer mixture of 2(S)-(2(S)-methoxypropyl)piperazine and 2(S)-(2(R)-methoxypropyl)piperazine (0.497 g, 3.14 mmol) to obtain the title compound as a mixture of isomers: mass spectrum (APCI): m/z 400.2 (M+1).

Example 362

10-[3(S)-(2(S)-Methoxy-propyl)piperazin-1-yl]-2-isopropyl-4H-3-thia-1,4,9-triaza-benzo[f]azulene dihydrochloride

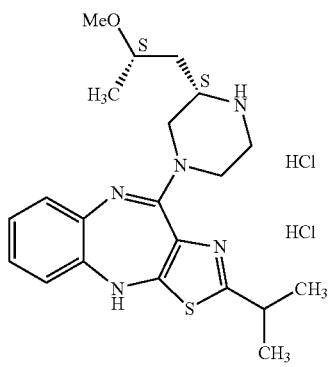

and

Example 363

10-[3(S)-(2(R)-Methoxy-propyl)piperazin-1-yl]-2-isopropyl-4H-3-thia-1,4,9-triaza-benzo[f]azulene dihydrochloride

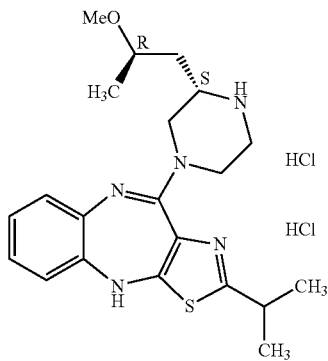

To a sample of 225 mg of diastereomerically mixed 10-[3(S)-(2(S)-methoxy-propyl)piperazin-1-yl]-2-isopropyl-4H-3-thia-1,4,9-triaza-benzo[f azulene dihydrochloride and 10-[3 (S)-(2(R)-methoxy-propyl)piperazin-1-yl]-2-isopropyl-4H-3-thia-1,4,9-triaza-benzo[f]azulene dihydrochloride apply chiral chromatography methods Chiralpak AD 4.6×150 mm Eluent: 0.2% DMEA, 15% MeOH, 15% 3A Alcohol in Heptane Flow: 0.6 mL/min WV: 280 nm to obtain isomer 1 (66 mg) and isomer 2 (54 mg) as yellow foams. Isolate both isomers (unknown stereochemistry) as the corresponding dihydrochlorides: Isomer 1 RT 7.75 min Exact Mass, Calc: 400.2171; Found: 400.2159. Isomer 2 RT 10.20 min Exact Mass, Calc: 400.2171; Found: 400.2159.

Example 364

10-[3(S)-(2(S)-Methoxy-propyl)-4-methyl-piperazin-1-yl]-2-isopropyl-4H-3-thia-1,4,9-triazabenzo[f]azulene dihydrochloride 10-[3(S)-(2(R)-Methoxy-propyl)-4-methyl-piperazin-1-Y]L-2-isopropyl-4H-3-thia-1,4,9-triazabenzo[f]azulene dihydrochloride

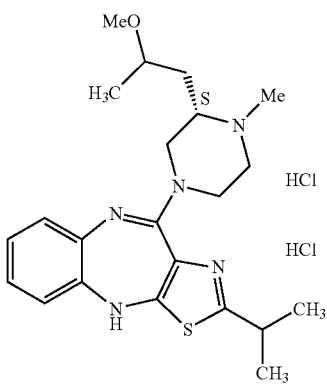

In a manner similar to that described in Example 360, using the mixture of diastereoisomers from Example 361 of 10-[3(S)-(2(S)-methoxy-propyl)-piperazin-1-yl]-2-isopropyl 4H-3-thia-1,4,9-triazabenzo[f]azulene and 10-[3(S)-(2(R)-methoxy-propyl)-piperazin-1-yl]-2-isopropyl 4H-3-thia-1,4,9-triazabenzo[f]azulene to obtain the free base of 10-[3(8)-(2(S)-methoxy-propyl)-4-methyl-piperazin-1-yl]-2-isopropyl-4H-3-thia-1,4,9-triazabenzo[f]azulene and 10-[3(S)-(2(R)-methoxy-propyl)-4-methyl-piperazin-1-yl]-2-isopropyl 4H-3-thia-1,4,9-triazabenzo[f]azulene (0.211 g, 0.510 mmol, 35%) as a yellow foam (mixture of diastereomers). Mass spectrum (APCI): m/z=414.2 (M+1). Isolate clean product as the corresponding dihydrochloride in the manner described in Example 319.

Example 365

10-[3(S)-(2(S)-Methoxy-propyl)-4-methyl-piperazin-1-yl]-2-isopropyl-4H-3-thia-1,4,9-triazabenzo[f]azulene dihydrochloride

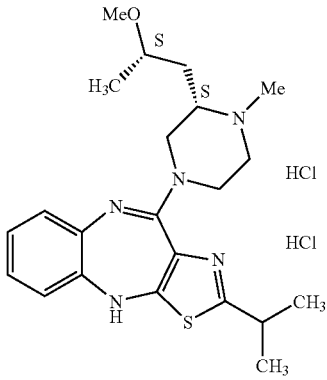

and

Example 366

10-[3 (S)-(2(R)-methoxy-propyl)-4-methyl-piperazin-1-yl]-2-isopropyl-4H-3-thia-1,4,9-triazabenzo[f]azulene dihydrochloride

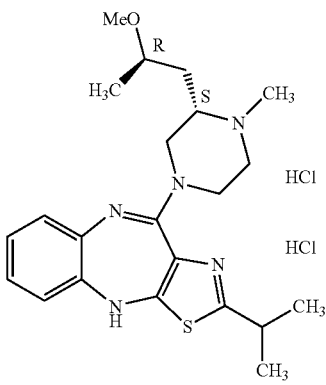

Separate individual isomers from diastereomeric mixture from above (203 mg) by using a Chiralpak AD 8×250 mm column. Elute with an 85:15 mixture of heptane:ethanol containing 0.2% dimethylethyl amine. Further purify each isomer by flash chromatography, eluting with a step gradient starting with dichloromethane going to 5% 2N ammonia-methanol in dichloromethane, to obtain isomer #1 (0.058 g) and isomer #2 (0.052 g). Isolate clean products as the corresponding dihydrochlorides in the manner described in Example 319. isomer #1: Exact Mass, Calc: 414.2328; Found: 414.2321. isomer #2: Exact Mass, Calc: 414.2328; Found: 414.2314.

Example 367

(S)-1-[4-(2-Isopropyl-4H-3-thia-1,4,9-triazabenzo[f]azulene-10-yl)-piperazin-2-yl]-2-methylpropan-2-ol dihydrochloride

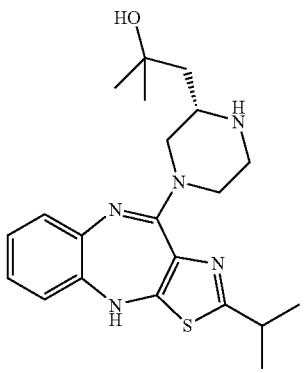

In a manner similar to that described in Example 359, combine 2-isopropyl-4,9-dihydro-3-thia-1,4,9-triazabenzo[f]azulene-10-thione (0.686 g, 2.49 mmol) and (S)-2-methyl-1-piperazin-2-yl-propan-2-ol (0.394 g, 2.49 mmol) to obtain the title compound: mass spectrum (APCI): m/z 400.2 (M+1).

Example 368

(S)-1-[4-(2-Isopropyl-4H-3-thia-1,4,9-triazabenzo[f]azulene-10-yl)-1-methylpiperazin-2-yl]-2-methyl-propan-2-ol dihydrochloride

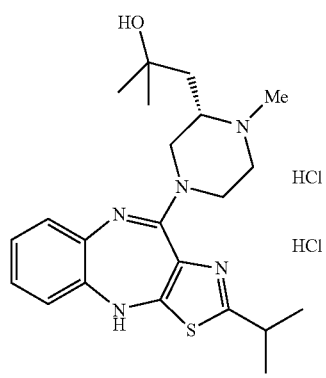

In a manner similar to that described in Example 360, using to (S)-1-[4-(2-Isopropyl-4H-3-thia-1,4,9-triazabenzo[f]azulene-10-yl)-piperazin-2-yl]-2-methylpropan-2-ol to obtain the free base of the title compound (0.122 g, 0.295 mmol, 16%) as a yellow oil: mass spectrum (APCI): m/z=414.2 (M+1). Isolate clean product as the corresponding dihydrochloride in the manner described in Example 319. Exact Mass, Calc: 414.2328; Found: 414.2313.

Example 369

(S)-2-Methyl-1-[4-(2-methyl-4H-3-thia-4,9-diazabenzo[f]azulen-10-yl)piperazin-2-yl]-propan-2-ol

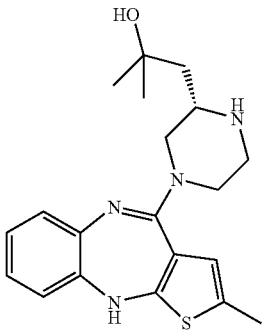

In a manner similar to that described in Example 359, combine 2-methyl-4,9-dihydro-3-thia-4,9-diazabenzo[f]azulene-10-thione (0.574 g, 2.33 mmol) and (S)-2-methyl-1-piperazin-2-yl-propan-2-ol (0.369 g, 2.33 mmol) to obtain the title compound: mass spectrum (APCI): m/z=371.2 (M+1).

Example 370

(S)-2-Methyl-1-[1-methyl-4-(2-methyl-4H-3-thia-4,9-diazabenzo[f]azulene-10-yl)-piperazin-2-yl]-propan-2-ol dihydrochloride 1p;2p

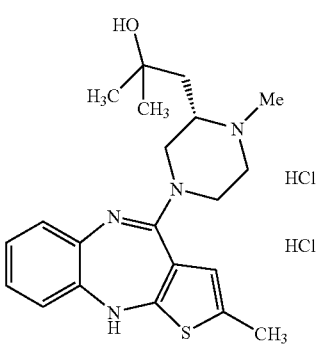

In a manner similar to that described in Example 360, using (S)-2-Methyl-1-[4-(2-methyl-4H-3-thia-4,9-diazabenzo[f]azulen-10-yl)piperazin-2-yl]-propran-2-ol to obtain the free base of the title compound (0.080 g, 0.208 mmol, 16%) as a yellow oil. Mass spectrum (APCI): m/z=385.2 (M+1). Isolate clean product as the corresponding dihydrochloride in the manner described in Example 319. Exact Mass, Calc: 385.2062; Found: 385.2053.

Example 371

1-[4-(2-Methyl-4H-3-thia-4,9-diazabenzo[f]azulen-10-yl]-piperazin-2(S)-yl]-propan-2(S)-ol dihydrochloride and 1-[4-(2-Methyl-4H-3-thia-4,9-diazabenzo[f]azulen-10-yl)-piperazin-2(S)-yl]-propan-2(R)-ol dihydrochloride

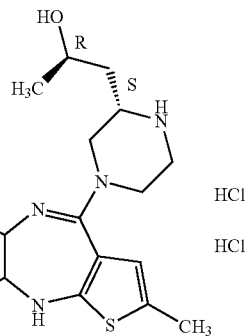

In a manner similar to that described (S)-10-[3-(2-methoxyethyl)piperazin-1-yl]-2-isopropyl-4H-3-thia-1,4,9-triazabenzo[f]azulene combine the diastereomeric mixture of 1-piperazin-2(S)-yl-propan-2(S)-ol and 1-piperazin-2(S)-yl-propan-2(R)-ol (477 mg, 3.3 mmoles) with 2-methyl-4,9-dihydro-3-thia-4,9-diazabenzo[f]azulene-10-thione (814 mg, 3.3 mmoles) to obtain a diastereomeric mixture of 1-[4-(2-methyl-4H-3-thia-4,9-diazabenzo[f]azulen-10-yl)-piperazin-2(S)-yl]propan-2(S)-ol dihydrochloride and 1-[4-(2-methyl-4H-3-thia-4,9-diazabenzo[f]azulen-10-yl)-piperazin-2(S)-yl]propan-2(R)-ol dihydrochloride as a brown oil.

Example 372

1-[4-(2-Methyl-4H-3-thia-4,9-diazabenzo[f]azulen-10-yl)-piperazin-2(S)-yl]-propan-2(S)-ol dihydrochloride

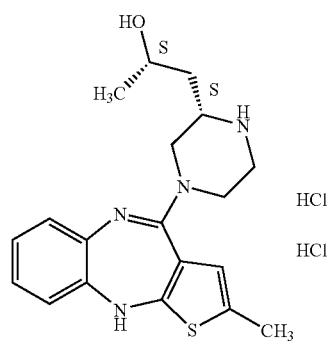

and

Example 373

1-[4-(2-Methyl-4H-3-thia-4,9-diazabenzo[f]azulen-10-yl)-piperazin-2(S)-yl]-propan-2(R)-ol dihydrochloride Using a column chromatography method to Example 365 and Example 366 separate the mixture of diastereoisomers from Example 371 via column chromatography using a step gradient from dichloromethane going to 5% 2N ammonia-methanol in dichloromethane to afford isomer 1 (184 mg, 16%) and isomer 2 (163 mg, 14%) as yellow foams. Isolate both isomers as the corresponding dihydrochlorides: isomer 1 Exact Mass, Calc: 357.1749; Found: 357.1720. isomer 2 Exact Mass, Calc: 357.1749; Found: 357.1743.

Example 374

1-[1-Methyl-4-(2-methyl-4H-3-thia-4,9-diazabenzo[f]azulen-10-yl)-piperazin-2(S)-yl]-propan-2-ol dihydrochloride (isomer 1, diastereomerically pure)

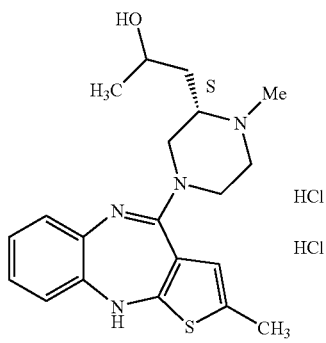

In a manner similar to that described in (S)-10-[3-(2-methoxyethyl)-4-methylpiperazin-1-yl]-2-isopropyl 4H-3-thia-1,4,9-triazabenzo[f]azulene dihydrochloride, convert isomer 1 from Example 372 and Example 373 (132 mg, 0.37 mmoles) into diastereomerically pure 1-[1-methyl-4-(2-methyl-4H-3-thia-4,9-diazabenzo[f]azulen-10-yl)piperazin-2(S)-yl]-propan-2-ol (isomer 1, 75 mg, 56%). Isolate as the title dihydrochloride: isomer 1 Exact Mass, Calc: 371.1906; Found: 371.1916.

Example 375

1-[1-Methyl-4-(2-methyl-4H-3-thia-4,9-diazabenzo[f]azulen-10-yl)-piperazin-2(S)-yl]-propan-2-ol dihydrochloride (isomer 2, diastereomerically pure)

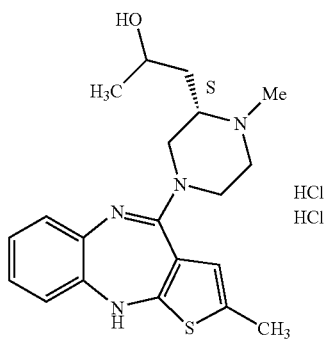

In a manner similar to that described (S)-10-[3-(2-methoxyethyl)-4-methylpiperazin-1-yl]-2-Isopropyl 4H-3-thia-1,4,9-triazabenzo[f]azulene dihydrochloride, convert isomer 2 from Example 372 and Example 373 (111 mg, 0.31 mmoles) into diastereomerically pure 1-[1-methyl-4-(2-methyl-4H-3-thia-4,9-diazabenzo[f]azulen-10-yl)piperazin-2(S)-yl]-propan-2-ol (isomer 2, 85 mg, 74%). Isolate as the title dihydrochloride: Isomer 2 Exact Mass, Calc: 371.1906; Found: 371.1924.

Example 380

(S)-5-[3-(2-Methoxy-ethyl)-piperazin-1-yl]-8-trifluoromethyl-11H-12-thia-6,11-diaza-dibenzo[a,f]azulene

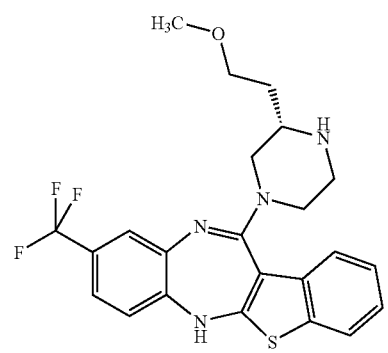

Add 8-trifluoromethyl-11H-12-thia-6,11-diaza-dibenzo[a,f]azulen-5-ylamine hydrochloride (0.75 g, 2.0 mmol) to a solution of (S)-2-(2-methoxy-ethyl)-piperazine (0.58 g, 4.1 mmol) in dimethyl sulfoxide: toluene (1:8, 0.2M). Add diisopropylethylamine (1 equiv), heat to 110° C., and stir. After 45 hours, cool to ambient temperature, and dilute with ethyl acetate and 0.1 N NaOH. Separate the aqueous layer and extract it with ethyl acetate (3×). Wash all organics with a saturated solution of sodium chloride, and then dry (sodium sulfate), filter, and concentrate them under reduced pressure. Purify the oil by flash chromatography, eluting with a gradient of a 3% solution of 2M ammonia in methanol, in dichloromethane (0-100% in dichloromethane). Reconstitute the material in ethyl acetate and wash it with a saturated solution of sodium chloride (2×) to remove residual dimethylsulfoxide. Back extract the combined aqueous layers with ethyl acetate. Dry (sodium sulfate) the organic phases, filter, and concentrate them under reduced pressure to give the title compound (0.331 g). Mass spectrum (APCI+, m/e): 461 (M+1).

Example 381

(S)-5-[3-(2-Methoxy-ethyl)-piperazin-1-yl]-8-trifluoromethyl-11H-12-thia-6,11-diaza-dibenzo[a,f]azulene dihydrochloride

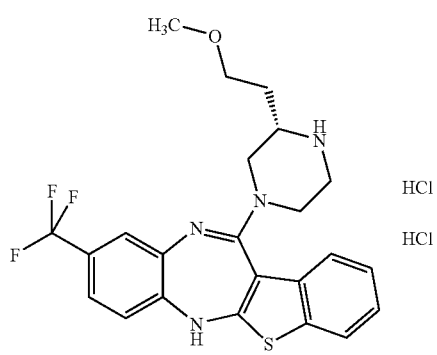

Add a solution of acetyl chloride (0.078 mL, 1.1 mmol) in absolute ethanol to a solution of (S)-5-[3-(2-methoxyethyl)-piperazin-1-yl]-8-trifluoromethyl-11H-12-thia-6,11-diaza-dibenzo[a,f]azulene (0.10 g, 0.22 mmol) in absolute ethanol and isolate the precipitated solid by suction filtration. Dry the solid under reduced pressure to give the title compound (0.095 g). Exact mass spectrum (ES+, m/e, $C_{23}H_{23}F_3N_4OS \cdot 2HCl$): calc. 461.1623 (M+1-2HCl), found 461.1613.

Example 382

(S)-5-[3-(2-Methoxy-ethyl)-4-methyl-piperazin-1-yl]-8-trifluoromethyl-11H-12-thia-6,11-diaza-dibenzo[a,f]azulene

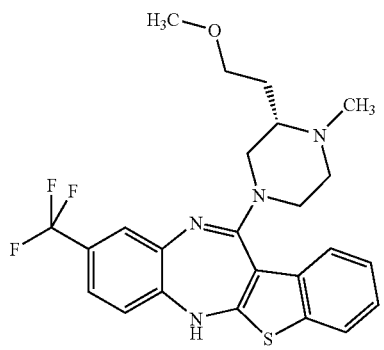

Add sodium triacetoxyborohydride (0.154 g; 0.727 mmol) and aqueous formaldehyde (37% w/w, 0.047 mL, 0.63 mmol) to a solution of (S)-5-[3-(2-methoxy-ethyl)-piperazin-1-yl]-8-trifluoromethyl-1H-12-thia-6,11-diaza-dibenzo[a,f]azulene (0.223 g, 0.484 mmol) in methanol:dichloroethane (1:1, 8 mL) and stir at ambient temperature. After an overnight period, add another 1.3 equivalents of aqueous formaldehyde (0.047 mL, 0.63 mmol) and 1.5 equivalents of sodium triacetoxyborohydride (0.154 g, 0.727 mmol), and rinse in with methanol. Stir a few hours at ambient temperature, and then dilute the reaction with a saturated solution of sodium bicarbonate and dichloromethane. Separate the aqueous layer and extract it with dichloromethane. Combine the organics and wash them with a saturated solution of sodium chloride. Dry (sodium sulfate), filter, and concentrate the organics under reduced pressure to a residue. Purify the residue by flash chromatography, eluting with a gradient of a solution of 2M ammonia in methanol and dichloromethane, in dichloromethane to give the title compound (0.225 g). Mass spectrum (APCI+, m/e): 475 (M+1).

Example 383

(S)-5-[3-(2-Methoxy-ethyl)-4-methyl-piperazin-1-yl]-8-trifluoromethyl-11H-12-thia-6,11-diaza-dibenzo[a,f]azulene dihydrochloride

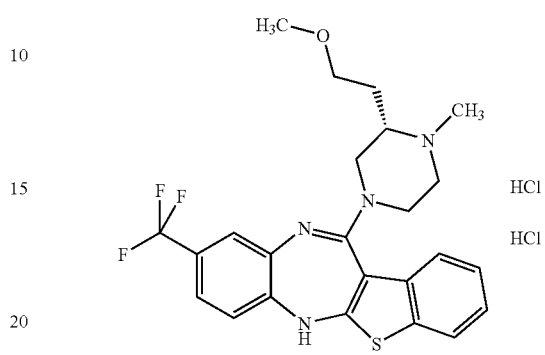

Using the method of Example 273 using (S)-5-[3-(2-methoxy-ethyl)-4-methyl-piperazin-1-yl]-8-trifluoromethyl-11H-12-thia-6,11-diaza-dibenzo[a,f]azulene (0.225 g, 0.474 mmol) and a solution of acetyl chloride (0.169 mL, 2.37 mmol) in absolute ethanol at ambient temperature gives the title compound (0.239 g). Mass spectrum (APCI+, m/e): 475 (M+1-2HCl); exact mass spectrum (ES+, m/e, $C_{24}H_{25}F_3N_4OS \cdot 2HCl$): calc. 475.1779 (M+1-2HCl), found 475.1765.

Example 384

(S)-5-[3-(2-Methoxy-ethyl)-piperazin-1-yl]-11H-12-thia-6,11-diaza-dibenzo[a,f]azulene

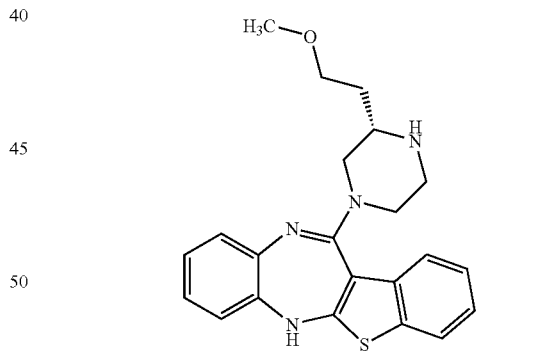

Following the method of Example 380, using 11H-12-thia-6,11-diaza-dibenzo[a,f]azulen-5-ylamine hydrochloride (0.40 g, 1.3 mmol) and (S)-2-(2-methoxy-ethyl)-piperazine (0.38 g, 2.7 mmol), stirring at 115° C. for 24 hours, wash the separated organic layer with 0.1 N NaOH (2×), and extract the combined aqueous layers with ethyl acetate. Combine the organics and wash them with a saturated solution of sodium chloride (3×), and then dry (sodium sulfate), filter, and concentrate under reduced pressure to a residue. Purify the residue by flash chromatography, eluting with a gradient of a solution of 5% 2M ammonia in methanol, in dichloromethane (in dichloromethane) to give the title compound (0.075 g). Mass spectrum (APCI+, m/e): 393 (M+1).

Example 385

(S)-5-[3-(2-Methoxy-ethyl)-4-methyl-piperazin-1-yl]-11H-12-thia-6,11-diaza-dibenzo[a,f]azulene

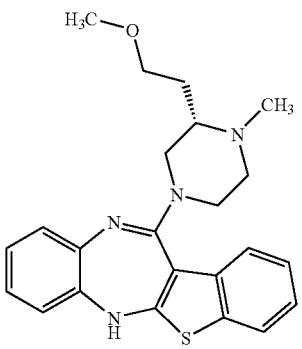

Following the method of Example 272 using (S)-5-[3-(2-Methoxy-ethyl)-piperazin-1-yl]-11H-12-thia-6,11-diaza-dibenzo[a,f]azulene (0.069 g, 0.18 mmol) gives partial conversion to the title compound after stirring at ambient temperature for 5.5 hours. Add another 1.3 equivalents of aqueous formaldehyde (0.0171 mL, 0.229 mmol) and 1.5 equivalents of sodium triacetoxyborohydride (0.0559 g, 0.264 mmol) with dichloroethane, and stir. After an overnight period, dilute the reaction with a saturated aqueous solution of sodium bicarbonate and dichloromethane, and separate the layers. Extract the aqueous layer with dichloromethane, combine organics, and wash them with a saturated solution of sodium chloride. Dry (sodium sulfate), filter, and concentrate the organics under reduced pressure to an oil. Purify the oil by flash chromatography, eluting with a gradient of a solution of 5% 2M ammonia in methanol, in dichloromethane (25-100% in dichloromethane over 43 minutes) to give the title compound (0.043 g). Mass spectrum (APCI+, m/e): 407 (M+1).

Example 386

(S)-5-[3-(2-Methoxy-ethyl)-4-methyl-piperazin-1-yl]-11H-12-thia-6,11-diaza-dibenzo[a,f]azulene dihydrochloride

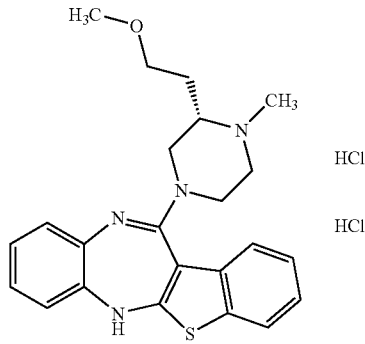

Using the method of Example 273 using (S)-5-[3-(2-methoxy-ethyl)-4-methyl-piperazin-1-yl]-11H-12-thia-6,11-diaza-dibenzo[a,f]azulene (0.039 g, 0.096 mmol) and a solution of acetyl chloride (0.0342 mL, 0.480 mmol) in absolute ethanol at ambient temperature gives the title compound (0.042 g). Mass spectrum (APCI+, m/e): 407 (M+1-2HCl); exact mass spectrum (ES+, m/e, $C_{23}H_{26}N_4OS \cdot 2HCl$): calc. 407.1906 (M+1-2HCl), found 407.1899.

Example 387

(S)-8-Fluoro-5-[3-(2-methoxy-ethyl)-piperazin-1-yl]-11H-12-thia-6,11-diaza-dibenzo[a,f]azulene

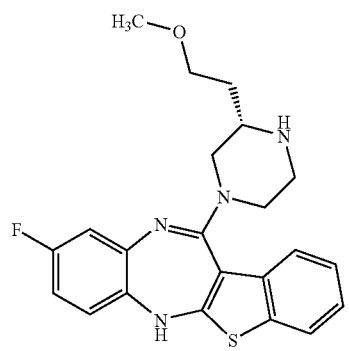

Following the method of Example 380 using 8-fluoro-11H-12-thia-6,11-diaza-dibenzo[a,f]azulen-5-ylamine hydrochloride (0.40 g, 1.3 mmol) and (S)-2-(2-methoxy-ethyl)-piperazine (0.36 g, 2.5 mmol), stirring at 115° C. for 24 hours, wash the separated organic layer with 0.1 N NaOH (2×), and extract the combined aqueous layers with ethyl acetate. Combine the organics and wash with a saturated solution of sodium chloride (3×), and then dry (sodium sulfate), filter, and concentrate under reduced pressure to a residue. Purify the residue by flash chromatography, eluting with a gradient of a solution of 5% 2M ammonia in methanol, in dichloromethane (in dichloromethane) to give the title compound (0.096 g). Mass spectrum (APCI+, m/e): 411 (M+1).

Example 388

(S)-8-Fluoro-5-[3-(2-methoxy-ethyl)-4-methyl-piperazin-1-yl]-11H-12-thia-6,11-diaza-dibenzo[a,f]azulene

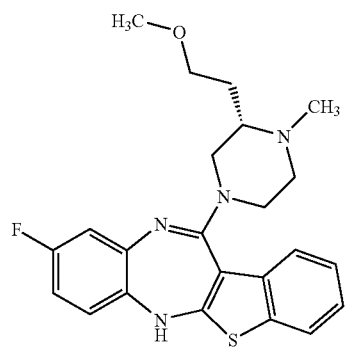

Following the method of Example 272 using (S)-8-fluoro-5-[3-(2-methoxy-ethyl)-piperazin-1-yl]-11H-12-thia-6,11- diaza-dibenzo[a,f]azulene (0.091 g, 0.22 mmol) gives partial conversion to the title compound after stirring at ambient temperature for 5.5 hours. Add another 1.3 equivalents of aqueous formaldehyde (0.0216 mL, 0.288 mmol) and 1.5 equivalents of sodium triacetoxyborohydride (0.0705 g, 0.333 mmol) with dichloroethane, and stir. After an overnight period, dilute the reaction with a saturated aqueous solution of sodium bicarbonate and dichloromethane, and separate the layers. Wash the organic layer with a saturated aqueous solution of sodium bicarbonate. Combine the aqueous layers and extract them with dichloromethane. Combine the organics, wash them with a saturated solution of sodium chloride, and dry (sodium sulfate), filter, and concentrate them under reduced pressure to an oil. Purify the oil by flash chromatography, eluting with a gradient of a 4% solution of 2M ammonia in methanol, in dichloromethane (25-100% in dichloromethane over 58 minutes) to give the title compound (0.047 g). Mass spectrum (APCI+, m/e): 425 (M+1).

Example 389

(S)-8-Fluoro-5-[3-(2-methoxy-ethyl)-4-methyl-piperazin-1-yl]-11H-12-thia-6,11-diaza-dibenzo[a f]azulene dihydrochloride

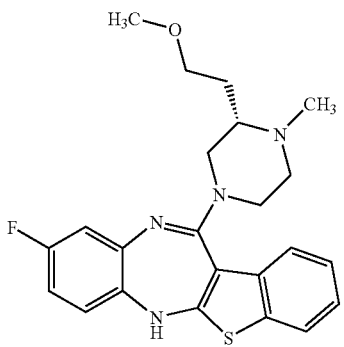

Using the method of Example 273 using (S)-8-fluoro-5-[3-(2-methoxy-ethyl)-4-methyl-piperazin-1-yl]-11H-12-thia-6,11-diaza-dibenzo[a,f]azulene (0.045 g, 0.11 mmol) and a solution of acetyl chloride (0.0378 mL, 0.530 mmol) in absolute ethanol at ambient temperature gives the title compound (0.050 g). Mass spectrum (APCI+, m/e): 425 (M+1-2HCl); exact mass spectrum (ES+, m/e, $C_{23}H_{25}FN_4OS \cdot 2HCl$): calc. 425.1811 (M+1-2HCl), found 425.1808.

Example 390

(S)-9-Fluoro-5-[3-(2-methoxy-ethyl)-piperazine-1-yl]-11H-12-thia-6,11-diaza-dibenzo[a,f]azulene

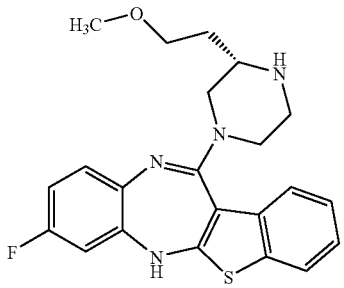

Combine 9-fluoro-11H-12-thia-6,11-diaza-dibenzo[a,f]azulen-5-ylamine hydrogen chloride (510.2 mg, 1.6 mmol, (S)-2-(2-methoxy-ethyl) piperazine (460.8 mg, 3.2 mmol) and diisopropylethyl amine (206 mg, 1.6 mmol) in DMSO (0.75 mL) and toluene (3.0 mL), stir and heat to 110° C. After 55 hours, cool the reaction to RT, dilute with $CH_2Cl_2$, wash with $H_2O$ and Brine. Dry the organic layer with by $Na_2SO_4$. The crude material pass through a 5 g SCX column, collect the 0.2 N $NH_3$/MeOH eluent, concentrate to a residue, which purified by chromatography on silica gel, gradient (100% $CH_2Cl_2$ to 100% $CH_2Cl_2$: 2N $NH_3$/MeOH=15:1), give 410 mg of title compound. Mass spectrum: ACPI (m/e): 411.2 (M+1).

Example 391

(S)-9-Fluoro-5-[3-(3-methoxy-propyl)-piperazin-1-yl]-11H-12-thia-6,11-diaza-dibenzo[a f]azulene

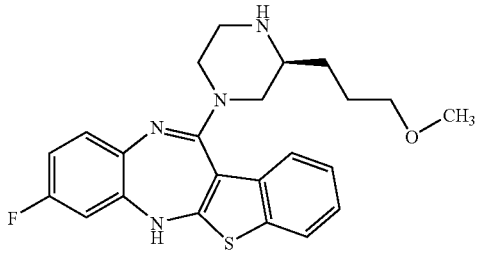

Using the method of (S)-1-[3-(3-Methoxy-propyl)-piperazin-1-yl]2-trifluoromethyl-5H-dibenzo[b,e][1,4]diazepine using 9-fluoro-11H-12-thia-6,11-diaza-dibenzo[a,f]azulen-5-ylamine to give the title compound: mass spectrum (m/e): 425.04 (M+1).

Example 392

(S)-9-Fluoro-5-[3-(2-methoxy-ethyl)-4-methyl-piperazine-1-yl]-1H-12-thia-6,11-diaza-dibenzo[a,f] azulene dihydrochloride

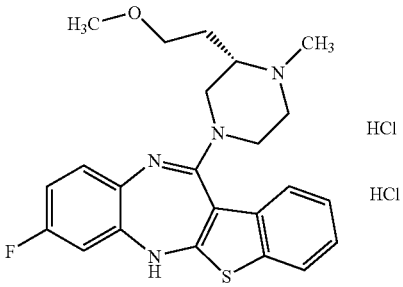

Combine (S)-9-fluoro-5-[3-(2-methoxy-ethyl)-piperazine-1-yl]-11H12-thia-6,11-diaza-dibenzo[a,f]azulene (300 mg, 0.73 mmol), formaldehyde (37%, w/w, aq) (71 mg, 0.88 mmol) and sodium triacetoxyborohydride (232 mg, 1.09 mmol) in 5.0 mL 1,2-dichloroethane and stir at RT for 5 hours. Quench the reaction by adding water, then extract with $CH_2Cl_2$, dry the combined organic solvents over $Na_2SO_4$. The crude material purify by flash chromatography on silica gel, gradient (100% $CH_2Cl_2$ to 100% $CH_2Cl_2$: 2N $NH_3$/MeOH 30:1) over 55 min, give 190 mg yellow foam, (S)-9-fluoro-5-[3-(2-methoxy-ethyl)-4-methyl-piperazine-1-yl]-11H-12-thia-6,11-diaza-dibenzo[a,f]azulene.
MS(APCI), (m/e) 425.2 (M+1). The dihydrochloric salt is form by adding 5 eq of acetyl chloride (175 mg, 2.25 mmol) to the free base (190 mg, 0.45 mmol) in ethanol 5 mL). After removing the solvent, the residue dissolve in 10 ml mix solvent of $CH_3CN/H_2O=50/50$, lyophilize overnight, afford 200 mg of brownish solid. Mass spectrum (electrospray) (m/e): $C_{23}H_{25}FN_4OS \cdot 2HCl$, Calc. Mass: 425.1811(M+1-2HCl); Found: 425.1818.

Example 393

(S)-9-Fluoro-5-[3-(3-methoxy-propyl)-4-methyl-piperazin-1-yl]-11H-12-thia-6,11-diaza-dibenzo[a,f]azulene

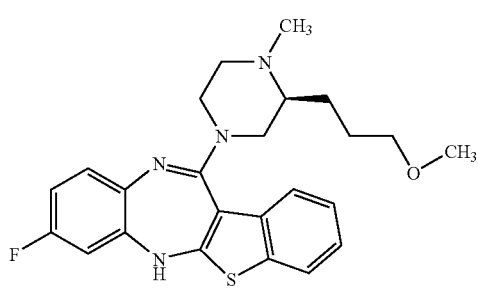

Using the method of Example 222 to give the title compound: mass spectrum (m/e):439.02 (M+1).

Example 394

(S)-9-Fluoro-5-[3-(3-methoxy-propyl)-4-methyl-piperazin-1-yl]-11H-12-thia-6,11-diaza-dibenzo[a f]azulene hydrochloride

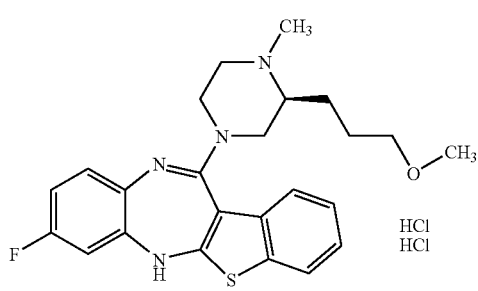

Using the method of Example 223 to give the title compound: mass spectrum (m/e):439.02 (M+1).

Example 395

(S)-8,9-Di-fluoro-5-[3-(2-methoxy-ethyl)-piperazine-1-yl]-11H-12-thia-6,11-diaza-dibenzo[a,f]azulene

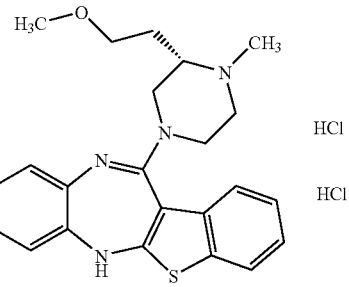

Combine 8,9-difluoro-1H-12-thia-6,11-diaza-dibenzo[a,f]azulen-5-ylamine hydrogen chloride (506 mg, 1.5 mmol, (S)-2-(2-methoxy ethyl) piperazine (432 mg, 3.0 mmol) and diisopropylethyl amine (193 mg, 1.5 mmol) in DMSO (1.0 mL) and toluene (3.0 mL), stir and heat to 110° C. After 48 hours, cool the reaction to RT, dilute with $CH_2Cl_2$, wash with $NaHCO_3$ (sat.) and brine. Dry the organic layer with by $Na_2SO_4$. The crude material purify by chromatography on silica gel, gradient (100% $CH_2Cl_2$ to 100% $CH_2Cl_2$: 2N $NH_3$/MeOH 20:1), give 137 mg of title compound.

Example 396

(S)-8,9-Di-fluoro-5-[3-(2-methoxy-ethyl)-4-methyl-piperazine-1-yl]-11H-12-thia-6,11-diaza-dibenzo[a,f]azulene dihydrochloride Combine 8,9-di-fluoro-5-[(S)-3-(2-methoxy-ethyl)-piperazine-1-yl]-11H12-thia-6,11-diaza-dibenzo[a,f]azulene (130 mg, 0.3 mmol), formaldehyde (37%, w/w, aq) (29.5 mg, 0.38 mmol) and sodium triacetoxyborohydride (95 mg, 0.45 mmol) in 5.0 mL 1,2-dichloroethane and stir at RT for 1 hours. Quench the reaction by adding water, then extract with $CH_2Cl_2$, dry the combined organic solvents over $Na_2SO_4$. The crude material purify by flash chromatography on silica gel, gradient (100% $CH_2Cl_2$ to 100% $CH_2Cl_2$: 2N $NH_3$/MeOH=30:1) over 55 min, give 125 mg yellow foam, (S)-8,9-diflouro-5-[3-(2-methoxy-ethyl)-4-methyl-piperazine-1-yl]-11H-12-thia-6,11-diaza-dibenzo[a,f]azulene. MS(APCI), (m/e) 443.1 (M+1). The dihydrochloric salt is form by adding 5 eq of acetyl chloride (111 mg, 1.40 mmol)

to the free base (125 mg, 0.28 mmol) in ethanol (5 mL). After removing the solvent, the residue dissolve in 10 ml mix solvent of $CH_3CN/H_2O=50/50$, lyophilize overnight, afford 130 mg of brownish solid. Mass spectrum (electrospray) (m/e): $C_{23}H_{24}F_2N_4OS \cdot 2HCl$, Calc. Mass: 443.1717 (M+1-2HCl); Found: 443.1729.

Receptor Binding Assays

Serotonin 5-HT$_6$, Dopamine D$_2$, and Histamine H$_1$ Binding Assay

The assay buffers used are 50 mM Tris-HCl pH 7.4, 120 mM NaCl, 5 mM KCl, 5 mM MgCl$_2$, 1 mM EDTA for the Dopamine D$_2$s receptor binding assay. The radioligand used is [$^{125}$I]iodospiperone from New England Nuclear Cat # NEX284-2200 Ci/mmole. The membranes used are from Receptor Biology (now owned by NEN), Cat # RBHD2CM for the D$_2$ receptor.

Compounds are obtained as 10 mM stocks in 100% DMSO. They are diluted to 1 mM in 100% DMSO by adding 180 μL DMSO to 20 μL of stock in 96 well plates using a multidrop. The 1 mM stocks are then diluted to make an 11 point concentration range from 125 μM down to 1.25 nM in half log increments using 10% DMSO as diluent. This is done using a TECAN robot. The final DMSO at this stage is 10-21.25% DMSO The radioligand is diluted in assay buffer to provide 0.1 nM for the D$_2$ assay. Each vial of membranes is diluted up to 92 mL in assay buffer. The final assay volume is 250 μL consisting of 210 μl of diluted membranes, 20 μL of compound or 10% DMSO for total binding, and 20 μL of diluted radioligand. The compounds are transferred from drug dilution plates into coming 96 well assay plates using a 96 well Multimek pipettor. Radioligand and membranes are added to assay plates using multidrop pipettors. Non-specific binding is determined in wells containing a final concentration of 5 μM haloperidol. The final drug concentration range in half logs is from 10 μM down to 0.1 nM. The final DMSO in the assay is 1-1.7%.

After addition of drug, membrane, and ligand, the plates are incubated for 2 hours at room temperature. During this time 96 well Millipore filter plates (MAFBNOB50) are soaked for a least 30 minutes with 200 μL per well of 0.5% polyethyleneimine.

The 0.5% PEI is removed from filterplate wells using a TiterTek MAP aspirator and 200 μL of the incubation mixture is transferred from the incubation plate to the filterplate after mixing. This transfer is done using the 96 tip Mutimek pipettor. After transfer to the filterplate filterplates are extracted and ished twice with 220 μL per well of cold buffer on the MAP aspirator. The peel away bottoms are removed from the filterplates and 60 μL per well of microscint 20 scintillation fluid is added per well using a multidrop. Plates are placed into suitable holders and are left at room temperature for 3 hours and are counted for $^3$H in either a Wallac Microbeta counter or on a Packard Topcount.

[$^{125}$I]DOI SPA Binding to Rhesus 5-HT$_{2A}$ Receptors Protocol

Incubations are performed in a total volume of 200 μl in 96 well assay plates. 50 μL [$^{125}$I]DOI (NEN, 2200 Ci/mmol, final concentration=0.075 nM) is added to 50 μL of test compounds dissolved in water (±DMSO and/or glacial acetic acid). 50 μL Wheat Germ Agglutinin (WGA) SPA beads, at 1 mg/well, (Amersham Life Sciences) in assay buffer (67 mM Tris-HCl pH 7.4, 13 mM MgCl$_2$, 0.67 mM EDTA) are then added. Membrane homogenate from cells expressing rhesus 5-HT$_{2A}$ receptors, approximately 0.9 million cells/ well, is added last. The plates are covered with sealing tape (FasCal) and allowed to incubate at room temperature for 2 hours. The plates are then centrifuged at approximately 200×g for 10 minutes at room temperature. The amount of $^{125}$I-DOI bound to the membranes, i.e. proximate to the WGA SPA beads, is then determined using a Wallac MicroBeta Trilux Scintillation Counter (Wallac, Inc.).

$^3$H-Pyrilamine SPA Binding to Human Histamine −1 Receptors Protocol

Incubations were performed in a total volume of 200 μl in 96 well assay plates. 50 μl $^3$H-pyrilamine (NEN, 20 Ci/mmol, final concentration=3.0 nM) was added to 50 μl of test compounds dissolved in water (±DMSO and/or glacial acetic acid). 50 μl Wheat Germ Agglutinin (WGA) bead, at 1 mg/well, (Amersham Life Sciences) in assay buffer (67 mM TrisCl pH 7.4) were then added. Membrane homogenate from cells expressing human Histamine-1 receptors, approximately 700,000 cells/well, was added last. The plates were covered with sealing tape (FasCal) and allowed to incubate at room temperature for 2 hours. The plates were then centrifuged at approximately 200×g for 10 minutes at room temperature. The amount of $^3$H-pyrilamine bound to the membranes, ie proximate to the WGA bead, was then determined using a Wallac MicroBeta Trilux Scintillation Counter (Wallac, Inc.).

Pharmaceutical Formulations

Capsule

A pulvule formulation is prepared by blending the active with silicone starch, and filling it into hard gelatin capsules.

|  | Per 300 mg capsule |
| --- | --- |
| Compound of formula (I) | 5.0 mg |
| Silicone | 2.9 mg |
| Starch flowable | 292.1 mg |

Tablet

A tablet formulation is made by granulating the active with appropriate diluent, lubricant, disintegrant and binder and compressing.

|  | Per 300 mg tablet |
| --- | --- |
| Compound of formula (I) | 10.0 mg |
| Magnesium stearate | 0.9 mg |
| Microcrystalline cellulose | 75.0 mg |
| Povidone | 15.0 mg |
| Starch, directly compressible | 199.1 mg |

Injection

An aqueous injection of active is prepared as a freeze-dried plug, for reconstitution in a suitable, sterile diluent before use (to a total volume of 10 ml).

| | |
|---|---|
| Compound of formula (I) | 20.0 mg |
| Mannitol | 20.0 mg |
| N Hydrochloric acid and/or N sodium hydroxide to adjust pH to 5-5.5. | |

Controlled Release Injection

A controlled release injection for intramuscular injection is formed from a sterile suspension of micronised active in an oleaginous vehicle.

| | |
|---|---|
| Compound of formula (I) | 65.0 mg |
| Aluminium stearate | 0.04 mg |
| Sesame oil | 2 ml |

We claim:

1. A compound of formula (I):

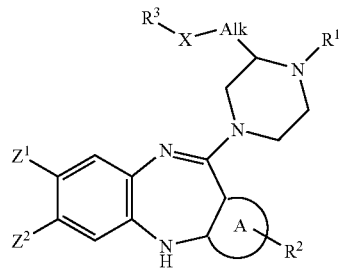

wherein:

is

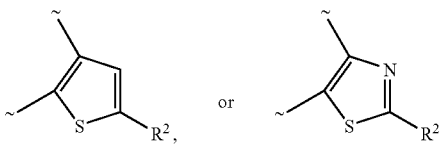

Alk is $(C_{1-4})$ alkylene or hydroxy substituted $(C_{1-4})$ alkylene;

X is oxygen or sulfur;

$R^1$ is $(C_{1-6})$ fluoroalkyl, $(C_{3-6})$ cycloalkyl, or $(C_{1-4})$ alkyl, wherein the $(C_{1-4})$ alkyl is unsubstituted or substituted with hydroxy, methoxy, ethoxy, $OCH_2CH_2OH$, or —CN;

$R^2$ is H, halogen, $(C_{1-6})$fluoroalkyl, $(C_{3-6})$ cycloalkyl, $OR^4$, $SR^4$, $NO_2$, CN, $COR^4$, $C(O)OR^4$, $CONR^5R^6$, $NR^5R^6$, $SO_2NR^5R^6$, $NR^5COR^4$, $NR^5SO_2R^4$, optionally substituted aromatic, or $(C_{1-6})$ alkyl, wherein the $(C_{1-6})$ alkyl is unsubstituted or substituted with hydroxy;

$R^3$ is hydrogen, $(C_{1-4})$ alkyl, $(C_{3-6})$ cycloalkyl, $(C_{2-6})$ alkenyl, Ar, or $(C_{1-4})$alkyl-Ar;

$R^4$ is hydrogen, $(C_{1-6})$ alkyl, $(C_{1-6})$ fluoroalkyl, or optionally substituted aromatic;

$R^5$ and $R^6$ are independently hydrogen, $(C_{1-6})$ alkyl, or optionally substituted aromatic, $R^7$ is hydrogen, $(C_{1-6})$ alkyl, $(C_{1-6})$ fluoroalkyl, or optionally substituted aromatic;

$R^8$ and $R^9$ are independently hydrogen, $(C_{1-6})$ alkyl, or optionally substituted aromatic;

Ar is optionally substituted phenyl, napthyl, monocyclic heteroaromatic or bicyclic heteroaromatic;

$Z^1$ and $Z^2$ are independently selected from hydrogen, halogen, $(C_{1-6})$ alkyl, $(C_{1-6})$ fluoroalkyl, $OR^7$, $SR^7$, $NO_2$, CN, $COR^7$, $CONR^8R^9$, $NR^8R^9$, and optionally substituted aromatic; or a pharmaceutically acceptable salt or hydrate thereof.

2. The compound of claim 1, wherein

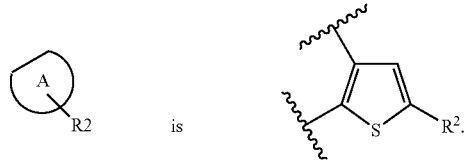

3. The compound of claim 2, wherein:

Alk is $(C_{1-4})$ alkylene;

$R^1$ is $(C_{1-4})$ alkyl;

$R^2$ is $(C_{1-6})$ alkyl or $(C_{1-6})$ fluoroalkyl;

$R^3$ is $(C_{1-4})$ alkyl;

X is O, and $Z^1$ and $Z^2$ are independently selected from hydrogen and halogen.

4. The compound of claim 1, wherein

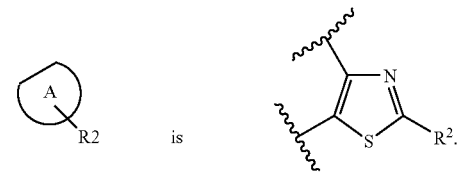

5. The compound of claim 4, wherein:

Alk is $(C_{1-4})$ alkylene;

X is oxygen;

$R^1$ is $(C_{1-4})$ alkyl;

$R^2$ is $(C_{1-6})$ fluoroalkyl$^4$, or $(C_{1-6})$ alkyl;

$R^3$ is $(C_{1-4})$ alkyl;

and $Z^1$ and $Z^2$ are hydrogen.

6. The compound of claim 1, wherein the stereo configuration is "S" about the carbon of the piperazine group bound to Alk.

7. The compound of claim 6, wherein Alk is $(C_{2-4})$ alkylene.

8. The compound of claim 1, wherein the stereo configuration is "R" about the carbon of the piperazine group bound to Alk.

9. The compound of claim 8, wherein Alk is methylene.

10. A pharmaceutical composition comprising an effective amount of a compound of claim 1 in association with a pharmaceutically acceptable carrier, diluent or excipient.

11. A method for treating a psychotic disorder, comprising administering to a mammal in need thereof an effective amount of a compound of claim 1.

12. The method of claim 11, wherein the psychotic disorder is schizophrenia.

13. The method of claim 11, wherein the psychotic disorder is schizophreniform.

14. The method of claim 11, wherein the psychotic disorder is schizoaffective disorder.

15. A method for treating a mood disorder, comprising administering to a mammal in need thereof an effective amount of a compound according to claim 1.

16. The method of claim 15, wherein the mood disorder is a bipolar disorder.

17. The method of claim 16, wherein the bipolar disorder is acute mania.

18. The method of claim 16, wherein the bipolar disorder is bipolar depression.

19. The compound (S)-6-Fluoro-10-[3-(2-methoxy-ethyl)-4-methyl-piperazin-1-yl]-2-methyl-4H-3-thia-4,9-diaza-benzo[f]azulene or a pharmaceutically acceptable salt or hydrate thereof.

20. The compound of claim 5 which is (S)-10-[3-(2-Methoxyethyl)-4-methylpiperazin-1-yl]-2-isopropyl-4H-3-thia-1,4,9-triazabenzo[f]azulene or a pharmaceutically acceptable salt or hydrate thereof.

21. A pharmaceutical composition of claim 10 comprising (S)-6-Fluoro-10-[3-(2-methoxy-ethyl)-4-methyl-piperazin-1-yl]-2-methyl-4H-3-thia-4,9-diaza-benzo[f]azulene a pharmaceutically acceptable salt or hydrate thereof.

* * * * *